(12) United States Patent
Tran et al.

(10) Patent No.: US 7,582,626 B2
(45) Date of Patent: Sep. 1, 2009

(54) 5,6-DIHYDRO-1H-PYRIDIN-2-ONE COMPOUNDS

(75) Inventors: Chinh V. Tran, San Diego, CA (US); Frank Ruebsam, San Diego, CA (US); Yuefen Zhou, San Diego, CA (US); Peter Dragovich, San Diego, CA (US); Alan X. Xiang, San Diego, CA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 11/955,144

(22) Filed: Dec. 12, 2007

(65) Prior Publication Data

US 2009/0111798 A1 Apr. 30, 2009

Related U.S. Application Data

(60) Provisional application No. 60/874,253, filed on Dec. 12, 2006, provisional application No. 60/907,479, filed on Apr. 3, 2007.

(51) Int. Cl.
*C07D 417/04* (2006.01)
*A61K 31/549* (2006.01)

(52) U.S. Cl. ............ 514/223.2; 544/12; 544/13
(58) Field of Classification Search ............ 544/12, 544/13; 514/223.2
See application file for complete search history.

(56) References Cited

U.S. PATENT DOCUMENTS

| 2005/0153877 A1 | 7/2005 | Miao et al. |
| 2006/0040927 A1 | 2/2006 | Blake et al. |
| 2006/0189602 A1 | 8/2006 | Zhou et al. |
| 2006/0211695 A1 | 9/2006 | Borzilleri et al. |
| 2006/0252785 A1 | 11/2006 | Blake et al. |

FOREIGN PATENT DOCUMENTS

| WO | WO-01/85172 A1 | 11/2001 |
| WO | WO-02/098424 A1 | 12/2002 |
| WO | WO-03/059356 A2 | 7/2003 |
| WO | WO-2006115221 | 11/2006 |

OTHER PUBLICATIONS

U.S. Appl. No. 11/766,668, Ellis et al.
U.S. Appl. No. 11/898,334, Zhou et al.
U.S. Appl. No. 11/861,678, Dragovich et al.
U.S. Appl. No. 11/955,144, Tran et al.
U.S. Appl. No. 11/955,193, Ruebsam et al.
U.S. Appl. No. 12/048,933, Ruebsam et al.
U.S. Appl. No. 12/061,499, Tran et al.
U.S. Appl. No. 11/845,515, Ellis et al.
Int'l Search Report of In'tl Appl. No. PCT/US05/45588, Oct. 13, 2006.
Tedesco et al., 3-(1,2,4)-benzothiadiazin-3-yl)-4-hydroxy-2(1H)-quinolinones, Potent Inhibitors of Hepatitis C Virus RNA-Dependent RNA Polymerase, J. Med. Chem. 49:971-983 (2006).
Int'l Search Report and Written Opinion of Int'l Appl. No. PCT/US07/87272, Apr. 16, 2008.
Int'l Search Report and Written Opinion of Int'l Appl. No. PCT/US07/87288, Apr. 17, 2008.
Fisyuk et al., Synthesis of 5,6-Dihydropyridin-2(1H)-ones, 1,5,6,8,8a-Hexahydroisoquinolin-3(2H)-ones and 4a,5,6,7,8,8a-Hexahydroquinolin-2(1H)-ones by Intramolecular Wittig Reaction. Molecules, Feb. 28, 2002, vol. 7, pp. 124-128.

*Primary Examiner*—Kahsay T Habte
(74) *Attorney, Agent, or Firm*—Connolly Bove Lodge & Hutz LLP

(57) ABSTRACT

The invention is directed to 5,6-dihydro-1H-pyridin-2-one compounds of Formula I and pharmaceutical compositions containing such compounds that are useful in treating hepatitis C virus infections:

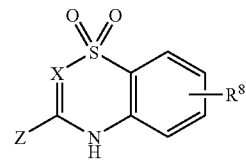

wherein
Z is

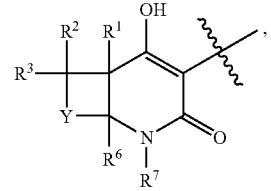

X is N or $CR^9$;
Y is $-(CR^4R^5)_n-$;
n is 2, 3, 4, or 5; and
$R^1$ through $R^9$ are defined herein.

20 Claims, No Drawings

5,6-DIHYDRO-1H-PYRIDIN-2-ONE COMPOUNDS

This application claims the benefit of U.S. Provisional Application No. 60/874,253, filed Dec. 12, 2006 and U.S. Provisional Application No. 60/907,479, filed Apr. 3, 2007.

FIELD OF THE INVENTION

The invention is directed to 5,6-dihydro-1H-pyridin-2-one compounds and pharmaceutical compositions containing such compounds that are useful in treating infections by hepatitis C virus.

BACKGROUND OF THE INVENTION

Hepatitis C is a major health problem world-wide. The World Health Organization estimates that 170 million people are chronic carriers of the hepatitis C virus (HCV), with 4 million carriers in the United States alone. In the United States, HCV infection accounts for 40% of chronic liver disease and HCV disease is the most common cause for liver transplantation. HCV infection leads to a chronic infection and about 70% of persons infected will develop chronic histological changes in the liver (chronic hepatitis) with a 10-40% risk of cirrhosis and an estimated 4% lifetime risk of hepatocellular carcinoma. The CDC estimates that each year in the United States there are 35,000 new cases of HCV infection and approximately ten thousand deaths attributed to HCV disease.

The current standard of care is a pegylated interferon/ribavirin combination at a cost of approximately $31,000/year. These drugs have difficult dosing problems and side-effects that preclude their use in almost half of diagnosed patients. Pegylated interferon treatment is associated with menacing flu-like symptoms, irritability, inability to concentrate, suicidal ideation, and leukocytopenia. Ribavirin is associated with hemolytic anemia and birth defects.

The overall response to this standard therapy is low; approximately one third of patients do not respond. Of those who do respond, a large fraction relapses within six months of completing 6-12 months of therapy. As a consequence, the long-term response rate for all patients entering treatment is only about 50%. The relatively low response rate and the significant side-effects of current therapy anti-HCV drug treatments, coupled with the negative long term effects of chronic HCV infection, result in a continuing medical need for improved therapy. Antiviral pharmaceuticals to treat RNA virus diseases like HCV are few, and as described above are often associated with multiple adverse effects.

A number of recent publications have described NS5B inhibitors useful in the treatment of hepatitis C infection. See, e.g., U.S. Patent Application Publication No. US 2006/0189602 (disclosing certain pyridazinones); U.S. Patent Application Publication No. US 2006/0252785 (disclosing selected heterocyclics); and International Publication Nos. WO 03/059356, WO 2002/098424, and WO 01/85172 (each describing a particular class of substituted thiadiazines).

While there are, in some cases, medicines available to reduce disease symptoms, there are few drugs to effectively inhibit replication of the underlying virus. The significance and prevalence of RNA virus diseases, including but not limited to chronic infection by the hepatitis C virus, and coupled with the limited availability and effectiveness of current antiviral pharmaceuticals, have created a compelling and continuing need for new pharmaceuticals to treat these diseases.

SUMMARY OF THE INVENTION

The present invention describes novel 5,6-dihydro-1H-pyridin-2-one compounds and pharmaceutically acceptable salts, which are useful in treating or preventing a hepatitis C virus infection in a patient in need thereof comprising administering to the patient a therapeutically or prophylactically effective amount of a 5,6-dihydro-1H-pyridin-2-one compound.

In a general aspect, the invention relates to compounds of Formula I

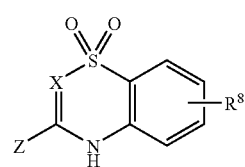

wherein

Z is

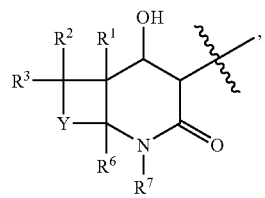

X is N or $CR^9$,

Y is $-(CR^4R^5)_n-$, n is 2, 3, 4, or 5, $R^1$ and $R^6$ are independently H or $C_1$-$C_6$ alkyl, $R^2$, $R^3$, $R^4$, and $R^5$ are independently H, $C_1$-$C_6$ alkyl, halo, or $R^2$ and $R^3$ or $R^4$ and $R^5$ combine with the atom to which they are attached to form a 3- to 6-membered spirocyclic ring, $R^7$ is H, $C_1$-$C_6$ alkyl, $C_3$-$C_8$ cycloalkyl, $-C_1$-$C_6$ alkylene($C_3$-$C_8$ cycloalkyl), $-C_1$-$C_6$ alkylene(aryl), $-C_1$-$C_6$ alkylene (heterocyclyl), aryl, heterocyclyl, or $-NR^{10}R^{11}$, wherein $R^{10}$ and $R^{11}$ are independently H, $C_1$-$C_6$ alkyl, $C_3$-$C_8$ cycloalkyl, or $C_2$-$C_6$ alkenyl $R^8$ is H, halo, nitro, $-CHR^{12}S(O)_2R^{13}$, $-C(S(O)_2R^{13})=CHR^{12}-$, $-NR^{13}R^{14}$, $-NR^{12}S(O)_2R^{13}$, or $-NR^{12}S(O)_2NR^{13}R^{14}$, wherein $R^{12}$, $R^{13}$, and $R^{14}$ are independently H, $C_1$-$C_6$ alkyl, $C_3$-$C_8$ cycloalkyl, aryl, or heterocyclyl, or $R^{12}$ and $R^{13}$ or $R^{13}$ and $R^{14}$ combine with the atom(s) to which they are attached to form a 5- or 6-membered heterocyclyl ring, $R^9$ is H, halo, or $C_1$-$C_6$ alkyl, wherein the above alkyl, alkylene, aryl, cycloalkyl, or heterocyclyl moieties provided in $R^1$, $R^2$, $R^3$, $R^4$, $R^5$, $R^6$, $R^7$, $R^9$, $R^{10}$, $R^{11}$, $R^{12}$, $R^{13}$, and $R^{14}$ are each optionally and independently substituted by 1-3 substituents selected from
  alkylamine,
  amino,
  aryl, cycloalkyl, heterocyclyl,
  $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms,
carboxyl,
cyano,
halo,
hydroxy,
nitro,
—C(O)OH, —C(O)$_2$—(C$_1$-C$_6$ alkyl), —C(O)$_2$—(C$_3$-C$_8$ cycloalkyl), —C(O)$_2$-(aryl),
—C(O)$_2$-(heterocyclyl), —C(O)$_2$—(C$_1$-C$_6$ alkylene)aryl, —C(O)$_2$—(C$_1$-C$_6$ alkylene)heterocyclyl, —C(O)$_2$—(C$_1$-C$_6$ alkylene)cycloalkyl, —C(O)(C$_1$-C$_6$ alkyl),
—C(O)(C$_3$-C$_8$ cycloalkyl), —C(O)(aryl), —C(O)(heterocyclyl), —C(O)(C$_1$-C$_6$ alkylene)aryl, —C(O)(C$_1$-C$_6$ alkylene)heterocyclyl, and —C(O)(C$_1$-C$_6$ alkylene)cycloalkyl, wherein each of the above optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, or a pharmaceutically acceptable salt, hydrate, tautomer or stereoisomer thereof.

In another embodiment, the invention relates to compounds of Formula I wherein Z is

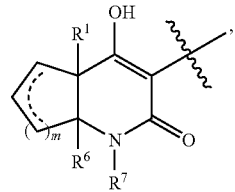

wherein m is 1 or 2, $R^1$, $R^6$ and $R^7$ are as defined previously, and one carbon-carbon double bond exists among the bonds indicated by the dotted line.

In one embodiment, the invention relates to compounds of Formula I wherein $R^8$ is —NR$^{12}$S(O)$_2$R$^{13}$, wherein $R^{12}$ and $R^{13}$ are independently H, $C_1$-$C_6$ alkyl or $C_3$-$C_8$ cycloalkyl.

In another embodiment, the invention relates to compounds of Formula I wherein $R^8$ is selected from

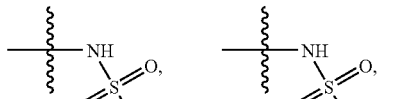

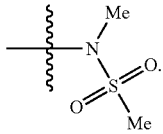

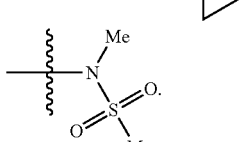

In yet another embodiment, the invention relates to compounds of Formula I wherein $R^8$ is selected from

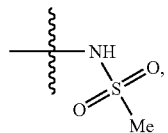 and 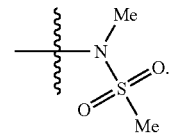

In one embodiment, the invention relates to compounds of Formula I wherein $R^7$ is selected from

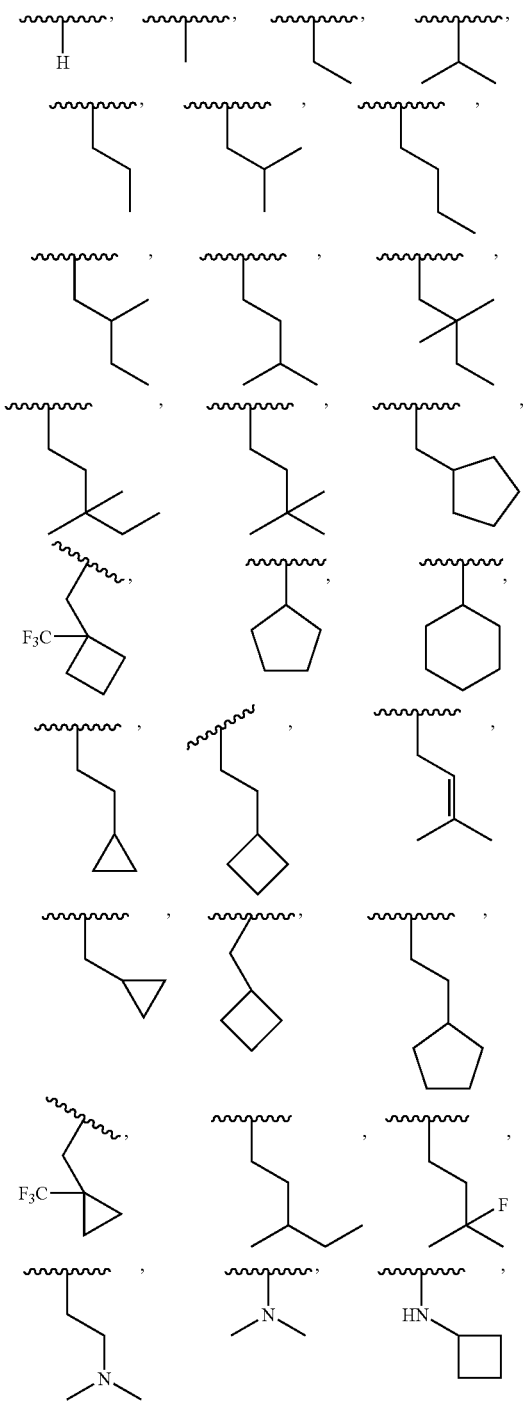

-continued
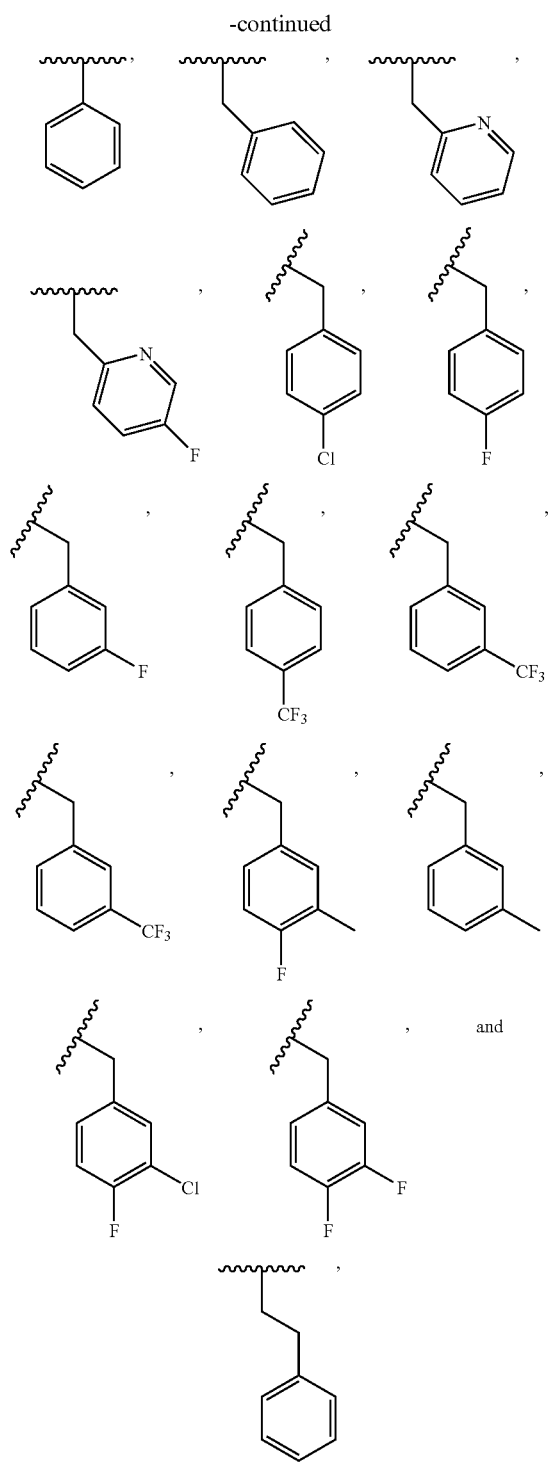
In another embodiment, the invention relates to compounds of Formula I wherein $R^7$ is selected from
-continued
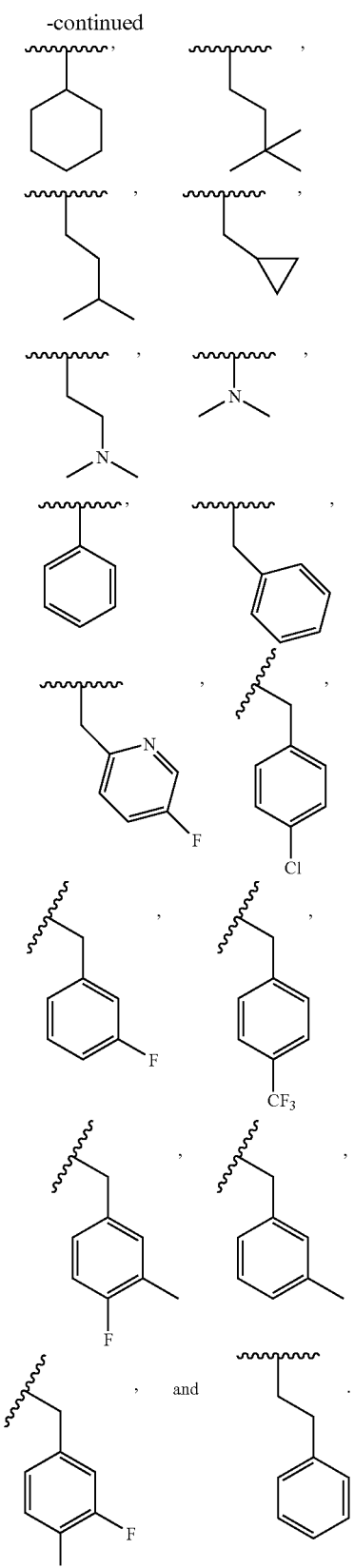
In a further embodiment, the invention relates to compounds of Formula I wherein $R^7$ is selected from

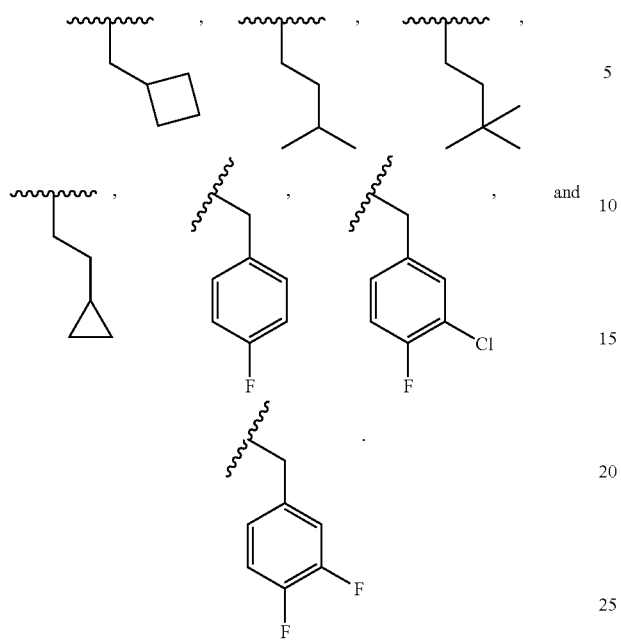

In one embodiment, the invention relates to compounds of Formula I wherein $R^9$ is H or $C_1$-$C_6$ alkyl.

In another embodiment, the invention relates to compounds of Formula I wherein $R^9$ is H.

In one embodiment, the invention relates to compounds of Formula I wherein $R^1$ and $R^6$ are H.

In one embodiment, the invention relates to compounds of Formula I wherein $R^2$, $R^3$, $R^4$, and $R^5$ are independently selected from

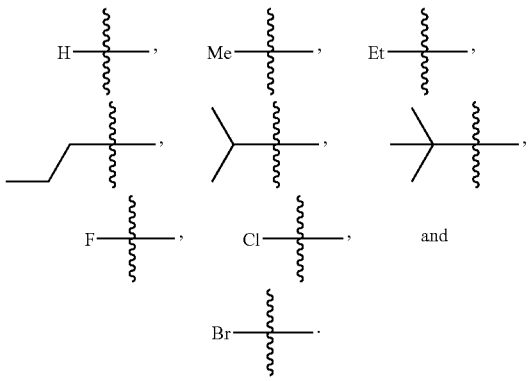

In a further embodiment, the invention relates to compounds of Formula I wherein $R^2$, $R^3$, $R^4$, and $R^5$ are independently selected from

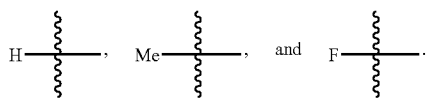

In yet another embodiment, the invention relates to compounds of Formula I wherein $R^2$, $R^3$, $R^4$, and $R^5$ are H.

In one embodiment n is 2 or 3.

In one embodiment, the invention relates to compounds of Formula I wherein Z is

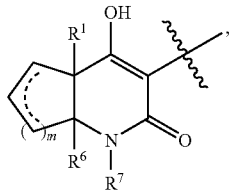

wherein m is 2, $R^1$, $R^6$ and $R^7$ are as defined previously, and one carbon-carbon double bond exists among the bonds indicated by the dotted line.

In another embodiment, the invention relates to compounds selected from cis-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1$\lambda^6$-benzo[1,2,4]thiadiazin-7-yl}-methanesulfonamide, N-{3-[1-(4-Fluoro-benzyl)-4-hydroxy-2-oxo-1,2,4a,5,6,7,8,9,10,10a-decahydro-cycloocta[b]pyridin-3-yl]-1,1-dioxo-1,4-dihydro-1$\lambda^6$-benzo[1,2,4]thiadiazin-7-yl}-methanesulfonamide, cis-N-[3-(4-Hydroxy-2-oxo-1-pyridin-2-ylmethyl-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide, cis-N-{3-[1-(5-Fluoro-pyridin-2-ylmethyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide, cis-N-{3-[1-(2-Dimethylamino-ethyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide, cis-N-[3-(1-Benzyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide, cis-N-[3-[1-(3-Fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide, cis-N-[3-(4-Hydroxy-2-oxo-1-phenethyl-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide, cis-N-[3-(1-Cyclopentyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide, (4aR,7aS)-N-{3-[1-(3-Chloro-4-fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide, (4aR,7aS)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide, (4aR,8aS)-N-{3-[1-(4-Fluoro-benzyl)-4-hydroxy-2-oxo-1, 2,4a,5,6,7,8,8a-octahydro-quinolin-3-yl]-1,1-dioxo-1,4-dihydro-1λ⁶-benzo[1,2,4]thiadiazin-7-yl}-methanesulfonamide, (4aR,7aS)-N-{3-[4-Hydroxy-2-oxo-1-(4-trifluoromethyl-benzyl)-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide, (4aR,7aS)-N-{3-[4-Hydroxy-2-oxo-1-(3-trifluoromethyl-benzyl)-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide, N-3-[1-(4-Fluoro-benzyl)-4-hydroxy-2-oxo-1,2,4a,5,6,8a-hexahydro-quinolin-3-yl]-1,1-dioxo-1,4-dihydro-1λ⁶-benzo[1,2,4]thiadiazin-7-yl}-methanesulfonamide, cis-N-{3-[2-(3-Methylbutyl)-5-hydroxy-3-oxo-2-aza-bi-cyclo[4.3.0]non-4-en-4-yl]-1,1-dioxo-1,4-dihydro-1λ⁶-benzo[1,2,4]thiadiazin-7-yl}-methanesulfonamide, cis-N-{3-[2-(3,3-Dimethylbutyl)-5-hydroxy-3-oxo-2-aza-bicyclo[4.3.0]non-4-en-4-yl]-1,1-dioxo-1,4-dihydro-1λ⁶-benzo[1,2,4]thiadiazin-7-yl}-methanesulfonamide, cis-N-{3-[2-Cyclopropylethyl-5-hydroxy-3-oxo-2-aza-bicyclo[4.3.0]non-4-en-4-yl]-1,1-dioxo-1,4-dihydro-1λ⁶-benzo[1,2,4]thiadiazin-7-yl}-methanesulfonamide, N-{3-[2-(3-Methylbutyl)-5-hydroxy-3-oxo-2-aza-bicyclo[4.4.0]dec-4-en-4-yl]-1,1-dioxo-1,4-dihydro-1λ⁶-benzo[1,2,4]thiadiazin-7-yl}-methanesulfonamide, N-{3-[2-(3,3-Dimethylbutyl)-5-hydroxy-3-oxo-2-aza-bicyclo[4.4.0]dec-4-en-4-yl]-1,1-dioxo-1,4-dihydro-1λ⁶-benzo[1,2,4]thiadiazin-7-yl}-methanesulfonamide, (4aR,7aS)-N-{3-[1-(4-Fluoro-3-methyl-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide, (4aR,7aS)-N-{3-[4-Hydroxy-1-(3-methyl-benzyl)-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide, cis-2-Amino-ethanesulfonic acid {3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-amide, cis-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,4]thiazin-7-yl}-methanesulfonamide, (4aS,7aR)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide, (4aR,7aS)-N-{3-[1-(3,4-Difluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide, (4aR,7aS)-N-{3-[4-Hydroxy-1-(3-methyl-butyl)-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide, (4aR,7aS)-N-{3-[1-(3,3-Dimethyl-butyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide, (4aR,7aS)-N-[3-(1-Cyclopropylmethyl-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide, (4aS,8aR)-N-{3-[1-(4-Fluoro-benzyl)-4-hydroxy-2-oxo-1,2,4a,5,6,7,8,8a-octahydro-quinolin-3-yl]-1,1-dioxo-1,4-dihydro-1λ⁶-benzo[1,2,4]thiadiazin-7-yl}-methanesulfonamide, N-{3-[1-(3,3-Dimethyl-butyl)-4-hydroxy-2-oxo-2,4a,5,6,7,8,9,9a-octahydro-1H-cyclohepta[b]pyridin-3-yl]-1,1-dioxo-1,4-dihydro-1λ⁶-benzo[1,2,4]thiadiazin-7-yl}-methanesulfonamide, N-{3-[4-Hydroxy-1-(3-methyl-butyl)-2-oxo-2,4a,5,6,7,8,9,9a-octahydro-1H-cyclohepta[b]pyridin-3-yl]-1,1-dioxo-1,4-dihydro-1λ⁶-benzo[1,2,4]thiadiazin-7-yl}-methanesulfonamide, N-{3-[4-Hydroxy-1-(3-methyl-butyl)-2-oxo-2,4a,5,6,7,8,9,9a-octahydro-1H-cyclohepta[b]pyridin-3-yl]-1,1-dioxo-1,4-dihydro-1λ⁶-benzo[1,2,4]thiadiazin-7-yl}-N-methyl-methanesulfonamide, N-{3-[1-(3,3-Dimethyl-butyl)-4-hydroxy-2-oxo-1,2,4a,5,6,7,8,9,10,10a-decahydro-cycloocta[b]pyridin-3-yl]-1,1-dioxo-1,4-dihydro-1λ⁶-benzo[1,2,4]thiadiazin-7-yl}-methanesulfonamide, N-{3-[1-(3,3-Dimethyl-butyl)-4-hydroxy-2-oxo-1,2,4a,5,6,7,8,9,10,10a-decahydro-cycloocta[b]pyridin-3-yl]-1,1-dioxo-1,4-dihydro-1λ⁶-benzo[1,2,4]thiadiazin-7-yl}-N-methyl-methanesulfonamide, cis-N-{3-[1-(4-Fluoro-benzyl)-4-hydroxy-2-oxo-1,2,4a,5,8,8a-hexahydro-quinolin-3-yl]-1,1-dioxo-1,4-dihydro-1λ⁶-benzo[1,2,4]thiadiazin-7-yl}-methanesulfonamide, cis-N-[3-(1-Dimethylamino-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide hydrochloride, (4aR,7aS)-1-(4-Fluoro-benzyl)-4-hydroxy-3-(7-iodo-1,1-dioxo-1,4-dihydro-1λ⁶-benzo[1,2,4]thiadiazin-3-yl)-1,4a,5,6,7,7a-hexahydro-[1]pyrindin-2-one, (4aR,7aS)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-benzenesulfonamide, cis-N-[3-(1-Cyclobutylamino-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide trifluoroacetic acid salt, (4aR,7aS)-3-(1,1-Dioxo-7-piperidin-1-yl-1,4-dihydro-1λ⁶-benzo[1,2,4]thiadiazin-3-yl)-1-(4-fluoro-benzyl)-4-hydroxy-1,4a,5,6,7,7a-hexahydro-[1]pyrindin-2-one, cis-N-[3-(1-Cyclohexyl-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide, (4aR,7aS)-3-[7-(1,1-Dioxo-4,5-dihydro-1H-1λ⁶-thiophen-2-yl)-1,1-dioxo-1,4-dihydro-1λ⁶-benzo[1,2,4]thiadiazin-3-yl]-1-(4-fluoro-benzyl)-4-hydroxy-1,4a,5,6,7,7a-hexahydro-[1]pyrindin-2-one, (4aR,7aS)-3-[7-(1,1-Dioxo-tetrahydro-1λ⁶-thiophen-2-yl)-1,1-dioxo-1,4-dihydro-1λ⁶-benzo[1,2,4]thiadiazin-3-yl]-1-(4-fluoro-benzyl)-4-hydroxy-1,4a,5,6,7,7a-hexahydro-[1]pyrindin-2-one, 1-(4-Fluoro-benzyl)-4-hydroxy-3-(7-iodo-1,1-dioxo-1,4-dihydro-1λ⁶-benzo[1,2,4]thiadiazin-3-yl)-1,4a,5,6,7,8,9,9a-octahydro-cyclohepta[b]pyridin-2-one, cis-N-[3-(1-Cyclobutylmethyl-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide, cis-N-[3-(4-Hydroxy-2-oxo-1-phenyl-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide, N-[3-(1-Cyclohexyl-4-hydroxy-2-oxo-1,2,4a,5,6,7,8,8a-oc-
   tahydro-quinolin-3-yl)-1,1-dioxo-1,4-dihydro-1$\lambda^6$-benzo
   [1,2,4]thiadiazin-7-yl]-methanesulfonamide,
1-(4-Fluoro-benzyl)-4-hydroxy-3-(7-iodo-1,1-dioxo-1,4-di-
   hydro-1$\lambda^6$-benzo[1,2,4]thiadiazin-3-yl)-4a,5,6,7,8,8a-
   hexahydro-1H-quinolin-2-one,
3-(1,1-Dioxo-1,4-dihydro-1$\lambda^6$-benzo[1,2,4]thiadiazin-3-yl)-
   1-(4-fluoro-benzyl)-4-hydroxy-1,4a,5,6,7,7a-hexahydro-
   [1]pyrindin-2-one,
(4aR,7aS)-N-{3-[1-(4-Fluoro-benzyl)-4-hydroxy-2-oxo-2,
   4a,5,6,7,7a-hexahydro-1H-[1]pyrindin-3-yl]-1,1-dioxo-1,
   4-dihydro-1$\lambda^6$-benzo[1,2,4]thiadiazin-7-yl}-C-phenyl-
   methanesulfonamide,
cis-N-[3-(4-Hydroxy-1-methyl-2-oxo-2,4a,5,6,7,7a-hexahy-
   dro-1H-[1]pyrindin-3-yl)-1,1-dioxo-1,4-dihydro-1$\lambda^6$-
   benzo[1,2,4]thiadiazin-7-yl]-methanesulfonamide,
cis-N-[3-(1-Ethyl-4-hydroxy-2-oxo-2,4a,5,6,7,7a-hexahy-
   dro-1H-[1]pyrindin-3-yl)-1,1-dioxo-1,4-dihydro-1$\lambda^6$-
   benzo[1,2,4]thiadiazin-7-yl]-methanesulfonamide,
cis-N-[3-(4-Hydroxy-1-isopropyl-2-oxo-2,4a,5,6,7,7a-
   hexahydro-1H-[1]pyrindin-3-yl)-1,1-dioxo-1,4-dihydro-
   1$\lambda^6$-benzo[1,2,4]thiadiazin-7-yl]-methanesulfonamide,
cis-N-{3-[1-(4-Chloro-benzyl)-4-hydroxy-2-oxo-2,4a,5,6,7,
   7a-hexahydro-1H-[1]pyrindin-3-yl]-1,1-dioxo-1,4-dihy-
   dro-1$\lambda^6$-benzo[1,2,4]thiadiazin-7-yl}-methanesulfona-
   mide,
cis-N-{3-[1-(4-Fluoro-benzyl)-4-hydroxy-2-oxo-2,4a,5,6,7,
   8,9,9a-octahydro-1H-cyclohepta[b]pyridin-3-yl]-1,1-di-
   oxo-1,4-dihydro-1$\lambda^6$-benzo[1,4]thiazin-7-yl}-methane-
   sulfonamide,
N-{3-[1-(2-Cyclopropyl-ethyl)-4-hydroxy-2-oxo-2,4a,5,6,
   7,8,9,9a-octahydro-1H-cyclohepta[b]pyridin-3-yl]-1,1-
   dioxo-1,4-dihydro-1$\lambda^6$-benzo[1,2,4]thiadiazin-7-yl}-
   methanesulfonamide,
N-[3-(4-Hydroxy-2-oxo-2,4a,5,6,7,8,9,9a-octahydro-1H-
   cyclohepta[b]pyridin-3-yl)-1,1-dioxo-1,4-dihydro-1$\lambda^6$-
   benzo[1,2,4]thiadiazin-7-yl]-methanesulfonamide, and
N-[3-(1-Cyclobutylamino-4-hydroxy-2-oxo-2,4a,5,6,7,8,9,
   9a-octahydro-1H-cyclohepta[b]pyridin-3-yl)-1,1-dioxo-
   1,4-dihydro-1$\lambda^6$-benzo[1,2,4]thiadiazin-7-yl]-methane-
   sulfonamide trifluoroacetic acid salt.

The invention is also directed to pharmaceutically accept-
able salts and pharmaceutically acceptable solvates of the
compounds of Formula I. Advantageous methods of making
the compounds of Formula I are also described.

In one aspect, the invention encompasses a method for
treating or preventing hepatitis C virus infection in a mammal
in need thereof, preferably in a human in need thereof, com-
prising administering to the patient a therapeutically or pro-
phylactically effective amount of a Formula I compound. In
one embodiment, the invention encompasses a method for
treating or preventing hepatitis C virus infection by adminis-
tering to a patient in need thereof a therapeutically or prophy-
lactically effective amount of a Formula I compound that is an
inhibitor of HCV NS5B polymerase.

In another aspect, the invention encompasses a method for
treating or preventing hepatitis C virus infection in a patient in
need thereof, comprising administering to the patient a thera-
peutically or prophylactically effective amount of a com-
pound of Formula I and a pharmaceutically acceptable excipi-
ent, carrier, or vehicle.

In another aspect, the invention encompasses a method for
treating or preventing hepatitis C virus infection in a patient in
need thereof, comprising administering to the patient a thera-
peutically or prophylactically effective amount of a com-
pound of Formula I and an additional therapeutic agent, pref-
erably an additional antiviral agent or an immunomodulatory
agent.

DETAILED DESCRIPTION OF THE INVENTION

Where the following terms are used in this specification,
they are used as defined below:

The terms "comprising," "having" and "including" are
used herein in their open, non-limiting sense.

The term "alkyl", as used herein, unless otherwise indi-
cated, includes saturated monovalent hydrocarbon radicals
having straight, branched, or cyclic moieties (including fused
and bridged bicyclic and spirocyclic moieties), or a combi-
nation of the foregoing moieties. For an alkyl group to have
cyclic moieties, the group must have at least three carbon
atoms.

The term "alkylene", as used herein, unless otherwise indi-
cated, includes a divalent radical derived from alkyl, as exem-
plified by —$CH_2CH_2CH_2CH_2$—.

The term "alkenyl", as used herein, unless otherwise indi-
cated, includes alkyl moieties having at least one carbon-
carbon double bond wherein alkyl is as defined above and
including E and Z isomers of said alkenyl moiety.

The term "alkynyl", as used herein, unless otherwise indi-
cated, includes alkyl moieties having at least one carbon-
carbon triple bond wherein alkyl is as defined above.

The term "alkoxy", as used herein, unless otherwise indi-
cated, includes O-alkyl groups wherein alkyl is as defined
above.

The term "Me" means methyl, "Et" means ethyl, and "Ac"
means acetyl.

The term "cycloalkyl", as used herein, unless otherwise
indicated refers to a non-aromatic, saturated or partially satu-
rated, monocyclic or fused, spiro or unfused bicyclic or tri-
cyclic hydrocarbon referred to herein containing a total of
from 3 to 10 carbon atoms, preferably 5-8 ring carbon atoms.
Exemplary cycloalkyls include monocyclic rings having
from 3-7, preferably 3-6, carbon atoms, such as cyclopropyl,
cyclobutyl, cyclopentyl, cyclohexyl, cycloheptyl and the like.
Illustrative examples of cycloalkyl are derived from, but not
limited to, the following:

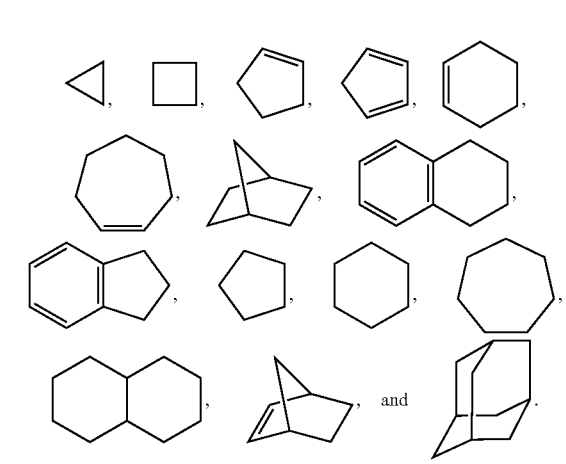

The term "aryl", as used herein, unless otherwise indicated,
includes an organic radical derived from an aromatic hydro-
carbon by removal of one hydrogen, such as phenyl or naph-
thyl.

The term "heterocyclic" or "heterocyclyl", as used herein, unless otherwise indicated, includes aromatic (e.g., heteroaryls) and non-aromatic heterocyclic groups containing one to four heteroatoms each selected from O, S and N, wherein each heterocyclic group has from 4-10 atoms in its ring system, and with the proviso that the ring of said group does not contain two adjacent O atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The 4- to 10-membered heterocyclic may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other illustrative examples of 4- to 10-membered heterocyclic are derived from, but not limited to, the following:

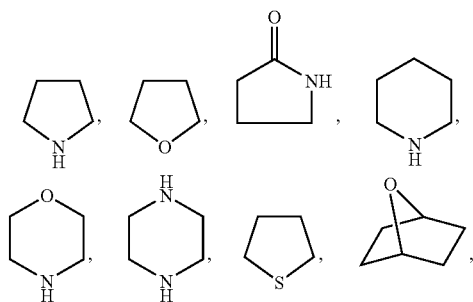

Unless defined otherwise, "alkyl," "alkylene," "alkenyl," "alkynyl," "aryl," "cycloalkyl," or "heterocyclyl" are each optionally and independently substituted by 1-3 substituents selected from alkylamine, amino, aryl, cycloalkyl, heterocyclyl, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms, carboxyl, cyano, halo, hydroxy, nitro, —C(O)OH, —C(O)$_2$—($C_1$-$C_6$ alkyl), —C(O)$_2$—($C_3$-$C_8$ cycloalkyl), —C(O)$_2$-(aryl), —C(O)$_2$-(heterocyclyl), —C(O)$_2$—($C_1$-$C_6$ alkylene)aryl, —C(O)$_2$—($C_1$-$C_6$ alkylene)heterocyclyl, —C(O)$_2$—($C_1$-$C_6$ alkylene)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkylene)aryl, —C(O)($C_1$-$C_6$ alkylene)heterocyclyl, and —C(O)($C_1$-$C_6$ alkylene)cycloalkyl, wherein each of these optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, e.g., $CF_3$.

The term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of HCV infection, the term "patient" or "subject" preferably means a monkey or a human, most preferably a human. In a specific embodiment the patient or subject is infected by or exposed to the hepatitis C virus. In certain embodiments, the patient is a human infant (age 0-2), child (age 2-17), adolescent (age 12-17), adult (age 18 and up) or geriatric (age 70 and up) patient. In addition, the patient includes immunocompromised patients such as HIV positive patients, cancer patients, patients undergoing immunotherapy or chemotherapy. In a particular embodiment, the patient is a healthy individual, i.e., not displaying symptoms of other viral infections.

The term a "therapeutically effective amount" refers to an amount of the compound of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term a "prophylactically effective amount" refers to an amount of a compound of the invention or other active ingredient sufficient to result in the prevention of infection, recurrence or spread of viral infection. A prophylactically effective amount may refer to an amount sufficient to prevent initial infection or the recurrence or spread of the infection or a disease associated with the infection. Used in connection with an amount of a compound of the invention, the term preferably encompasses a non-toxic amount that improves overall prophylaxis or enhances the prophylactic efficacy of or synergies with another prophylactic or therapeutic agent.

The term "in combination" refers to the use of more than one prophylactic and/or therapeutic agents simultaneously or sequentially and in a manner that their respective effects are additive or synergistic.

The term "treating" refers to:

(i) preventing a disease, disorder, or condition from occurring in an animal that may be predisposed to the disease, disorder and/or condition, but has not yet been diagnosed as having it;

(ii) inhibiting the disease, disorder, or condition, i.e., arresting its development; and (iii) relieving the disease, disorder, or condition, i.e., causing regression of the disease, disorder, and/or condition.

The terms "R" and "S" indicate the specific stereochemical configuration of a substituent at an asymmetric carbon atom in a chemical structure as drawn.

The term "rac" indicates that a compound is a racemate, which is defined as an equimolar mixture of a pair of enantiomers. A "rac" compound does not exhibit optical activity. The chemical name or formula of a racemate is distinguished from those of the enantiomers by the prefix (±)- or rac- (or racem-) or by the symbols RS and SR.

The terms "cis" and "trans" are descriptors which show the relationship between two ligands attached to separate atoms that are connected by a double bond or are contained in a ring. The two ligands are said to be located cis to each other if they lie on the same side of a plane. If they are on opposite sides, their relative position is described as trans. The appropriate reference plane of a double bond is perpendicular to that of the relevant σ-bonds and passes through the double bond. For a ring it is the mean plane of the ring(s).

The compounds of the invention may exhibit the phenomenon of tautomerism. While Formula I cannot expressly depict all possible tautomeric forms, it is to be understood that Formula I is intended to represent any tautomeric form of the depicted compound and is not to be limited merely to a specific compound form depicted by the formula drawings. For illustration, and in no way limiting the range of tautomers, the compounds of Formula I may exist as the following:

When X=N:

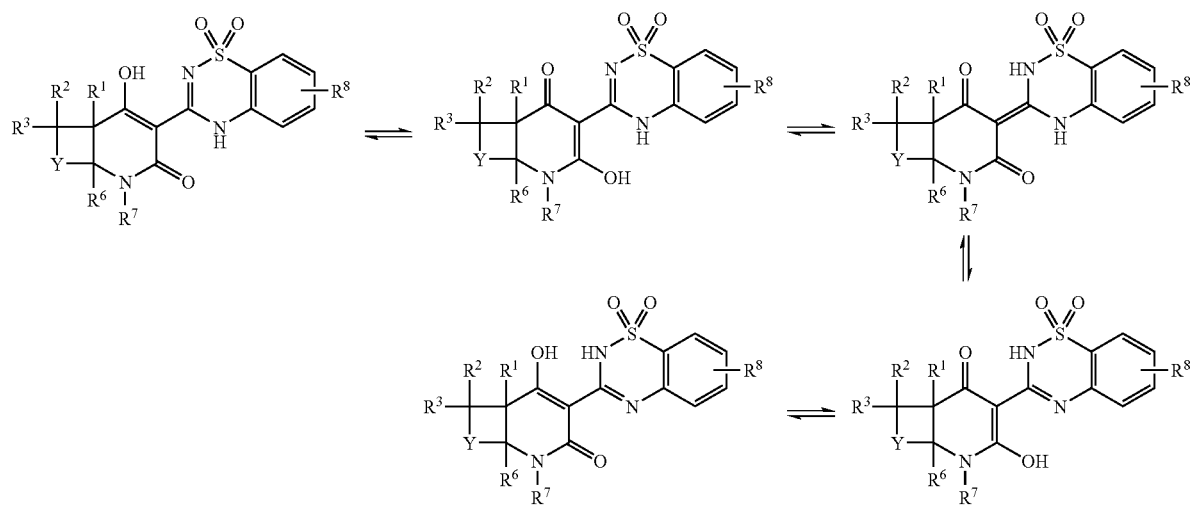

When X=CR$^9$:

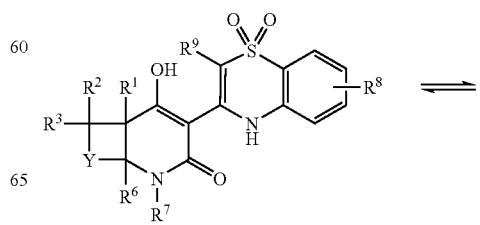

-continued

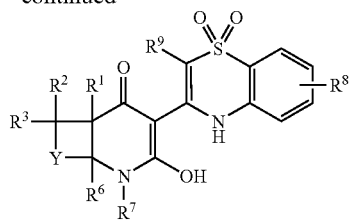

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% free of other enantiomers or diastereomers of the compounds, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the Formula I is intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

"A pharmaceutically acceptable prodrug" is a compound that may be converted under physiological conditions or by solvolysis to the specified compound or to a pharmaceutically acceptable salt of such compound prior to exhibiting its pharmacological effect (s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the compounds of Formula I using methods known in the art, such as those described by *Burger's Medicinal Chemistry and Drug Chemistry*, 1, 172-178, 949-982 (1995). See also Bertolini et al., *J. Med. Chem.*, 40, 2011-2016 (1997); Shan, et al., *J. Pharm. Sci.*, 86 (7), 765-767; Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, Design and Application of Prodrugs, Drug Design and Development (Krogsgaard-Larsen et al., eds., Harwood Academic Publishers, 1991); Dear et al., *J. Chromatogr. B*, 748, 281-293 (2000); Spraul et al., *J. Pharmaceutical & Biomedical Analysis*, 10, 601-605 (1992); and Prox et al., *Xenobiol.*, 3, 103-112 (1992).

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the Formula I compounds, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal, co-crystal, or polymorphic forms, all of which are intended to be within the scope of the present invention and specified formulas.

Methods of Treatment and Prevention of Hepatitis C Viral Infections

The present invention provides methods for treating or preventing a hepatitis C virus infection in a patient in need thereof.

The present invention further provides methods for introducing a therapeutically effective amount of the Formula I compound or combination of such compounds into the blood stream of a patient in the treatment and/or prevention of hepatitis C viral infections.

The magnitude of a prophylactic or therapeutic dose of a Formula I compound of the invention or a pharmaceutically acceptable salt, solvate, or hydrate, thereof in the acute or chronic treatment or prevention of an infection will vary, however, with the nature and severity of the infection, and the route by which the active ingredient is administered. The dose, and in some cases the dose frequency, will also vary according to the infection to be treated, the age, body weight, and response of the individual patient. Suitable dosing regimens can be readily selected by those skilled in the art with due consideration of such factors.

The methods of the present invention are particularly well suited for human patients. In particular, the methods and doses of the present invention can be useful for immunocompromised patients including, but not limited to cancer patients, HIV infected patients, and patients with an immunodegenerative disease. Furthermore, the methods can be useful for immunocompromised patients currently in a state of remission. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Doses

Toxicity and efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture; alternatively, the dose of the Formula I compound may be formulated in animal models to achieve a circulating plasma concentration range of the compound that corresponds to the concentration required to achieve a fixed magnitude of response. Such information can be used to more accurately determine useful doses in humans. Levels in plasma may be measured, for example, by high performance liquid chromatography.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of the Formula I compounds are exposed to the ligand and the magnitude of response is measured by an appropriate technique. The assessment of the Formula I compound is then evaluated with respect to the Formula I compound potency, and the degree of conversion of the Formula I compound prodrug. Compounds for use in methods of the invention can be tested in suitable animal model systems prior to testing in humans, including but not limited to in rats, mice, chicken, cows, monkeys, rabbits, hamsters, etc. The compounds can then be used in the appropriate clinical trials.

The magnitude of a prophylactic or therapeutic dose of a prodrug of a Formula I compound of the invention or a pharmaceutically acceptable salt, solvate, or hydrate thereof in the acute or chronic treatment or prevention of an infection or condition will vary with the nature and severity of the infection, and the route by which the active ingredient is administered. The dose, and perhaps the dose frequency, will also vary according to the infection to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. Also, the dose may differ for various particular Formula I compounds; suitable doses can be predicted on the basis of the aforementioned in vitro measurements and on the basis of animal studies, such that smaller doses will be suitable for those Formula I compounds that show effectiveness at lower concentrations than other Formula I compounds when measured in the systems described or referenced herein. In general, the dose per day is in the range of from about 0.001 to 100 mg/kg, preferably about 1 to 25 mg/kg, more preferably about 5 to 15 mg/kg. For treatment of humans infected by hepatitis C viruses, about 0.1 mg to about 15 g per day is administered in about one to four divisions a day, preferably 100 mg to 12 g per day, more preferably from 100 mg to 8000 mg per day.

Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered once time per week, two times per week, three times per week, four times per week or five times per week.

In one embodiment, the compounds of the invention are administered to provide systemic distribution of the compound within the patient. In a related embodiment, the compounds of the invention are administered to produce a systemic effect in the body.

In another embodiment the compounds of the invention are administered via oral, mucosal (including sublingual, buccal, rectal, nasal, or vaginal), parenteral (including subcutaneous, intramuscular, bolus injection, intraarterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intraarterial, or intravenous), transdermal, or topical administration. In a further specific embodiment, the compounds of the invention are administered via oral administration. In a further specific embodiment, the compounds of the invention are not administered via oral administration.

Different therapeutically effective amounts may be applicable for different infections, as will be readily known by those of ordinary skill in the art. Similarly, amounts sufficient to treat or prevent such infections, but insufficient to cause, or sufficient to reduce, adverse effects associated with conventional therapies are also encompassed by the above described dosage amounts and dose frequency schedules.

Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, antiemetic agents, antidepressants, and antifungal agents, anti-inflammatory agents, antiviral agents, anticancer agents, immunomodulatory agents, α-interferons, β-interferons, ribavirin, alkylating agents, hormones, cytokines, or toll receptor-like modulators. In one embodiment the invention encompasses the administration of an additional therapeutic agent that is HCV specific or demonstrates anti-HCV activity.

The Formula I compounds of the invention can be administered or formulated in combination with antibiotics. For example, they can be formulated with a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)),aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The Formula I compounds of the invention can also be administered or formulated in combination with an antiemetic agent. Suitable antiemetic agents include, but are not limited to, metoclopramide, domperidone, prochlorperazine, promethazine, chlorpromazine, trimethobenzamide, ondensetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

The Formula I compounds of the invention can be administered or formulated in combination with an antidepressant. Suitable antidepressants include, but are not limited to, binedaline, caroxazone, citalopram, dimethazan, fencamine, indalpine, indeloxazine hydrochloride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazapine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The Formula I compound s of the invention can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofulvin.

The Formula I compounds of the invention can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The Formula I compounds of the invention can be administered or formulated in combination with another antiviral agent. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, acyclovir, gangcyclovir, vidarabine, idoxuridine, trifluridine, levovirin, viramidine and ribavirin, as well as foscamet, amantadine, rimantadine, saquinavir, indinavir, amprenavir, lopinavir, ritonavir, the α-interferons; β-interferons; adefovir, clevadine, entecavir, pleconaril.

The Formula I compound of the invention can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boehringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), anti-B7 antibodies (e.g., IDEC-114 (IDEC)), CTLA4-immunoglobulin, and toll receptor-like (TLR) modulators. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies).

The Formula I compounds of the invention can be administered or formulated in combination with an agent which inhibits viral enzymes, including but not limited to inhibitors of HCV protease, such as BILN 2061, SCH-503034, ITMN-191 or VX-950; and inhibitors of NS5B polymerase such as NM107 (and its prodrug NM283), R1626, R7078, BILN1941, GSK625433, GILD9128 or HCV-796.

The Formula I compounds of the invention can be administered or formulated in combination with an agent which inhibits HCV polymerase such as those described in Wu, *Curr Drug Targets Infect Disord.* 2003; 3(3):207-19 or in combination with compounds that inhibit the helicase function of the virus such as those described in Bretner M, et al *Nucleosides Nucleotides Nucleic Acids.* 2003; 22(5-8):1531, or with inhibitors of other HCV specific targets such as those described in Zhang X., *IDrugs,* 5(2), 154-8 (2002).

The Formula I compounds of the invention can be administered or formulated in combination with an agent which inhibits viral replication.

The Formula I compounds of the invention can be administered or formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-α, and IFN-γ).

The Formula I compounds of the invention can be administered or formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

The Formula I compounds of the invention can be administered or formulated in combination with β-interferons which include, but are not limited to, interferon β-1a, interferon β-1b.

The Formula I compounds of the invention can be administered or formulated in combination with α-interferons which include, but are not limited to, interferon α-1, interferon α-2a (roferon), interferon α-2b, intron, Peg-Intron, Pegasys, consensus interferon (infergen) and albuferon.

The Formula I compounds of the invention can be administered or formulated in combination with an absorption enhancer, particularly those which target the lymphatic system, including, but not limited to sodium glycocholate; sodium caprate; N-lauryl-β-D-maltopyranoside; EDTA; mixed micelle; and those reported in Muranishi *Crit. Rev. Ther. Drug Carrier Syst.*, 7, 1-33, which is hereby incorporated by reference in its entirety. Other known absorption enhancers can also be used. Thus, the invention also encompasses a pharmaceutical composition comprising one or more Formula I compounds of the invention and one or more absorption enhancers.

The Formula I compounds of the invention can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The compounds of the invention and the other therapeutics agent can act additively or, more preferably, synergistically. In one embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent, particularly an antiviral agent.

In one embodiment, the methods of the invention comprise the administration of one or more Formula I compounds of the invention without an additional therapeutic agent.

Pharmaceutical Compositions and Dosage Forms

Pharmaceutical compositions and single unit dosage forms comprising a Formula I compound of the invention, or a pharmaceutically acceptable salt, or hydrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, pharmaceutical composition encompassed by this embodiment includes a Formula I compound of the invention, or a pharmaceutically acceptable salt, or hydrate thereof, and at least one additional therapeutic agent. Examples of additional therapeutic agents include, but are not limited to, those listed above.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990). Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise Formula I compounds of the invention, or a pharmaceutically acceptable salt or hydrate thereof comprise 0.1 mg to 1500 mg per unit to provide doses of about 0.01 to 200 mg/kg per day.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophilized products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the invention include, but are not limited to, creams, lotions, ointments, gels, solutions, emulsions, suspensions, or other forms known to one of skill in the art. See, e.g., *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985).

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the invention include, but are not limited to, ophthalmic solutions, sprays and aerosols, or other forms known to one of skill in the art. See, e.g., *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The Formula I compounds of the invention may also be administered directly to the lung by inhalation. For administration by inhalation, a Formula I compound can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a Formula I compound directly to the lung. MDI devices are available from a number of suppliers such as 3M Corporation, Aventis, Boehringer Ingelheim, Forest Laboratories, Glaxo-Wellcome, Schering Plough and Vectura.

Alternatively, a Dry Powder Inhaler (DPI) device can be used to administer a Formula I compound to the lung (see, e.g., Raleigh et al., *Proc. Amer. Assoc. Cancer Research Annual Meeting,* 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a Formula I compound to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver a Formula I compound to the lung. Nebulizers create aerosols from liquid drug formulations by using, for example, ultrasonic energy to form fine particles that can be readily inhaled (See e.g., Verschoyle et al., *British J. Cancer,* 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In one embodiment, an electrohydrodynamic ("EHD") aerosol device is used to deliver Formula I compounds to the lung. EHD aerosol devices use electrical energy to aerosolize liquid drug solutions or suspensions (see, e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the Formula I compounds formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of Formula I compounds will be known to the skilled artisan and are within the scope of the invention.

Liquid drug formulations suitable for use with nebulizers and liquid spray devices and EHD aerosol devices will typically include a Formula I compound with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the Formula I compound. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. Nos. 5,112,598; Biesalski, 5,556,611, which are herein incorporated by reference) A Formula I compound can also be formulated in rectal or vaginal compositions such as suppositories or retention enemas, e.g., containing conventional suppository bases such as cocoa butter or other glycerides.

In addition to the formulations described previously, a Formula I compound can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver Formula I compounds. Certain organic solvents such as dimethylsulfoxide can also be employed, although usually at the cost of greater toxicity. A Formula I compound can also be delivered in a controlled release system. In one embodiment, a pump can be used (Sefton, *CRC Crit. Ref Biomed Eng.,* 1987, 14, 201; Buchwald et al., *Surgery,* 1980, 88, 507; Saudek et al., *N. Engl. J. Med.*, 1989, 321, 574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.*, 1983, 23, 61; see also Levy et al., *Science*, 1985, 228, 190; During et al., *Ann. Neurol.*, 1989, 25, 351; Howard et al., *J. Neurosurg.*, 71, 105 (1989). In yet another embodiment, a controlled-release system can be placed in proximity of the target of the compounds of the invention, e.g., the lung, thus requiring only a fraction of the systemic dose (see, e.g., Goodson, in *Medical Applications of Controlled Release*, supra, vol. 2, pp. 115 (1984)). Other controlled-release system can be used (see, e.g., Langer, *Science*, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The invention provides a pharmaceutical pack or kit comprising one or more containers comprising a Formula I compound useful for the treatment or prevention of a Hepatitis C virus infection. In other embodiments, the invention provides a pharmaceutical pack or kit comprising one or more containers comprising a Formula I compound useful for the treatment or prevention of a Hepatitis C virus infection and one or more containers comprising an additional therapeutic agent, including but not limited to those listed above, in particular an antiviral agent, an interferon, an agent which inhibits viral enzymes, or an agent which inhibits viral replication, preferably the additional therapeutic agent is HCV specific or demonstrates anti-HCV activity.

The invention also provides a pharmaceutical pack or kit comprising one or more containers comprising one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The inventive agents may be prepared using the reaction routes and synthesis schemes as described below, employing the general techniques known in the art using starting materials that are readily available. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

Preparation of Compounds

In the synthetic schemes described below, unless otherwise indicated all temperatures are set forth in degrees Celsius and all parts and percentages are by weight.

Reagents were purchased from commercial suppliers such as Aldrich Chemical Company or Lancaster Synthesis Ltd. and were used without further purification unless otherwise indicated. All solvents were purchased from commercial suppliers such as Aldrich, EMD Chemicals or Fisher and used as received.

The reactions set forth below were done generally under a positive pressure of argon or nitrogen at an ambient temperature (unless otherwise stated) in anhydrous solvents, and the reaction flasks were fitted with rubber septa for the introduction of substrates and reagents via syringe. Glassware was oven dried and/or heat dried.

The reactions were assayed by TLC and/or analyzed by LC-MS and terminated as judged by the consumption of starting material. Analytical thin layer chromatography (TLC) was performed on glass-plates precoated with silica gel 60 $F_{254}$ 0.25 mm plates (EMD Chemicals), and visualized with UV light (254 nm) and/or iodine on silica gel and/or heating with TLC stains such as ethanolic phosphomolybdic acid, ninhydrin solution, potassium permanganate solution or ceric sulfate solution. Preparative thin layer chromatography (prepTLC) was performed on glass-plates precoated with silica gel 60 $F_{254}$ 0.5 mm plates (20×20 cm, from Thomson Instrument Company) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $MgSO_4$ prior to filtration and evaporation of the solvents under reduced pressure on a rotary evaporator and noted as solvents removed in vacuo. Column chromatography was completed under positive pressure using Merck silica gel 60, 230-400 mesh or 50-200 mesh neutral alumina, ISCO Flash chromatography using prepacked RediSep silica gel columns, or Analogix flash column chromatography using prepacked SuperFlash silica gel columns. Hydrogenolysis was done at the pressure indicated in the examples or at ambient pressure.

$^1$H NMR spectra and $^{13}$C NMR were recorded on a Varian Mercury-VX400 instrument operating at 400 MHz. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), bs (broad singlet), dd (doublet of doublets), dt (doublet of triplets). Coupling constants, when given, are reported in Hertz (Hz).

Infrared (IR) spectra were recorded on an ATR FT-IR Spectrometer as neat oils or solids, and when given are reported in wave numbers (cm$^{-1}$). Mass spectra reported are (+)-ES or APCI (+) LC/MS conducted by the Analytical Chemistry Department of Anadys Pharmaceuticals, Inc. Elemental analyses were conducted by the Atlantic Microlab, Inc. in Norcross, Ga. Melting points (mp) were determined on an open capillary apparatus, and are uncorrected.

The described synthetic pathways and experimental procedures utilize many common chemical abbreviations, 2,2-DMP (2,2-dimethoxypropane), Ac (acetyl), ACN (acetonitrile), Bn (benzyl), Boc (tert-butoxycarbonyl), Boc$_2$O (di-tert-butyl dicarbonate), Bz (benzoyl), DBU (1,8-diazabicyclo[5,4,0]undec-7-ene), DCC (N,N'-dicyclohexylcarbodiimide), DCE (1,2-dichloroethane), DCM (dichloromethane), DEAD (diethylazodicarboxylate), DIEA (diisopropylethylamine), DMA (N,N-dimethylacetamide), DMAP (4-(N,N-dimethylamino)pyridine), DMF (N,N-dimethylformamide), DMSO (dimethyl sulfoxide), EDC (1-(3-dimethylaminopropyl)-3-ethylcarbodiimide hydrochloride), Et (ethyl), EtOAc (ethyl acetate), EtOH (ethanol), HATU (O-(7-azabenzotriazol-1-yl)-1,1,3,3-tetramethyluronium hexafluorophosphate), HBTU (O-benzotriazol-1-yl-N,N,N',N'-tetramethyluronium hexafluorophosphate), HF (hydrogen fluoride), HOAc (acetic acid), HOBT (1-hydroxybenzotriazole hydrate), HPLC (high pressure liquid chromatography), IPA (isopropyl alcohol), KHMDS (potassium bis(trimethylsilyl)amide), KN(TMS)$_2$ (potassium bis(trimethylsilyl)amide), KO$^t$Bu (potassium tert-butoxide), LDA (lithium diisopropylamine), MCPBA (3-chloroperbenzoic acid), Me (methyl), MeCN (acetonitrile), MeOH (methanol), NaBH(OAc)$_3$ (sodium triacetoxyborohydride), NaCNBH$_3$ (sodium cyanoborohydride), NaH (sodium hydride), NIS (N-iodosuccinimide), NaN(TMS)$_2$ (sodium bis(trimethylsilyl)amide), NaOAc (sodium acetate), NaOEt (sodium ethoxide), NMM (N-methylmorpholine), Phe (phenylalanine), PPTS (pyridinium p-toluenesulfonate), PS (polymer supported), Py (pyridine), pyBOP (benzotriazol-1-yloxy)tripyrrolidinophosphonium hexafluorophosphate), TEA (triethylamine), TFA (trifluoroacetic acid), TFAA (trifluoroacetic anhydride), THF (tetrahydrofuran), TLC (thin layer chromatography), TMS (trimethylsilyl), Tol (toluoyl), Val (valine), and the like.

Scheme 1 provides a general procedure that can be used to prepare 5,6-dihydro-1H-pyridin-2-one compounds of Formula I.

Scheme 1

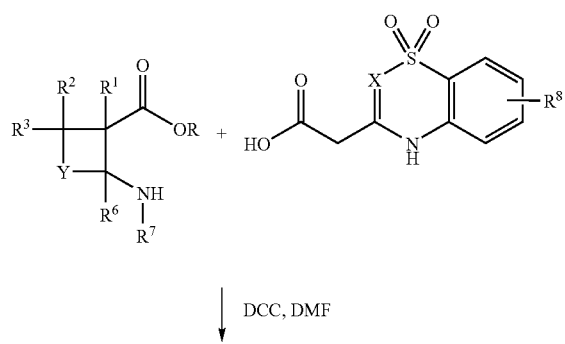

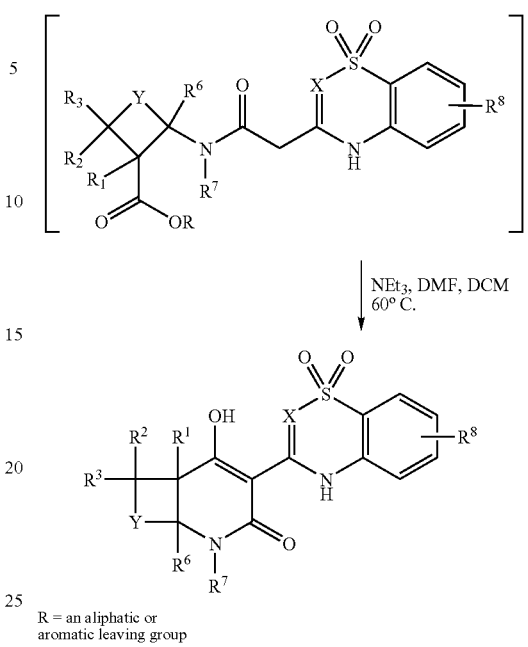

R = an aliphatic or aromatic leaving group

The β-amino acid ester intermediate, which can be obtained as described by one of the methods in schemes 4 to 14, can be condensed with a carboxylic acid intermediate using standard peptide coupling conditions used for the formation of amide bonds, such as DCC, to yield the shown amide. This intermediate can be cyclized without isolation in the presence of a base (e.g., triethylamine) to give the desired 5,6-dihydro-1H-pyridin-2-one compounds.

Scheme 2 provides a general procedure that can be used to prepare 5,6-dihydro-1H-pyridin-2-one compounds of Formula I.

Scheme 2

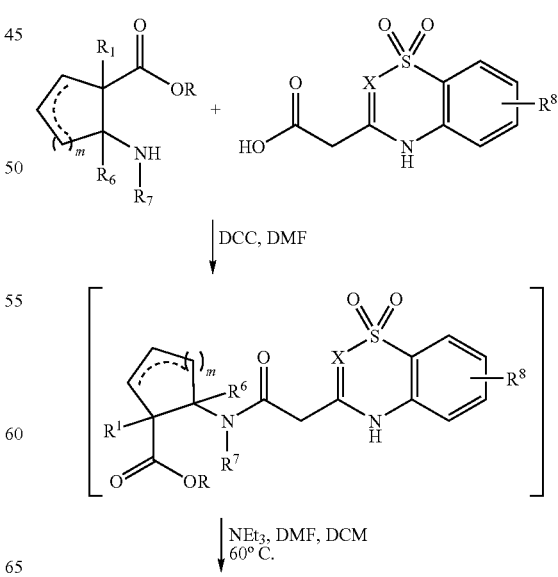

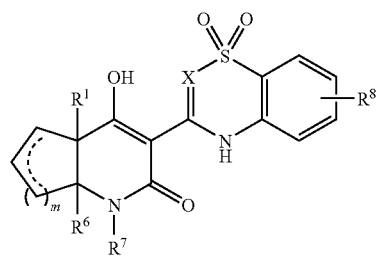

R = an aliphatic or aromatic leaving group

The β-amino acid ester intermediate, which can be obtained as described by one of the methods in schemes 4 to 14, can be condensed with a carboxylic acid intermediate using standard peptide coupling conditions used for the formation of amide bonds, such as DCC, to yield the shown amide. This intermediate can be cyclized without isolation in the presence of a base (e.g., triethylamine) to give the desired 5,6-dihydro-1H-pyridin-2-one compounds.

Scheme 3 provides a specific procedure that was used to prepare 5,6-dihydro-1H-pyridin-2-one compounds of Formula I.

Scheme 3

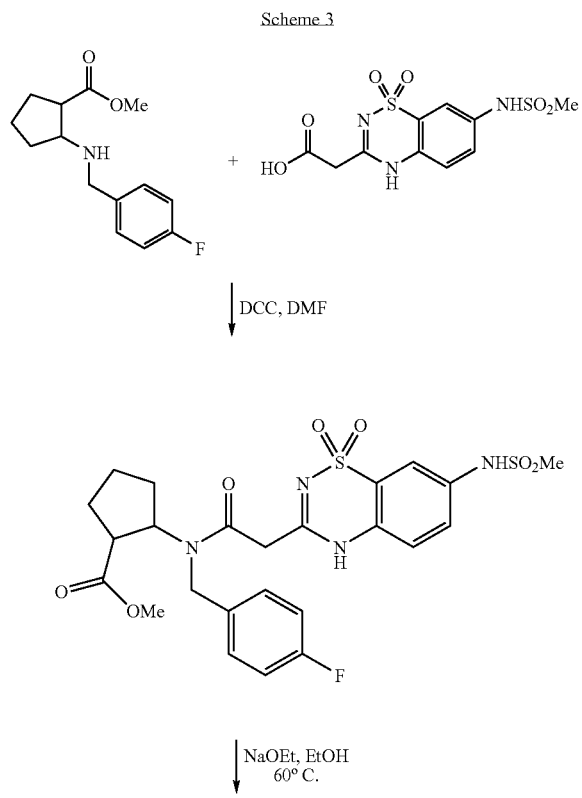

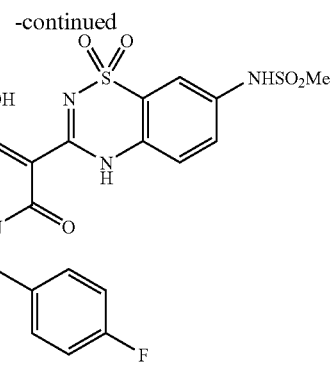

The β-amino acid ester intermediate, which can be obtained as described below, can be condensed with a carboxylic acid intermediate using standard peptide coupling conditions used for the formation of amide bonds, such as DCC, to yield the shown amide. The amide can be cyclized in the presence of a base (e.g., NaOEt) to give the desired 5,6-dihydro-1H-pyridin-2-one compounds.

Scheme 4 provides a general procedure that can be used to prepare the β-amino acid ester intermediates.

Scheme 4

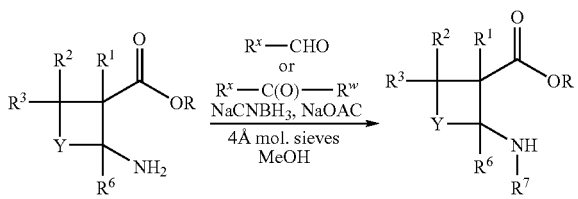

In cases where the cyclic β-amino acid esters (or their salts, e.g., hydrochlorides) are not commercially available, the commercially available cyclic β-amino acids, where Y is $-(CR^4R^5)_n-$ and n is 4 or 5, can be converted to an ester, such as a methyl ester, using known methods for the formation of esters from carboxylic acids (e.g., TMS-diazomethane). Also, in some cases the optically active cyclic β-amino acids are commercially available. The cyclic β-amino acid ester can then be treated with aldehydes or ketones, where $R^x$ and $R^w$ are $C_1$-$C_5$ alkyl, $C_3$-$C_8$ cycloalkyl, $-C_1$-$C_5$ alkylene($C_3$-$C_8$ cycloalkyl), $-C_1$-$C_5$ alkylene (aryl), $-C_1$-$C_5$ alkylene(heterocyclyl), aryl, or heterocyclyl, or $R^w$ can combine with $R^x$ to form a 3- to 8-membered ring, in the presence of a reducing agent (such as sodium cyanoborohydride) to afford the desired β-amino acid ester intermediates.

Scheme 5 provides a general procedure that can be used to prepare the β-amino acid ester intermediates.

Scheme 5

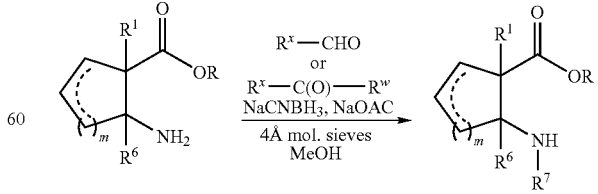

In cases where the cyclic β-amino acid esters (or their salts, e.g., hydrochlorides) are not commercially available, the commercially available cyclic β-amino acids, can be converted to an ester, such as a methyl ester, using known methods for the formation of esters from carboxylic acids (e.g., TMS-diazomethane). Also, in some cases the optically active cyclic β-amino acids are commercially available. The cyclic β-amino acid ester can then be treated with aldehydes or ketones, where $R^x$ and $R^w$ are $C_1$-$C_5$ alkyl, $C_3$-$C_8$ cycloalkyl, —$C_1$-$C_5$ alkylene($C_3$-$C_8$ cycloalkyl), —$C_1$-$C_5$ alkylene (aryl), —$C_1$-$C_5$ alkylene(heterocyclyl), aryl, or heterocyclyl, or $R^w$ can combine with $R^x$ to form a 3- to 8-membered ring, in the presence of a reducing agent (such as sodium cyanoborohydride) to afford the desired β-amino acid ester intermediates.

Scheme 6 provides a specific procedure that was used to prepare the β-amino acid ester intermediates.

omethane). Also, in some cases the optically active cyclic β-amino acids are commercially available. The cyclic β-amino acid ester can then be treated with halides or pseudohalides $X^a$ (e.g., chlorides, bromides, iodides, mesylates, tosylates or triflates), where $R^v$ is aryl or heterocyclyl, in the presence of metal catalyst such as copper (e.g., under Ullmann reaction conditions) or palladium (e.g., under Buchwald-Hartwig reaction conditions), to afford the desired β-amino acid ester intermediates.

Scheme 8 provides an alternate general procedure that can be used to prepare the β-amino acid ester intermediates.

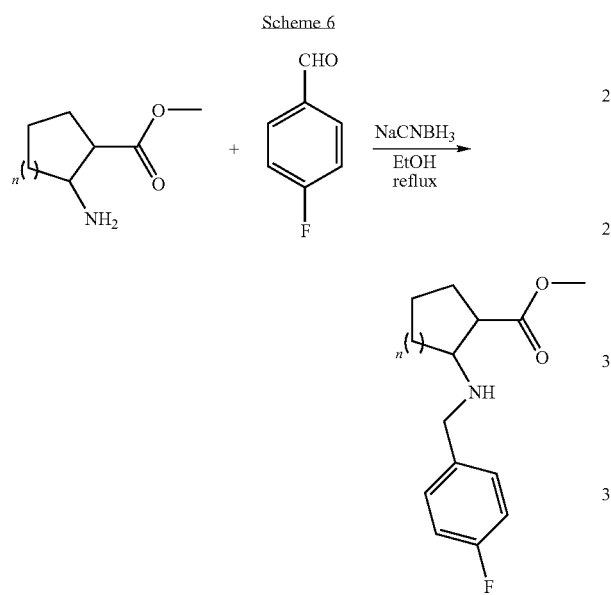

$n$ = 0, 1, 2, 3, 4, or 5

Commercially available cyclic β-amino acids, such as shown above, can be treated with aliphatic or aromatic aldehydes in the presence of a reducing agent (such as sodium cyanoborohydride) to undergo reductive alkylation to afford the desired β-amino acid ester intermediates.

Scheme 7 provides a general procedure that can be used to prepare the β-amino acid ester intermediates.

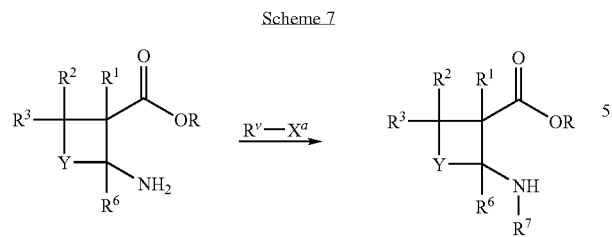

In cases where the cyclic β-amino acid esters (or their salts, e.g., hydrochlorides) are not commercially available, the commercially available cyclic β-amino acids, where Y is —$(CR^4R^5)_n$— and n is 4 or 5, can be converted to an ester, such as a methyl ester, using known methods for the formation of esters from carboxylic acids (e.g., TMS-diaz-

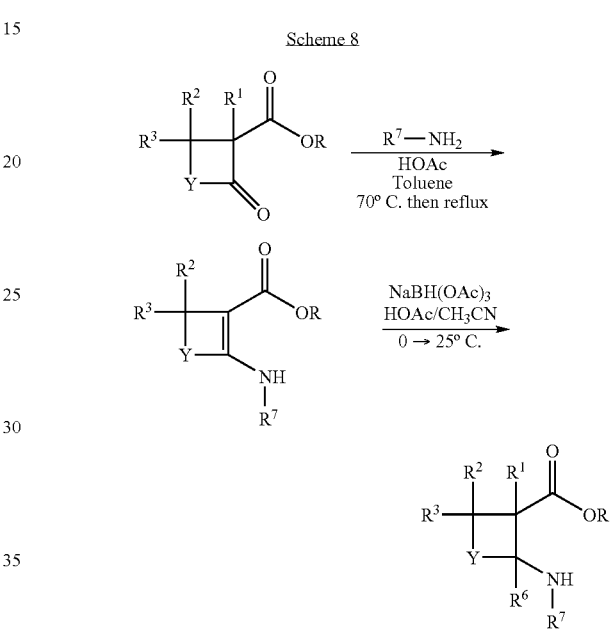

Alternatively, commercially available β-ketoesters can be treated with a primary amine to form enamines. The enamines can then be reduced to the desired corresponding amine compounds using standard methods for the reduction of a C—N double bond, such as sodium triacetoxyborohydride, yielding predominantly the cis isomers. The other isomer (trans) can be separated and isolated by chromatography.

Scheme 9 provides an alternate general procedure that can be used to prepare the β-amino acid ester intermediates.

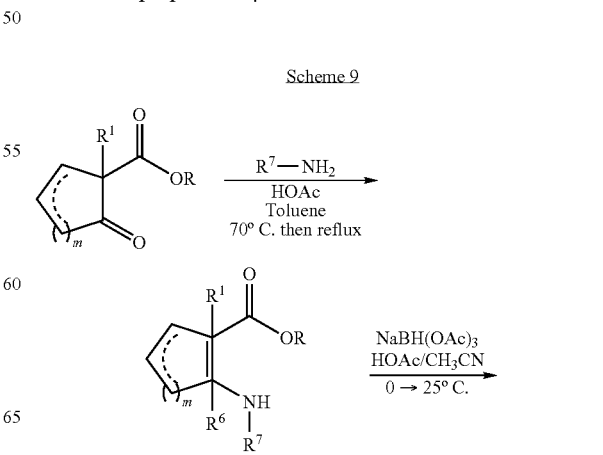

-continued

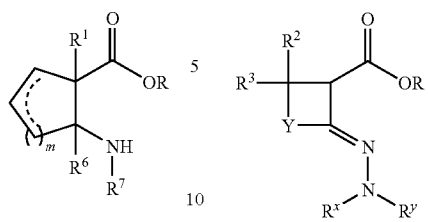

Alternatively, cyclic β-ketoesters can be treated with a primary amine to form enamines. The enamines can then be reduced to the desired corresponding amine compounds using standard methods for the reduction of a C—N double bond, such as sodium triacetoxyborohydride.

Scheme 10 provides a general procedure that was used to prepare the β-amino acid ester intermediates.

Scheme 10

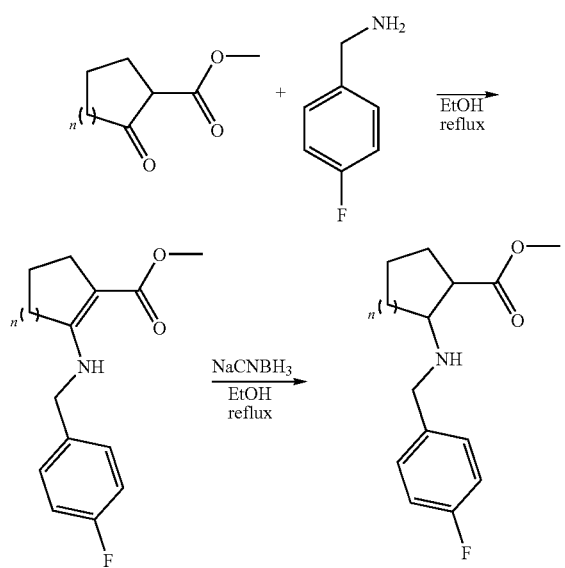

The commercially available β-ketoesters can be treated with a primary amine, such as an aliphatic or benzylic amine, to form enamines. The enamines can then be reduced to the desired corresponding amine compounds using standard methods for the reduction of a C—N double bond, such as sodium cyanoborohydride.

Scheme 11 provides an alternate general procedure that can be used to prepare the β-amino acid ester intermediates derived from hydrazines.

Scheme 11

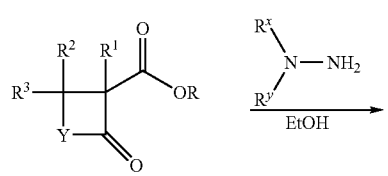

-continued

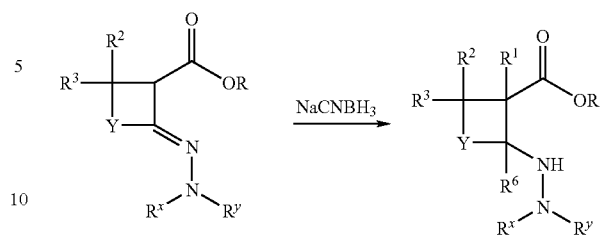

Commercially available β-ketoesters can be treated with optionally substituted hydrazines to afford hydrazones (where $R^x$ and $R^y$ are independently hydrogen, $C_1$-$C_6$ alkyl, $C_3$-$C_8$ cycloalkyl, or $C_2$-$C_6$ alkenyl). The hydrazones can then be reduced to the desired corresponding hydrazine compounds using standard methods for the reduction of a C—N double bond, such as sodium cyanoborohydride, to afford the desired β-amino acid ester intermediates. Alternatively, the desired β-amino acid ester intermediates can be synthesized in one step from the commercially available β-ketoesters and optionally substituted hydrazines in the presence of a reducing agent, such as sodium cyanoborohydride.

Scheme 12 provides an alternate general procedure that can be used to prepare the β-amino acid ester intermediates derived from hydrazines.

Scheme 12

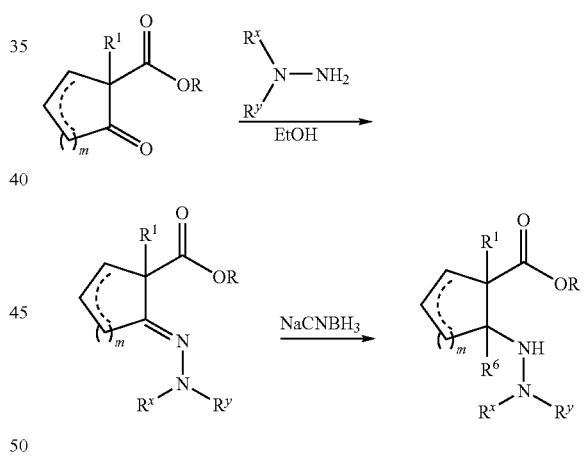

Cyclic β-ketoesters can be treated with optionally substituted hydrazines to afford hydrazones (where $R^x$ and $R^y$ are independently hydrogen, $C_1$-$C_6$ alkyl, $C_3$-$C_8$ cycloalkyl, or $C_2$-$C_6$ alkenyl). The hydrazones can then be reduced to the desired corresponding hydrazine compounds using standard methods for the reduction of a C—N double bond, such as sodium cyanoborohydride, to afford the desired β-amino acid ester intermediates. Alternatively, the desired β-amino acid ester intermediates can be synthesized in one step from the cyclic β-ketoesters and optionally substituted hydrazines in the presence of a reducing agent, such as sodium cyanoborohydride.

Scheme 13 provides a general scheme describing a method that can be used to separate the cis enantiomers through kinetic resolution of diastereomeric salts.

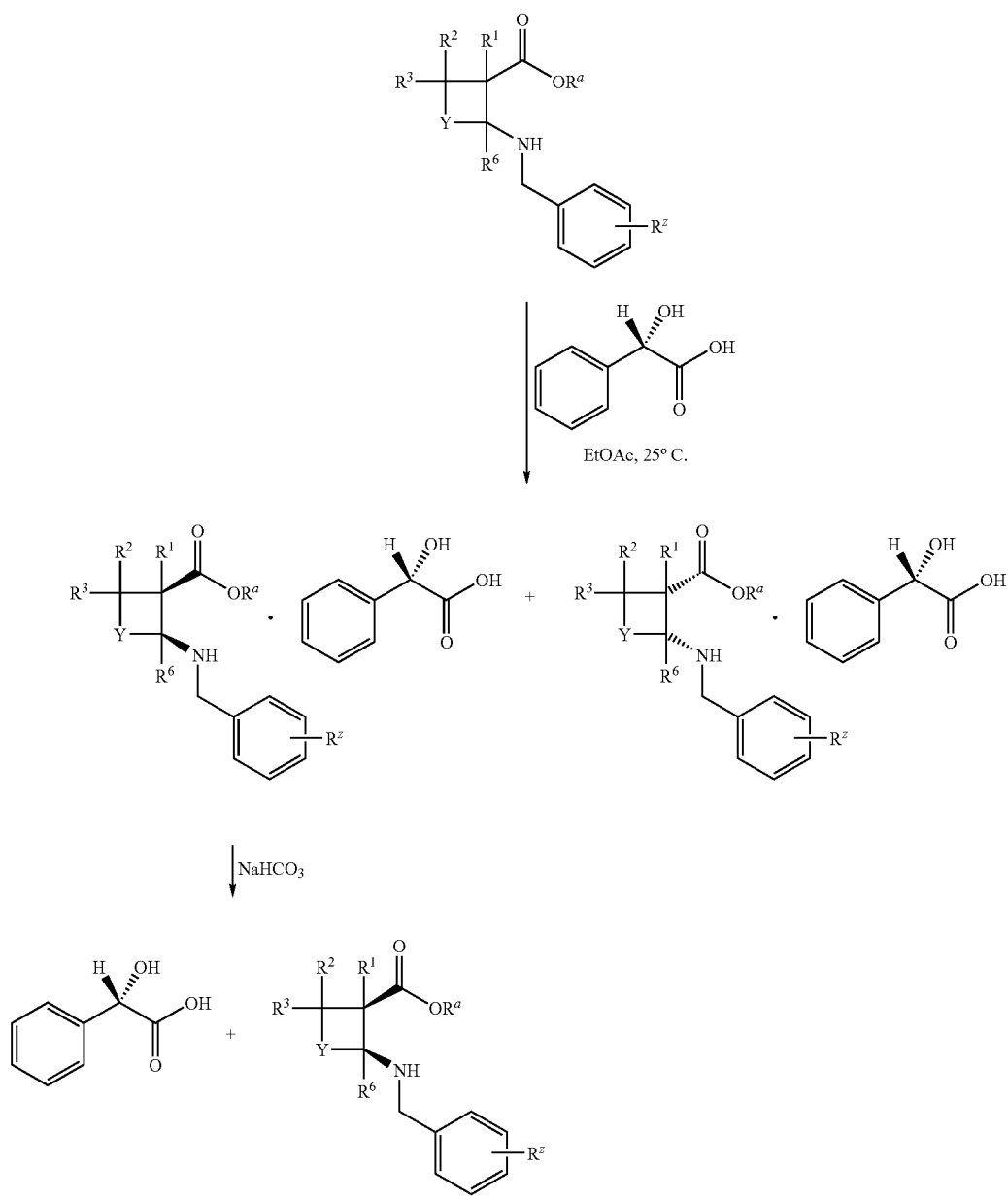

Scheme 13

$R^a$ = Me, Et

The pure racemic cis-β-amino acid ester derivatives obtained as described above (here shown with substituent $R^z$), can be resolved by forming diastereomeric salts with an optically pure acid, such as (S)-(+)-mandelic acid. The salt of the (1R,2S)-β-amino acid ester derivative forms a crystalline precipitate with (S)-(+)-mandelic acid that could be selectively isolated by filtration from an appropriate solvent (e.g., ethyl acetate) and treated with a base, such as sodium bicarbonate, to afford the free enantiomerically pure (1R,2S)-β-amino acid ester derivative. The corresponding salt of the (1S,2R)-β-amino acid ester with (S)-(+)-mandelic acid remains soluble in ethyl acetate, where $R^z$ is one to three independent substituents selected from $C_1$-$C_6$ alkyl, $C_3$-$C_8$ cycloalkyl, $C_1$-$C_6$ alkoxy, $C_2$-$C_6$ alkenyl, and $C_2$-$C_6$ alkynyl, wherein each of which may be interrupted by one or more hetero atoms, and wherein each of these substituents can be optionally substituted by 1-5 substituents selected from halo, cyano, hydroxy, and nitro.

Scheme 14 provides a general scheme describing a method that can be used to isolate the (1S,2R)-enantiomer of the β-amino acid ester derivative through formation of a different diastereomeric salt.

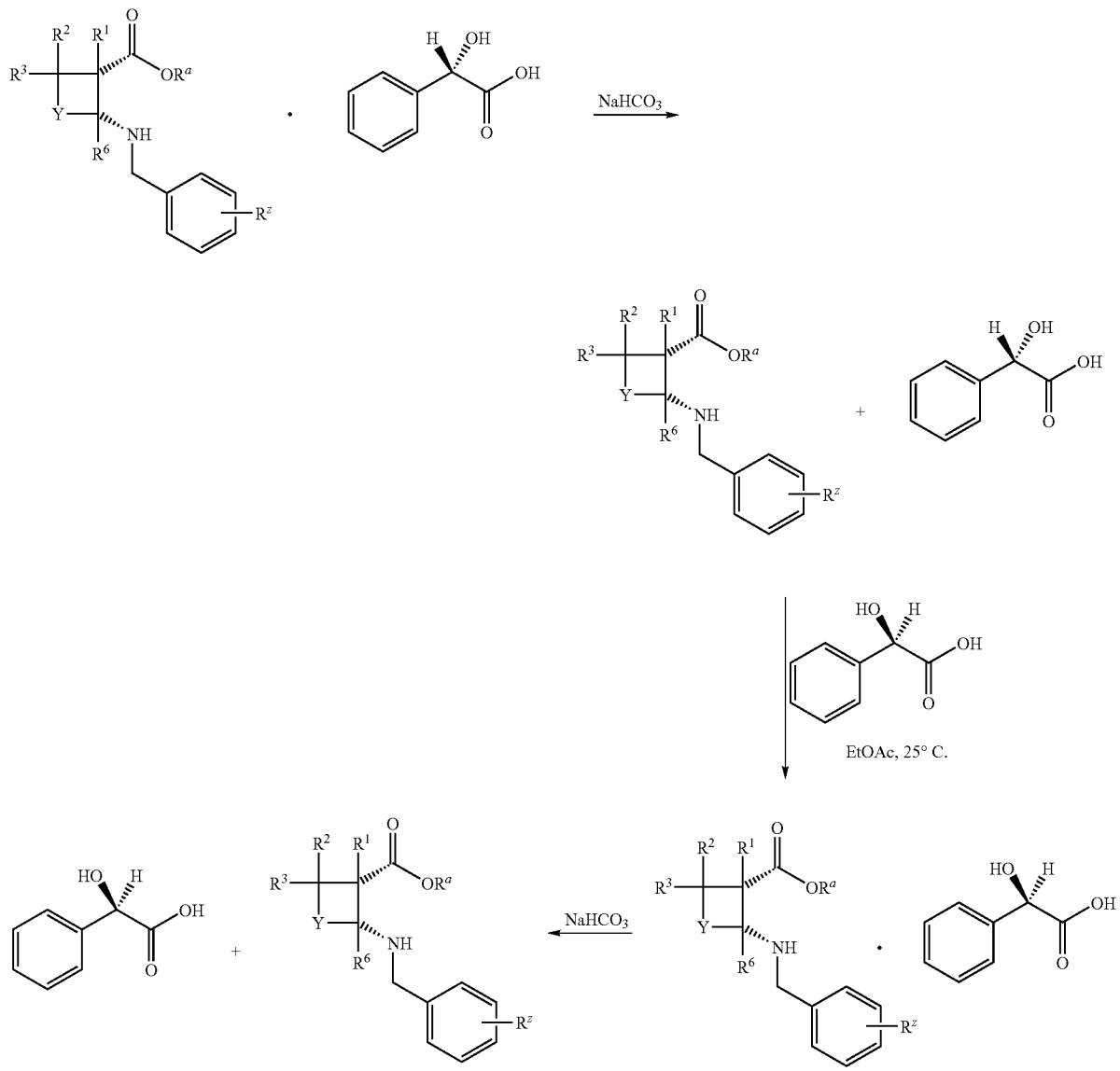

Scheme 14

$R^a$ = Me, Et

The solution of the salt of the (1S,2R)-β-amino acid ester (as prepared in scheme 13) can be treated with a base, such as sodium bicarbonate, to afford the free enantiomerically pure (1S,2R)-β-amino acid ester derivative in a non-crystalline form. At this stage the (S)-(+)-mandelic acid can also be recovered. Treatment of the (1S,2R)-β-amino acid ester with (R)-(−)-mandelic acid affords the crystalline diastereomeric salt, which can be isolated by filtration from an appropriate solvent (e.g., ethyl acetate). The isolated salt can be treated with a base, such as sodium bicarbonate, to afford the free enantiomerically pure (1S,2R)-β-amino acid ester derivative. (R)-(−)-mandelic acid can be recovered at this stage as well.

Scheme 15 provides a procedure that was used to prepare 7-substituted-1,1-dioxo-1,4-dihydro-1λ$^6$-benzo[1,4]thiazin-3-yl-acetic acid intermediates.

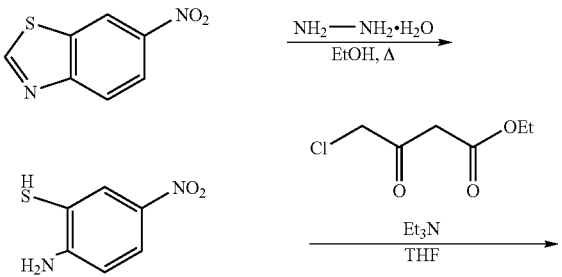

Scheme 15

47

-continued

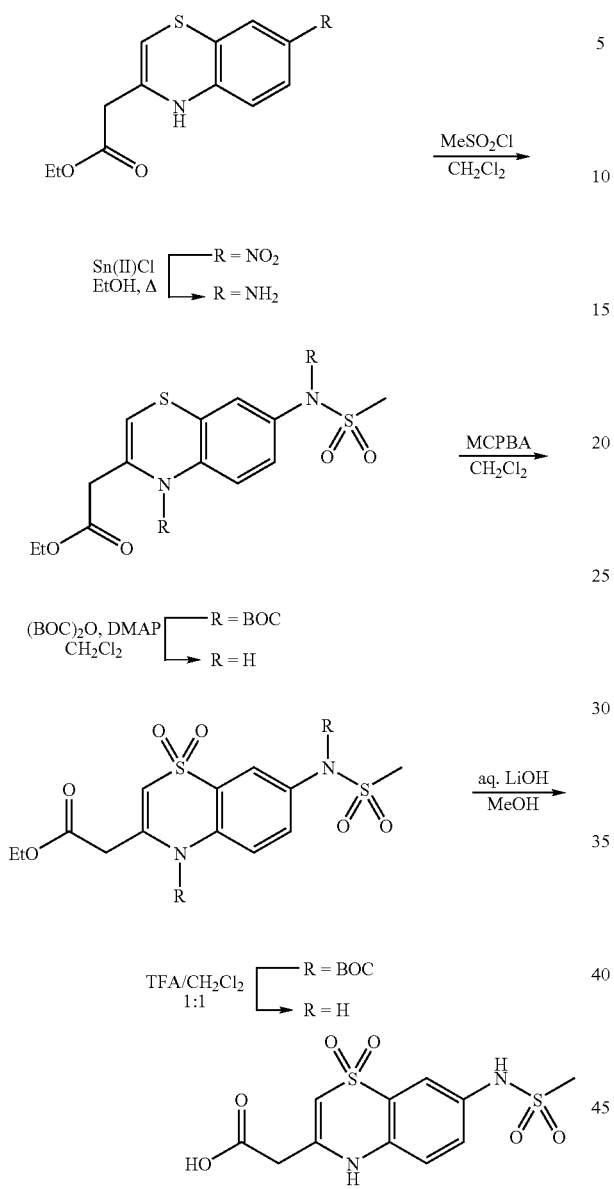

48

Scheme 16 provides a general procedure that can be used to prepare 7-substituted-, 1,1-dioxo-1,4-dihydro-1λ$^6$-benzo[1,2,4]thiadiazin-3-yl-acetic acid intermediates.

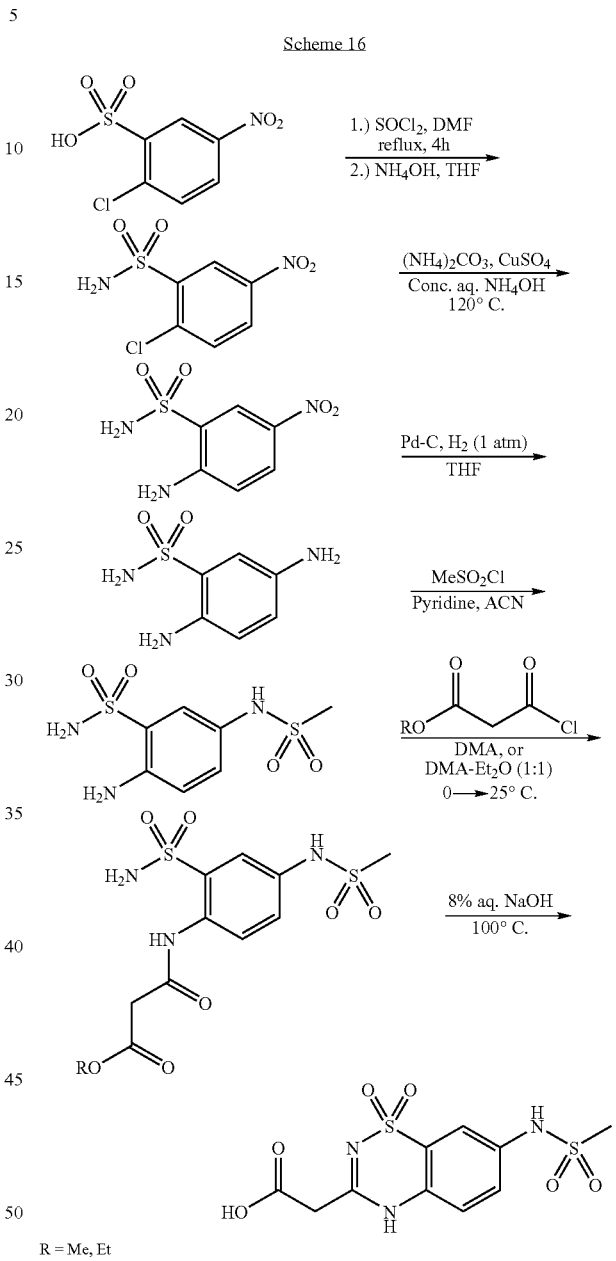

Commercially available 6-nitrobenzothiazole can be treated with hydrazine to obtain the 2-amino-5-nitro-benzenethiol, which can subsequently be reacted with chloroacetoacetate to give the (7-nitro-4H-benzo[1,4]thiazin-3-yl)-acetic acid ethyl ester. Reduction of the nitro group to the amino group can be accomplished by reaction with tin(II) chloride. Subsequent reaction with a sulfonyl chloride, such as methylsulfonyl chloride, can be used to obtain the corresponding sulfonamides. Protection of both nitrogens with a suitable protecting group such as a Boc group can be achieved by using standard methods for protecting amino groups. The sulfides can be oxidized using as suitable oxidizing reagent (e.g., MCPBA) to give the sulfones. Finally, deprotection of the amino groups using trifluoroacetic acid, followed by hydrolysis of the esters can be used to afford the desired acid intermediates.

Commercially available 2-chloro-5-nitro-benzenesulfonic acid can be treated with thionyl chloride to give the sulfonylchloride, which can be further treated with ammonia to afford the sulfonamide intermediate. The chloride can be displaced with ammonia by treatment with ammonium hydroxide and ammonium carbonate in the presence of copper(II)sulfate. Reduction of the nitro group under standard hydrogenation conditions affords the aniline intermediate, which can be treated with a sulfonyl chloride, such as methylsulfonyl chloride, to yield the corresponding sulfonamide. Acylation of the 2-amino moiety with malonyl chlorides, e.g., ethyl 3-chloro-3-oxo-propionate, gives the corresponding amide, which can simultaneously be cyclized to the thiadiazine-dioxide and hydrolyzed to the desired acid intermediate.

Scheme 17 provides an alternate procedure that can be used to prepare the 2-amino-5-methanesulfonylamino-benzenesulfonamide intermediate.

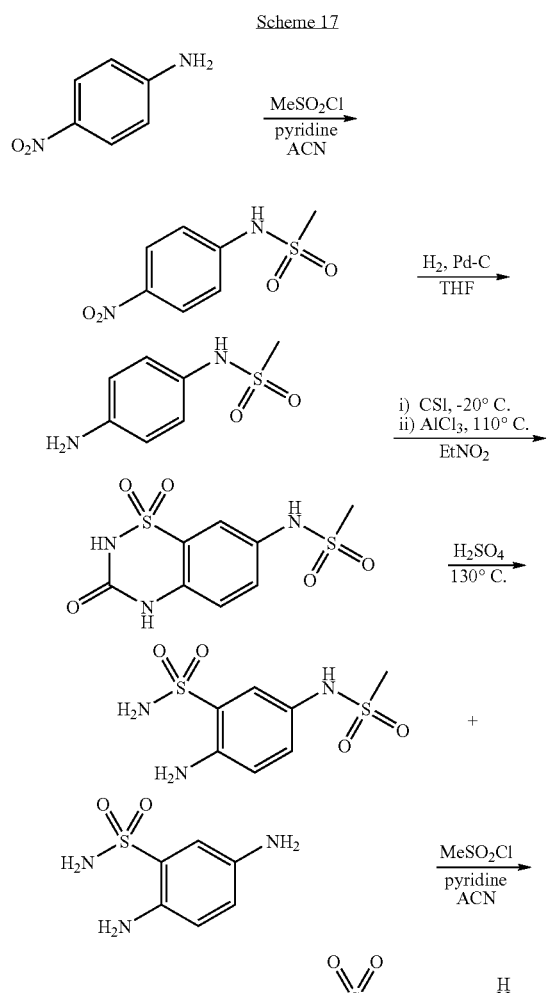

In a preferred route, commercially available 4-nitroaniline can be treated with sulfonyl chlorides, e.g., methanesulfonyl chloride, to obtain the corresponding sulfonamides. Reduction of the nitro group using standard conditions affords the corresponding anilines, which can be treated with chlorosulfonyl isocyanate followed by aluminum chloride to give the corresponding 1,1-dioxo-1,4-dihydro-2H-1$\lambda^6$-benzo[1,2,4]thiadiazin-3-ones. Opening of the cyclicureas with a strong acid (e.g., sulfuric acid) gives the desired 2-amino-5-sulfonylamino-benzenesulfonamide intermediates along with some of the hydrolyzed 2,5-diaminobenzenesulfonamide, which can be converted back by treatment with sulfonyl chlorides, e.g., methanesulfonyl chloride, to obtain the desired 2-amino-5-sulfonylamino-benzenesulfonamide intermediates.

Scheme 18 provides an alternative procedure that can be used to prepare the 2-chloro-5-nitro-benzenesulfonamide intermediate.

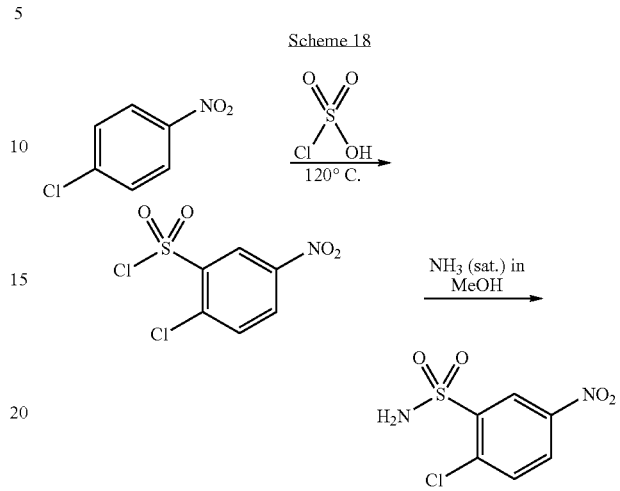

Commercially available 1-chloro-4-nitro-benzene can be reacted with chlorosulfonic acid to afford the corresponding sulfonylchloride. Treatment with a saturated solution of ammonia in methanol affords the desired the 2-chloro-5-nitro-benzenesulfonamide intermediate.

Scheme 19 provides an alternative procedure that can be used to prepare the 2,5-diamino-benzenesulfonamide intermediate.

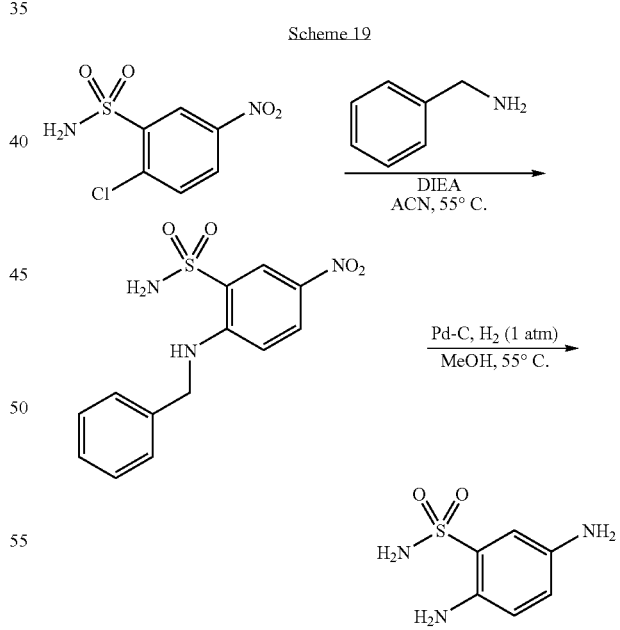

The 2-chloro-5-nitro-benzenesulfonamide intermediate (prepared as described in schemes 16 and 18) can be treated with a benzylic amine, such as benzylamine, to displace the chloro moiety. Hydrogenation under standard conditions can be used to remove the benzylic group and to reduce the nitro group at the same time to afford the desired 2,5-diamino-benzenesulfonamide intermediate.

Scheme 20 provides an alternative procedure that can be used to prepare the 2-amino-5-nitro-benzenesulfonamide intermediate.

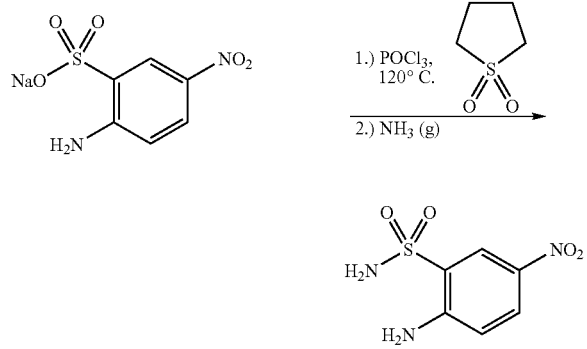

The commercially available sodium salt of 2-amino-5-nitro-benzenesulfonic acid can be converted to the corresponding sulfonyl chloride with phosphoryl chloride in the presence of a suitable co-solvent, such as sulfolane. Treatment with ammonia, e.g., ammonia solution in methanol or ammonia gas, affords the desired 2-amino-5-nitro-benzenesulfonamide intermediate.

Scheme 21 provides an alternative procedure that can be used to prepare the 2-amino-5-nitro-benzenesulfonamide intermediate.

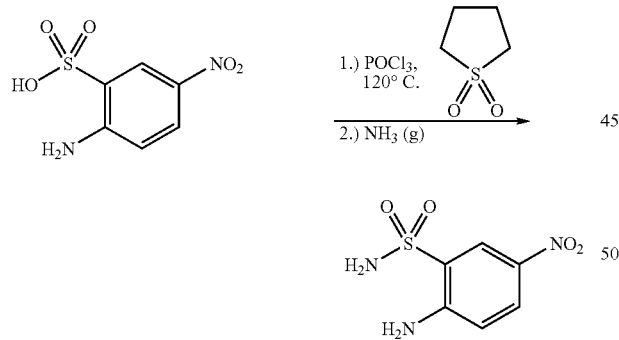

Commercially available 2-amino-5-nitro-benzenesulfonic acid can be converted to the corresponding sulfonyl chloride with phosphoryl chloride in the presence of a suitable co-solvent, such as sulfolane. Treatment with ammonia, e.g., aqueous ammonium hydroxide solution or ammonia gas, affords the desired 2-amino-5-nitro-benzenesulfonamide intermediate.

Scheme 22 provides an alternative procedure that can be used to prepare the N-(4-methanesulfonylamino-2-sulfamoyl-phenyl)-malonamic acid ethyl ester intermediate.

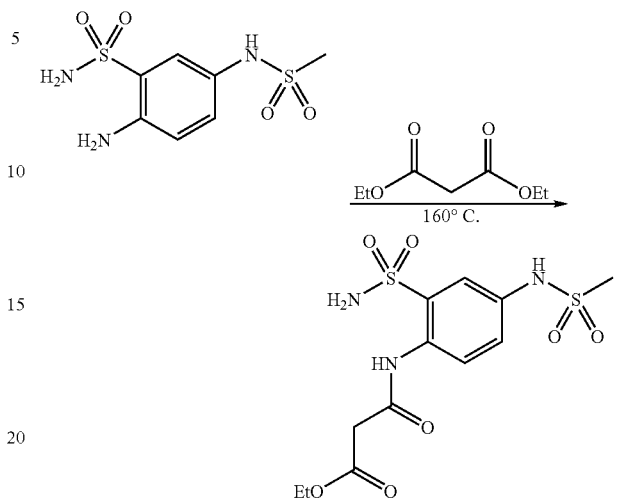

2-Amino-5-methanesulfonylamino-benzenesulfonamide (prepared as described in schemes 16 and 17) can be treated with a dialkyl malonate, such as diethyl malonate, to afford the desired N-(4-methanesulfonylamino-2-sulfamoyl-phenyl)-malonamic acid ethyl ester intermediate.

Scheme 23 provides a procedure that was used to prepare the (7-iodo-1,1-dioxo-1,4-dihydro-1$\lambda^6$-benzo[1,2,4]thiadiazin-3-yl)-acetic acid intermediate.

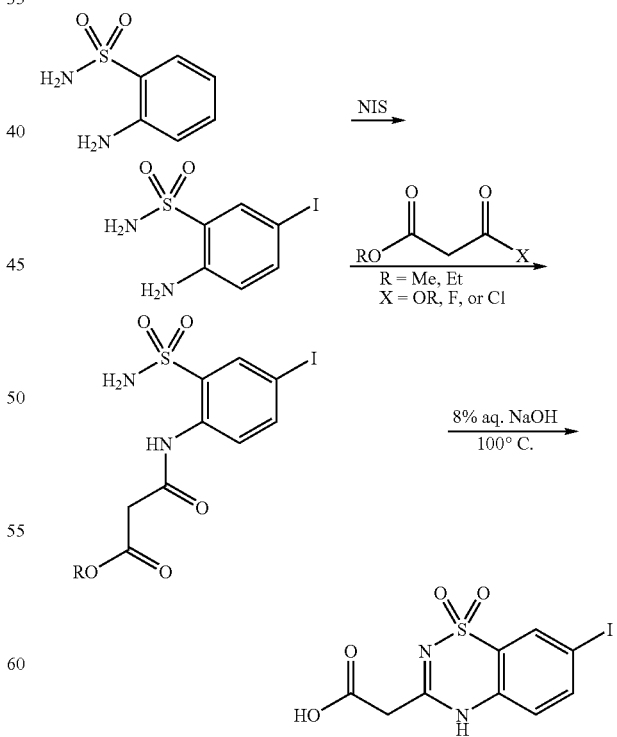

Commercially available 2-aminobenzenesulfonamide can be treated with N-iodosuccinimide (NIS) to afford 2-amino-5-iodo-benzenesulfonamide. Acylation with a malonyl halide monoester, such as ethyl 3-chloro-3-oxo-propionate, or with a dialkyl malonate, such as diethyl malonate, affords the corresponding amide, which can simultaneously be cyclized to the thiadiazine-dioxide and hydrolyzed to the desired acid intermediate.

Scheme 24 provides a procedure that was used to prepare the (1,1-dioxo-1,4-dihydro-1λ$^6$-benzo[1,2,4]thiadiazin-3-yl)-acetic acid intermediate.

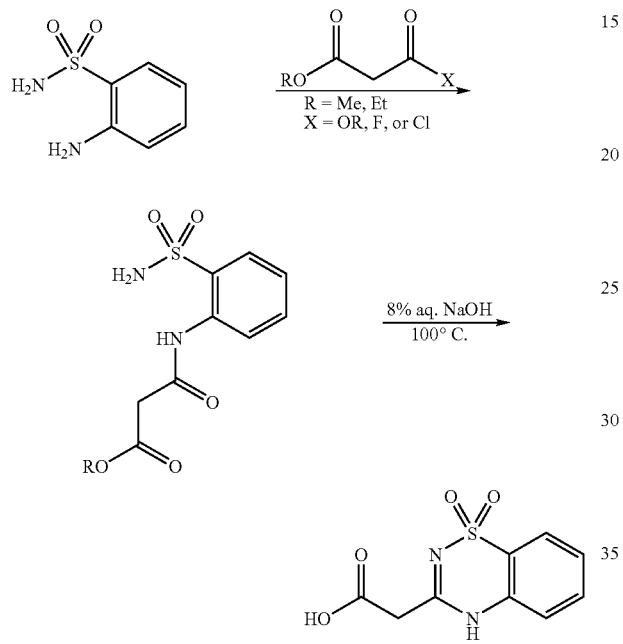

Commercially available 2-aminobenzenesulfonamide can be acylated with a malonyl halide monoester, such as ethyl 3-chloro-3-oxo-propionate, or with a dialkyl malonate, such as diethyl malonate, to afford the corresponding amide, which can simultaneously be cyclized to the thiadiazine-dioxide and hydrolyzed to the desired acid intermediate.

Scheme 25 provides a general procedure that was used to prepare 3-(1,1-dioxo-1,4-dihydro-1λ$^6$-benzo[1,2,4]thiadiazin-3-yl)-4-hydroxy-5,6-dihydro-1H-pyridin-2-one compounds of Formula I from the corresponding iodo precursors.

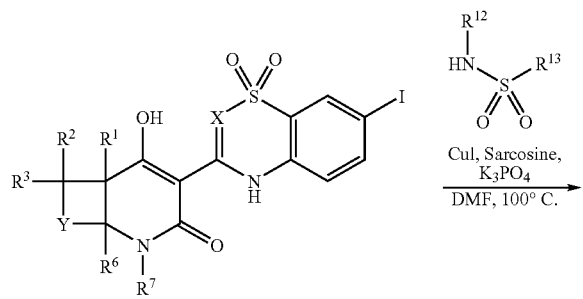

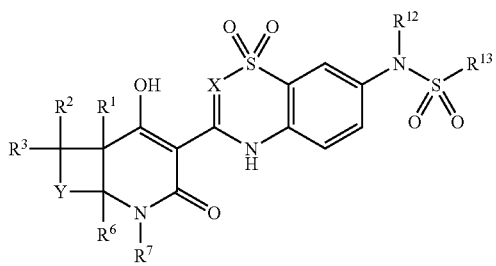

Optionally substituted 4-hydroxy-3-(7-iodo-1,1-dioxo-1,4-dihydro-1λ6-benzo[1,2,4]thiadiazin-3-yl)-5,6-dihydro-1H-pyridin-2-ones can be treated with substituted sulfonamides in a copper-mediated displacement reaction to afford the desired 3-(1,1-dioxo-1,4-dihydro-1λ$^6$-benzo[1,2,4]thiadiazin-3-yl)-4-hydroxy-5,6-dihydro-1H-pyridin-2-one compounds of Formula I.

Scheme 26 provides a general procedure that was used to prepare N-substituted 3-(1,1-dioxo-1,4-dihydro-1λ$^6$-benzo[1,2,4]thiadiazin-3-yl)-4-hydroxy-5,6-dihydro-1H-pyridin-2-one compounds of Formula I.

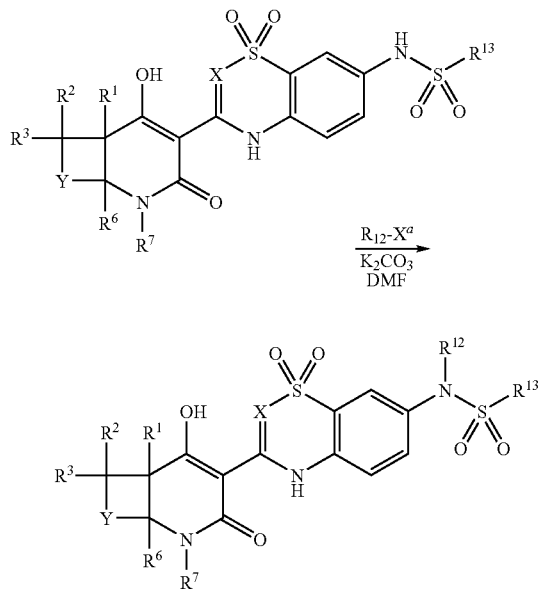

The sulfonamide moiety of optionally substituted 3-(1,1-dioxo-1,4-dihydro-1λ$^6$-benzo[1,2,4]thiadiazin-3-yl)-4-hydroxy-5,6-dihydro-1H-pyridin-2-ones can be N-alkylated by treatment with an alkylating agent, such as alkyl halides or pseudohalides X$^a$ (e.g., chlorides, bromides, iodides, mesylates, tosylates or triflates), in the presence of a base (e.g., potassium carbonate) to afford the desired N-substituted 3-(1,1-dioxo-1,4-dihydro-1λ$^6$-benzo[1,2,4]thiadiazin-3-yl)-4-hydroxy-5,6-dihydro-1H-pyridin-2-one compounds of Formula I.

Scheme 27 provides a procedure that was used to prepare the 3-(1,1-dioxo-1,4-dihydro-1λ⁶-benzo[1,2,4]thiadiazin-3-yl)-4-hydroxy-5,6-dihydro-1H-pyridin-2-one compounds of Formula I from the corresponding iodo precursors.

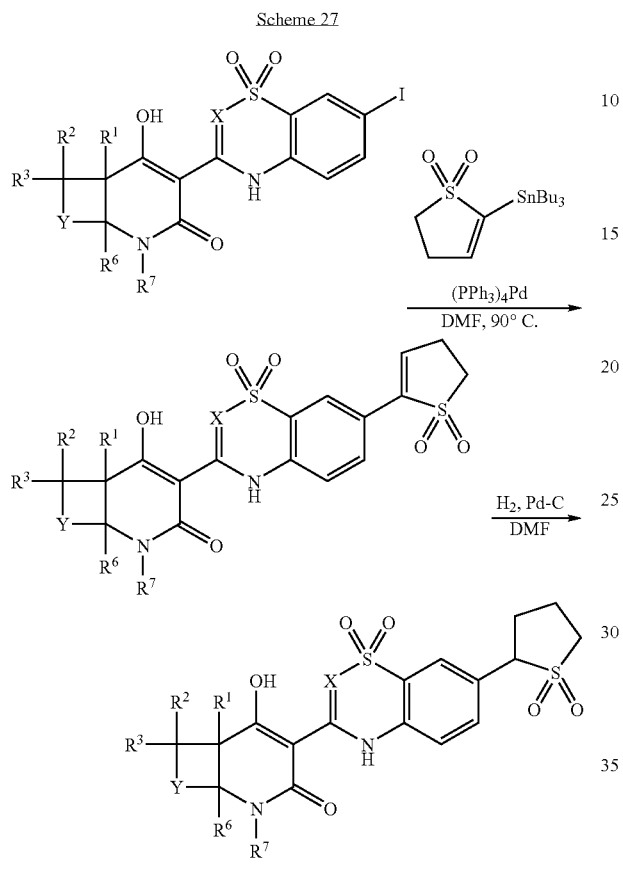

Optionally substituted 4-hydroxy-3-(7-iodo-1,1-dioxo-1,4-dihydro-1λ⁶-benzo[1,2,4]thiadiazin-3-yl)-5,6-dihydro-1H-pyridin-2-ones can be treated with stannanes, such as the unsaturated cyclic sulfone shown above, in a Stille-type palladium-catalyzed reaction to afford the unsaturated intermediates shown. Reduction of the alkene using standard hydrogenation conditions affords the desired 3-(1,1-dioxo-1,4-dihydro-1λ⁶-benzo[1,2,4]thiadiazin-3-yl)-4-hydroxy-5,6-dihydro-1H-pyridin-2-one compounds of Formula I.

Scheme 28 provides a general procedure that was used to prepare the 3-(1,1-dioxo-1,4-dihydro-1λ⁶-benzo[1,2,4]thiadiazin-3-yl)-4-hydroxy-5,6-dihydro-1H-pyridin-2-one compounds of Formula I from the corresponding iodo precursors.

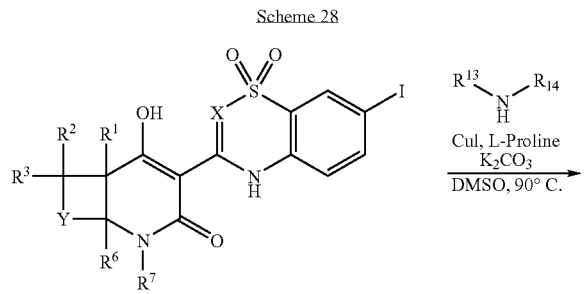

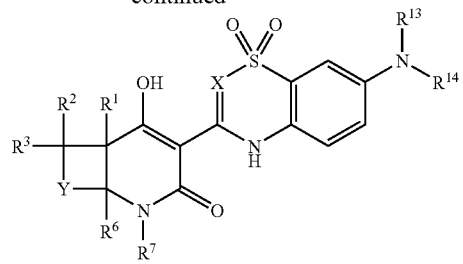

Optionally substituted 4-hydroxy-3-(7-iodo-1,1-dioxo-1,4-dihydro-1λ⁶-benzo[1,2,4]thiadiazin-3-yl)-5,6-dihydro-1H-pyridin-2-ones can be treated with amines in a copper-mediated displacement reaction to afford the desired 3-(1,1-dioxo-1,4-dihydro-1λ⁶-benzo[1,2,4]thiadiazin-3-yl)-4-hydroxy-5,6-dihydro-1H-pyridin-2-one compounds of Formula I.

EXAMPLE 1 cis-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide

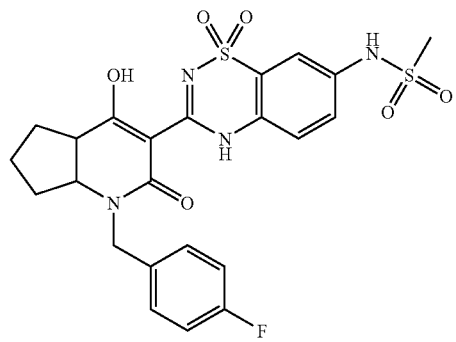

a) N-(4-Nitro-phenyl)-methanesulfonamide

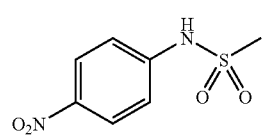

A solution of methanesulfonylchloride (47.1 mL, 0.61 mol) in acetonitrile (160 mL) was added over 40 min to a solution of 4-nitroaniline (80.0 g, 0.58 mol) and pyridine (70.2 mL, 0.87 mol) in acetonitrile (400 mL) at 25° C. The mixture was stirred at 25° C. for 19 h, and then water (800 mL) was added. The resulting suspension was stirred at 25° C. for 30 min, and then was filtered through medium paper using a Büchner funnel. The collected solid was washed with water (2×150 mL) and air-dried overnight to afford the desired product, N-(4-nitro-phenyl)-methanesulfonamide (111.4 g, 0.52 mol, 89%) as a pale yellow solid. $^1$H NMR (400 MHz, DMSO-d$_6$) δ 3.17 (3H, s), 7.35 (2H, d, J=9.4 Hz), 8.20 (2H, d, J=9.1 Hz), 10.69 (1H, s).

b) N-(4-Amino-phenyl)-methanesulfonamide

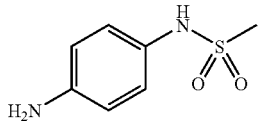

5% Palladium on carbon ("wet", 11.1 g) was added to a solution of N-(4-nitro-phenyl)-methanesulfonamide (111.4 g, 0.52 mol) in tetrahydrofuran (900 mL) at 25° C. The atmosphere above the resulting suspension was replaced with hydrogen gas and the reaction mixture was maintained under 1 atmosphere of hydrogen at 25° C. for 4 days using several balloons. The mixture was then filtered through Celite and the Celite was washed with tetrahydrofuran (3×100 mL). The combined filtrate and washings were concentrated in vacuo to approximately 300 mL volume and heptane (500 mL) was added dropwise via addition funnel over 45 min at 25° C. with vigorous stirring. The resulting suspension was stirred for an additional 45 min at 25° C., and then was filtered through medium paper using a Büchner funnel. The collected solid was washed with heptane (1×150 mL) and was air-dried to afford the desired product, N-(4-amino-phenyl)-methanesulfonamide (90.7 g, 0.49 mol, 95%) as a beige powder. $^1$H NMR (400 MHz, DMSO-d$_6$) δ 2.79 (3H, s), 5.00 (2H, s), 6.49 (2H, d, J=8.5 Hz), 6.87 (2H, d, J=8.6 Hz), 8.87 (1H, s).

c) N-(1,1,3-Trioxo-1,2,3,4-tetrahydro-1λ$^6$-benzo[1,2,4]thiadiazin-7-yl)-methanesulfonamide

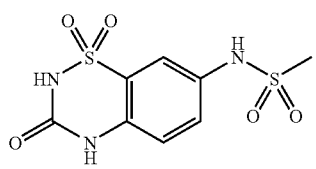

A solution of N-(4-amino-phenyl)-methanesulfonamide (90.7 g, 0.49 mol) in nitroethane (900 mL) was added dropwise over 1.5 h to a mechanically stirred solution of chlorosulfonylisocyanate (50.6 mL, 0.54 mol) in nitroethane (150 mL) at −20° C. The resulting suspension was stirred at −20° C. for 30 min, then aluminum chloride (77.9 g, 0.58 mol) was added in one portion over 1 min. The resulting brown solution was warmed to 25° C., and then was heated at 110° C. for 1 h (considerable gas evolution was noted during this time). After cooling to −5° C., water (300 mL) was added dropwise via addition funnel over 15 min, followed by the rapid addition of more water (700 mL). The resulting suspension was allowed to warm to 25° C. and vigorously stirred for 30 min, and then was filtered through medium paper using a Büchner funnel. The collected solid was washed with water (1×300 mL) and was air-dried to afford the desired product, N-(1,1,3-trioxo-1,2,3,4-tetrahydro-1λ$^6$-benzo[1,2,4]thiadiazin-7-yl)-methanesulfonamide (115.2 g, 0.40 mmol, 81%) as a beige solid. $^1$H NMR (400 MHz, DMSO-d$_6$) δ 3.00 (3H, s), 7.22 (1H, d, J=8.5 Hz), 7.46 (1H, dd, J$_2$=8.8 Hz, J$_2$=2.7 Hz), 7.51 (1H, d, J=2.4 Hz), 9.92 (1H, s), 11.20 (1H, s).

d) 2-Amino-5-methanesulfonylamino-benzenesulfonamide

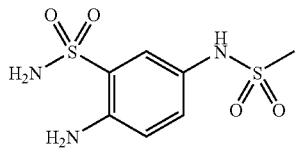

A mechanically stirred suspension of N-(1,1,3-trioxo-1,2,3,4-tetrahydro-1λ$^6$-benzo[1,2,4]thiadiazin-7-yl)-methanesulfonamide (115.2 g, 0.40 mol) in 9.0 M aqueous sulfuric acid (500 mL) was heated to 130° C. for 2.5 h (considerable gas evolution was noted during this time). The resulting brown solution was cooled to 0° C. and an aqueous solution of sodium hydroxide (351 g in 750 mL water; ca. 11.7 M) was added via addition funnel over 45 min. The pH of the reaction mixture was then adjusted to approximately 7.0 by the dropwise addition of 3.0 M aqueous sodium carbonate solution. The resulting suspension was allowed to warm to 25° C. and stirred for 1 h, then was filtered through medium paper using a Büchner funnel. The collected solid was washed with water (1×300 mL) and was dried in a vacuum oven at 50° C. to afford a mixture of 2-amino-5-methanesulfonylamino-benzenesulfonamide and 2,5-diamino-benzenesulfonamide (1.5:1.0 ratio, 70.0 g, 75%) as a brown solid. $^1$H NMR (400 MHz, DMSO-d$_6$) δ: 2.86 (3H, s), 4.54 (2H, bs), 4.98 (2H, bs), 5.77 (2H, s), 6.55-6.60 (2H, m), 6.76 (1H, d, J=8.6 Hz), 6.87 (1H, d, J=2.2 Hz), 6.99 (2H, bs), 7.11 (1H, dd, J$_1$=8.6 Hz, J$_2$=2.4 Hz), 7.25 (2H, bs), 7.43 (1H, d, J=3.1 Hz), 9.16 (1H, s).

A solution of methanesulfonylchloride (8.2 mL, 0.11 mol) in acetonitrile (100 mL) was added over 15 min to a solution of the above mixture of 2-amino-5-methanesulfonylamino-benzenesulfonamide and 2,5-diamino-benzenesulfonamide (1.5:1.0 ratio, 60.0 g) and pyridine (12.0 mL, 0.15 mol) in acetonitrile (500 mL) at 25° C. The mixture was stirred at 25° C. for 15 h, and then was concentrated in vacuo to approximately 300 mL volume. Ethyl acetate (300 mL) was added and the resulting suspension was stirred at 25° C. for 10 min, and then was filtered through medium paper using a Büchner funnel. The collected solid was washed with water (1×200 mL) and was dried in a vacuum oven at 50° C. to afford the desired product, 2-amino-5-methanesulfonylamino-benzenesulfonamide (54.0 g, 0.20 mol, 80%) as a beige solid. $^1$H NMR (400 MHz, DMSO-d$_6$) δ 2.86 (3H, s), 5.77 (2H, s), 6.76 (1H, d, J=8.6 Hz), 7.11 (1H, dd, J$_1$=8.6 Hz, J$_2$=2.4 Hz), 7.25 (2H, bs), 7.43 (1H, d, J=3.1 Hz), 9.16 (1H, s).

e) 2-Chloro-5-nitrobenzenesulfonamide

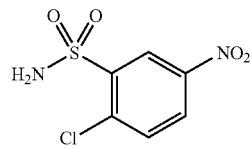

To a solution of thionyl chloride (11 mL) and 2-chloro-5-nitro-benzenesulfonic acid (4.78 g, 20.1 mmol) was added N,N-dimethylformamide (0.92 µL) and the reaction mixture was heated to reflux for 4 h. Upon cooling, the reaction mixture was azeotroped with toluene (2-3×). The sulfonyl chloride was dissolved in a minimal amount of toluene and then added to a mixture of concentrated aqueous ammonium hydroxide solution (25 mL) and tetrahydrofuran (25 mL) at −10° C. After stirring for 2 h the reaction was quenched by adding a 6.0 M aqueous hydrochloric acid solution until pH 4 was reached. The layers were separated and the organic layer was concentrated in vacuo to a slurry. Pentane was added and the product was isolated by vacuum filtration to afford the desired product, 2-chloro-5-nitrobenzenesulfonamide (2.0 g, 8.48 mmol, 42.4%) as a solid.

Alternatively, 2-chloro-5-nitrobenzenesulfonamide can be prepared as follows:

4-Chloronitrobenzene (10 g, 63.5 mmol) was charged into a flask, followed by addition of chlorosulfonic acid (21.1 mL, 317 mmol), and heated at 120° C. for 100 h. The reaction mixture was quenched by pouring it into ice (300 mL) containing a 8.0 N aqueous ammonium hydroxide solution (200 mL), and the mixture was allowed to stir at 25° C. for 18 h. The desired product was extracted with ethyl acetate (400 mL) and filtered through Merck silica gel 60, 40-63 µm and concentrated in vacuo. The crude product was slurried in toluene (70 mL) at 70° C. for 2 h before filtering to afford the desired product, 2-chloro-5-nitro-benzenesulfonamide (4.75 g, 20.1 mmol, 29%) as a dark, brown solid. $^1$H NMR (400 MHz, DMSO-d$_6$) δ: 7.94 (d, 1H, J=8.8 Hz), 7.97 (bs, 2H), 8.40 (dd, 1H, J$_1$=8.6 Hz, J$_2$=3.1 Hz), 8.64 (d, 1H, J=3.1 Hz).

f) 2-Amino-5-nitrobenzenesulfonamide

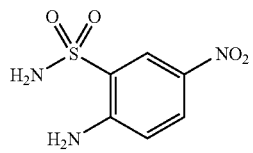

A mixture of 2-chloro-5-nitrobenzenesulfonamide (0.88 g, 3.72 mmol), ammonium carbonate (0.88 g, 9.16 mmol), and copper(II) sulfate (0.175 g, 1.10 mmol) in concentrated aqueous ammonium hydroxide solution (4.4 mL) was heated for 4 h at 120° C. in a pressure reaction vessel. The mixture was allowed to cool to 25° C. and the resulting solid was collected by vacuum filtration, washed with water and dried to afford the desired product, 2-amino-5-nitrobenzenesulfonamide (0.295 g, 1.36 mmol, 36.5%) as a tan solid.

Alternatively, 2-amino-5-nitrobenzenesulfonamide can be prepared as follows:

To a suspension of 4-nitroanline-2-sulfonic acid sodium salt (20.00 g, 83.27 mmol) in sulfolane (83 mL) was slowly added phosphorous oxychloride (23 mL, 249.82 mmol) at 25° C. The mixture was heated at 120° C. for 3.5 h, allowed to cool to 25° C. and diluted with dichloromethane (300 mL). The mixture was filtered and the precipitate was washed with dichloromethane (200 mL). The filtrate was treated with ammonia gas for 10 minutes while cooling in an ice bath and then stirred at 25° C. for 5 minutes. The yellow solid was collected by vacuum filtration and the precipitate was further washed with dichloromethane (300 mL, then 200 mL), cold water (2×150 mL) and dried in vacuo for 16 h at 60° C. to afford the desired product, 2-amino-5-nitrobenzenesulfonamide (8.06 g, 37.14 mmol, 44%) as a yellow solid. $^1$H NMR (400 MHz, DMSO-d$_6$) δ: 6.89 (d, J=9.3 Hz, 1H), 7.12 (bs, 2H), 7.57 (bs, 2H), 8.07 (dd, J$_1$=9.0 Hz, J$_2$=2.6 Hz, 1H), 8.43 (d, J=3.0 Hz, 1H).

Alternatively, 2-amino-5-nitrobenzenesulfonamide can be prepared as follows:

To a suspension of 4-nitroanline-2-sulfonic acid sodium salt (20.00 g, 83.27 mmol) in sulfolane (83 mL) was slowly added phosphorous oxychloride (23 mL, 249.82 mmol) at 25° C. The mixture was heated at 120° C. for 3.5 h, allowed to cool to 25° C. and diluted with toluene (300 mL). The mixture was filtered and the precipitate was washed with toluene (200 mL). The filtrate was treated with ammonia gas for 10 minutes while cooling in an ice bath and then stirred at 25° C. for 5 minutes. The yellow solid was collected by vacuum filtration and the precipitate was further washed with toluene (300 mL, then 200 mL), cold water (2×150 mL) and dried in vacuo for 16 h at 60° C. to afford the desired product, 2-amino-5-nitrobenzenesulfonamide (7.39 g, 34.05 mmol, 41%) as a yellow solid. $^1$H NMR (400 MHz, DMSO-d$_6$) δ: 6.89 (d, J=9.3 Hz, 1H), 7.12 (bs, 2H), 7.57 (bs, 2H), 8.07 (dd, J$_1$=9.0 Hz, J$_2$=2.6 Hz, 1H), 8.43 (d, J=3.0 Hz, 1H).

Alternatively, 2-amino-5-nitrobenzenesulfonamide can be prepared as follows:

To a suspension of 2-amino-5-nitro-benzenesulfonic acid (3.00 g, 13.75 mmol) in sulfolane (10 mL) was slowly added phosphorous oxychloride (3.43 mL, 37.47 mmol) at 25° C. The mixture was heated at 120° C. for 3.5 h, allowed to cool to 25° C. and diluted with dichloromethane (50 mL). The mixture was filtered and the precipitate was washed with dichloromethane (50 mL). The filtrate was treated with ammonia gas for 10 minutes while cooling in an ice bath and then stirred at 25° C. for 5 minutes. The yellow solid was collected by vacuum filtration and the precipitate was further washed with dichloromethane (2×50 mL), cold water (2×50 mL) and dried in vacuo for 16 h at 60° C. to afford the desired product, 2-amino-5-nitrobenzenesulfonamide (1.46 g, 6.73 mmol, 49%) as a brown solid. $^1$H NMR (400 MHz, DMSO-d$_6$) δ: 6.89 (d, J=9.1 Hz, 1H), 7.19 (bs, 2H), 7.37 (bs, 2H), 8.07 (dd, J$_1$=8.9 Hz, J$_2$=2.3 Hz, 1H), 8.43 (d, J=3.0 Hz, 1H).

Alternatively, 2-amino-5-nitrobenzenesulfonamide can be prepared as follows: To a suspension of 2-amino-5-nitro-benzenesulfonic acid (3.00 g, 13.75 mmol) in sulfolane (10 mL) was slowly added phosphorous oxychloride (3.43 mL, 37.47 mmol) at 25° C. The mixture was heated at 120° C. for 3.5 h, allowed to cool to 25° C. and slowly poured into aqueous ammonium hydroxide solution (30 mL) at 25° C. The pH of the solution was adjusted to ca. 6-7 upon which a solid precipitated. The solid was collected by vacuum filtration and the precipitate was washed water (100 mL) and dried in vacuo for 16 h at 60° C. to afford the desired product, 2-amino-5-nitrobenzenesulfonamide (1.87 g, 8.62 mmol, 63%) as a yellow-brown solid. $^1$H NMR (400 MHz, DMSO-d$_6$) δ: 6.89 (d, J=9.1 Hz, 1H), 7.19 (bs, 2H), 7.37 (bs, 2H), 8.07 (dd, J$_1$=8.9 Hz, J$_2$=2.3 Hz, 1H), 8.43 (d, J=3.0 Hz, 1H).

g) 2,5-Diaminobenzenesulfonamide

A mixture of 2-amino-5-nitrobenzenesulfonamide (10 g, 46.08 mmol), 10% palladium on charcoal (~1 g) in tetrahydrofuran (250 mL) was hydrogenated for 26 h at 25° C. under 1 atmosphere of hydrogen gas via balloon. The mixture was then filtered through Celite, washed with tetrahydrofuran, and the solvent removed in vacuo to afford the desired product. The catalyst/Celite mixture was slurried in methanol (400 mL) for 16 h, filtered and the solvent was removed in vacuo to afford a second batch of the desired product, 2,5-diaminobenzenesulfonamide (combined: 7.79 g, 41.65 mmol, 90.4%) as a light-brown solid. $^1$H NMR (400 MHz, DMSO-$d_6$) δ: 4.54 (2H, bs), 4.98 (2H, bs), 6.55-6.60 (2H, m), 6.87 (1H, d, J=2.2 Hz), 6.99 (2H, bs). LC-MS (ESI) calcd for $C_6H_9N_3O_2S$ 187.04, found 188.3 [M+H$^+$].

Alternatively, 2,5-diaminobenzenesulfonamide can be prepared as follows:

a') 2-Benzylamino-5-nitro-benzenesulfonamide

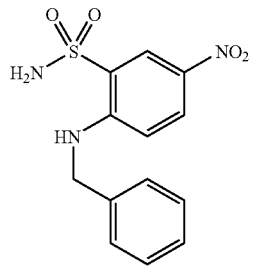

A solution of 2-chloro-5-nitro-benzenesulfonamide (20 g, 84.52 mmol) in acetonitrile (169 mL) was treated with benzylamine (13.85 mL, 126.78 mmol), diisopropyl ethylamine (29.44 mL, 169.04 mmol) and stirred for 16 h at 55° C. The reaction was cooled to 25° C., poured into water (1.0 L) then placed in an ice bath while stirring. After 4 h a precipitate was filtered off and washed with the mother liquor to afford the desired product, 2-benzylamino-5-nitro-benzenesulfonamide (21.65 g, 70.45 mmol, 83.3%) as a yellow solid. $^1$H NMR (400 MHz, DMSO-$d_6$) δ: 4.64 (2H, d, J=4.6 Hz), 6.81 (1H, d, J=9.4 Hz), 7.23-7.44 (6H, m), 7.77 (2H, bs), 8.11 (1H, dd, $J_1$=9.4 Hz, $J_2$=2.3 Hz), 8.49 (1H, d, J=3.1 Hz). LC-MS (ESI) calcd for $C_{13}H_{13}N_3O_4S$ 307.06, found 308.2 [M+H$^+$] (100%), 615.2 [2M+H$^+$] (81%).

b') 2,5-Diamino-benzenesulfonamide

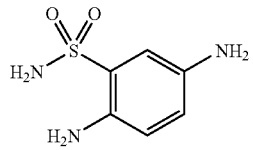

A mixture of 2-benzylamino-5-nitro-benzenesulfonamide (15 g, 48.81 mmol) and 5% palladium on activated carbon powder (wet, nominally 50% water, 6 g) in methanol (500 mL) was heated to 55° C. The mixture was degassed while stirring and the flask was charged with hydrogen gas via balloon. After stirring for 16 h under 1 atmosphere of hydrogen gas, the reaction was filtered through Celite and concentrated in vacuo to afford the desired product, 2,5-diaminobenzenesulfonamide (8.55 g, 45.67 mmol, 93.6%) as a tan solid. $^1$H NMR (400 MHz, DMSO-$d_6$) δ: 4.56 (2H, bs), 4.98 (2H, bs), 6.58-6.59 (2H, m), 6.87 (1H, d, J=1.6 Hz), 7.00 (2H, s). LC-MS (ESI) calcd for $C_6H_9N_3O_2S$ 187.04, found 188.2 [M+H$^+$].

c') 2-Amino-5-methanesulfonylamino-benzenesulfonamide

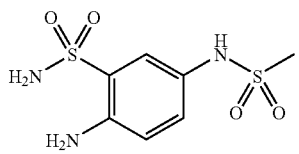

2,5-Diaminobenzenesulfonamide (14.5 g, 77.2 mmol) was dissolved in acetonitrile (150 mL) and pyridine (9.37 mL, 115.9 mmol) was added. Methanesulfonyl chloride (6.28 mL, 81.1 mmol) was added dropwise over a period of 15 min and the reaction mixture was stirred for 20 h at 25° C. after which time a precipitate had formed. Most of the acetonitrile (approximately 110 mL) was removed in vacuo and water (120 mL) was added to afford a clear solution. A purple solid precipitated from this solution over the next 2 h. This precipitate was collected by vacuum filtration, washed with methyl-tert-butyl ether (3×30 mL) and dried in vacuo overnight at 50° C. to afford the desired product, 2-amino-5-methanesulfonylamino-benzenesulfonamide (also made in Example 1d) (18.2 g, 68.7 mmol, 89%) as a purple solid. $^1$H NMR (400 MHz, CD$_3$OD) δ: 2.89 (3H, s), 6.82 (1H, d, J=8.5 Hz), 7.20 (1H, dd, $J_1$=8.5 Hz, $J_2$=2.5 Hz), 7.58 (1H, d, J=2.5 Hz). LC-MS (ESI) calcd for $C_7H_{11}N_3O_4S_2$ 265.02, found 266.0 [M+H$^+$].

h) N-(4-Methanesulfonylamino-2-sulfamoyl-phenyl)-malonamic acid ethyl ester

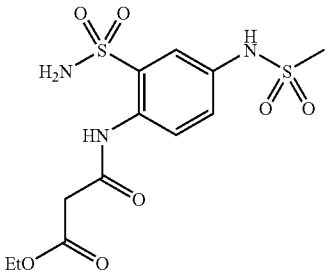

2-Amino-5-methanesulfonylamino-benzenesulfonamide (prepared as described in Examples 1d or 1gc', 23.27 g, 87.81 mmol) was dissolved in N,N-dimethylacetamide (100 mL) and diethyl ether (100 mL). Ethyl 3-chloro-3-oxo-propionate (13.88 g, 92.20 mmol) was added and the reaction mixture was stirred at 25° C. for 1 h. The reaction mixture was diluted with ethyl acetate (400 mL) and was extracted with water (400 mL). The aqueous layer was back-extracted with ethyl acetate (2×200 mL). The combined organic layers were dried over sodium sulfate, filtered and most of the solvent was removed in vacuo to a volume of ~100 mL. To the stirred solution was added hexanes (~100 mL) upon which a precipitate formed. The precipitate was collected by vacuum filtration, washed with hexanes and dried under high vacuum to afford the analytically pure product, N-(4-methanesulfonylamino-2-sulfamoyl-phenyl)-malonamic acid ethyl ester (31.22 g, 85.53 mmol, 97.4%) as a light-brown solid. $^1$H NMR (400 MHz, CD$_3$OD) δ: 1.31 (3H, t, J=7.0 Hz), 3.00 (3H, s), 3.59 (2H, s), 4.25 (2H, quartet, J=6.9 Hz), 7.42-7.45 (1H, m), 7.86 (1H, m), 7.92 (1H, d, J=8.8 Hz).

Alternatively, N-(4-methanesulfonylamino-2-sulfamoyl-phenyl)-malonamic acid ethyl ester can be prepared as follows:

To 2-amino-5-methanesulfonylamino-benzenesulfonamide (prepared as described in Examples 1d or 1gc', 175 mg, 0.66 mmol) was added diethyl malonate (297 mg, 1.66 mmol) and heated at 160° C. for 60 min. After cooling down to 25° C., a 1:1 mixture of ethyl acetate/hexanes (5 mL) was added, upon which as a white solid precipitated out. The solid was collected by vacuum filtration, washed twice with a 1:1 mixture of ethyl acetate/hexanes, and dried under high vacuum to afford the desired product, N-(4-methanesulfonylamino-2-sulfamoyl-phenyl)-malonamic acid ethyl ester (179 mg, 0.47 mmol, 72%) as an off-white solid. $^1$H NMR (400 MHz, CD$_3$OD) δ: 1.32 (t, 3H, J=7.0 Hz), 3.00 (s, 3H), 3.60 (s, 2H), 4.25 (quartet, 2H, J=6.8 Hz), 7.44 (dd, 1H, J$_1$=3.2 Hz, J$_2$=8.4 Hz), 7.87 (d, 1H, J=5.6 Hz), 7.92 (d, 1H, J=8.4 Hz). LC-MS (ESI$^+$) calcd for C$_{12}$H$_{17}$N$_3$O$_7$S$_2$ 379.05, found 380.1 [M+H$^+$].

i) N-(4-Methanesulfonylamino-2-sulfamoylphenyl) malonamic acid methyl ester

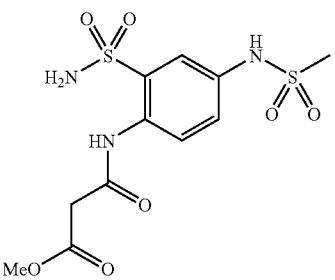

Methyl malonyl chloride (9.05 mL, 84.4 mmol) was added dropwise over 10 min to a solution of 2-amino-5-methanesulfonylamino-benzenesulfonamide (prepared as described in Example 1d, 20.35 g, 76.7 mmol) in N,N-dimethylacetamide (90 mL) at 0° C. The mixture was allowed to warm to 25° C. and stirred at that temperature for 1 h. A solution of sodium bicarbonate (7.09 g, 84.4 mmol) in water (200 mL) was then added via addition funnel over 15 min (gas evolution and a mild exotherm were noted) followed by the rapid addition of an additional volume of water (200 mL). The resulting solution was then seeded with a small amount of N-(4-methanesulfonylamino-2-sulfamoylphenyl)malonamic acid methyl ester (ca. 15 mg). The mixture was stirred for 21 h at 25° C. during which time a tan precipitate formed. This material was collected by filtration, washed with water (150 mL), and was dried in a vacuum oven at 50° C. to afford the desired product, N-(4-methanesulfonylamino-2-sulfamoylphenyl)-malonamic acid methyl ester (24.33 g, 66.6 mmol, 87%) as a tan solid. $^1$H NMR (400 MHz, DMSO-d$_6$) δ: 3.02 (3H, s), 3.60 (2H, s), 3.66 (3H, s), 7.38 (1H, dd, J$_1$=2.3 Hz, J$_2$=8.6 Hz), 7.53 (2H, bs), 7.73 (1H, d, J=2.4 Hz), 7.83 (1H, d, J=8.7 Hz), 9.43 (1H, s), 9.99 (1H, s).

j) (7-Methanesulfonylamino-1,1-dioxo-1,4-dihydro-1λ$^6$-benzo[1,2,4]thiadiazin-3-yl)-acetic acid

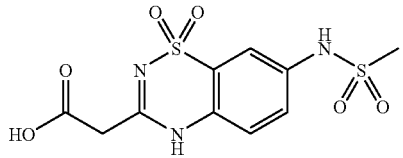

N-(4-Methanesulfonylamino-2-sulfamoyl-phenyl)-malonamic acid ethyl ester (9.55 g, 26.16 mmol) was dissolved in 8% aqueous sodium hydroxide solution (262 mL) and heated at 100° C. for 1.5 h. The reaction mixture was cooled to 0° C. and the solution was acidified by slowly adding 12.0 M aqueous hydrochloric acid solution until pH 1-2 was reached. A precipitate started to form and the suspension was allowed to stir for 30 min at 0° C. The precipitate was collected by vacuum filtration, washed with cold water, and dried under high vacuum to afford (7-methanesulfonylamino-1,1-dioxo-1,4-dihydro-1λ$^6$-benzo[1,2,4]thiadiazin-3-yl)-acetic acid (7.20 g, 21.621 mmol, 82.6%) as a pinkish solid. $^1$H NMR (400 MHz, DMSO-d$_6$) δ: 3.03 (3H, s), 3.56 (2H, s), 7.33 (1H, d, J=9.1 Hz), 7.52-7.54 (2H, m), 10.09 (1H, s), 12.24 (1H, s), 13.02 (1H, bs). LC-MS (ESI) calcd for C$_{10}$H$_{11}$N$_3$O$_6$S$_2$ 333.01, found 334.1 [M+H$^+$].

Alternatively, (7-methanesulfonylamino-1,1-dioxo-1,4-dihydro-1λ$^6$-benzo[1,2,4]thiadiazin-3-yl)-acetic acid can be prepared from Example 11 as follows:

N-(4-Methanesulfonylamino-2-sulfamoylphenyl)-malonamic acid methyl ester (prepared as described in Example 1i, 21.75 g, 59.53 mmol) was dissolved in an aqueous solution of sodium hydroxide (7.14 g, 178.5 mmol; dissolved in 180 mL water) at 25° C. The reaction mixture was heated to 100° C. for 1 h, then was gradually cooled over 30 min to 0° C. 12.0 M Aqueous hydrochloric acid solution (20 mL, 240 mmol) was added dropwise over 10 min via addition funnel resulting in the formation of a tan precipitate. The mixture was allowed to warm to 25° C. and was stirred at that temperature for 21 h. The precipitate was collected by filtration, washed with water (150 mL), and was dried in a vacuum oven at 45° C. for 22 h to afford (7-methanesulfonylamino-1,1-dioxo-1,4-dihydro-1λ$^6$-benzo[1,2,4]thiadiazin-3-yl)-acetic acid (18.36 g, 55.1 mmol, 93%) as a tan solid. $^1$H NMR (400 MHz, DMSO-d$_6$) δ: 3.03 (3H, s), 3.56 (2H, s), 7.32-7.34 (1H, m), 7.51-7.54 (2H, m), 10.09 (1H, s), 12.26 (1H, s), 13.01 (1H, bs). LC-MS (ESI) calcd for C$_{10}$H$_{11}$N$_3$O$_6$S$_2$ 333.01, found 334.1 [M+H$^+$].

k) 2-(4-Fluoro-benzylamino)-cyclopent-1-enecarboxylic acid ethyl ester

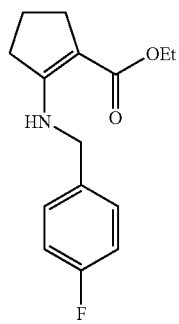

4-Fluorobenzylamine (12.1 g, 97.5 mmol) was added to a solution of 2-oxo-cyclopentanecarboxylic acid ethyl ester (15.25 g, 97.6 mmol) in toluene (225 mL) at 23° C. Glacial acetic acid (6.15 mL, 107 mmol) was then added, producing a large amount of white solid. The reaction mixture was heated to 70° C. in an oil bath, whereupon most of the solids dissolved. After stirring for 2 h at 70° C., a Dean-Stark apparatus and reflux condenser were fitted to the reaction flask and approximately 40 mL of liquid (predominantly toluene) was removed by distillation over 45 min (oil bath temperature=145° C.). The mixture was allowed to cool to 23° C. and was used in the next step. A small aliquot of the crude reaction mixture was concentrated under reduced pressure to afford the desired product, 2-(4-fluoro-benzylamino)-cyclopent-1-enecarboxylic acid ethyl ester as an orange oil: $^1$H NMR (CDCl$_3$) δ: 1.28 (3H, t, J=7.5), 1.79-1.86 (2H, m), 2.51-2.56 (4H, m), 4.15 (2H, q, J=6.9), 4.34-4.36 (2H, m), 6.98-7.03 (2H, m), 7.19-7.23 (2H, m), 7.73 (1H, bs).

l) 2-(4-Fluoro-benzylamino)-cyclopentanecarboxylic acid ethyl ester

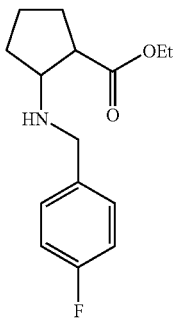

Sodium triacetoxyborohydride (62.1 g, 293 mmol) was suspended in a 1:1 mixture of glacial acetic acid and actonitrile (200 mL) at 0° C. The crude 2-(4-fluoro-benzylamino)-cyclopent-1-enecarboxylic acid ethyl ester was added via cannula over 15 min and the resulting orange/brown suspension was allowed to warm to 23° C. over 19 h. A 4.0 M aqueous hydrochloric acid solution (60 mL) was then carefully added and the mixture was stirred at 23° C. for 20 min. The mixture was transferred to a large Erlenmeyer flask containing a stirbar and was cooled to 0° C. Aqueous sodium hydroxide (98 g dissolved in 350 mL; approx. 8.0 M) was then added over 20 min with gentle stirring and continued external cooling (large exotherm noted; melted ice was replenished). After the exotherm subsided, the mixture was transferred to a separatory funnel and the phases were separated. The aqueous phase was extracted with ethyl acetate (1×300 mL) and the combined organic layers were washed with half-saturated aqueous sodium bicarbonate solution (1×200 mL), dried over sodium sulfate, filtered and were concentrated in vacuo. Purification of the residue by flash chromatography (Teledyne Isco RediSep Column; 15-40% ethyl acetate in hexanes) afforded the desired product, cis-2-(4-fluoro-benzylamino)-cyclopentanecarboxylic acid ethyl ester (19.9 g, 77% over two steps), as a pale yellow oil. $^1$H NMR (CDCl$_3$) δ: 1.27 (3H, t, J=7.0), 1.55-1.71 (2H, m), 1.81-1.91 (4H, m), 1.98-2.06 (1H, m), 2.90-2.96 (1H, m), 3.26-3.31 (1H, m), 3.73 (1H, d, J=13.1), 3.77 (1H, d, J=13.2), 4.15 (2H, q, J=7.3), 6.94-7.00 (2H, m), 7.24-7.28 (2H, m). $^{13}$C NMR (CDCl$_3$) δ: 14.8, 22.7, 27.9, 32.2, 48.0, 51.9, 60.5, 61.7, 115.2 (d, J=21.5), 129.6 (d, J=8.4), 136.5 (d, J=3.1), 161.9 (d, J=243.8), 174.7. Anal. calcd for C$_{15}$H$_{20}$FNO$_2$: C, 67.90; H, 7.60; N, 5.28; Found: C, 67.92; H, 7.88; N, 5.55. Continued elution of the silica gel column with increasing amounts of ethyl acetate (up to 100% of eluent concentration) afforded trans-2-(4-fluoro-benzylamino)-cyclopentanecarboxylic acid ethyl ester (3.2 g, 12%) as a dark orange oil. $^1$H NMR (CDCl$_3$) δ: 1.26 (3H, t, J=7.0), 1.40-1.49 (1H, m), 1.67-1.77 (2H, m), 1.82-1.91 (1H, m), 1.97-2.05 (2H, m), 2.58 (1H, q, J=7.9), 3.31 (1H, q, J=7.3), 3.72 (1H, d, J=13.2), 3.77 (1H, d, J=12.5), 4.14 (2H, q, J=7.0), 6.96-7.01 (2H, m), 7.24-7.29 (2H, m).

m) cis-2-{(4-Fluoro-benzyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester

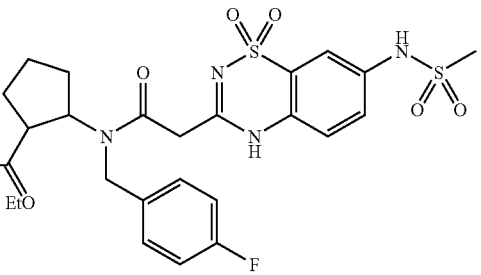

To a solution of (7-methanesulfonylamino-1,1-dioxo-1,4-dihydro-1λ$^6$-benzo[1,2,4]thiadiazin-3-yl)-acetic acid (prepared as described in Example 1j, 0.140 g, 0.241 mmol) and cis-2-(4-fluoro-benzylamino)-cyclopentanecarboxylic acid ethyl ester (0.064 g, 0.241 mmol) in N,N-dimethylformamide (10 mL) was added a 2.0 M solution of N,N'-dicyclohexylcarbodiimide in N,N-dimethylformamide (121 μL, 0.241 mmol) and the reaction mixture was stirred at 25° C. for 16 h. The solvent was removed in vacuo and the residue was purified by flash column chromatography (Teledyne Isco RediSep Flash Column 4 g; 0-10% methanol in dichloromethane) to afford the desired product, cis-2-{(4-fluoro-benzyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester (0.04 g, 0.0689 mmol, 28.6%). LC-MS (ESI) calcd for C$_{25}$H$_{29}$FN$_4$O$_7$S$_2$ 580.15, found 581.2 [M+H$^+$].

n) cis-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

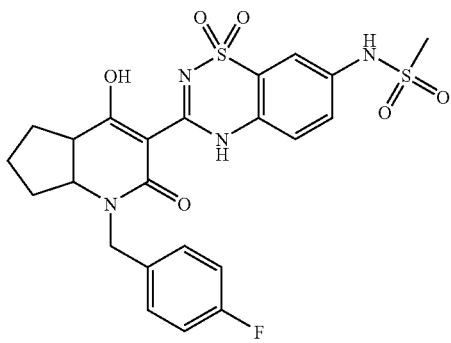

To a solution of cis-2-{(4-fluoro-benzyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester (0.044 g, 0.076 mmol) in ethanol (10 mL) was added a 21% w/w solution of sodium ethoxide in ethanol (0.0981 g, 0.303 mmol) and the reaction mixture was heated at 60° C. for 16 h. Upon cooling the reaction mixture was quenched with a 1.0 M aqueous hydrochloric acid solution and extracted with ethyl acetate. The organic layer was dried over sodium sulfate, filtered and the solvent was removed in vacuo to afford the crude product, which was further purified by prep-HPLC to afford cis-N-{3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide (0.0241 g, 0.045 mmol, 59.4%), as a solid. $^1$H NMR (400 MHz, DMSO-d$_6$) δ: 1.48-1.55 (4H, m), 1.95-2.10 (4H, m), 3.07 (3H, s), 3.34 (1H, bs), 3.86 (1H, bs), 4.48 (1H, d, J=14.7 Hz), 4.91 (1H, d, J=14.8 Hz), 7.16 (2H, t, J=8.9 Hz), 7.40 (2H, t, J=6.6 Hz), 7.52 (1H, d, J=10.7 Hz), 7.59 (2H, d, J=8.4 Hz), 10.18 (1H, s). LC-MS (ESI) calcd for C$_{23}$H$_{23}$FN$_4$O$_6$S$_2$ 534.10, found 535.4 [M+H$^+$].

EXAMPLE 2

N-{3-[1-(4-Fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide

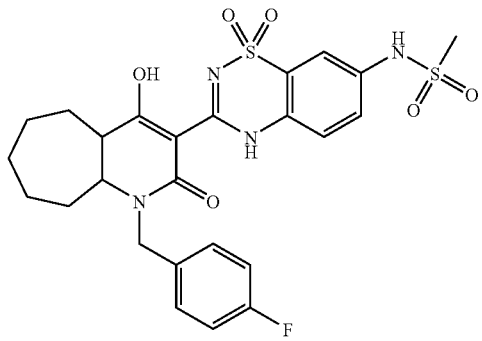

a) cis-2-Amino-cycloheptanecarboxylic acid methyl ester hydrochloride

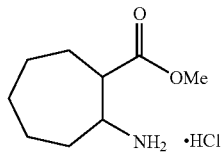

cis-2-Amino-cycloheptanecarboxylic acid hydrochloride (0.75 g, 3.89 mmol) was dissolved in methanol (5 mL). Benzene (7.5 mL) was added followed by the dropwise addition of a 2.0 M solution of (trimethylsilyl)diazomethane in dichloromethane (3.5 mL). The yellow solution continued to stir at 25° C. for 20 min. The solution was concentrated in vacuo to afford a yellow powder. The powder was suspended in methanol (20 mL) and concentrated in vacuo to afford the desired product, cis-2-amino-cycloheptanecarboxylic acid methyl ester hydrochloride (0.8 g, 3.86 mmol, 99%), as a white powder. $^1$H NMR (400 MHz, D$_2$O) δ: 1.33-1.86 (8H, m), 2.60-2.62 (1H, m), 2.75-2.78 (1H, m), 3.27-3.30 (1H, m), 3.39-3.44 (1H, m), 3.62 (3H, s).

b) cis-2-(4-Fluoro-benzylamino)-cycloheptanecarboxylic acid methyl ester

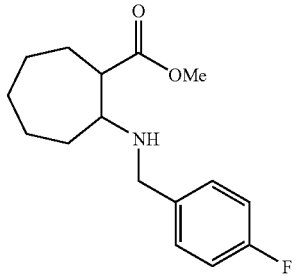

cis-2-Amino-cycloheptanecarboxylic acid methyl ester hydrochloride (0.8 g, 3.86 mmol) was suspended in methanol (20 mL). Sodium acetate (0.63 g, 7.7 mmol) was added followed by 4 Å powdered molecular sieves (0.8 g) followed by 4-fluoro-benzaldehyde (0.48 g, 3.86 mmol). Sodium cyanoborohydride (0.48 g, 7.7 mmol) was added and the mixture stirred at 25° C. for 16 h. The mixture was poured into a 1:1 mixture of saturated aqueous sodium bicarbonate solution (200 mL) and ethyl acetate (200 mL). After shaking, both layers were passed through a plug of Celite. The organic layer was further washed with saturated aqueous brine solution (50 mL), dried over magnesium sulfate and concentrated in vacuo to afford the crude product, cis-2-(4-fluoro-benzylamino)-cycloheptanecarboxylic acid methyl ester (0.56 g, 2 mmol, 52%), as a clear oil. LC-MS (ESI) calcd for C$_{16}$H$_{22}$FNO$_2$ 279.16, found 280.3 [M+H$^+$].

c) N-{3-[1-(4-Fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide

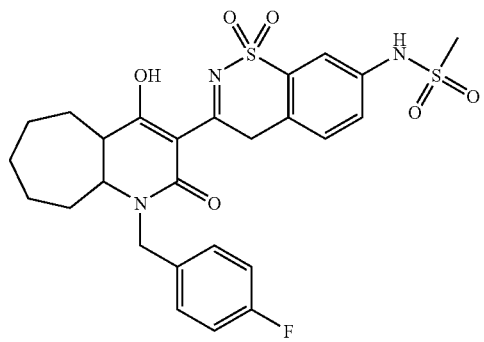

(7-Methanesulfonylamino-1,1-dioxo-1,4-dihydro-1λ$^6$-benzo[1,2,4]thiadiazin-3-yl)-acetic acid (prepared as described in Example 1j, 0.1 g, 0.299 mmol) was dissolved in anhydrous N,N-dimethylformamide (1.5 mL). cis-2-(4-Fluoro-benzylamino)-cycloheptanecarboxylic acid methyl ester (0.084 g, 0.299 mmol) was added followed by a 1.0 M solution of N,N'-dicyclohexylcarbodiimide in dichloromethane (0.314 mL, 0.314 mmol). The mixture stirred at 25° C. for 1.5 h. Triethylamine (0.122 mL, 0.897 mmol) was added and the mixture stirred at 50° C. for 16 h. Upon cooling, the mixture was poured into 1.0 M aqueous hydrochloric acid solution (100 mL). The product was extracted into ethyl acetate (100 mL). The organic layer was filtered to remove the N,N'-dicyclohexylurea precipitate and then further washed with 1.0 M aqueous hydrochloric acid solution (50 mL), saturated aqueous brine solution (25 mL), dried over magnesium sulfate, filtered and concentrated in vacuo. Purification by flash column chromatography (Merck silica gel 60, 40-63 μm; column 1: 50-70% ethyl acetate in hexanes; column 2: 1-5% methanol in dichloromethane) afforded the desired product, N-{3-[1-(4-fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1$\lambda^6$-benzo[1,2,4]thiadiazin-7-yl}-methanesulfonamide (0.049 g, 0.087 mmol, 29%), as a pale yellow powder. $^1$H NMR (400 MHz, DMSO-$d_6$) δ: 1.23-1.38 (3H, m), 1.46-1.73 (6H, m), 1.93-2.02 (1H, m), 2.72-2.80 (1H, m), 2.98 (3H, s), 3.03 (1H, s), 4.07 (1H, d, J=14.9 Hz), 5.01 (1H, d, J=15.5 Hz), 7.12 (2H, t, J=9.1 Hz), 7.18-7.25 (1H, m), 7.33-7.37 (3H, m), 7.43 (1H, s), 7.51-7.56 (1H, m), 9.81 (1H, s). LC-MS (ESI) calcd for $C_{25}H_{27}FN_4O_6S_2$ 562.14, found 563.2 [M+H$^+$].

EXAMPLE 3

N-{3-[1-(4-Fluoro-benzyl)-4-hydroxy-2-oxo-1,2,4a,5,6,7,8,9,10,10a-decahydro-cycloocta[b]pyridin-3-yl]-1,1-dioxo-1,4-dihydro-1$\lambda^6$-benzo[1,2,4]thiadiazin-7-yl}-methanesulfonamide

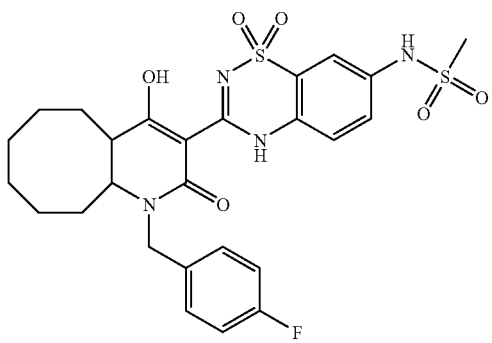

a) cis-2-Amino-cyclooctanecarboxylic acid methyl ester

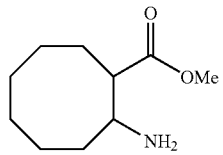

cis-2-Amino-cyclooctanecarboxylic acid (0.65 g, 3.8 mmol) was dissolved in methanol (5 mL). Benzene (7.5 mL) was added followed by dropwise addition of a 2.0 M solution of (trimethylsilyl)diazomethane in diethyl ether (3.5 mL). The yellow solution was stirred at 25° C. for 45 min. The solution was concentrated in vacuo. The residue was dissolved in methanol (20 mL) and concentrated in vacuo to afford the desired product, cis-2-amino-cyclooctanecarboxylic acid methyl ester (0.66 g, 3.56 mmol, 94%), as a colorless oil. LC-MS (ESI) calcd for $C_{10}H_{19}NO_2$ 185.14, found 186.2 [M+H$^+$].

b) cis-2-(4-Fluoro-benzylamino)-cyclooctanecarboxylic acid methyl ester

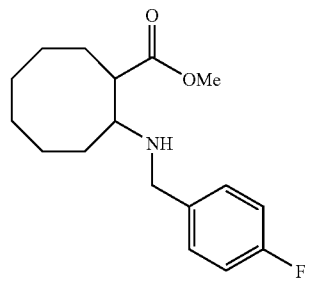

cis-2-Amino-cyclooctanecarboxylic acid methyl ester (0.66 g, 3.56 mmol) was dissolved in methanol (20 mL). 4-Fluoro-benzaldehyde (0.44 g, 3.56 mmol) was added followed by acetic acid (1 mL). The solution was stirred at 25° C. for 10 min. Sodium cyanoborohydride (0.56 g, 8.9 mmol) was added and the mixture was stirred at 25° C. for 16 h. The mixture was poured into 1/2 saturated aqueous sodium bicarbonate solution (150 mL). The aqueous layer was extracted with ethyl acetate (2×150 mL). The organic layer was dried over sodium sulfate and concentrated in vacuo to afford the crude product, cis-2-(4-fluoro-benzylamino)-cyclooctanecarboxylic acid methyl ester (0.7 g, 2.39 mmol, 67%), as a clear oil. LC-MS (ESI) calcd for $C_{17}H_{24}FNO_2$ 293.18, found 294.3 [M+H$^+$].

d) cis-2-{(4-Fluoro-benzyl)-[2-(7-methanesulfonylamino-1,1-dioxo-1,4-dihydro-1$\lambda^6$-benzo[1,2,4]thiadiazin-3-yl)-acetyl]-amino}-cyclooctanecarboxylic acid methyl ester

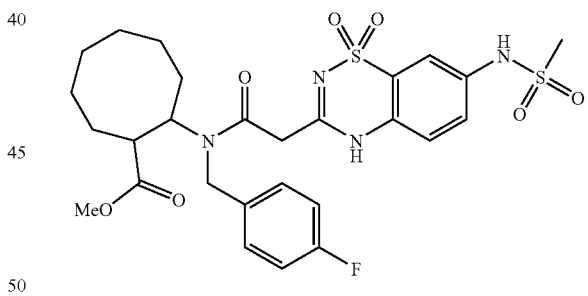

(7-Methanesulfonylamino-1,1-dioxo-1,4-dihydro-1$\lambda^6$-benzo[1,2,4]thiadiazin-3-yl)-acetic acid (prepared as described in Example 1j, 0.132 g, 0.396 mmol) was dissolved in anhydrous N,N-dimethylformamide (4 mL). cis-2-(4-Fluoro-benzylamino)-cyclooctanecarboxylic acid methyl ester (0.117 g, 0.396 mmol) was added followed by 1-(3-dimethylaminopropyl)-3-ethylcarbodiimide hydrochloride (0.08 g, 0.416 mmol). Then N-methylmorpholine (0.84 g, 0.832 mmol) was added. The mixture was stirred at 25° C. for 5 h. The solution was poured into 1.0 M aqueous hydrochloric acid solution (100 mL). The aqueous layer was extracted with ethyl acetate (2×100 mL). The organic layer was dried over sodium sulfate and concentrated in vacuo to afford the crude product, cis-2-{(4-fluoro-benzyl)-[2-(7-methanesulfonylamino-1,1-dioxo-1,4-dihydro-1$\lambda^6$-benzo[1,2,4]thiadiazin-3-yl)-acetyl]-amino}-cyclooctanecarboxylic acid methyl ester (0.241 g, 0.396 mmol), as an orange oil. LC-MS (ESI) calcd for $C_{27}H_{33}FN_4O_7S_2$ 608.18, found 609.4 [M+H$^+$].

e) N-{3-[1-(4-Fluoro-benzyl)-4-hydroxy-2-oxo-1,2, 4a,5,6,7,8,9,10,10a-decahydro-cycloocta[b]pyridin-3-yl]-1,1-dioxo-1,4-dihydro-1λ$^6$-benzo[1,2,4]thiadiazin-7-yl}-methanesulfonamide

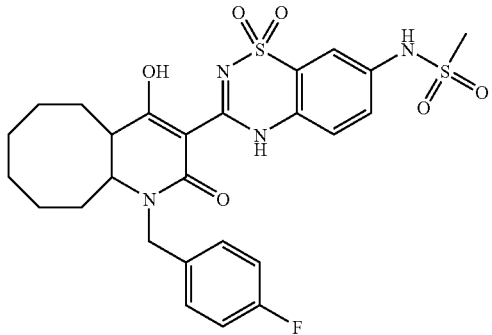

cis-2-{(4-Fluoro-benzyl)-[2-(7-methanesulfonylamino-1, 1-dioxo-1,4-dihydro-1λ$^6$-benzo[1,2,4]thiadiazin-3-yl)-acetyl]-amino}-cyclooctanecarboxylic acid methyl ester (0.241 g, 0.396 mmol) was dissolved in ethanol (4 mL), a 21% w/w solution of sodium ethoxide in ethanol (0.739 mL, 1.98 mmol) was added. The mixture was stirred at 60° C. for 4 h and allowed to cool to 25° C. The mixture was poured into a 0.5 M aqueous hydrochloric acid solution (100 mL). The product started to precipitate and was collected by vacuum filtration. The precipitate was washed with water and dried under high vacuum to afford the pure product N-{3-[1-(4-fluoro-benzyl)-4-hydroxy-2-oxo-1,2,4a,5,6,7,8,9,10,10a-decahydro-cycloocta[b]pyridin-3-yl]-1,1-dioxo-1,4-dihydro-1λ$^6$-benzo[1,2,4]thiadiazin-7-yl}-methanesulfonamide (0.07 g, 0.121 mmol, 31%), as a light yellow solid. $^1$H NMR (400 MHz, DMSO-d$_6$) δ: 1.24-1.83 (12H, m), 3.04 (3H, s), 3.73-3.58 (2H, m), 4.21-4.46 (1H, m), 4.99 (1H, d, J=16 Hz), 7.18 (2H, t, J=8 Hz), 7.47-7.53 (6H, m), 10.08 (1H, s). LC-MS (ESI) calcd for $C_{26}H_{29}FN_4O_6S_2$ 576.15, found 577.5 [M+H$^+$].

EXAMPLE 4 cis-N-[3-(4-Hydroxy-2-oxo-1-pyridin-2-ylmethyl-2, 4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide

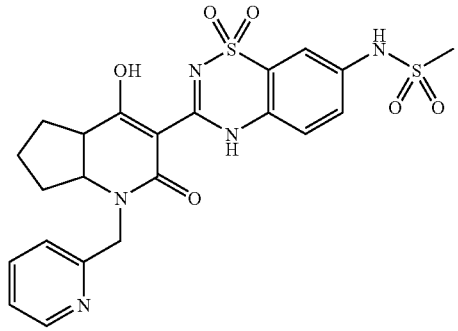

a) 2-[(Pyridin-2-ylmethyl)-amino]-cyclopent-1-en-ecarboxylic acid ethyl ester

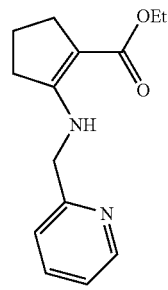

A solution of 2-oxo-cyclopentanecarboxylic acid ethyl ester (3.72 g, 23.8 mmol) in ethanol (50 mL) was treated with pyridin-2-yl-methylamine (2.58 g, 23.8 mmol). The solution was heated at reflux at 80° C. for 16 h. After cooling to 25° C. the solvent was removed in vacuo, and the residue was purified by flash column chromatography (Teledyne Isco RediSep Flash Column 40 g; 0-50 ethyl acetate in hexanes) to afford the desired product, 2-[(pyridin-2-ylmethyl)-amino]-cyclopent-1-enecarboxylic acid ethyl ester (4.78 g, 19.4 mmol, 81%), as a light yellow oil. $^1$H NMR (400 MHz, DMSO-d$_6$) δ: 1.18 (3H, t, J=7.0 Hz), 1.69-1.76 (2H, m), 2.42 (2H, t, J=7.0 Hz), 2.57 (2H, t, J=7.7 Hz), 4.04 (2H, q, J=7.0 Hz), 4.50 (2H, d, J=6.1 Hz), 7.25-7.30 (2H, m), 7.74-7.79 (1H, m), 8.00 (1H, t, J=5.8 Hz), 8.51-8.53 (1H, m).

b) 2-[(Pyridin-2-ylmethyl)-amino]-cyclopentanecarboxylic acid ethyl ester

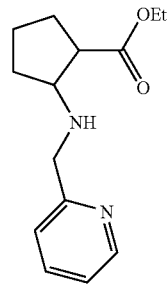

A solution of 2-[(pyridin-2-ylmethyl)-amino]-cyclopent-1-enecarboxylic acid ethyl ester (4.78 g, 19.4 mmol) in acetic acid (70 mL) was treated with a 8.0 M solution of borane in pyridine (2.67 mL, 21.4 mmol) and stirred under a nitrogen atmosphere for 30 min. The reaction was quenched with 1.0 M aqueous hydrochloric acid solution (40 mL) for 16 h. The reaction was then poured into a mixture of saturated aqueous sodium bicarbonate solution (200 mL) and ethyl acetate (200 mL) and extracted. The organic layer was dried over sodium sulfate, filtered, concentrated in vacuo, and purified by flash column chromatography (Teledyne Isco RediSep Flash Column 40 g; 0-10% methanol in dichloromethane) to afford the desired product, 2-[(pyridin-2-ylmethyl)-amino]-cyclopentanecarboxylic acid ethyl ester (3.30 g, 13.3 mmol, 68.6%), as a light yellow oil. $^1$H NMR (400 MHz, DMSO-d$_6$) δ: 1.16 (3H, t, J=7.4 Hz), 1.38-1.79 (4H, m), 1.82-1.96 (2H, m), 2.56 (1H, dd, J$_1$=15.5 Hz, J$_2$=7.0 Hz), 2.88 (1H, dd, J$_1$=14.9 Hz, J$_2$=7.1 Hz), 3.21 (1H, dd, J$_1$=13.7 Hz, J$_2$=6.7 Hz), 4.04 (2H, q, J=7.0 Hz), 3.78 (2H, s), 7.19-7.22 (2H, m), 7.38 (1H, d, J=7.6 Hz), 7.68-7.73 (1H, m), 8.45 (1H, d, J=4.7 Hz). LC-MS (ESI) calcd for $C_{14}H_{20}N_2O_2$ 248.15, found 249.2 [M+H$^+$].

c) 2-{[2-(7-Methanesulfonylamino-1,1-dioxo-1,4-dihydro-1λ⁶-benzo[1,2,4]thiadiazin-3-yl)-acetyl]-pyridin-2-ylmethyl-amino}-cyclopentanecarboxylic acid ethyl ester

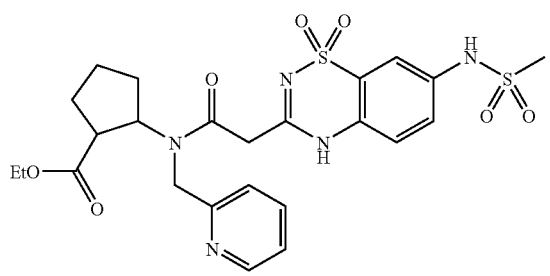

A solution of (7-methanesulfonylamino-1,1-dioxo-1,4-dihydro-1λ⁶-benzo[1,2,4]thiadiazin-3-yl)-acetic acid (prepared as described in Example 1j, 0.10 g, 0.30 mmol) and N,N'-dicyclohexylcarbodiimide (0.068 g, 0.33 mmol) in N,N-dimethylformamide (10 mL) was treated with 2-[(pyridin-2-ylmethyl)-amino]-cyclopentanecarboxylic acid ethyl ester and stirred for 16 h. The mixture was filtered, the filtrate was concentrated in vacuo, and purified by flash column chromatography (Teledyne Isco RediSep Flash Column 40 g; 0-10% methanol in dichloromethane) to afford the desired product, 2-{[2-(7-methanesulfonylamino-1,1-dioxo-1,4-dihydro-1λ⁶-benzo[1,2,4]thiadiazin-3-yl)-acetyl]-pyridin-2-ylmethyl-amino}-cyclopentanecarboxylic acid ethyl ester (0.043 g, 0.076 mmol, 25.3%), as a pale white solid. LC-MS (ESI) calcd for $C_{24}H_{29}N_5O_7S_2$ 563.15, found 564.6 [M+H⁺].

d) cis-N-[3-(4-Hydroxy-2-oxo-1-pyridin-2-ylmethyl-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide

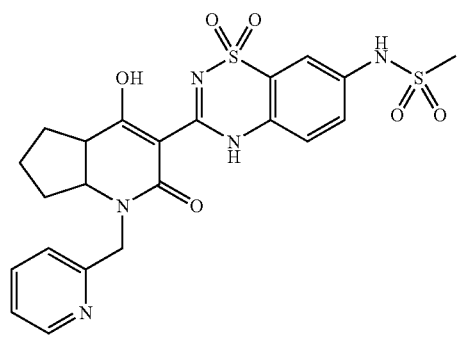

A solution of 2-{[2-(7-methanesulfonylamino-1,1-dioxo-1,4-dihydro-1λ⁶-benzo[1,2,4]thiadiazin-3-yl)-acetyl]-pyridin-2-ylmethyl-amino}-cyclopentanecarboxylic acid ethyl ester (0.043 g, 0.076 mmol) in ethanol (5 mL) was treated with a 21% w/w solution of sodium ethoxide in ethanol (0.114 mL) and stirred for 16 h at 60° C. Glacial acetic acid (0.100 mL) was added, the solvents were removed in vacuo, and the residue was purified by prep-HPLC [Column Luna 5μ C18 (2) 100 Å AXIA 50×21.2 mm, 5 micron, 30%-90% in 7 min @ 30 mL/min flow rate, 0.05% trifluoroacetic acid in acetonitrile/0.05% trifluoroacetic acid in water] to afford the desired product, cis-N-[3-(4-hydroxy-2-oxo-1-pyridin-2-yl-methyl-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide (8.7 mg, 0.017 mmol, 22.4%), as a pale brown solid. ¹H NMR (400 MHz, DMSO-d₆) δ: 1.47-1.71 (3H, m), 1.99-2.15 (3H, m), 3.06 (3H, s), 3.97-4.03 (1H, m), 4.61-4.65 (1H, m), 4.99 (1H, d, J=15.3 Hz), 7.32-7.35 (1H, m), 7.42 (1H, d, J=7.8 Hz), 7.49-7.52 (1H, m), 7.56-7.58 (2H, m), 7.80-7.84 (1H, m), 8.54 (1H, d, J=4.7 Hz), 10.18 (1H, s). LC-MS (ESI) calcd for $C_{22}H_{23}N_5O_6S_2$ 517.11, found 518.1 [M+H⁺].

EXAMPLE 5 cis-N-{3-[1-(5-Fluoro-pyridin-2-ylmethyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide

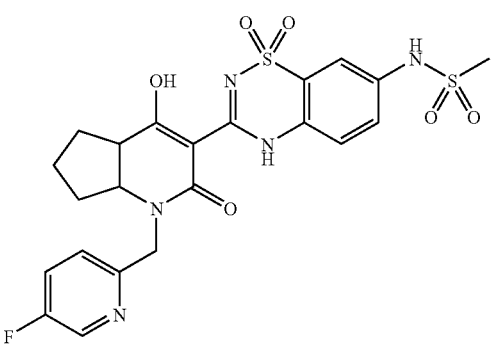

a) cis-2-[(5-Fluoro-pyridin-2-ylmethyl)-amino]-cyclopentanecarboxylic acid ethyl ester

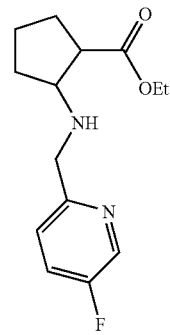

A solution of ethyl cis-2-amino-1-cyclopentane carboxylate hydrochloride (0.250 g, 1.29 mmol) in ethanol (10 mL) was treated with 5-fluoro-pyridine-2-carbaldehyde, glacial acetic acid (10 drops), sodium cyanoborohydride (0.162 g, 2.58 mmol) and stirred for 72 h at 50° C. The reaction was extracted with ethyl acetate (100 mL) and washed with saturated aqueous sodium bicarbonate solution (100 mL). The organic layer was dried over sodium sulfate, filtered, concentrated in vacuo, and purified by flash column chromatography (Teledyne Isco RediSep Flash Column 10 g; 0-10% methanol in dichloromethane) to afford the desired product, cis-2-[(5-fluoro-pyridin-2-ylmethyl)-amino]-cyclopentanecarboxylic acid ethyl ester (0.179 g, 0.678 mmol, 52.5%), as a light yellow oil. LC-MS (ESI) calcd for $C_{14}H_{19}FN_2O_2$ 266.14, found 267.2 [M+H$^+$].

b) cis-2-{(5-Fluoro-pyridin-2-ylmethyl)-[2-(7-methanesulfonylamino-1,1-dioxo-1,4-dihydro-1$\lambda^6$-benzo[1,2,4]thiadiazin-3-yl)-acetyl]-amino}-cyclopentanecarboxylic acid ethyl ester

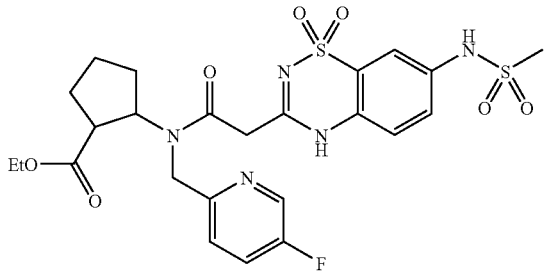

A solution of (7-methanesulfonylamino-1,1-dioxo-1,4-dihydro-1$\lambda^6$-benzo[1,2,4]thiadiazin-3-yl)-acetic acid (prepared as described in Example 1j, 0.100 g, 0.300 mmol) and cis-2-[(5-fluoro-pyridin-2-ylmethyl)-amino]-cyclopentanecarboxylic acid ethyl ester (0.080 g, 0.300 mmol) in N,N-dimethylformamide (1.5 mL) was treated with a 1.0 M solution of N,N'-dicyclohexylcarbodiimide in dichloromethane (0.315 mL, 0.315 mmol). The reaction was stirred for 6 h at 25° C., the urea byproduct was filtered off and the crude material was purified by prep-HPLC [Column Luna 5μ C18 (2) 100 Å AXIA 50×21.2 mm, 5 micron, 30%-90% in 7 min @ 30 mL/min flow rate, 0.05% trifluoroacetic acid in acetonitrile/0.05% trifluoroacetic acid in water] to afford the desired product, cis-2-{(5-fluoro-pyridin-2-ylmethyl)-[2-(7-methanesulfonylamino-1,1-dioxo-1,4-dihydro-1$\lambda^6$-benzo[1,2,4]thiadiazin-3-yl)-acetyl]-amino}-cyclopentanecarboxylic acid ethyl ester (0.085 g, 0.146 mmol, 48.7%), as a white solid. LC-MS (ESI) calcd for $C_{24}H_{28}FN_5O_7S_2$ 581.14, found 582.2 [M+H$^+$].

c) cis-N-{3-[1-(5-Fluoro-pyridin-2-ylmethyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide

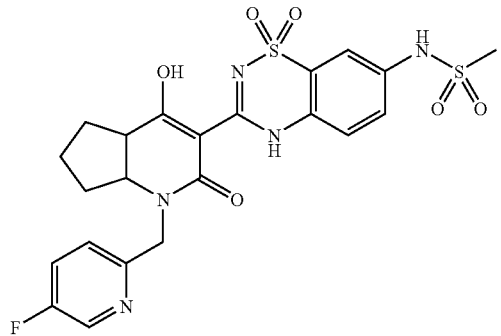

A solution of cis-2-{(5-fluoro-pyridin-2-ylmethyl)-[2-(7-methanesulfonylamino-1,1-dioxo-1,4-dihydro-1$\lambda^6$-benzo[1,2,4]thiadiazin-3-yl)-acetyl]-amino}-cyclopentane-carboxylic acid ethyl ester (0.085 g, 0.146 mmol) in ethanol (2 mL) was treated with a 21% w/w solution of sodium ethoxide in ethanol (0.218 mL) and stirred for 2 h at 60° C. Glacial acetic acid (0.200 mL) was added, the solvents were removed in vacuo, and the residue was purified by prep-HPLC [Column Luna 5μ C18 (2) 100 Å AXIA 50×21.2 mm, 5 micron, 30%-90% in 7 min @ 30 mL/min flow rate, 0.05% trifluoroacetic acid in acetonitrile/0.05% trifluoroacetic acid in water] to afford the desired product, cis-N-{3-[1-(5-fluoro-pyridin-2-ylmethyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide (0.052 g, 0.097 mmol, 66.5%), as a white solid. $^1$H NMR (400 MHz, DMSO-d$_6$) δ: 1.47-1.69 (3H, m), 1.96-2.14 (3H, m), 3.06 (3H, s), 3.95-4.01 (1H, m), 4.61 (1H, bs), 4.96 (1H, d, J=16.5 Hz), 7.46-7.52 (2H, m), 7.56-7.58 (2H, m), 7.67-7.72 (1H, m), 8.51 (1H, d, J=3.5 Hz), 10.18 (1H, s). LC-MS (ESI) calcd for $C_{22}H_{22}FN_5O_6S_2$ 535.10, found 536.4 [M+H$^+$].

EXAMPLE 6 cis-N-{3-[1-(2-Dimethylamino-ethyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide

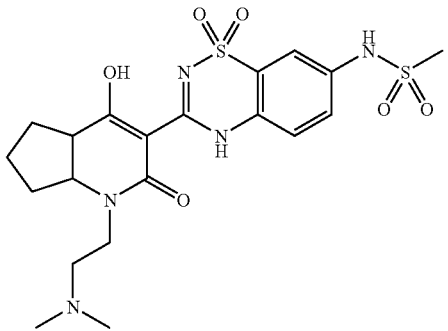

a) 2-(2-Dimethylamino-ethylamino)-cyclopent-1-enecarboxylic acid ethyl ester

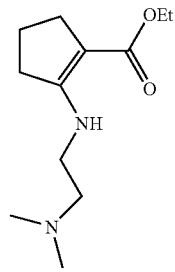

A solution of 2-oxo-cyclopentanecarboxylic acid ethyl ester (5.00 g, 32.0 mmol) in ethanol (50 mL) was treated with N,N-dimethylethylenediamine (3.85 mL, 35.2 mmol). The solution was heated at reflux at 80° C. for 16 h. After cooling to 25° C. the solvent was removed in vacuo, and the residue was purified by flash column chromatography (Teledyne Isco RediSep Flash Column 40 g; 0-100% ethyl acetate in hexanes) to afford the desired product, 2-(2-dimethylamino-ethylamino)-cyclopent-1-enecarboxylic acid ethyl ester (6.7 g, 29.6 mmol, 92.5%), as a light yellow oil. The product was used immediately in the following step without characterization.

b) 2-(2-Dimethylamino-ethylamino)-cyclopentan-ecarboxylic acid ethyl ester

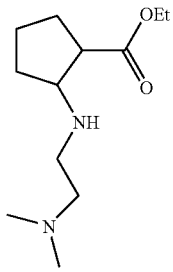

A solution of 2-(2-dimethylamino-ethylamino)-cyclopent-1-enecarboxylic acid ethyl ester (2.18 g, 9.63 mmol) in ethanol (100 mL) was treated with glacial acetic acid (10 drops), sodium cyanoborohydride (1.21 g, 19.26 mmol) and stirred for 16 h at 50° C. The reaction was diluted with ethyl acetate (100 mL) and washed twice with saturated aqueous sodium bicarbonate solution (100 mL). The organic layer was dried over sodium sulfate, filtered, concentrated in vacuo to afford the desired product, 2-(2-dimethylamino-ethylideneamino)-cyclopentanecarboxylic acid ethyl ester (1.84 g, 8.06 mmol, 83.7%), as a light yellow oil. LC-MS (ESI) calcd for $C_{12}H_{24}N_2O_2$ 228.18, found 229.3 [M+H$^+$].

c) 2-{(2-Dimethylamino-ethyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester

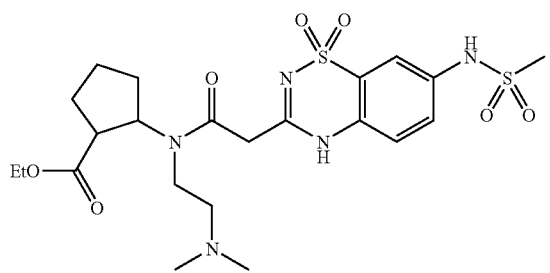

A solution of (7-methanesulfonylamino-1,1-dioxo-1,4-dihydro-1λ$^6$-benzo[1,2,4]thiadiazin-3-yl)-acetic acid (prepared as described in Example 1j, 0.100 g, 0.300 mmol) and 2-(2-dimethylamino-ethylideneamino)-cyclopentanecarboxylic acid ethyl ester (0.069 g, 0.300 mmol) in N,N-dimethylformamide (1.5 mL) was treated with a 1.0 M solution N,N'-dicyclohexylcarbodiimide in dichloromethane (0.315 mL, 0.315 mmol). The reaction was stirred for 6 h at 25° C., the urea byproduct was filtered off and the crude material was purified by prep-HPLC [Column Luna 5μ C18 (2) 100 Å AXIA 50×21.2 mm, 5 micron, 30%-90% in 7 min @ 30 mL/min flow rate, 0.05% trifluoroacetic acid in acetonitrile/ 0.05% trifluoroacetic acid in water] to afford the desired product, 2-{(2-dimethylamino-ethyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester (25.4 mg, 0.047 mmol, 15.6%), as a white solid. LC-MS (ESI) calcd for $C_{22}H_{33}N_5O_7S_2$ 543.18, found 544.4 [M+H$^+$].

d) cis-N-{3-[1-(2-Dimethylamino-ethyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

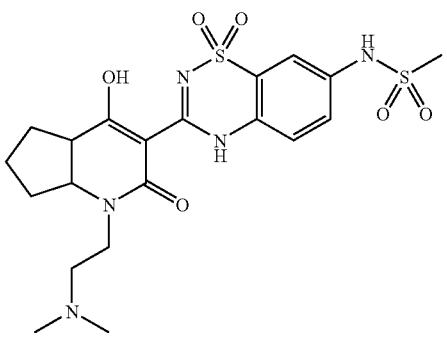

A solution of 2-{(2-dimethylamino-ethyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester (25.4 mg, 0.047 mmol) in ethanol (2 mL) was treated with a 21% w/w solution of sodium ethoxide in ethanol (0.070 mL) and stirred for 2 h at 60° C. Glacial acetic acid (0.100 mL) was added, the solvents were removed in vacuo, and the crude material was purified by prep-HPLC [Column Luna 5μ C18 (2) 100 Å AXIA 50×21.2 mm, 5 micron, 30%-90% in 7 min @ 30 mL/min flow rate, 0.05% trifluoroacetic acid in acetonitrile/0.05% trifluoroacetic acid in water] to afford the desired product, cis-N-{3-[1-(2-dimethylamino-ethyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide (5.7 mg, 0.011 mmol, 23.4%), as a white solid. $^1$H NMR (400 MHz, DMSO-d$_6$) δ: 1.53-1.67 (3H, m), 2.02-2.19 (3H, m), 2.88 (6H, s), 3.07 (3H, s), 3.24-3.33 (2H, m), 3.38-3.45 (2H, m), 3.92-3.98 (1H, m), 4.08-4.15 (1H, m), 7.52-7.58 (3H, m), 9.27 (1H, s), 10.20 (1H, s). LC-MS (ESI) calcd for $C_{20}H_{27}N_5O_6S_2$ 497.14, found 498.3 [M+H$^+$].

EXAMPLE 7 cis-N-[3-(1-Benzyl-4-hydroxy-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide

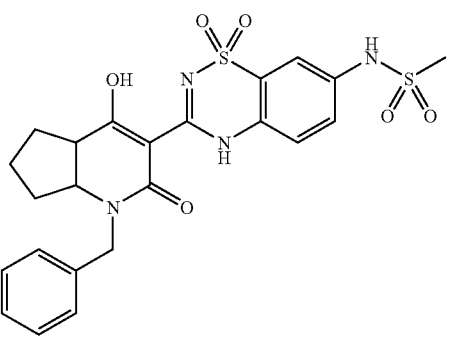

a) 2-Benzylamino-cyclopentanecarboxylic acid ethyl ester

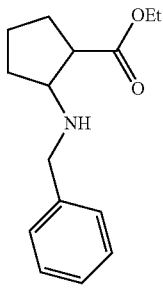

A solution of 2-oxo-cyclopentanecarboxylic acid ethyl ester (3.00 g, 19.2 mmol) in ethanol (20 mL) was treated with benzylamine (2.10 mL, 19.2 mmol), sodium cyanoborohydride (2.42 g, 38.4 mmol), glacial acetic acid (10 drops) and stirred for 16 h at 50° C. After cooling to 25° C. the solvent was removed in vacuo, the crude material was redissolved in ethyl acetate (100 mL) and washed with saturated aqueous sodium bicarbonate solution (100 mL). The aqueous layer was discarded and the organic layer was washed with 1.0 M aqueous hydrochloric acid solution (50 mL). The organic layer was discarded, 1.0 M aqueous sodium hydroxide solution (75 mL) was added and the aqueous layer was extracted with ethyl acetate (100 mL). The organic layer was dried over sodium sulfate, filtered and the solvent was removed in vacuo to afford the desired product, 2-benzylamino-cyclopentanecarboxylic acid ethyl ester (2.10 g, 8.49 mmol, 44.2%), as a light yellow oil. LC-MS (ESI) calcd for $C_{15}H_{21}NO_2$ 247.16, found 248.2 $[M+H^+]$.

b) cis-N-[3-(1-Benzyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide

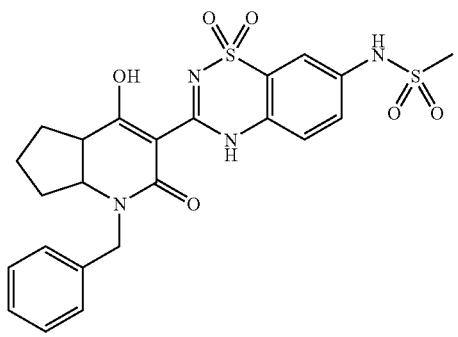

A solution of (7-methanesulfonylamino-1,1-dioxo-1,4-dihydro-1$\lambda^6$-benzo[1,2,4]thiadiazin-3-yl)-acetic acid (prepared as described in Example 1j, 0.100 g, 0.300 mmol) and 2-benzylamino-cyclopentanecarboxylic acid ethyl ester (0.074 g, 0.300 mmol) in N,N-dimethylformamide (1.5 mL) was treated with N-methylmorpholine (63.7 mg, 0.63 mmol), 1-(3-dimethylaminopropyl)-3-ethylcarbodiimide hydrochloride (60.4 mg, 0.315 mmol) and stirred at 25° C. for 4 h. The solvent was removed in vacuo. The crude material was redissolved in ethyl acetate (75 mL) and washed twice with 1.0 M aqueous hydrochloric acid solution (50 mL). The organic layer was then dried over sodium sulfate, filtered and concentrated in vacuo. The crude intermediate was redissolved in ethanol (5 mL) and treated with a 21% w/w solution of sodium ethoxide in ethanol (448 µL, 1.2 mmol) and stirred for 2 h at 60° C. The reaction was allowed to cool to 25° C., treated with glacial acetic acid (0.4 mL), the solvents were removed in vacuo, and the residue was purified by prep-HPLC [Column Luna 5µ C18 (2) 100 Å AXIA 50×21.2 mm, 5 micron, 30%-90% in 7 min @ 30 mL/min flow rate, 0.05% trifluoroacetic acid in acetonitrile/0.05% trifluoroacetic acid in water] to afford the desired product, cis-N-[3-(1-benzyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide (47.0 mg, 0.091 mmol, 30.3%), as a white solid. $^1$H NMR (400 MHz, DMSO-$d_6$) δ: 1.43-1.61 (3H, m), 1.93-2.15 (3H, m), 3.06 (3H, s), 3.80-3.90 (1H, m), 4.40-4.52 (1H, m), 4.96 (1H, d, J=14.8 Hz), 7.27-7.34 (5H, m), 7.50-7.60 (3H, m), 10.18 (1H, s). LC-MS (ESI) calcd for $C_{23}H_{24}N_4O_6S_2$ 516.11, found 517.2 $[M+H^+]$.

EXAMPLE 8 cis-N-{3-[1-(3-Fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide

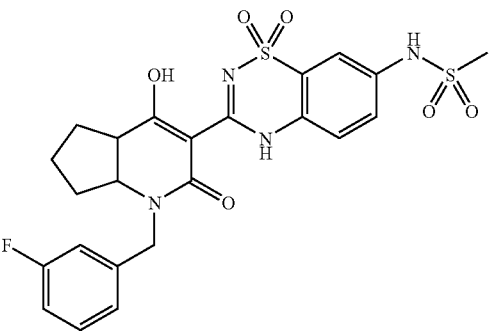

a) 2-(3-Fluoro-benzylamino)-cyclopentanecarboxylic acid ethyl ester

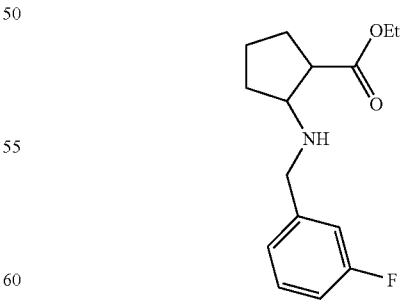

A solution of 2-oxo-cyclopentanecarboxylic acid ethyl ester (3.00 g, 19.2 mmol) in ethanol (20 mL) was treated with benzylamine (2.19 mL, 19.2 mmol), sodium cyanoborohydride (2.42 g, 38.4 mmol), and glacial acetic acid (10 drops) and stirred for 16 h at 50° C. After cooling to 25° C. the solvent was removed in vacuo, the crude material was redissolved in ethyl acetate (100 mL and washed with saturated aqueous sodium bicarbonate solution (100 mL). The aqueous layer was discarded and the organic layer was washed with 1.0 M aqueous hydrochloric acid solution (50 mL). The organic layer was discarded, 1.0 M aqueous sodium hydroxide solution (75 mL) was added and the aqueous layer was extracted with ethyl acetate (100 mL). The organic layer was dried over sodium sulfate, filtered and the solvent was removed in vacuo to afford the desired product, 2-(3-fluoro-benzylamino)-cyclopentanecarboxylic acid ethyl ester (0.754 g, 2.84 mmol, 14.8%), as a light yellow oil. LC-MS (ESI) calcd for $C_{15}H_{20}FNO_2$ 265.15, found 266.0 [M+H$^+$].

b) cis-N-{3-[1-(3-Fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide

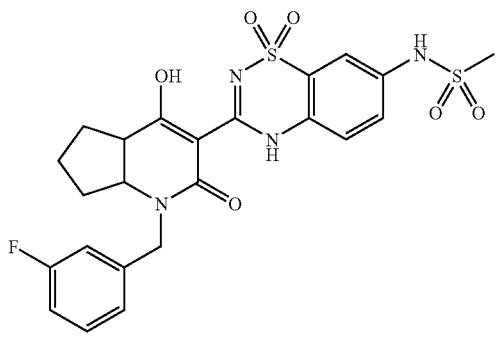

A solution of (7-methanesulfonylamino-1,1-dioxo-1,4-dihydro-1$\lambda^6$-benzo[1,2,4]thiadiazin-3-yl)-acetic acid (prepared as described in Example 1j, 0.100 g, 0.300 mmol) and 2-(3-fluoro-benzylamino)-cyclopentanecarboxylic acid ethyl ester (0.080 g, 0.300 mmol) in N,N-dimethylformamide (1.5 mL) was treated with N-methylmorpholine (63.7 mg, 0.63 mmol), 1-(3-dimethylaminopropyl)-3-ethylcarbodiimide hydrochloride (60.4 mg, 0.315 mmol) and stirred at 25° C. for 4 h. The solvent was removed in vacuo. The crude material was redissolved in ethyl acetate (75 mL) and washed twice with 1.0 M aqueous hydrochloric acid solution (50 mL). The organic layer was then dried over sodium sulfate, filtered and concentrated in vacuo. The crude intermediate was redissolved in ethanol (5 mL) and treated with a 21% w/w solution of sodium ethoxide in ethanol (448 µL, 1.2 mmol) and stirred for 2 h at 60° C. The reaction was allowed to cool to 25° C., treated with glacial acetic acid (0.4 mL), the solvents were removed in vacuo, and the residue was purified by prep-HPLC [Column Luna 5µ C18 (2) 100 Å AXIA 50×21.2 mm, 5 micron, 30%-90% in 7 min @ 30 mL/min flow rate, 0.05% trifluoroacetic acid in acetonitrile/0.05% trifluoroacetic acid in water] to afford the desired product, cis-N-{3-[1-(3-fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide (50.9 mg, 0.095 mmol, 31.7%), as a white solid. $^1$H NMR (400 MHz, DMSO-d$_6$) δ: 1.46-1.62 (3H, m), 1.97-2.19 (3H, m), 3.06 (3H, s), 3.86-3.93 (1H, m), 4.46-4.55 (1H, m), 4.94 (1H, d, J=15.6 Hz), 7.07-7.12 (1H, m), 7.18-7.20 (2H, m), 7.35-7.41 (1H, m), 7.50-7.53 (1H, m), 7.58-7.60 (2H, m), 10.18 (1H, s). LC-MS (ESI) calcd for $C_{23}H_{23}FN_4O_6S_2$ 534.10, found 535.4 [M+H$^+$].

EXAMPLE 9 cis-N-[3-(4-Hydroxy-2-oxo-1-phenethyl-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide

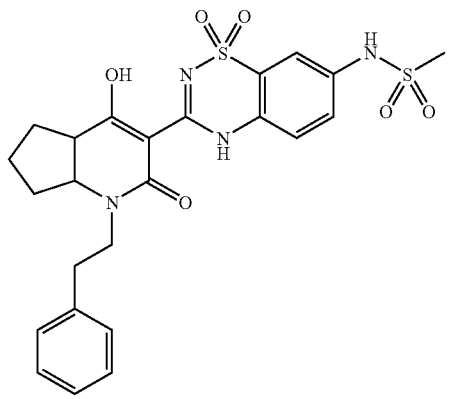

a) 2-Phenethylamino-cyclopentanecarboxylic acid ethyl ester

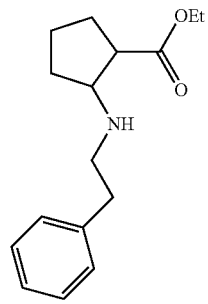

A solution of 2-oxo-cyclopentanecarboxylic acid ethyl ester (3.00 g, 19.2 mmol) in ethanol (20 mL) was treated with phenethylamine (2.41 mL, 19.2 mmol), sodium cyanoborohydride (2.42 g, 38.4 mmol), and glacial acetic acid (10 drops) and stirred for 16 h at 50° C. After cooling to 25° C. the solvent was removed in vacuo, the crude material was redissolved in ethyl acetate (100 mL and washed with saturated aqueous sodium bicarbonate solution (100 mL). The aqueous layer was discarded and the organic layer was washed with 1.0 M aqueous hydrochloric acid solution (50 mL). The organic layer was discarded, 1.0 M aqueous sodium hydroxide solution (75 mL) was added and the aqueous layer was extracted with ethyl acetate (100 mL). The organic layer was dried over sodium sulfate, filtered and the solvent was removed in vacuo to afford the desired product, 2-phenethylamino-cyclopentanecarboxylic acid ethyl ester (1.94 g, 7.42 mmol, 38.6%), as a light yellow solid. LC-MS (ESI) calcd for $C_{16}H_{23}NO_2$ 261.17, found 262.2 [M+H$^+$].

b) cis-N-[3-(4-Hydroxy-2-oxo-1-phenethyl-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide

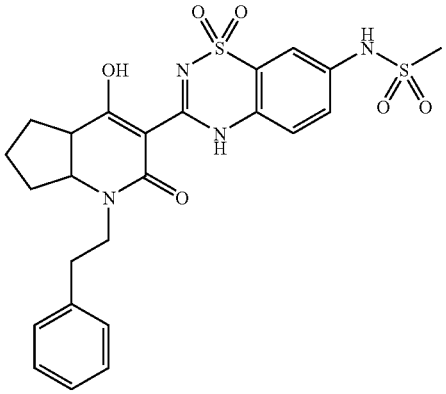

A solution of (7-methanesulfonylamino-1,1-dioxo-1,4-dihydro-1λ⁶-benzo[1,2,4]thiadiazin-3-yl)-acetic acid (prepared as described in Example 1j, 0.100 g, 0.300 mmol) and 2-phenethylamino-cyclopentanecarboxylic acid ethyl ester (0.078 g, 0.300 mmol) in N,N-dimethylformamide (1.5 mL) was treated with N-methylmorpholine (63.7 mg, 0.63 mmol), 1-(3-dimethylaminopropyl)-3-ethylcarbodiimide hydrochloride (60.4 mg, 0.315 mmol) and stirred at 25° C. for 4 h. The solvent was removed in vacuo. The crude material was redissolved in ethyl acetate (75 mL) and washed twice with 1.0 M aqueous hydrochloric acid solution (50 mL). The organic layer was then dried over sodium sulfate, filtered and concentrated in vacuo. The crude intermediate was redissolved in ethanol (5 mL) and treated with a 21% w/w solution of sodium ethoxide in ethanol (448 µL, 1.2 mmol) and stirred for 2 h at 60° C. The reaction was allowed to cool to 25° C., treated with glacial acetic acid (0.4 mL), the solvents were removed in vacuo, and the residue was and purified by prep-HPLC [Column Luna 5µ C18 (2) 100 Å AXIA 50×21.2 mm, 5 micron, 30%-90% in 7 min @ 30 mL/min flow rate, 0.05% trifluoroacetic acid in acetonitrile/0.05% trifluoroacetic acid in water] to afford the desired product, cis-N-[3-(4-hydroxy-2-oxo-1-phenethyl-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide (35.9 mg, 0.068 mmol, 22.6%), as a white solid. ¹H NMR (400 MHz, DMSO-d₆) δ: 1.48-1.65 (3H, m), 1.97-2.26 (3H, m), 2.83-2.99 (4H, m), 3.06 (3H, s), 3.88 (2H, bs), 7.21-7.34 (8H, m), 7.50-7.83 (5H, m), 10.17 (1H, bs). LC-MS (ESI) calcd for $C_{24}H_{26}N_4O_6S_2$ 530.13, found 531.3 [M+H⁺].

EXAMPLE 10 cis-N-[3-(1-Cyclopentyl-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide

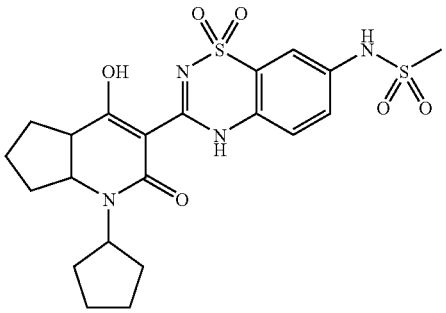

a) 2-Cyclopentylamino-cyclopentanecarboxylic acid ethyl ester

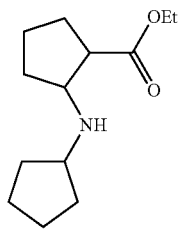

A solution of 2-oxo-cyclopentanecarboxylic acid ethyl ester (3.00 g, 19.2 mmol) in ethanol (20 mL) was treated with cyclopentylamine (1.90 mL, 19.2 mmol), sodium cyanoborohydride (2.42 g, 38.4 mmol), and glacial acetic acid (10 drops) and stirred for 16 h at 50° C. After cooling to 25° C. the solvent was removed in vacuo, the crude material was redissolved in ethyl acetate (100 mL) and washed with saturated aqueous sodium bicarbonate solution (100 mL). The aqueous layer was discarded and the organic layer was washed with 1.0 M aqueous hydrochloric acid solution (50 mL). The organic layer was discarded, 1.0 M aqueous sodium hydroxide solution (75 mL) was added and the aqueous layer was extracted with ethyl acetate (100 mL). The organic layer was dried over sodium sulfate, filtered and the solvent was removed in vacuo to afford the desired product, 2-cyclopentylamino-cyclopentanecarboxylic acid ethyl ester (1.48 g, 6.57 mmol, 34.2%), as a light yellow oil. LC-MS (ESI) calcd for $C_{13}H_{23}NO_2$ 225.17, found 226.2 [M+H⁺].

b) cis-N-[3-(1-Cyclopentyl-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide

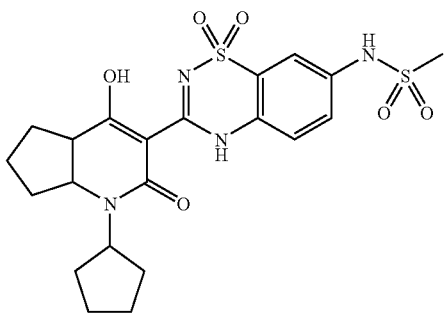

A solution of (7-methanesulfonylamino-1,1-dioxo-1,4-dihydro-1λ⁶-benzo[1,2,4]thiadiazin-3-yl)-acetic acid (prepared as described in Example 1j, 0.100 g, 0.300 mmol) and 2-cyclopentylamino-cyclopentanecarboxylic acid ethyl ester (0.068 g, 0.300 mmol) in N,N-dimethylformamide (1.5 mL) was treated with N-methylmorpholine (63.7 mg, 0.63 mmol), 1-(3-dimethylaminopropyl)-3-ethylcarbodiimide hydrochloride (60.4 mg, 0.315 mmol) and stirred at 25° C. for 4 h. The solvent was removed in vacuo. The crude material was redissolved in ethyl acetate (75 mL) and washed twice with 1.0 M aqueous hydrochloric acid solution (50 mL). The organic layer was then dried over sodium sulfate, filtered and concentrated in vacuo. The crude intermediate was redissolved in ethanol (5 mL) and treated with a 21% w/w solution of sodium ethoxide in ethanol (448 μL, 1.2 mmol) and stirred for 2 h at 60° C. The reaction was allowed to cool to 25° C., treated with glacial acetic acid (0.4 mL), the solvents were removed in vacuo, and the residue was and purified by prep-HPLC [Column Luna 5μ C18 (2) 100 Å AXIA 50×21.2 mm, 5 micron, 30%-90% in 7 min @ 30 mL/min flow rate, 0.05% trifluoroacetic acid in acetonitrile/0.05% trifluoroacetic acid in water] to afford the desired product, cis-N-[3-(1-cyclopentyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide (2.5 mg, 0.005 mmol, 1.7%), as a white solid. $^1$H NMR (400 MHz, DMSO-d$_6$) δ: 1.51-2.11 (13H, m), 3.06 (3H, s), 3.84-4.03 (1H, m), 4.52-4.67 (1H, m), 7.49-7.57 (3H, m), 10.17 (1H, s). LC-MS (ESI) calcd for $C_{21}H_{26}N_4O_6S_2$ 494.13, found 495.5 [M+H$^+$].

EXAMPLE 11

(4aR,7aS)-N-{3-[1-(3-Chloro-4-fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide

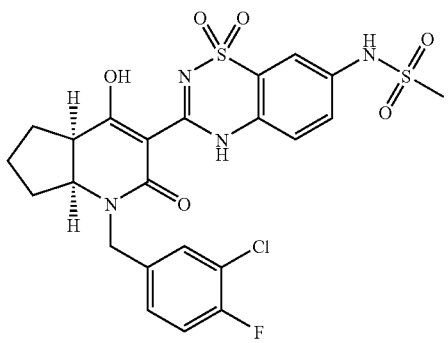

a) (1R,2S)-2-Amino-cyclopentanecarboxylic acid methyl ester hydrochloride

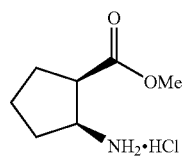

(1R,2S)-2-Amino-cyclopentanecarboxylic acid hydrochloride (96 mg, 0.58 mmol) was dissolved in a 1:1 mixture of benzene and methanol (6 mL). The mixture was cooled to 0° C. A 2.0 M solution of (trimethylsilyl)diazomethane in hexanes (0.44 mL, 0.87 mmol) was added and the reaction was stirred at 25° C. for 30 min. The mixture was concentrated and dried in vacuo. The crude product was directly used in the next step.

b) (1R,2S)-2-(3-Chloro-4-fluoro-benzylamino)-cyclopentanecarboxylic acid methyl ester

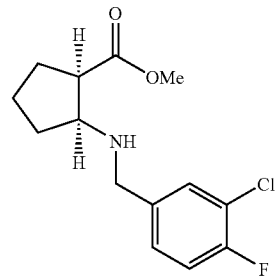

(1R,2S)-2-Amino-cyclopentanecarboxylic acid methyl ester hydrochloride (prepared as described in Example 11a, 0.2 g, 1.27 mmol) was dissolved in methanol (5.5 mL), followed by addition of 4-fluoro-3-chlorobenzaldehyde (0.201 g, 1.27 mmol) and stirred at 25° C. for 10 min. After this time, 5.2 M acetic acid (0.245 mL) was added, stirred at 25° C. for 5 min before placing in an ice-bath. Once at 0° C., sodium borohydride (0.203 mg, 3.2 mmol) was added portionwise after which time the mixture was allowed to warm to 25° C. and continued to stir for 17 h. The reaction mixture was quenched by pouring into saturated aqueous sodium bicarbonate solution (200 mL) and extracted with ethyl acetate (200 mL). The organic layer was concentrated in vacuo and purified by flash column chromatography (Teledyne Isco RediSep Flash Column; 0-80% ethyl acetate in hexanes) to afford the desired product, (1R,2S)-2-(3-chloro-4-fluoro-benzylamino)-cyclopentanecarboxylic acid methyl ester (256 mg, 0.898 mmol, 70% as a yellow oil, containing residual ethyl acetate. $^1$H NMR (400 MHz, CDCl$_3$) δ: 1.55-1.97 (m, 6H), 2.86 (dd, 1H, J$_1$=14.2 Hz, J$_2$=7.0 Hz), 3.19 (dd, 1H, J$_1$=13.1 Hz, J$_2$=6.9 Hz), 3.62 (s, 3H), 3.64 (d, 2H, J=6.2 Hz), 6.96 (t, 1H, J=8.5 Hz), 7.04-7.08 (m, 1H), 7.26-7.28 (m, 1H). LC-MS (ESI) calcd for $C_{14}H_{17}ClFNO_2$ 285.09, found 286.0 [M+H$^+$].

c) (1R,2S)-2-{(3-Chloro-4-fluoro-benzyl)-[2-(7-methanesulfonylamino-1,1-dioxo-1,4-dihydro-1$\lambda^6$-benzo[1,2,4]thiadiazin-3-yl)-acetyl]-amino}-cyclopentanecarboxylic acid methyl ester

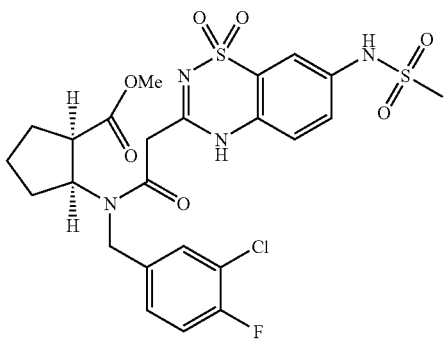

(1R,2S)-2-(3-Chloro-4-fluoro-benzylamino)-cyclopentanecarboxylic acid methyl ester (0.12 g, 0.42 mmol) was dissolved in anhydrous N,N-dimethylformamide (4.2 mL). (7-Methanesulfonylamino-1,1-dioxo-1,4-dihydro-1$\lambda^6$- benzo[1,2,4]thiadiazin-3-yl)-acetic acid (prepared as described in Example 1j, 0.154 g, 0.46 mmol) was added followed by N-methylmorpholine (0.101 mL, 0.92 mmol). The mixture was stirred until everything dissolved, approximately 5 min. 1-(3-Dimethylaminopropyl)-3-ethylcarbodiimide hydrochloride (0.088 g, 0.46 mmol) was added portionwise and the mixture was stirred at 25° C. for 15 h. The reaction mixture was quenched by pouring into 1.0 M aqueous hydrochloric acid solution (100 mL) and extracted with ethyl acetate (200 mL). The organic layer was concentrated in vacuo to afford the crude product, (1R,2S)-2-{(3-chloro-4-fluoro-benzyl)-[2-(7-methanesulfonylamino-1,1-dioxo-1,4-dihydro-1$\lambda^6$-benzo[1,2,4]thiadiazin-3-yl)-acetyl]-amino}-cyclopentanecarboxylic acid methyl ester, which was used directly in the next step without further purification. LC-MS (ESI) calcd for $C_{24}H_{26}ClFN_4O_7S_2$ 600.09, found 601.1 [M+H$^+$].

d) (4aR,7aS)-N-{3-[1-(3-Chloro-4-fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide

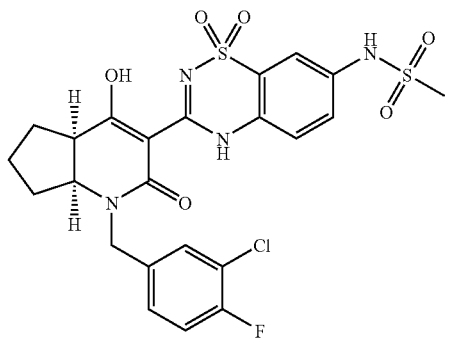

(1R,2S)-2-{(3-Chloro-4-fluoro-benzyl)-[2-(7-methanesulfonylamino-1,1-dioxo-1,4-dihydro-1$\lambda^6$-benzo[1,2,4]thiadiazin-3-yl)-acetyl]-amino}-cyclopentanecarboxylic acid methyl ester (crude from Example 11b, 0.252 g, 0.42 mmol) was dissolved in ethanol (8.4 mL), followed by addition of a 21% w/w solution of sodium ethoxide in ethanol (0.545 mL, 1.68 mmol), and heated to 60° C. for 1 h. Upon cooling, the reaction mixture was then quenched with 1.0 M aqueous hydrochloric acid solution (2 mL) and extracted with ethyl acetate (2×50 mL). The combined organic layers were dried over magnesium sulfate, filtered, and dried in vacuo. Recrystallization from 10-20% ethyl acetate in hexanes afforded the desired product, (4aR,7aS)-N-{3-[1-(3-chloro-4-fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide (0.147 g, 0.259 mmol, 61%), as a white solid. $^1$H NMR (400 MHz, DMSO-d$_6$) δ: 1.51-1.58 (m, 3H), 1.99-2.00 (m, 3H), 3.06 (s, 3H), 3.30 (bs, 1H), 3.88 (bs, 1H), 4.47 (d, 1H, J=15.0 Hz), 4.89 (d, 1H, J=15.4 Hz), 7.36 (d, 2H, J=7.3 Hz), 7.50 (dd, 1H, J$_1$=8.6 Hz, J$_2$=2.4 Hz), 7.57-7.59 (m, 3H), 10.17 (bs, 1H). LC-MS (ESI) calcd for $C_{23}H_{22}ClFN_4O_6S_2$ 568.07, found 569.03 [M+H$^+$].

EXAMPLE 12

(4aR,7aS)—N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide

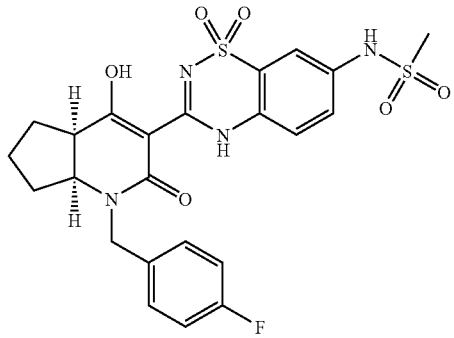

a) (1R,2S)-2-(4-Fluoro-benzylamino)-cyclopentanecarboxylic acid methyl ester

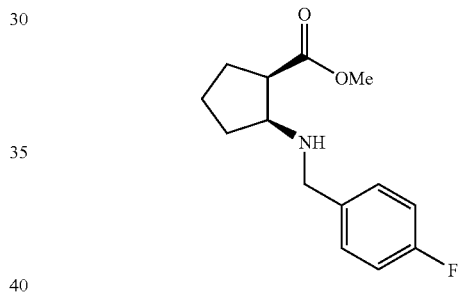

To a solution of (1R,2S)-2-amino-cyclopentanecarboxylic acid methyl ester hydrochloride (prepared as described in Example 11a, 104 mg, 0.58 mmol) in tetrahydrofuran (6 mL) at 25° C. was added magnesium sulfate (200 mg), triethylamine (0.085 mL, 0.61 mmol), and 4-fluorobenzaldehyde (0.13 mL, 1.19 mmol) sequentially. The reaction was stirred at 25° C. for 16 h. The mixture was passed through a short pad of Celite and the filtrate was concentrated and dried in vacuo. The residue was re-dissolved in methanol (10 mL) at 25° C. To this solution was added slowly sodium borohydride (45 mg, 1.19 mmol). The mixture was stirred at 25° C. for 1 h. It was then poured into a saturated sodium bicarbonate aqueous solution (10 mL) and the mixture was extracted into ethyl acetate (20 mL). The organic layer was dried over magnesium sulfate, filtered, and concentrated in vacuo to afford a clear oil. Purification by flash column chromatography (Merck silica gel 60, 40-63 μm; 0-15% ethyl acetate in hexanes) afforded the desired product, (1R,2S)-2-(4-fluoro-benzylamino)-cyclopentanecarboxylic acid methyl ester (116 mg, 0.46 mmol, 79%), as a clear oil. $^1$H NMR (400 MHz, CDCl$_3$) δ: 1.55-1.73 (2H, m), 1.83-1.93 (3H, m), 1.99-2.08 (1H, m), 2.97 (1H, dd, J$_1$=14.4 Hz, J$_2$=8.0 Hz), 3.31 (1H, dd, J$_1$=14.4 Hz, J$_2$=7.2 Hz), 3.70 (3H, s), 3.77 (2H, dd, J$_1$=19.6 Hz, J$_2$=12.0 Hz), 4.67 (1H, s), 6.96-7.06 (2H, m), 7.26-7.35 (2H, m). LC-MS (ESI) calcd for $C_{14}H_{18}FNO_2$ 251.30, found 252.1 [M+H$^+$].

c) (1R,2S)-2-{(4-Fluoro-benzyl)-[2-(7-methane-sulfonylamino-1,1-dioxo-1,4-dihydro-1λ⁶-benzo[1,2,4]thiadiazin-3-yl)-acetyl]-amino}-cyclopentanecarboxylic acid methyl ester

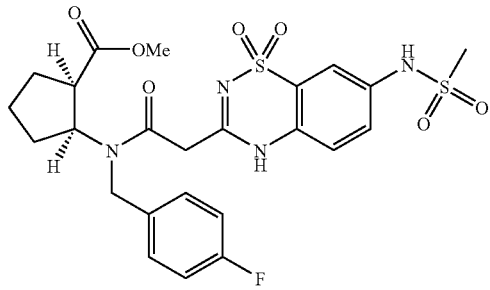

(1R,2S)-2-(4-Fluoro-benzylamino)-cyclopentanecarboxylic acid methyl ester (106 mg, 0.42 mmol) and (7-methanesulfonylamino-1,1-dioxo-1,4-dihydro-1λ⁶-benzo[1,2,4]thiadiazin-3-yl)-acetic acid (prepared as described in Example 1j, 140 mg, 0.42 mmol) were dissolved in a 1:1 mixture of dichloromethane and N,N'-dimethylformamide (6 mL). A 1.0 M solution of N,N'-dicyclohexylcarbodiimide in dichloromethane (0.46 mL, 0.46 mmol) was added. The reaction was stirred at 25° C. for 16 h. The mixture was concentrated in vacuo and purified by flash column chromatography (Merck silica gel 60, 40-63 μm; 0-85% ethyl acetate in hexanes) to afford the desired product, (1R,2S)-2-{(4-fluoro-benzyl)-[2-(7-methanesulfonylamino-1,1-dioxo-1,4-dihydro-1λ⁶-benzo[1,2,4]thiadiazin-3-yl)-acetyl]-amino}-cyclopentanecarboxylic acid methyl ester (127 mg, 0.22 mmol, 52%), as a white solid. ¹H NMR (400 MHz, CDCl₃) δ: 1.80-2.22 (6H, m), 3.07 (3H, s), 3.24 (1H, dd, J₁=18.8 Hz, J₂=8.0 Hz), 3.32 (1H, dd, J₁=15.6 Hz, J₂=8.0 Hz), 3.69 (1H, s), 4.63 (2H, d, J=4.8 Hz), 4.67-4.74 (1H, m), 4.82-4.89 (1H, m), 6.99-7.14 (5H, m), 7.51-7.64 (2H, m). LC-MS (ESI) calcd for $C_{24}H_{27}FN_4O_7S_2$ 566.62, found 567.1 [M+H⁺].

d) (4aR,7aS)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide

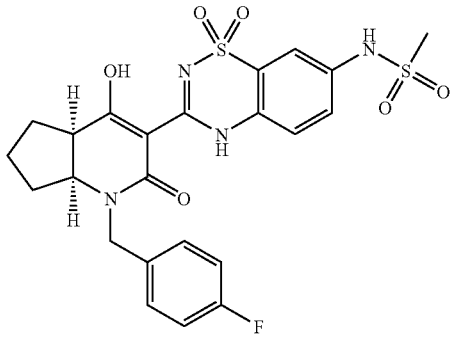

(1R,2S)-2-{(4-Fluoro-benzyl)-[2-(7-methanesulfonylamino-1,1-dioxo-1,4-dihydro-1λ⁶-benzo[1,2,4]thiadiazin-3-yl)-acetyl]-amino}-cyclopentanecarboxylic acid methyl ester (117 mg, 0.21 mmol) was dissolved in ethanol (10 mL). A 21% w/w solution of sodium ethoxide in ethanol (0.17 mL, 0.46 mmol) was added and the mixture was stirred at 60° C. for 4 h. The reaction was allowed to cool to 25° C. and quenched with 1.0 M aqueous hydrochloric acid solution (10 mL). The mixture was extracted with ethyl acetate (3×20 mL). The organic layers were combined, dried over magnesium sulfate, filtered, and concentrated in vacuo. The crude material was purified by flash column chromatography (Merck silica gel 60, 40-63 μm; 0-5% methanol in dichloromethane) to afford the desired product, (4aR,7aS)-N-{3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide (80 mg, 0.15 mmol, 71%), as a white solid. ¹H NMR (400 MHz, DMSO-d₆) δ: 1.46-1.61 (4H, m), 1.95-2.12 (2H, m), 3.07 (3H, s), 3.85 (1H, bs), 4.48 (1H, bs), 4.91 (1H, d, J=14.8 Hz), 7.16 (2H, t, J=8.4 Hz), 7.40 (2H, bs), 7.50-7.61 (3H, m), 10.18 (1H, s). LC-MS (ESI) calcd for $C_{23}H_{23}FN_4O_6S_2$ 534.58, found 535.1 [M+H⁺]. e.e. =98% [HPLC-analysis: Chiralpak AS-RH 4.6× 250 mm, 5 micron at 25° C., 0.7 mL/min, 310 nm, t1=14.89 min, t2=22.20 min (major)]. α_D=−40.76 (c=0.92, dichloromethane/methanol 1:1). Anal. calcd for $C_{23}H_{23}FN_4O_6S_2$ 0.3H₂O 0.3EtOAc 0.2Et₂O: C, 51.66; H, 4.86; N, 9.64, found C, 51.64; H, 4.90; N, 9.56.

EXAMPLE 13

(4aR,8aS)-N-{3-[1-(4-Fluoro-benzyl)-4-hydroxy-2-oxo-1,2,4a,5,6,7,8,8a-octahydro-quinolin-3-yl]-1,1-dioxo-1,4-dihydro-1λ⁶-benzo[1,2,4]thiadiazin-7-yl}-methanesulfonamide

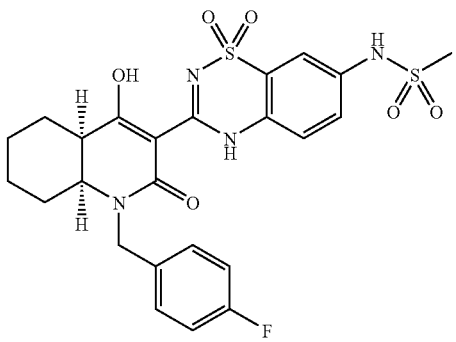

a) (1S,2R)-Cyclohexane-1,2-dicarboxylic acid monomethyl ester

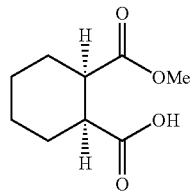

(1S,2R)-Cyclohexane-1,2-dicarboxylic acid monomethyl ester was prepared as described in *J. Org. Chem.* 2000, 65, 6984-6991. cis-1,2-Cyclohexanedicarboxylic anhydride (4.48 g, 29.1 mmol) was suspended in a 1:1 mixture of toluene and carbon tetrachloride (582 mL). The mixture was stirred for 20 min. Quinine (10.38 g, 32 mmol) was added and the flask was degassed and backfilled with nitrogen. The solution was cooled to −55° C. While stirring, methanol (3.55 mL, 87.3 mmol) was added dropwise. The mixture was stirred at −55° C. for 20 h. Upon warming to 25° C., the mixture was concentrated in vacuo to dryness. The resulting residue was dissolved in ethyl acetate (400 mL), washed with 3.0 M aqueous hydrochloric acid solution (2×150 mL), saturated aqueous brine solution (100 mL), dried over magnesium sulfate, filtered, and concentrated in vacuo to afford the desired product, (1S,2R)-cyclohexane-1,2-dicarboxylic acid monomethyl ester (5.41 g, 29.1 mmol, 100%), as a light yellow oil. $^1$H NMR (400 MHz, CDCl$_3$) δ: 1.37-2.05 (8H, m), 2.84-2.86 (2H, m), 3.68 (3H, s), 11.47 (1H, s).

c) (1R,2S)-2-Benzyloxycarbonylamino-cyclohexanecarboxylic acid methyl ester

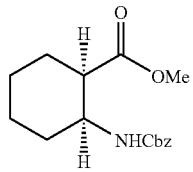

(1S,2R)-Cyclohexane-1,2-dicarboxylic acid monomethyl ester (5.41 g, 29.1 mmol) was dissolved in anhydrous tetrahydrofuran (47 mL). The flask was degassed and backfilled with nitrogen and the mixture was cooled to −20° C. Triethylamine (12.2 mL, 87.3 mmol) was added followed by the dropwise addition of ethyl chloroformate (5.56 mL, 58.2 mmol) with vigorous stirring. The mixture was stirred at −20° C. for 1 h. Sodium azide (5.67 g, 87.3 mmol) was dissolved in water (35 mL) and added to the reaction mixture at −10° C. The mixture was gradually warmed to 25° C. and was stirred for 2 h. The mixture was poured into water (350 mL) and the product was extracted into ethyl acetate (350 mL). The organic layer was further washed with 1/2 saturated sodium bicarbonate solution (2×100 mL), saturated aqueous brine solution (100 mL), dried over magnesium sulfate, filtered, and concentrated in vacuo to afford a light yellow oil. The oil was dissolved in anhydrous benzene (35 mL) and heated at reflux while stirring under nitrogen for 2 h. Upon cooling to 25° C. the solution was concentrated in vacuo to afford a slightly yellow oil. The oil was dissolved in dichloromethane (35 mL) and benzyl alcohol (3.31 mL, 32 mmol) was added followed by triethylamine (8.12 mL, 58.2 mmol). The mixture was heated at reflux under nitrogen for 16 h. Upon cooling to 25° C. the solution was concentrated in vacuo to afford an oil. Purification by flash column chromatography (Teledyne Isco RediSep Flash Column; 50% ethyl acetate in hexanes) afforded the desired product, (1R,2S)-2-benzyloxycarbonylamino-cyclohexanecarboxylic acid methyl ester (5.78 g, 19.8 mmol, 68%), as a light yellow oil. LC-MS (ESI) calcd for C$_{16}$H$_{21}$NO$_4$ 291.15, found 292.2 [M+H$^+$].

c) (1R,2S)-2-Amino-cyclohexanecarboxylic acid methyl ester

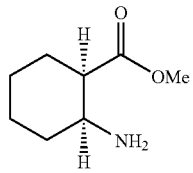

(1R,2S)-2-Benzyloxycarbonylamino-cyclohexanecarboxylic acid methyl ester (5.78 g, 19.8 mmol) was dissolved in methanol (200 mL). 10% Palladium on charcoal (0.21 g) was added. The flask was degassed and backfilled with hydrogen gas via balloon. The mixture was stirred at 25° C. for 5 h. The mixture was passed through a plug of Celite and the filtrate was concentrated in vacuo to afford the desired product, (1R,2S)-2-amino-cyclohexanecarboxylic acid methyl ester (2.5 g, 15.9 mmol, 80%), as a clear oil. LC-MS (ESI) calcd for C$_8$H$_{15}$NO$_2$ 157.11, found 158.1 [M+H$^+$].

d) (1R,2S)-2-(4-Fluoro-benzylamino)-cyclohexanecarboxylic acid methyl ester

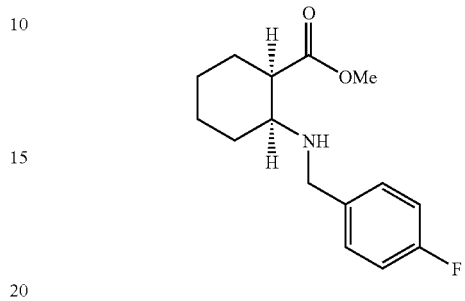

(1R,2S)-2-Amino-cyclohexanecarboxylic acid methyl ester (1 g, 6.4 mmol) was dissolved in methanol (70 mL). 4-Fluoro-benzaldehyde (0.794 g, 6.4 mmol) was added followed by acetic acid (1 mL). The solution was stirred at 25° C. for 10 min. Sodium cyanoborohydride (1 g, 16 mmol) was added and the mixture was stirred at 25° C. for 16 h. The mixture was poured into 1/2 saturated aqueous sodium bicarbonate solution (150 mL). The aqueous layer was extracted with ethyl acetate (2×150 mL). The organic layer was dried over sodium sulfate, filtered, and concentrated in vacuo to afford the crude product, (1R,2S)-2-(4-fluoro-benzylamino)-cyclohexanecarboxylic acid methyl ester (0.8 g, 3 mmol, 47%), as a light yellow oil. LC-MS (ESI) calcd for C$_{15}$H$_{20}$FNO$_2$ 265.15, found 266.2 [M+H$^+$].

e) (1R,2S)-2-{(4-Fluoro-benzyl)-[2-(7-methanesulfonylamino-1,1-dioxo-1,4-dihydro-1λ$^6$-benzo[1,2,4]thiadiazin-3-yl)-acetyl]-amino}-cyclohexanecarboxylic acid methyl ester

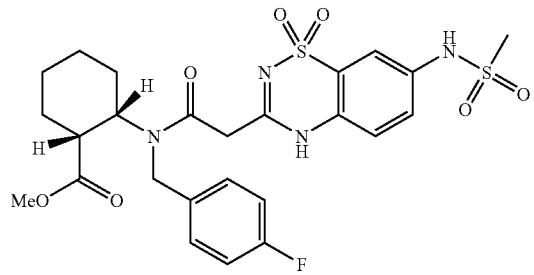

(7-Methanesulfonylamino-1,1-dioxo-1,4-dihydro-1λ$^6$-benzo[1,2,4]thiadiazin-3-yl)-acetic acid (prepared as described in Example 1j, 0.1 g, 0.3 mmol) was dissolved in anhydrous N,N-dimethylformamide (4 mL). (1R,2S)-2-(4-Fluoro-benzylamino)-cyclohexanecarboxylic acid methyl ester (0.79 g, 0.3 mmol) was added followed by 1-(3-dimethylaminopropyl)-3-ethylcarbodiimide hydrochloride (0.06 g, 0.315 mmol). Then N-methylmorpholine (0.07 mL, 0.63 mmol) was added into the above reaction mixture. The mixture was stirred at 25° C. for 2 h. The solution was poured into 1.0 M aqueous hydrochloric acid solution (50 mL). The aqueous layer was extracted with ethyl acetate (2×50 mL). The organic layer was dried over sodium sulfate, filtered and concentrated in vacuo to afford the crude product, (1R,2S)-2-{(4-fluoro-benzyl)-[2-(7-methanesulfonylamino-1,1-dioxo-1,4-dihydro-1λ$^6$-benzo[1,2,4]thiadiazin-3-yl)-acetyl]- amino}-cyclohexanecarboxylic acid methyl ester (0.3 mmol), as a yellow oil. LC-MS (ESI) calcd for $C_{25}H_{29}FN_4O_7S_2$ 580.15, found 581.3 [M+H$^+$].

f) (4aR,8aS)-N-{3-[1-(4-Fluoro-benzyl)-4-hydroxy-2-oxo-1,2,4a,5,6,7,8,8a-octahydro-quinolin-3-yl]-1,1-dioxo-1,4-dihydro-1λ$^6$-benzo[1,2,4]thiadiazin-7-yl}-methanesulfonamide

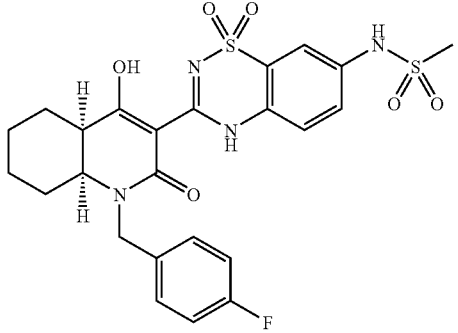

The crude (1R,2S)-2-{(4-fluoro-benzyl)-[2-(7-methanesulfonylamino-1,1-dioxo-1,4-dihydro-1λ$^6$-benzo[1,2,4]thiadiazin-3-yl)-acetyl]-amino}-cyclohexanecarboxylic acid methyl ester (0.3 mmol) was dissolved in ethanol (4 mL). A 21% w/w solution of sodium ethoxide in ethanol (0.448 mL, 1.2 mmol) was added into the above solution. The mixture was stirred at 60° C. for 4 h. Upon cooling to 25° C., the mixture was poured into 1.0 M aqueous hydrochloric acid solution (50 mL). The aqueous layer was extracted with ethyl acetate (2×50 mL). The organic layer was dried over sodium sulfate, filtered and concentrated in vacuo to afford a light yellow solid. Purification by flash column chromatography (Teledyne Isco RediSep Flash Column; 5% methanol in dichloromethane) afforded the desired product, (4aR,8aS)-N-{3-[1-(4-fluoro-benzyl)-4-hydroxy-2-oxo-1,2,4a,5,6,7,8,8a-octahydro-quinolin-3-yl]-1,1-dioxo-1,4-dihydro-1λ$^6$-benzo[1,2,4]thiadiazin-7-yl}-methanesulfonamide (49.7 mg, 0.09 mmol, 30% over two steps), as a light yellow solid. $^1$H NMR (400 MHz, DMSO-d$_6$) δ: 1.13-2.34 (8H, m), 3.06 (3H, s), 3.46-3.69 (1H, m), 4.24-4.66 (2H, m), 4.98 (1H, d, J=16 Hz), 7.16 (2H, t, J=8 Hz), 7.39-7.59 (5H, m), 10.15 (1H, s). LC-MS (ESI) calcd for $C_{24}H_{25}FN_4O_6S_2$ 548.12, found 549.2 [M+H$^+$].

EXAMPLE 14

(4aR,7aS)-N-{3-[4-Hydroxy-2-oxo-1-(4-trifluoromethyl-benzyl)-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

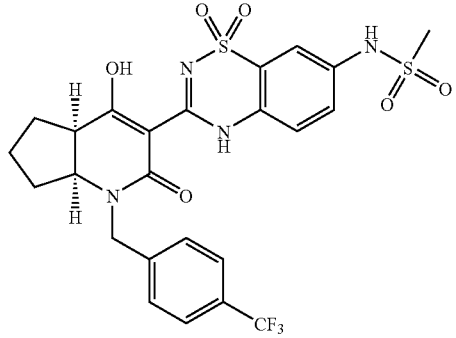

a) (1R,2S)-2-(4-Trifluoromethyl-benzylamino)-cyclopentanecarboxylic acid methyl ester

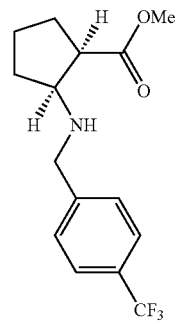

(1R,2S)-2-Amino-cyclopentanecarboxylic acid methyl ester hydrochloride (prepared as described in Example 11a, 130 mg, 0.91 mmol) was dissolved in methanol (5 mL). 4-Trifluoromethyl-benzaldehyde (160 mg, 0.91 mmol) was added, stirred at 25° C. for 15 min, then acetic acid (0.2 mL) was added, followed by sodium cyanoborohydride (150 mg, 2.3 mmol) and the mixture was stirred at 25° C. for 16 h. The mixture was poured into a mixture of saturated aqueous sodium bicarbonate solution (100 mL) and ethyl acetate (200 mL). The organic layer was washed with saturated aqueous sodium bicarbonate solution (100 mL), saturated aqueous brine solution (100 mL), dried over magnesium sulfate, filtered, and concentrated in vacuo to afford the crude product (1R,2S)-2-(4-trifluoromethyl-benzylamino)-cyclopentanecarboxylic acid methyl ester (200 mg, 0.664 mmol, 73%) as a clear oil. LC-MS (ESI) calcd for $C_{15}H_{18}F_3NO_2$ 301.13, found 302.2 [M+H$^+$].

b) (4aR,7aS)-N-{3-[4-Hydroxy-2-oxo-1-(4-trifluoromethyl-benzyl)-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

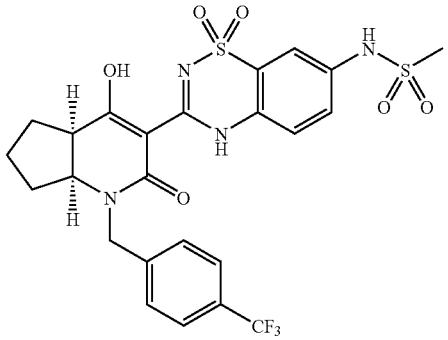

2-(4-Trifluoromethyl-benzylamino)-cyclopentanecarboxylic acid methyl ester (0.1 g, 0.33 mmol) was dissolved in anhydrous N,N-dimethylformamide (5 mL). (7-Methanesulfonylamino-1,1-dioxo-1,4-dihydro-1λ$^6$-benzo[1,2,4]thiadiazin-3-yl)-acetic acid (prepared as described in Example 1j, 0.108 g, 0.33 mmol) was added followed by N-methylmorpholine (0.087 mL, 0.66 mmol). The mixture was stirred until everything dissolved, approximately 5 min. 1-(3-Dimethylaminopropyl)-3-ethylcarbodiimide hydrochloride (0.069 g, 0.36 mmol) was added and the mixture was stirred at 25° C. for 3 h. The solution was diluted with ethyl acetate (25 mL) and washed with 1.0 M aqueous hydrochloric acid solution (2×25 mL), saturated aqueous brine solution (10 mL), dried over magnesium sulfate, filtered, and concentrated in vacuo to afford a golden oil. The oil was dissolved in ethanol (4 mL)

and a 21% w/w solution of sodium ethoxide in ethanol (1.3 mL, 3.6 mmol) was added, and the reaction mixture was heated to 60° C. for 2 h. Upon cooling to 25° C., the reaction mixture was acidified to pH 2-3 with 2.0 M aqueous hydrochloric acid solution, upon which the product precipitated while stirring. The solid was collected by vacuum filtration and purified by prep-HPLC [Column Luna 5μ C18 (2) 100 Å AXIA 50×21.2 mm, 5 micron, 50%-70% in 8 min @ 30 mL/min flow rate, 0.05% trifluoroacetic acid in acetonitrile/0.05% trifluoroacetic acid in water] to afford the desired product, (4aR,7aS)-N-{3-[4-hydroxy-2-oxo-1-(4-trifluoromethyl-benzyl)-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide (0.1 g, 0.171 mmol, 52%), as a white powder. $^1$H NMR (400 MHz, DMSO-d$_6$) δ: 1.42-1.62 (3H, m), 1.96-2.15 (3H, m), 3.06 (3H, s), 3.90 (1H, d, J=7.2 Hz), 4.58 (1H, d, J=14.8 Hz), 5.00 (1H, d, J=15.6 Hz), 7.49 (4H, q, J=2.4 Hz), 7.57 (4H, m), 7.68 (2H, m), 10.18 (1H, s). LC-MS (ESI) calcd for $C_{24}H_{23}F_3N_4O_6S_2$ 584.10, found 585.1 [M+H$^+$]. [α]$_D$=−50.6863.

EXAMPLE 15

(4aR,7aS)-N-{3-[4-Hydroxy-2-oxo-1-(3-trifluoromethyl-benzyl)-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

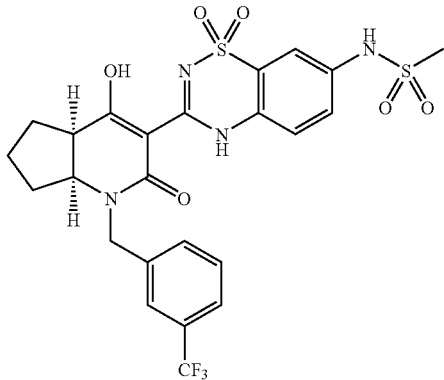

a) (1R,2S)-2-(3-Trifluoromethyl-benzylamino)-cyclopentanecarboxylic acid methyl ester

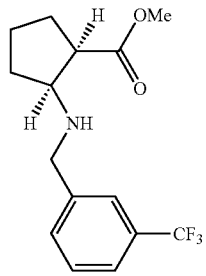

(1R,2S)-2-Amino-cyclopentanecarboxylic acid methyl ester hydrochloride (prepared as described in Example 11a, 130 mg, 0.91 mmol) was dissolved in methanol (5 mL). 3-Trifluoromethyl-benzaldehyde (160 mg, 0.91 mmol) was added, stir at 25° C. for 15 min, acetic acid (0.2 mL) added, followed with sodium cyanoborohydride (150 mg, 2.3 mmol) was added and the mixture was stirred at 25° C. for 16 h. The mixture was poured into a mixture of saturated aqueous sodium bicarbonate solution (100 mL) and ethyl acetate (200 mL). The organic layer was washed with saturated aqueous sodium bicarbonate solution (100 mL), saturated aqueous brine solution (100 mL), dried over magnesium sulfate, filtered, and concentrated in vacuo to afford the crude product (1R,2S)-2-(3-trifluoromethyl-benzylamino)-cyclopentanecarboxylic acid methyl ester (200 mg, 0.664 mmol, 73%), as a clear oil. LC-MS (ESI) calcd for $C_{15}H_{18}F_3NO_2$ 301.13, found 302.2 [M+H$^+$].

b) (4aR,7aS)-N-{3-[4-Hydroxy-2-oxo-1-(3-trifluoromethyl-benzyl)-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

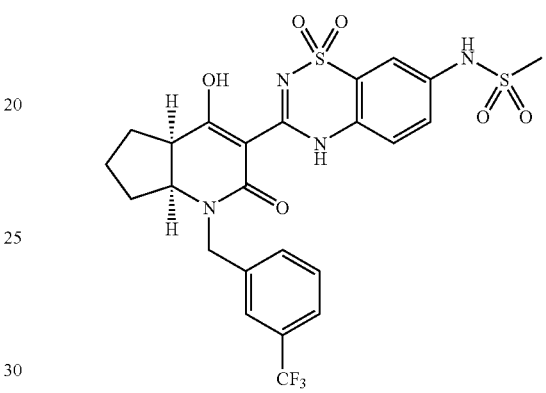

2-(3-Trifluoromethyl-benzylamino)-cyclopentanecarboxylic acid methyl ester (0.046 g, 0.15 mmol) was dissolved in anhydrous N,N-dimethylformamide (2 mL). (7-Methanesulfonylamino-1,1-dioxo-1,4-dihydro-1λ$^6$-benzo[1,2,4]thiadiazin-3-yl)-acetic acid (prepared as described in Example 1j, 0.051 g, 0.15 mmol) was added followed by N-methylmorpholine (0.04 mL, 0.33 mmol). The mixture was stirred until everything dissolved, approximately 5 min. 1-(3-Dimethylaminopropyl)-3-ethylcarbodiimide hydrochloride (0.033 g, 0.16 mmol) was added and the mixture was stirred at 25° C. for 3 h. The solution was diluted with ethyl acetate (25 mL) and washed with 1.0 M aqueous hydrochloric acid solution (2×25 mL), saturated aqueous brine solution (10 mL), dried over magnesium sulfate, filtered, and concentrated in vacuo to afford a golden oil. The oil was dissolved in ethanol (4 mL) and a 21% w/w solution of sodium ethoxide in ethanol (0.3 mL, 0.8 mmol) was added, and the reaction mixture was heated to 60° C. for 2 h. Upon cooling to 25° C., the reaction mixture was acidified to pH 2-3 with 2.0 M aqueous hydrochloric acid solution, upon which the product precipitated while stirring. The solid was collected by vacuum filtration and purified by prep-HPLC [Column Luna 5μ C18 (2) 100 Å AXIA 50×21.2 mm, 5 micron, 30%-95% in 9 min @ 30 mL/min flow rate, 0.05% trifluoroacetic acid in acetonitrile/0.05% trifluoroacetic acid in water] to afford the desired product, (4aR,7aS)-N-{3-[4-hydroxy-2-oxo-1-(3-trifluoromethyl-benzyl)-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide (0.04 g, 0.068 mmol, 46%), as a white powder. $^1$H NMR (400 MHz, DMSO-d$_6$) δ: 1.42-1.64 (3H, m), 1.96-2.18 (3H, m), 3.04 (3H, s), 3.95 (1H, d, J=7.2 Hz), 4.62 (1H, d, J=16.4 Hz), 5.00 (1H, d, J=15.6 Hz), 7.50 (4H, q, J=2.4 Hz), 7.57 (4H, m), 7.68 (2H, m), 10.18 (1H, s). LC-MS (ESI) calcd for $C_{24}H_{23}F_3N_4O_6S_2$ 584.10, found 585.0 [M+H$^+$]. [α]$_D$=−47.7083.

EXAMPLE 16

N-{3-[1-(4-Fluoro-benzyl)-4-hydroxy-2-oxo-1,2,4a,5,6,8a-hexahydro-quinolin-3-yl]-1,1-dioxo-1,4-dihydro-1λ$^6$-benzo[1,2,4]thiadiazin-7-yl}-methanesulfonamide

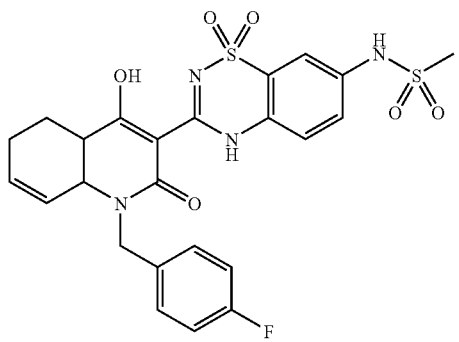

a) cis-2-Amino-cyclohex-3-enecarboxylic acid methyl ester hydrochloride

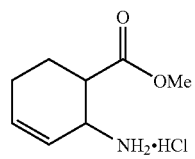

cis-2-Amino-cyclohex-3-enecarboxylic acid hydrochloride (0.5 g, 2.8 mmol) was dissolved in a mixture of methanol (12 mL) and benzene (12 mL) at 25° C., cooled to 0° C., a 2.0 M solution of (trimethylsilyl)diazomethane in diethyl ether (4.2 mL, 8.4 mmol) was added slowly, and, after removing the ice-bath, the reaction mixture was stirred at 25° C. for 6 h. The reaction mixture was concentrated in vacuo, to afford the desired crude product, 2-amino-cyclohex-3-enecarboxylic acid methyl ester hydrochloride, which was used in the next step without further purification.

b) cis-2-(4-Fluoro-benzylamino)-cyclohex-3-enecarboxylic acid methyl ester

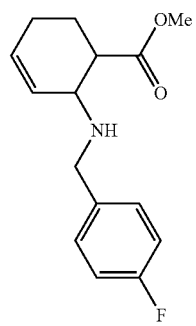

The crude cis-2-amino-cyclohex-3-enecarboxylic acid methyl ester hydrochloride (2.8 mmol) was dissolved in methanol (5 mL). 4-Fluoro-benzaldehyde (37.3 mg, 0.3 mmol) was added, followed by 4 Å molecular sieves (0.5 g) and sodium acetate (0.46 g, 5.6 mmol). After stirring at 25° C. for 15 min, sodium cyanoborohydride (0.37 g, 5.9 mmol) was added and the mixture was stirred at 25° C. for 16 h. The mixture was poured into a mixture of saturated aqueous sodium bicarbonate solution (100 mL) and ethyl acetate (200 mL). After shaking, both layers were passed through a plug of Celite. The organic layer was washed with saturated aqueous sodium bicarbonate solution (100 mL), followed by saturated aqueous brine solution (100 mL), dried over magnesium sulfate, filtered, and concentrated in vacuo to afford the crude product, cis-2-(4-fluoro-benzylamino)-cyclohex-3-enecarboxylic acid methyl ester (250 mg, 0.95 mmol, 34%), as a clear oil. LC-MS (ESI) calcd for $C_{15}H_{18}FNO_2$ 263.13, found 264.04 [M+H$^+$].

c) N-{3-[1-(4-Fluoro-benzyl)-4-hydroxy-2-oxo-1,2,4a,5,6,8a-hexahydro-quinolin-3-yl]-1,1-dioxo-1,4-dihydro-1λ$^6$-benzo[1,2,4]thiadiazin-7-yl}-methanesulfonamide

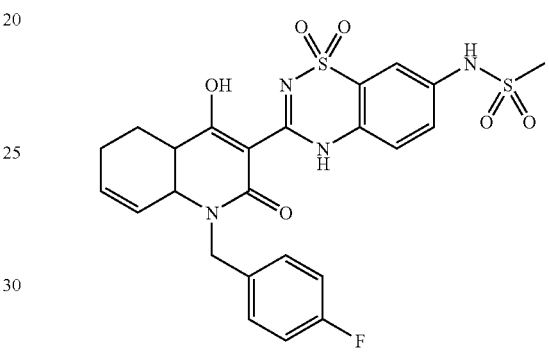

2-(4-Fluoro-benzylamino)-cyclohex-3-enecarboxylic acid methyl ester (0.051 g, 0.19 mmol) was dissolved in anhydrous N,N-dimethylformamide (2 mL). (7-Methanesulfonylamino-1,1-dioxo-1,4-dihydro-1λ$^6$-benzo[1,2,4]thiadiazin-3-yl)-acetic acid (prepared as described in Example 1j, 0.065 g, 0.19 mmol) was added followed by N-methylmorpholine (0.05 mL, 0.43 mmol). The mixture was stirred until everything dissolved, approximately 5 min. 1-(3-Dimethylaminopropyl)-3-ethylcarbodiimide hydrochloride (0.041 g, 0.21 mmol) was added and the mixture was stirred at 25° C. for 3 h. The solution was diluted with ethyl acetate (25 mL) and washed with 1.0 M aqueous hydrochloric acid solution (2×25 mL), saturated aqueous brine solution (10 mL), dried over magnesium sulfate, filtered, and concentrated in vacuo to afford a golden oil. The oil was dissolved in ethanol (4 mL) and a 21% w/w solution of sodium ethoxide in ethanol (0.3 mL, 0.8 mmol) was added, and the reaction mixture was heated to 60° C. for 2 h. Upon cooling to 25° C., the reaction mixture was acidified to pH 2-3 with 2.0 M aqueous hydrochloric acid solution, upon which the product precipitated while stirring. The solid was collected by vacuum filtration and purified by prep-HPLC [Column Luna 5µ C18 (2) 100 Å AXIA 50×21.2 mm, 5 micron, 30%-95% in 9 min @ 30 mL/min flow rate, 0.05% trifluoroacetic acid in acetonitrile/0.05% trifluoroacetic acid in water] to afford the desired product, N-{3-[1-(4-fluoro-benzyl)-4-hydroxy-2-oxo-1,2,4a,5,6,8a-hexahydro-quinolin-3-yl]-1,1-dioxo-1,4-dihydro-1λ$^6$-benzo[1,2,4]thiadiazin-7-yl}-methanesulfonamide (0.025 g, 0.046 mmol, 25%), as a white powder. $^1$H NMR (400 MHz, DMSO-d$_6$) δ: 1.65-2.24 (4H, m), 3.04 (3H, s), 4.10-4.21 (1H, m), 5.01 (1H, d, J=16.0 Hz), 5.45 (1H, d, J=10.0 Hz), 5.86 (1H, d, J=8.8 Hz), 7.16 (2H, dd, J=8.8 Hz), 7.42 (2H, m), 7.51 (1H, m), 7.57 (12H, m), 10.20 (1H, s). LC-MS (ESI) calcd for $C_{24}H_{23}FN_4O_6S_2$ 546.10, found 547.3 [M+H$^+$].

EXAMPLE 17 cis-N-{3-[2-(3-Methylbutyl)-5-hydroxy-3-oxo-2-aza-bicyclo[4.3.0]non-4-en-4-yl]-1,1-dioxo-1,4-dihydro-1$\lambda^6$-benzo[1,2,4]thiadiazin-7-yl}-methanesulfonamide

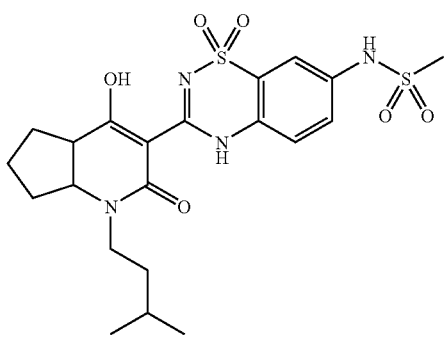

a) 2-(3-Methylbutylamino)-cyclopent-1-enecarboxylic acid ethyl ester

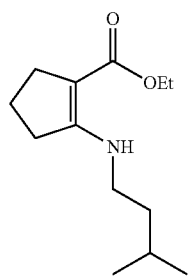

To a solution of ethyl 2-oxocyclopentanecarboxylate (5.00 mL, 32.1 mmol) in ethanol (50 mL) was added isoamylamine (3.8 mL, 32.3 mmol) at 25° C. The mixture was heated at reflux for 12 h. The reaction mixture was allowed to cool to 25° C. and concentrated in vacuo. The crude material was purified by flash column chromatography (Teledyne Isco RediSep Flash Column; 0-30% ethyl acetate in hexanes) to afford the desired product, 2-(3-methylbutylamino)-cyclopent-1-enecarboxylic acid ethyl ester (6.84 g, 30.4 mmol, 95%), as a yellowish oil. $^1$H NMR (400 MHz, CDCl$_3$) δ 0.92 (6H, d, J=6.1 Hz), 1.28 (3H, t, J=6.9 Hz), 1.44 (2H, q, J=7.2 Hz), 1.63-1.74 (1H, m), 1.80-1.87 (2H, m), 2.50-2.58 (4H, m), 3.19 (2H, q, J=6.7 Hz), 4.14 (2H, q, J=7.1 Hz), 7.34 (1H, bs).

b) 2-(3-Methylbutylamino)-cyclopentanecarboxylic acid ethyl ester

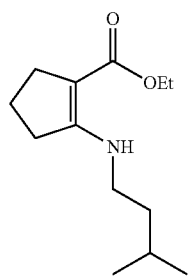

To a solution of 2-(3-methylbutylamino)-cyclopent-1-enecarboxylic acid ethyl ester (6.84 g, 30.4 mmol) in acetic acid (100 mL) was added a 8.0 M solution of borane in pyridine (4.6 mL, 36.8 mmol) at 25° C. After stirring for 15 min, the reaction mixture was concentrated in vacuo. The crude material was triturated with 1.0 M aqueous hydrochloric acid solution (25 mL) and stirred for 0.5 h (until the gas evolution ceased). The mixture was extracted with ethyl acetate (3×50 mL) and the combined organic layers were dried over anhydrous magnesium sulfate and concentrated in vacuo. The crude material was purified by flash column chromatography (Teledyne Isco RediSep Flash Column; 0-10% methanol in dichloromethane) to afford cis-2-(3-methylbutylamino)-cyclopentanecarboxylic acid ethyl ester (2.37 g, 10.4 mmol, 34%) as a colorless oil and trans-2-(3-methylbutylamino)-cyclopentanecarboxylic acid ethyl ester (1.18 g, 5.2 mmol, 17%) as a white solid. cis-2-(3-Methylbutylamino)-cyclopentanecarboxylic acid ethyl ester: $^1$H NMR (400 MHz, CDCl$_3$) δ 0.90 (6H, d, J=6.3 Hz), 1.26 (3H, t, J=7.0 Hz), 1.34-1.46 (3H, m), 1.57-1.74 (4H, m), 1.81-1.90 (1H, m), 1.94-2.04 (2H, m), 2.53 (1H, q, J=8.1 Hz), 2.59 (2H, t, J=7.5 Hz), 3.27 (1H, q, J=7.6 Hz), 4.11-4.17 (2H, m). trans-2-(3-Methylbutylamino)-cyclopentanecarboxylic acid ethyl ester: $^1$H NMR (400 MHz, CDCl$_3$) δ: 0.92 (6H, d, J=6.8 Hz), 1.28 (3H, t, J=7.3 Hz), 1.41-1.47 (2H, m), 1.51-1.90 (5H, m), 2.00-2.09 (3H, m), 2.62-2.74 (3H, m), 3.38 (1H, q, J=7.2 Hz), 4.16 (2H, q, J=7.0 Hz). LC-MS (ESI) calcd for C$_{13}$H$_{25}$NO$_2$ 227.19, found 228.3 [M+H$^+$].

c) cis-2-[2-(7-Methanesulfonylamino-1,1-dioxo-1,4-dihydro-1$\lambda^6$-benzo[1,2,4]thiadiazin-3-yl)-acetyl]-(3-methylbutyl)amino]-cyclopentanecarboxylic acid ethyl ester

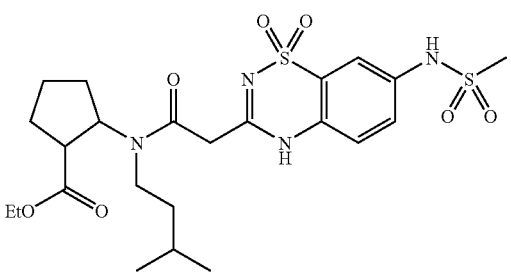

To a solution of cis-2-(3-methylbutylamino)-cyclopentanecarboxylic acid ethyl ester (53.5 mg, 0.237 mmol) in N,N-dimethylformamide (3.0 mL) was added (7-methanesulfonylamino-1,1-dioxo-1,4-dihydro-1λ⁶-benzo[1,2,4]thiadiazin-3-yl)-acetic acid (prepared as described in Example 1j, 157.4 mg, 0.472 mmol) and a 1.0 M solution of N,N'-dicyclohexylcarbodiimide in dichloromethane (0.47 mL, 0.47 mmol). After stirring at 25° C. for 12 h, the mixture was diluted with dichloromethane and the precipitated N,N'-dicyclohexylurea byproduct was removed by filtration. The filtrate was concentrated and dried in vacuo to afford the crude product, cis-2-[2-(7-methanesulfonylamino-1,1-dioxo-1,4-dihydro-1λ⁶-benzo[1,2,4]thiadiazin-3-yl)-acetyl]-(3-methylbutyl)amino]-cyclopentanecarboxylic acid ethyl ester, which was used in the next step without further purification. LC-MS (ESI) calcd for $C_{23}H_{34}N_4O_7S_2$ 542.19, found 543.2 [M+H⁺].

d) cis-N-{3-[2-(3-Methylbutyl)-5-hydroxy-3-oxo-2-aza-bicyclo[4.3.0]non-4-en-4-yl]-1,1-dioxo-1,4-dihydro-1λ⁶-benzo[1,2,4]thiadiazin-7-yl}-methanesulfonamide

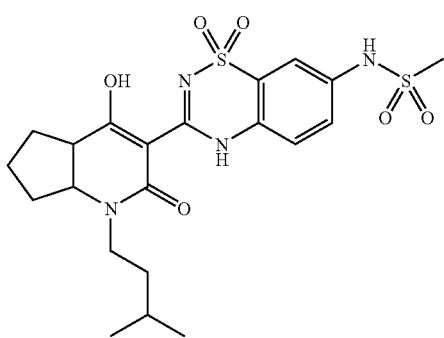

To a solution of cis-2-[2-(7-methanesulfonylamino-1,1-dioxo-1,4-dihydro-1λ⁶-benzo[1,2,4]thiadiazin-3-yl)-acetyl]-(3-methylbutyl)amino]-cyclopentanecarboxylic acid ethyl ester (128.6 mg, 0.237 mmol) in absolute ethanol (10 mL) was added a 21% w/w solution of sodium ethoxide in ethanol (0.51 mL, 1.37 mmol). After stirring at 60° C. for 12 h, the mixture was diluted with ethyl acetate and acidified with 1.0 M aqueous hydrochloric acid solution to pH 1. The organic layer was separated and the aqueous layer was extracted with ethyl acetate (2×20 mL). The combined organic layers were dried over anhydrous magnesium sulfate and concentrated in vacuo. The crude mixture was purified by flash column chromatography (Teledyne Isco RediSep Flash Column; 0-100% ethyl acetate in hexanes) to afford the desired product, cis-N-{3-[2-(3-methylbutyl)-5-hydroxy-3-oxo-2-aza-bicyclo[4.3.0]non-4-en-4-yl]-1,1-dioxo-1,4-dihydro-1λ⁶-benzo[1,2,4]thiadiazin-7-yl}-methanesulfonamide (72.2 mg, 0.145 mmol, 61%), as an off-white solid. ¹H NMR (400 MHz, DMSO-d₆) δ 0.92 (6H, d, J=6.3 Hz), 1.43-1.60 (6H, m), 2.11-2.16 (3H, m), 3.05 (3H, s), 3.17 (1H, bs), 3.35 (1H, bs), 3.65-3.72 (1H, m), 3.90 (1H, bs), 7.48-7.59 (3H, m), 10.17 (1H, bs). LC-MS (ESI) calcd for $C_{21}H_{28}N_4O_6S_2$ 496.15, found 497.3 [M+H⁺]. Anal. calcd for $C_{21}H_{28}N_4O_6S_2$·0.6H₂O: C, 49.71; H, 5.80; N, 11.04; S, 12.64, found C, 50.06; H, 5.81; N, 10.79; S, 12.20.

EXAMPLE 18 cis-N-{3-[2-(3,3-Dimethylbutyl)-5-hydroxy-3-oxo-2-aza-bicyclo[4.3.0]non-4-en-4-yl]-1,1-dioxo-1,4-dihydro-1λ⁶-benzo[1,2,4]thiadiazin-7-yl}-methanesulfonamide

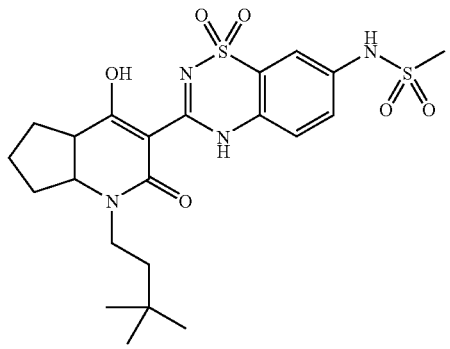

a) 2-(3,3-Dimethylbutylamino)-cyclopent-1-enecarboxylic acid ethyl ester

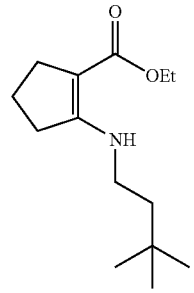

To a solution of ethyl 2-oxocyclopentanecarboxylate (4.10 mL, 26.3 mmol) in ethanol (50 mL) was added 3,3-dimethylbutylamine (2.80 g, 26.8 mmol) at 25° C. The mixture was heated at reflux for 12 h. The reaction mixture was allowed to cool to 25° C. and concentrated in vacuo. The crude material was purified by flash column chromatography (Teledyne Isco RediSep Flash Column; 0-20% ethyl acetate in hexanes) to afford the desired product, 2-(3,3-dimethylbutylamino)-cyclopent-1-enecarboxylic acid ethyl ester (5.59 g, 23.4 mmol, 89%), as a yellowish oil. ¹H NMR (400 MHz, CDCl₃) δ 0.94 (9H, s), 1.28 (3H, t, J=7.0 Hz), 1.46-1.50 (2H, m), 1.80-1.88 (2H, m), 2.51-2.58 (4H, m), 3.16-3.21 (2H, m), 4.14 (2H, q, J=7.0 Hz).

b) 2-(3,3-Dimethylbutylamino)-cyclopentanecarboxylic acid ethyl ester

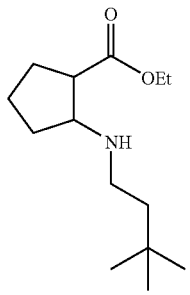

To a solution of 2-(3,3-dimethylbutylamino)-cyclopent-1-enecarboxylic acid ethyl ester (5.59 g, 23.4 mmol) in acetic acid (70 mL) was added a 8.0 M solution of borane in pyridine (3.2 mL, 25.6 mmol) at 25° C. After stirring for 15 min, the reaction mixture was concentrated in vacuo. The crude material was triturated with 1.0 M aqueous hydrochloric acid solution (25 mL) and stirred for 0.5 h (until the gas evolution ceased). The mixture was extracted with ethyl acetate (3×50 mL) and the combined organic layers were dried over anhydrous magnesium sulfate and concentrated in vacuo. The crude material was purified by flash column chromatography (Teledyne Isco RediSep Flash Column; 0-10% methanol in dichloromethane) to afford cis-2-(3,3-dimethylbutylamino)-cyclopentanecarboxylic acid ethyl ester as a yellowish oil (0.40 g, 1.7 mmol, 7%) and trans-2-(3,3-dimethylbutylamino)-cyclopentanecarboxylic acid ethyl ester and an off-white solid (2.37 g, 9.8 mmol, 42%). cis-2-(3,3-Dimethylbutylamino)-cyclopentanecarboxylic acid ethyl ester: $^1$H NMR (400 MHz, CDCl$_3$) δ 0.91 (9H, s), 1.28 (3H, t, J=7.0 Hz), 1.35-1.50 (2H, m), 1.56-1.73 (2H, m), 1.80-2.03 (4H, m), 2.60-2.75 (2H, m), 2.98-3.02 (1H, m), 3.35 (1H, q, J=7.4 Hz), 4.15 (2H, q, J=6.9 Hz), 6.38 (1H, s). trans-2-(3,3-Dimethylbutylamino)-cyclopentanecarboxylic acid ethyl ester: $^1$H NMR (400 MHz, CDCl$_3$) δ 0.94 (9H, s), 1.29 (3H, t, J=7.0 Hz), 1.66-2.01 (6H, m), 2.11-2.27 (2H, m), 2.86 (2H, t, J=8.6 Hz), 3.10 (1H, q, J=7.8 Hz), 3.68 (1H, q, J=7.0 Hz), 4.18 (2H, q, J=7.0 Hz). LC-MS (ESI) calcd for $C_{14}H_{27}NO_2$ 241.20, found 242.4 [M+H$^+$].

c) cis-2-{(3,3-Dimethylbutyl)-[2-(7-methanesulfonylamino-1,1-dioxo-1,4-dihydro-1λ$^6$-benzo[1,2,4]thiadiazin-3-yl)acetyl]amino}-cyclopentanecarboxylic acid ethyl ester

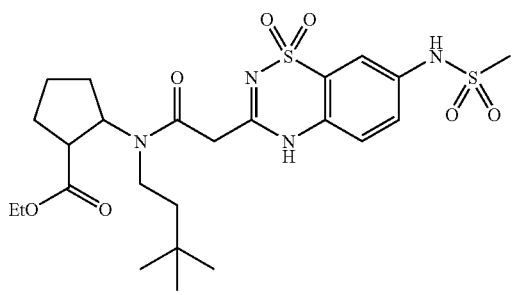

To a solution of cis-2-(3,3-dimethylbutylamino)-cyclopentanecarboxylic acid ethyl ester (54.5 mg, 0.226 mmol) in N,N-dimethylformamide (5.0 mL) was added (7-methanesulfonylamino-1,1-dioxo-1,4-dihydro-1λ$^6$-benzo[1,2,4]thiadiazin-3-yl)-acetic acid (prepared as described in Example 1j, 150.6 mg, 0.452 mmol) and a 1.0 M solution of N,N'-dicyclohexylcarbodiimide in dichloromethane (0.23 mL, 0.23 mmol). After stirring at 25° C. for 12 h, the mixture was diluted with dichloromethane and the precipitated N,N'-dicyclohexylurea byproduct was removed by filtration. The filtrate was concentrated and dried in vacuo to afford the crude product, cis-2-{(3,3-dimethylbutyl)-[2-(7-methanesulfonylamino-1,1-dioxo-1,4-dihydro-1λ$^6$-benzo[1,2,4]thiadiazin-3-yl)acetyl]amino}-cyclopentanecarboxylic acid ethyl ester as a yellowish oil. The crude product was used in the next step without further purification. LC-MS (ESI) calcd for $C_{24}H_{36}N_4O_7S_2$ 556.20, found 557.3 [M+H$^+$].

d) cis-N-{3-[2-(3,3-Dimethylbutyl)-5-hydroxy-3-oxo-2-aza-bicyclo[4.3.0]non-4-en-4-yl]-1,1-dioxo-1,4-dihydro-1λ$^6$-benzo[1,2,4]thiadiazin-7-yl}-methanesulfonamide

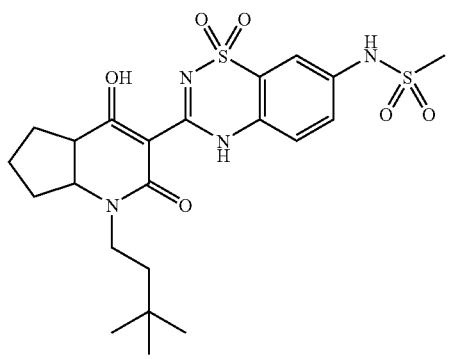

To a solution of cis-2-{(3,3-dimethylbutyl)-[2-(7-methanesulfonylamino-1,1-dioxo-1,4-dihydro-1λ$^6$-benzo[1,2,4]thiadiazin-3-yl)acetyl]amino}-cyclopentanecarboxylic acid ethyl ester (125.8 mg, 0.226 mmol) in absolute ethanol (10 mL) was added a 21% w/w solution of sodium ethoxide in ethanol (0.84 mL, 2.25 mmol). After stirring at 60° C. for 4 h, the mixture was diluted with ethyl acetate and acidified with 1.0 M aqueous hydrochloric acid solution to pH 1. The organic layer was separated and the aqueous layer was extracted with ethyl acetate (2×20 mL). The combined organic layers were dried over anhydrous magnesium sulfate and concentrated in vacuo. The crude mixture was purified by flash column chromatography (Teledyne Isco RediSep Flash Column; 0-100% ethyl acetate in hexanes) to afford the desired product, cis-N-{3-[2-(3,3-dimethylbutyl)-5-hydroxy-3-oxo-2-aza-bicyclo[4.3.0]non-4-en-4-yl]-1,1-dioxo-1,4-dihydro-1λ$^6$-benzo[1,2,4]thiadiazin-7-yl}-methanesulfonamide (52.7 mg, 0.103 mmol, 46%), as an off-white solid. $^1$H NMR (400 MHz, DMSO-d$_6$) δ 0.94 (9H, s), 1.56-1.57 (5H, m), 2.08-2.15 (3H, m), 3.05 (3H, s), 3.17 (1H, bs), 3.34 (1H, bs), 3.64-3.72 (1H, m), 3.90 (1H, bs), 7.48-7.60 (3H, m), 10.17 (1H, bs). LC-MS (ESI) calcd for $C_{22}H_{30}N_4O_6S_2$ 510.16, found 511.4 [M+H$^+$]. Anal. calcd for $C_{22}H_{30}N_4O_6S_2$ 0.3H$_2$O: C, 51.20; H, 5.98; N, 10.86; S, 12.43, found C, 51.39; H, 5.81; N, 10.65; S, 12.26.

EXAMPLE 19 cis-N-{3-[2-Cyclopropylethyl-5-hydroxy-3-oxo-2-aza-bicyclo[4.3.0]non-4-en-4-yl]-1,1-dioxo-1,4-dihydro-1$\lambda^6$-benzo[1,2,4]thiadiazin-7-yl}-methanesulfonamide

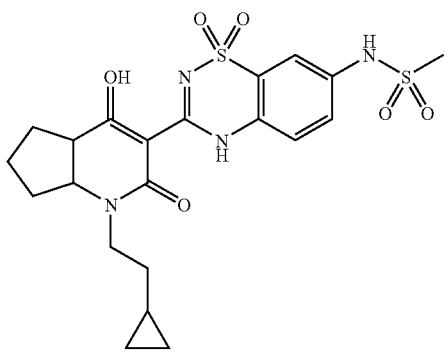

a) Cyclopropylacetaldehyde

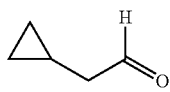

To a 2.0 M solution of oxalyl chloride in dichloromethane (9.8 mL, 19.6 mmol) at −78° C. was added dimethyl sulfoxide dropwise. After stirring for 15 min at −78° C., a solution of cyclopropylethyl alcohol (1.5 g, 17.4 mmol) in dichloromethane (3.5 mL) was added. After stirring for an additional 1 h, triethylamine (13.8 mL, 98.3 mmol) was added. The reaction mixture was allowed to warm to 25° C. and diluted with water. The organic layer was separated and the aqueous layer was extracted with dichloromethane (3×50 mL). The combined organic layers were dried over anhydrous magnesium sulfate and concentrated in vacuo at 0° C. to afford the crude cyclopropylacetaldehyde, which was used in the next step without further purification. $^1$H NMR (400 MHz, CDCl$_3$) δ 0.19 (2H, dd, J$_1$=10.3 Hz, J$_2$=5.2 Hz), 0.62 (2H, dd, J$_1$=13.2 Hz, J$_2$=5.3 Hz), 1.03-0.97 (1H, m), 2.30 (2H, d, J=5.1 Hz), 9.79 (1H, d, J=1.7 Hz).

b) cis-2-(2-Cyclopropylethylamino)-cyclopentanecarboxylic acid ethyl ester

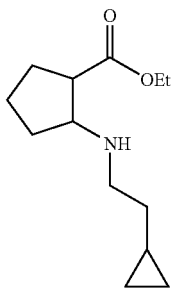

To a solution of cis-ethyl 2-amino-1-cyclopentanecarboxylate hydrochloride (250.0 mg, 1.28 mmol) in ethanol (5 mL) was added triethylamine (0.2 mL, 1.42 mmol), cyclopropylacetaldehyde (288.0 mg, 1.92 mmol), and sodium cyanoborohydride (59.2 mg, 0.895 mmol) at 25° C. After stirring for 12 h, the mixture was concentrated in vacuo and the residue was dissolved in ethyl acetate. The organic layer was washed with water, dried over anhydrous magnesium sulfate, and concentrated in vacuo. The crude material was purified by flash column chromatography (Teledyne Isco RediSep Flash Column; 0-50% ethyl acetate in hexanes) to afford cis-2-(2-cyclopropylethylamino)-cyclopentanecarboxylic acid ethyl ester as a yellowish oil (42.7 mg, 0.189, 15%) and trans-2-(2-cyclopropylethylamino)-cyclopentanecarboxylic acid ethyl ester as a yellowish oil (130.5 mg, 0.579 mmol, 45%). cis-2-(2-Cyclopropylethylamino)-cyclopentanecarboxylic acid ethyl ester: $^1$H NMR (400 MHz, CDCl$_3$) δ 0.08-0.12 (2H, m), 0.45-0.49 (2H, m), 0.63-0.72 (1H, m), 1.29 (3H, t, J=7.0 Hz), 1.46-1.52 (2H, m), 1.58-1.77 (2H, m), 1.85-2.10 (4H, m), 2.73-2.87 (2H, m), 3.03 (1H, q, J=6.7 Hz), 3.36 (1H, q, J=7.3 Hz), 4.17 (2H, q, J=7.0 Hz). LC-MS (ESI) calcd for C$_{13}$H$_{23}$NO$_2$ 225.17, found 226.2 [M+H$^+$]. trans-2-(2-Cyclopropylethylamino)-cyclopentanecarboxylic acid ethyl ester: $^1$H NMR (400 MHz, CDCl$_3$) δ 0.12-0.16 (2H, m), 0.50-0.55 (2H, m), 0.65-0.72 (1H, m), 1.31 (3H, t, J=7.1 Hz), 1.53-1.59 (2H, m), 1.64-1.84 (2H, m), 1.89-2.13 (4H, m), 2.81-2.87 (1H, m), 2.95-3.01 (1H, m), 3.07 (1H, q, J=7.1 Hz), 3.44 (1H, q, J=7.2 Hz), 4.20 (2H, q, J=7.0 Hz). LC-MS (ESI) calcd for C$_{13}$H$_{23}$NO$_2$ 225.17, found 226.2 [M+H$^+$].

c) cis-2-{(2-Cyclopropylethyl)-[2-(7-methanesulfonylamino-1,1-dioxo-1,4-dihydro-1$\lambda^6$-benzo[1,2,4]thiadiazin-3-yl)acetyl]amino}-cyclopentanecarboxylic acid ethyl ester

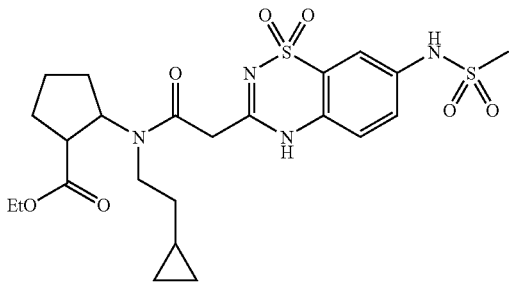

To a solution of cis-2-(2-cyclopropylethylamino)-cyclopentanecarboxylic acid ethyl ester (42.7 mg, 0.189 mmol) in N,N-dimethylformamide (3.0 mL) was added (7-methanesulfonylamino-1,1-dioxo-1,4-dihydro-1$\lambda^6$-benzo[1,2,4]thiadiazin-3-yl)-acetic acid (prepared as described in Example 1j, 94.8 mg, 0.284 mmol), 1-(3-dimethylaminopropyl)-3-ethylcarbodiimide hydrochloride (73.9 mg, 0.378 mmol), and 4-dimethylaminopyridine (5.8 mg, 0.047 mmol). After stirring at 25° C. for 14 h, the mixture was diluted with ethyl acetate and acidified with 1.0 M aqueous hydrochloric acid solution. The layers were separated and the organic layer was dried over magnesium sulfate, filtered, and concentrated in vacuo to afford the crude product, cis-2-{(2-cyclopropylethyl)-[2-(7-methanesulfonylamino-1,1-dioxo-1,4-dihydro-1$\lambda^6$-benzo[1,2,4]thiadiazin-3-yl)acetyl]amino}-cyclopentanecarboxylic acid ethyl ester, as a yellowish oil. The crude product was used in the next step without further purification. LC-MS (ESI) calcd for C$_{23}$H$_{32}$N$_4$O$_7$S$_2$ 540.17, found 541.4 [M+H$^+$].

d) cis-N-{3-[2-Cyclopropylethyl-5-hydroxy-3-oxo-2-aza-bicyclo[4.3.0]non-4-en-4-yl]-1,1-dioxo-1,4-dihydro-1λ⁶-benzo[1,2,4]thiadiazin-7-yl}-methanesulfonamide

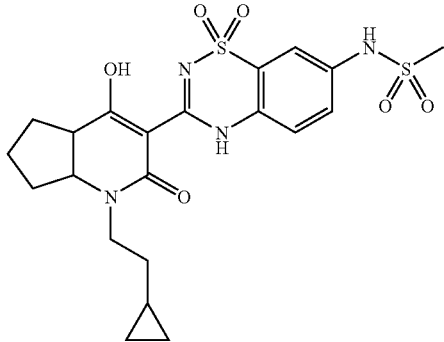

To a solution of cis-2-{(2-cyclopropylethyl)-[2-(7-methanesulfonylamino-1,1-dioxo-1,4-dihydro-1λ⁶-benzo[1,2,4]thiadiazin-3-yl)acetyl]amino}-cyclopentanecarboxylic acid ethyl ester (102.2 mg, 0.189 mmol) in absolute ethanol (10 mL) was added a 21% w/w solution of sodium ethoxide in ethanol (0.35 mL, 0.938 mmol). After stirring at 60° C. for 12 h, the mixture was diluted with ethyl acetate and acidified with 1.0 M aqueous hydrochloric acid solution to pH 1. The organic layer was separated and the aqueous layer was extracted with ethyl acetate (2×20 mL). The combined organic layers were dried over anhydrous magnesium sulfate and concentrated in vacuo. The crude mixture was purified by flash column chromatography (Teledyne Isco RediSep Flash Column; 0-100% ethyl acetate in hexanes) to afford the desired product, cis-N-{3-[2-cyclopropylethyl-5-hydroxy-3-oxo-2-aza-bicyclo[4.3.0]non-4-en-4-yl]-1,1-dioxo-1,4-dihydro-1λ⁶-benzo[1,2,4]thiadiazin-7-yl}-methanesulfonamide (58.5 mg, 0.118 mmol, 62%), as an off-white solid. $^1$H NMR (400 MHz, DMSO-$d_6$) δ 0.09 (2H, d, J=4.1 Hz), 0.42 (2H, d, J=7.8 Hz), 0.71 (1H, bs), 1.44-1.55 (6H, m), 2.11-2.15 (2H, m), 3.05 (3H, s), 3.22 (1H, bs), 3.29 (1H, bs), 3.78 (1H, bs), 3.93 (1H, bs), 7.48-7.55 (3H, m), 10.16 (1H, bs). LC-MS (ESI) calcd for $C_{21}H_{26}N_4O_6S_2$ 494.13, found 495.3 [M+H⁺]. Anal. calcd for $C_{21}H_{26}N_4O_6S_2$: C, 51.00; H, 5.30; N, 11.33; S, 12.97, found C, 51.36; H, 5.77; N, 11.28; S, 12.58.

EXAMPLE 20

N-{3-[2-(3-Methylbutyl)-5-hydroxy-3-oxo-2-aza-bicyclo[4.4.0]dec-4-en-4-yl]-1,1-dioxo-1,4-dihydro-1λ⁶-benzo[1,2,4]thiadiazin-7-yl}-methanesulfonamide

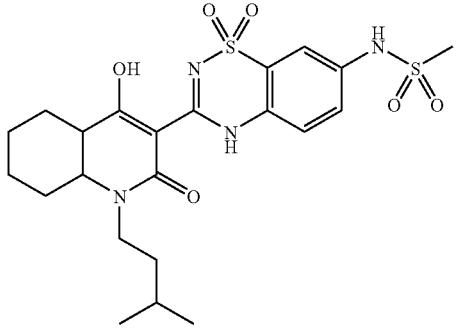

a) (2-(3-Methylbutylamino)-cyclohexanecarboxylic acid ethyl ester

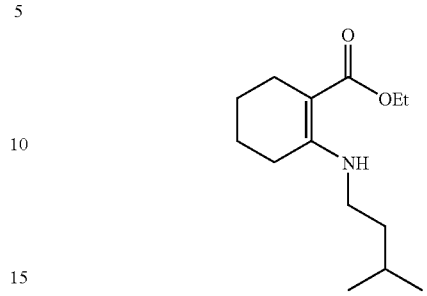

To a solution of ethyl 2-oxocyclohexanecarboxylate (3.0 mL, 17.8 mmol) in ethanol (30 mL) was added isoamylamine (2.1 mL, 17.9 mmol) at 25° C. The mixture was heated at reflux for 12 h. The reaction mixture was allowed to cool to 25° C. and concentrated in vacuo. The crude material was purified by flash column chromatography (Teledyne Isco RediSep Flash Column; 0-30% ethyl acetate in hexanes) to afford the desired product, (2-(3-methylbutylamino)-cyclohexanecarboxylic acid ethyl ester (3.23 g, 13.5 mmol, 76%), as a yellowish oil. LC-MS (ESI) calcd for $C_{14}H_{25}NO_2$ 239.19, found 240.3 [M+H⁺].

b) (2-(3-Methylbutylamino)-cyclohexanecarboxylic acid ethyl ester

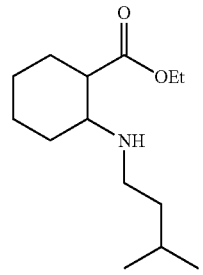

To a solution of (2-(3-methylbutylamino)-cyclohexanecarboxylic acid ethyl ester (3.23 g, 13.5 mmol) in acetic acid (40 mL) was added a 8.0 M solution of borane in pyridine (1.9 mL, 15.2 mmol) at 25° C. After stirring for 30 min, the reaction mixture was concentrated in vacuo. The crude material was triturated with 1.0 M aqueous hydrochloric acid solution (25 mL) and stirred for 0.5 h (until the gas evolution ceased). The mixture was extracted with ethyl acetate (3×50 mL) and the combined organic layers were dried over anhydrous magnesium sulfate and concentrated in vacuo. The crude material was purified by flash column chromatography (Teledyne Isco RediSep Flash Column; 0-10% methanol in dichloromethane) to afford trans-(2-(3-methylbutylamino)-cyclohexanecarboxylic acid ethyl ester as a yellowish oil (1.98 g, 8.2 mmol, 61%) and cis-(2-(3-methylbutylamino)-cyclohexanecarboxylic acid ethyl ester and an off-white solid (0.53 g, 2.2 mmol, 16%). cis-(2-(3-Methylbutylamino)-cyclohexanecarboxylic acid ethyl ester: $^1$H NMR (400 MHz, CDCl$_3$) δ 0.96 (6H, d, J=6.2 Hz), 1.22-1.45 (2H, m), 1.32 (3H, t, J=7.0 Hz), 1.53-1.81 (6H, m), 1.89-1.95 (1H, m), 2.17-2.21 (1H, m), 2.35-2.39 (1H, m), 2.90-2.97 (1H, m), 3.01-3.07 (1H, m), 3.25-3.30 (1H, m), 3.41-3.42 (1H, m), 4.20-4.30 (2H, m). LC-MS (ESI) calcd for $C_{14}H_{27}NO_2$ 241.20, found 242.4 [M+H$^+$].

c) cis-2-[2-(7-Methanesulfonylamino-1,1-dioxo-1,4-dihydro-1$\lambda^6$-benzo[1,2,4]thiadiazin-3-yl)-acetyl]-(3-methylbutyl)amino]-cyclohexanecarboxylic acid ethyl ester

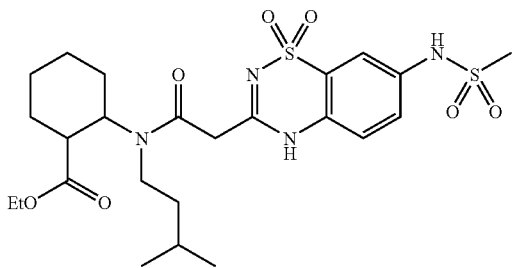

To a solution of cis-(2-(3-methylbutylamino)-cyclohexanecarboxylic acid ethyl ester (58.7 mg, 0.243 mmol) in N,N-dimethylformamide (5.0 mL) was added (7-methanesulfonylamino-1,1-dioxo-1,4-dihydro-1$\lambda^6$-benzo[1,2,4]thiadiazin-3-yl)-acetic acid (prepared as described in Example 1j, 162.0 mg, 0.486 mmol) and a 1.0 M solution of N,N'-dicyclohexylcarbodiimide in dichloromethane (0.49 mL, 0.49 mmol). After stirring at 25° C. for 12 h, the mixture was diluted with dichloromethane and the precipitated N,N'-dicyclohexylurea byproduct was removed by filtration. The filtrate was concentrated and dried in vacuo to afford the crude product, cis-2-[2-(7-methanesulfonylamino-1,1-dioxo-1,4-dihydro-1$\lambda^6$-benzo[1,2,4]thiadiazin-3-yl)-acetyl]-(3-methylbutyl)amino]-cyclohexanecarboxylic acid ethyl ester, as a yellowish oil. The crude product was used in the next step without further purification. LC-MS (ESI) calcd for $C_{24}H_{36}N_4O_7S_2$ 556.20, found 557.3 [M+H$^+$].

d) N-{3-[2-(3,3-Methylbutyl)-5-hydroxy-3-oxo-2-aza-bicyclo[4.4.0]dec-4-en-4-yl]-1,1-dioxo-1,4-dihydro-1$\lambda^6$-benzo[1,2,4]thiadiazin-7-yl}-methanesulfonamide

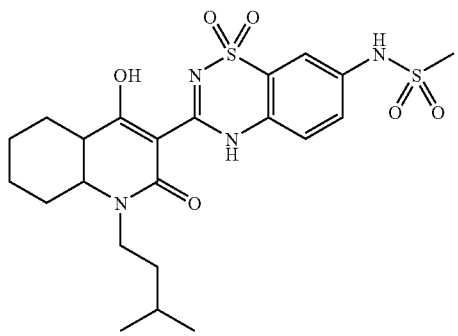

To a solution of cis-2-[2-(7-methanesulfonylamino-1,1-dioxo-1,4-dihydro-1$\lambda^6$-benzo[1,2,4]thiadiazin-3-yl)-acetyl]-(3-methylbutyl)amino]-cyclohexanecarboxylic acid ethyl ester (135.3 mg, 0.243 mmol) in absolute ethanol (10 mL) was added a 21% w/w solution of sodium ethoxide in ethanol (1.5 mL, 4.02 mmol). After stirring at 80° C. for 12 h, the mixture was diluted with ethyl acetate and acidified with 1.0 M aqueous hydrochloric acid solution to pH 1. The organic layer was separated and the aqueous layer was extracted with ethyl acetate (2×20 mL). The combined organic layers were dried over anhydrous magnesium sulfate and concentrated in vacuo. The crude mixture was purified by flash column chromatography (Teledyne Isco RediSep Flash Column; 0-100% ethyl acetate in hexanes) to afford the desired product, N-{3-[2-(3-methylbutyl)-5-hydroxy-3-oxo-2-aza-bicyclo[4.4.0]dec-4-en-4-yl]-1,1-dioxo-1,4-dihydro-1$\lambda^6$-benzo[1,2,4]thiadiazin-7-yl}-methanesulfonamide (31.2 mg, 0.061 mmol, 25%), as an off-white solid. $^1$H NMR (400 MHz, DMSO-d$_6$) δ 0.93 (6H, d, J=6.3 Hz), 1.13-1.85 (10H, m), 2.31 (1H, bs), 2.94-3.83 (4H, m), 3.05 (3H, s), 7.48-7.59 (3H, m), 10.14 (1H, d, J=18.6 Hz). LC-MS (ESI) calcd for $C_{22}H_{30}N_4O_6S_2$ 510.16, found 511.3 [M+H$^+$]. Anal. calcd for $C_{22}H_{30}N_4O_6S_{20}$ 0.7H$_2$O: C, 50.50; H, 6.05; N, 10.71; S, 12.26, found C, 50.77; H, 5.82; N, 10.20; S, 11.92.

EXAMPLE 21

N-{3-[2-(3,3-Dimethylbutyl)-5-hydroxy-3-oxo-2-aza-bicyclo[4.4.0]dec-4-en-4-yl]-1,1-dioxo-1,4-dihydro-1$\lambda^6$-benzo[1,2,4]thiadiazin-7-yl}-methanesulfonamide

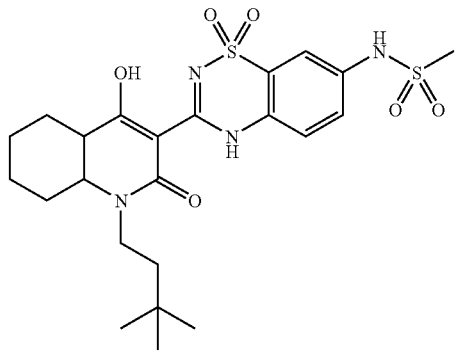

a) cis-2-(3,3-Dimethylbutylamino)-cyclohexanecarboxylic acid ethyl ester

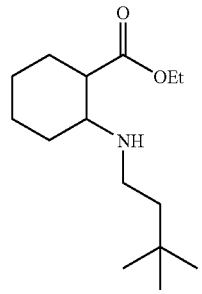

To a solution of ethyl cis-2-amino-1-cyclohexanecarboxylate hydrochloride (1.00 g, 4.6 mmol) in methanol (10 mL) was added triethylamine (0.72 mL, 5.1 mmol), 3,3-dimethylbutyraldehyde (0.67 mL, 5.1 mmol), and sodium cyanoborohydride (213.0 mg, 3.2 mmol) at 25° C. After stirring for 18 h, the mixture was concentrated in vacuo and the residue was dissolved in ethyl acetate. The organic layer was washed with water, dried over anhydrous magnesium sulfate, and concentrated in vacuo. The crude material was purified by flash column chromatography (Teledyne Isco RediSep Flash Column; 0-50% ethyl acetate in hexanes) to afford the desired product, cis-2-(3,3-dimethylbutylamino)-cyclohexanecarboxylic acid ethyl ester (31.2 mg, 0.061 mmol, 25%), as a white solid. $^1$H NMR (400 MHz, CDCl$_3$) δ 0.99 (9H, s), 1.22-1.29 (1H, m), 1.35 (3H, t, J=7.0 Hz), 1.40-1.51 (1H, m), 1.58-1.77 (5H, m), 1.90-1.94 (1H, m), 2.12-2.15 (1H, m), 2.37-2.40 (1H, m), 2.96 (1H, bs), 3.09 (1H, bs), 3.22-3.33 (2H, m), 4.21-4.35 (2H, m). LC-MS (ESI) calcd for C$_{15}$H$_{29}$NO$_2$ 255.22, found 256.3 [M+H$^+$].

b) cis-2-{(3,3-Dimethylbutyl)-[2-(7-methanesulfonylamino-1,1-dioxo-1,4-dihydro-1λ$^6$-benzo[1,2,4]thiadiazin-3-yl)acetyl]amino}-cyclohexanecarboxylic acid ethyl ester

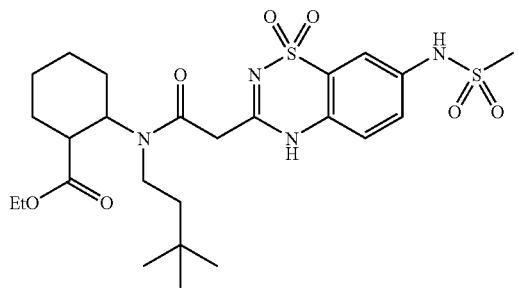

To a solution of cis-2-(3,3-dimethylbutylamino)-cyclohexanecarboxylic acid ethyl ester (60.0 mg, 0.243 mmol) in N,N-dimethylformamide (5.0 mL) was added (7-methanesulfonylamino-1,1-dioxo-1,4-dihydro-1λ$^6$-benzo[1,2,4]thiadiazin-3-yl)-acetic acid (prepared as described in Example 1j, 162.0 mg, 0.486 mmol) and a 1.0 M solution of N,N'-dicyclohexylcarbodiimide in dichloromethane (0.49 mL, 0.49 mmol). After stirring at 25° C. for 12 h, the mixture was diluted with dichloromethane and the precipitated N,N'-dicyclohexylurea byproduct was removed by filtration. The filtrate was concentrated and dried in vacuo to afford the crude product, cis-2-{(3,3-dimethylbutyl)-[2-(7-methanesulfonylamino-1,1-dioxo-1,4-dihydro-1λ$^6$-benzo[1,2,4]thiadiazin-3-yl)acetyl]amino}-cyclohexanecarboxylic acid ethyl ester, as a yellowish oil. The crude product was used in the next step without further purification. LC-MS (ESI) calcd for C$_{25}$H$_{38}$N$_4$O$_7$S$_2$ 570.22, found 571.4 [M+H$^+$].

c) N-{3-[2-(3,3-Dimethylbutyl)-5-hydroxy-3-oxo-2-aza-bicyclo[4.4.0]dec-4-en-4-yl]-1,1-dioxo-1,4-dihydro-1λ$^6$-benzo[1,2,4]thiadiazin-7-yl}-methanesulfonamide

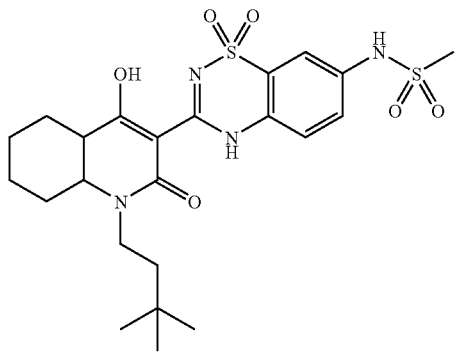

To a solution of cis-2-{(3,3-dimethylbutyl)-[2-(7-methanesulfonylamino-1,1-dioxo-1,4-dihydro-1λ$^6$-benzo[1,2,4]thiadiazin-3-yl)acetyl]amino}-cyclohexanecarboxylic acid ethyl ester (138.7 mg, 0.243 mmol) in absolute ethanol (10 mL) was added a 21% w/w solution of sodium ethoxide in ethanol (0.91 mL, 2.44 mmol). After stirring at 60° C. for 13 h, the mixture was diluted with ethyl acetate and acidified with 1.0 M aqueous hydrochloric acid solution to pH 1. The organic layer was separated and the aqueous layer was extracted with ethyl acetate (2×20 mL). The combined organic layers were dried over anhydrous magnesium sulfate and concentrated in vacuo. The crude mixture was purified by flash column chromatography (Teledyne Isco RediSep Flash Column; 0-100% ethyl acetate in hexanes) to afford the desired product, N-{3-[2-(3,3-dimethylbutyl)-5-hydroxy-3-oxo-2-aza-bicyclo[4.4.0]dec-4-en-4-yl]-1,1-dioxo-1,4-dihydro-1λ$^6$-benzo[1,2,4]thiadiazin-7-yl}-methanesulfonamide (44.3 mg, 0.084 mmol, 35%), as an off-white solid. $^1$H NMR (400 MHz, DMSO-d$_6$) δ 0.94 (9H, s), 1.10-1.87 (9H, m), 2.32 (1H, bs), 3.04 (3H, s), 2.92-3.82 (4H, m), 7.47-7.58 (3H, m), 10.13 (1H, bs). LC-MS (ESI) calcd for C$_{23}$H$_{32}$N$_4$O$_6$S$_2$ 524.18, found 525.3 [M+H$^+$]. Anal. calcd for C$_{23}$H$_{32}$N$_4$O$_6$S$_2$: C, 52.65; H, 6.15; N, 10.68; S, 12.22, found C, 52.56; H, 6.10; N, 10.71; S, 12.16.

EXAMPLE 22

(4aR,7aS)-N-{3-[1-(4-Fluoro-3-methyl-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

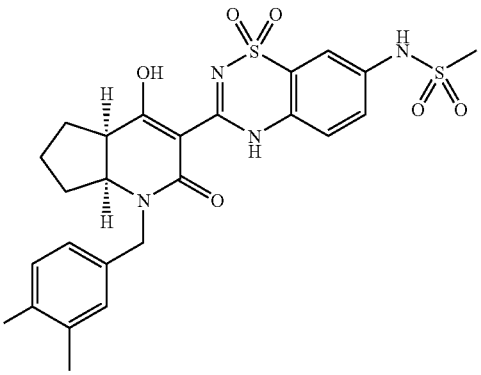

a) (1S,2R)-2-(Methoxycarbonyl)cyclopentanecarboxylic acid

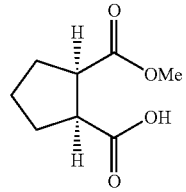

(1S,2R)-2-(Methoxycarbonyl)cyclopentanecarboxylic acid was prepared as described in *J. Org. Chem.* 2000, 65, 6984-6991. Tetrahydro-cyclopenta[c]furan-1,3-dione (5.0 g, 35.7 mmol) was dissolved in a 1:1 mixture of toluene and carbon tetrachloride (720 mL). The mixture was cooled to −55° C. under a nitrogen atmosphere, and then quinine (12.7 g, 39.3 mmol) was added. A solution of methanol (4.33 mL, 107 mmol) in toluene-carbon tetrachloride (1:1, 30 mL) was slowly added via an addition funnel. The suspension was stirred at −55° C. for 36 h, and then allowed to warm to 25° C. The mixture was concentrated in vacuo and the residue was dissolved in ethyl acetate (400 mL), washed with 1.0 M aqueous hydrochloric acid solution (2×400 mL) and saturated aqueous brine solution, dried over magnesium sulfate and filtered. The filtrate was concentrated in vacuo to afford the desired product, (1S,2R)-2-(methoxycarbonyl)cyclopentanecarboxylic acid (6.2 g, 35.7 mmol, quantitative), as a clear oil. $^1$H NMR (400 MHz, CD$_3$OD) δ: 1.67 (1H, m), 1.84 (1H, m), 1.99 (4H, m), 3.08 (2H, m), 3.63 (3H, s).

b) Methyl (1R,2S)-2-{[(benzyloxy)carbonyl]amino}cyclopentanecarboxylate

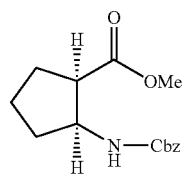

(1S,2R)-2-(Methoxycarbonyl)cyclopentanecarboxylic acid (6.2 g, 35.7 mmol) was dissolved in anhydrous tetrahydrofuran (100 mL) and cooled to −10° C. under a nitrogen atmosphere. Triethylamine (14.9 mL, 107.1 mmol) was added followed by the dropwise addition of ethyl chloroformate (6.83 mL, 71.5 mmol) with vigorous stirring. Immediate precipitation was observed. The mixture was stirred at −10° C. for 1 h. Sodium azide (6.96 g, 107.1 mmol) was dissolved in water (50 mL) and added to the reaction mixture at −10° C. The mixture was stirred at −10° C. for 15 min, and then was allowed to warm to 25° C. and stirred for 2 h. The mixture was poured into water (150 mL) and extracted with ethyl acetate. The combined organic layers were washed with saturated aqueous sodium bicarbonate solution and saturated aqueous brine solution, dried over magnesium sulfate and filtered. The filtrate was concentrated in vacuo to afford the acyl azide intermediate as a clear oil. The oil was dissolved in anhydrous benzene (100 mL) and heated at reflux for 2 h under a nitrogen atmosphere. The solution was allowed to cool to 25° C., and concentrated in vacuo to afford a yellow oil. The oil was dissolved in dichloromethane (100 mL), triethylamine (9.9 mL, 71.4 mmol) and benzyl alcohol (3.69 mL, 35.7 mmol) were added sequentially. The resulting mixture was heated at reflux for 16 h under a nitrogen atmosphere. The mixture was allowed to cool to 25° C., concentrated in vacuo and the residue was purified by flash column chromatography (Teledyne Isco RediSep Flash Column; 0-50% ethyl acetate in hexanes) to afford the desired product, methyl (1R,2S)-2-{[(benzyloxy)carbonyl]amino}cyclopentanecarboxylate (7.37 g, 26.59 mmol, 75%), as a clear oil. $^1$H NMR (400 MHz, CDCl$_3$) δ: 1.70 (2H, m), 1.84 (1H, m), 1.99 (3H, m), 3.02 (1H, m), 3.64 (3H, s), 4.29 (1H, m), 5.10 (2H, s), 7.36 (5H, m).

c) Methyl (1R,2S)-2-aminocyclopentanecarboxylate

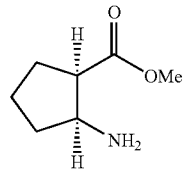

To a solution of methyl (1R,2S)-2-{[(benzyloxy)carbonyl]amino}cyclopentanecarboxylate (6.5 g, 23.5 mmol) in ethyl acetate (200 mL), 5% Palladium on carbon (1.3 g, 20% w/w) was added. The flask was degassed and backfilled with hydrogen gas via balloon. The mixture was stirred at 25° C. for 1.5 h, passed through a plug of Celite and rinsed with ethyl acetate. The filtrate was concentrated in vacuo to afford the desired product, methyl (1R,2S)-2-aminocyclopentanecarboxylate (4.30 g, 30.05 mmol, quantitative), as a clear oil. $^1$H NMR (400 MHz, CDCl$_3$) δ: 1.57 (2H, m), 1.90 (3H, m), 2.05 (1H, m), 2.81 (1H, m), 3.61 (1H, m), 3.72 (3H, s).

d) Methyl (1R,2S)-2-[(4-fluoro-3-methylbenzyl)amino]cyclopentanecarboxylate

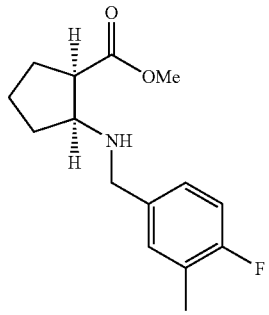

To a stirred solution of methyl (1R,2S)-2-aminocyclopentanecarboxylate (310 mg, 2.17 mmol) in methanol (10 mL) under a nitrogen atmosphere, 4-fluoro-3-methyl-benzaldehyde (0.27 mL, 2.17 mmol) was added. The mixture was stirred for 10 min, and then acetic acid (0.4 mL) was added followed by sodium cyanoborohydride (340 mg, 5.42 mmol). The resulting mixture was stirred at 25° C. for 16 h, and then poured into a mixture of saturated aqueous sodium bicarbonate solution (50 mL) and ethyl acetate (100 mL). Two layers were separated and the aqueous layer was extracted with ethyl acetate. The combined organic layers were washed with saturated aqueous brine solution, dried over magnesium sulfate and filtered. The filtrate was concentrated in vacuo to afford the desired product, methyl (1R,2S)-2-[(4-fluoro-3-methylbenzyl)amino]cyclopentanecarboxylate (460 mg, 1.73 mmol, 80%), as a clear oil. $^1$H NMR (400 MHz, CDCl$_3$) δ: 1.68 (2H, m), 1.89 (3H, m), 2.04 (1H, m), 2.28 (3H, d, J=2.0 Hz), 2.97 (1H, m), 3.31 (1H, m), 3.71 (3H, s), 3.72 (2H, m), 6.93 (1H, t, J=8.4 Hz), 7.07 (1H, m), 7.11 (1H, m).

e) (4aR,7aS)-N-{3-[1-(4-Fluoro-3-methyl-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide

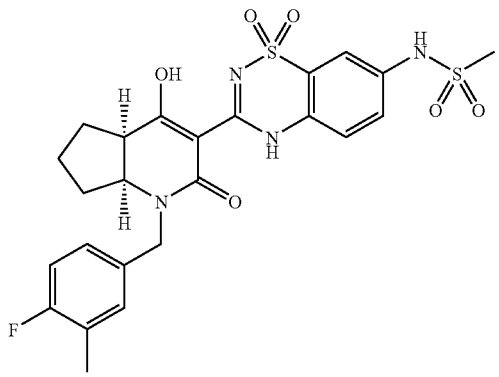

To a stirred solution of methyl (1R,2S)-2-[(4-fluoro-3-methylbenzyl)amino]cyclopentanecarboxylate (120 mg, 0.45 mmol) and (7-methanesulfonylamino-1,1-dioxo-1,4-dihydro-1λ⁶-benzo[1,2,4]thiadiazin-3-yl)-acetic acid (prepared as described in Example 1j, 150 mg, 0.45 mmol) in anhydrous N,N-dimethylformamide (4 mL) under a nitrogen atmosphere, N-methylmorpholine (0.15 mL, 1.40 mmol) and 1-(3-dimethylaminopropyl)-3-ethylcarbodiimide hydrochloride (86 mg, 0.45 mmol) were added sequentially. The mixture was stirred at 25° C. for 2.5 h, and then poured into 1.0 M aqueous hydrochloric acid solution and extracted with ethyl acetate. The combined organic layers were washed with saturated aqueous brine solution, dried over magnesium sulfate and filtered. The filtrate was concentrated in vacuo to afford the amide intermediate, which was used directly in the next step without further purification.

The above intermediate was dissolved in ethanol (8 mL), a 21% w/w solution of sodium ethoxide in ethanol (0.7 mL, 1.8 mmol) was added and the mixture was stirred at 60° C. for 1 h. The reaction mixture was cooled to 0° C., and then 1.0 M aqueous hydrochloric acid solution (4 mL) was slowly added. The mixture was diluted with ethyl acetate, washed with water and saturated aqueous brine solution, dried over magnesium sulfate and filtered. The filtrate was concentrated in vacuo and the residue was purified by flash column chromatography (Teledyne Isco RediSep Flash Column; 0-10% methanol in dichloromethane) to afford the desired product, (4aR,7aS)-N-{3-[1-(4-fluoro-3-methyl-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide (170 mg, 0.31 mmol, 69% over two steps), as a slightly yellow solid. ¹H NMR (400 MHz, DMSO-d₆) δ: 1.52 (3H, m), 1.97 (2H, m), 2.10 (1H, m), 2.22 (3H, d, J=1.6 Hz), 3.05 (3H, s), 3.29 (1H, m), 3.82 (1H, m), 4.38 (1H, d, J=14.8 Hz), 4.88 (d, 1H, J=14.8 Hz), 7.07 (2H, m), 7.18 (1H, m), 7.23 (1H, m), 7.56-7.48 (3H, m), 10.15 (1H, s). LC-MS (ESI) calcd for $C_{24}H_{25}FN_4O_6S_2$ 548.12, found 549.3 [M+H⁺]. e.e. >95% [HPLC-analysis: Chiralpak AS-RH 4.6× 250 mm, 5 micron].

EXAMPLE 23

(4aR,7aS)-N-{3-[4-Hydroxy-1-(3-methyl-benzyl)-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide

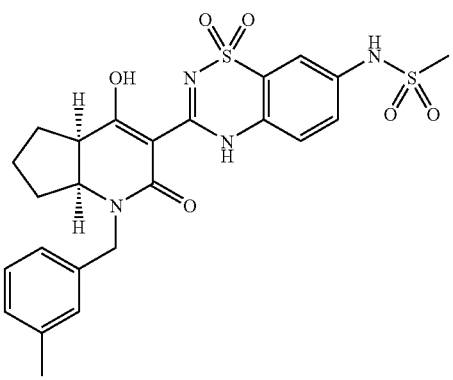

a) Methyl (1R,2S)-2-[(3-methylbenzyl)amino]cyclopentanecarboxylate

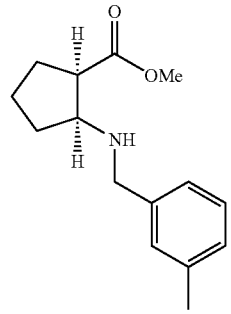

To a stirred solution of methyl (1R,2S)-2-aminocyclopentanecarboxylate (240 mg, 1.68 mmol) in methanol (10 mL) under a nitrogen atmosphere, 3-methyl-benzaldehyde (202 mg, 1.68 mmol) was added. The mixture was stirred for 10 min, and then acetic acid (0.4 mL) was added followed by sodium cyanoborohydride (265 mg, 4.2 mmol). The resulting mixture was stirred at 25° C. for 16 h, and then poured into a mixture of saturated aqueous sodium bicarbonate solution (50 mL) and ethyl acetate (100 mL). The layers were separated and the aqueous layer was extracted with ethyl acetate. The combined organic layers were washed with saturated aqueous brine solution, dried over magnesium sulfate and filtered. The filtrate was concentrated in vacuo to afford the desired product, methyl (1R,2S)-2-[(3-methylbenzyl)amino]cyclopentanecarboxylate (330 mg, 1.34 mmol, 80%), as a clear oil. ¹H NMR (400 MHz, CDCl₃) δ: 1.62 (1H, m), 1.71 (1H, m), 1.91 (3H, m), 2.05 (1H, m), 2.37 (3H, s), 2.99 (1H, m), 3.34 (1H, m), 3.72 (3H, s), 3.77 (1H, d, J=12.8 Hz), 3.82 (1H, d, J=12.8 Hz), 7.24-7.07 (4H, m).

b) (4aR,7aS)-N-{3-[4-Hydroxy-1-(3-methyl-benzyl)-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide

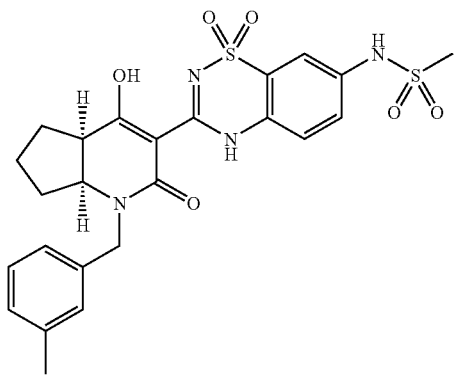

To a stirred solution of methyl (1R,2S)-2-[(3-methylbenzyl)amino]cyclopentane-carboxylate (74 mg, 0.30 mmol) and (7-methanesulfonylamino-1,1-dioxo-1,4-dihydro-1λ⁶-benzo[1,2,4]thiadiazin-3-yl)-acetic acid (prepared as described in Example 1j, 100 mg, 0.30 mmol) in anhydrous N,N-dimethylformamide (3 mL) under a nitrogen atmosphere, N-methylmorpholine (0.10 mL, 0.9 mmol) and 1-(3-dimethylaminopropyl)-3-ethylcarbodiimide hydrochloride (63 mg, 0.33 mmol) were added sequentially. The mixture was stirred at 25° C. for 16 h, diluted with ethyl acetate, washed with 1.0 M aqueous hydrochloric acid and saturated aqueous brine solution, dried over magnesium sulfate and filtered. The filtrate was concentrated in vacuo to afford the amide intermediate, which was used directly in the next step without further purification.

Above intermediate was dissolved in ethanol (5 mL), a 21% w/w solution of sodium ethoxide in ethanol) 0.44 mL, 1.2 mmol) was added and the mixture was stirred at 60° C. for 1.5 h. The reaction mixture was cooled to 0° C., 0.3 M aqueous hydrochloric acid solution (10 mL) was slowly added, upon which the product precipitated while stirring. The solid was collected by vacuum filtration, washed with water, and further dried in vacuo to afford the desired product, (4aR,7aS)-N-{3-[4-hydroxy-1-(3-methyl-benzyl)-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide (90 mg, 0.17 mmol, 56% over two steps), as a off-white solid. ¹H NMR (400 MHz, DMSO-d₆) δ: 1.62-1.44 (3H, m), 2.07-1.96 (3H, m), 2.29 (3H, s), 3.06 (3H, s), 3.33 (1H, bs), 3.83 (1H, bs), 4.38 (1H, bs), 4.94 (1H, d, J=15.6 Hz), 7.10 (3H, m), 7.19 (1H, m), 7.54 (3H, m), 10.17 (1H, s). LC-MS (ESI) calcd for $C_{24}H_{26}N_4O_6S_2$ 530.13, found 531.2 [M+H⁺].

EXAMPLE 24 cis-2-Amino-ethanesulfonic acid {3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-amide

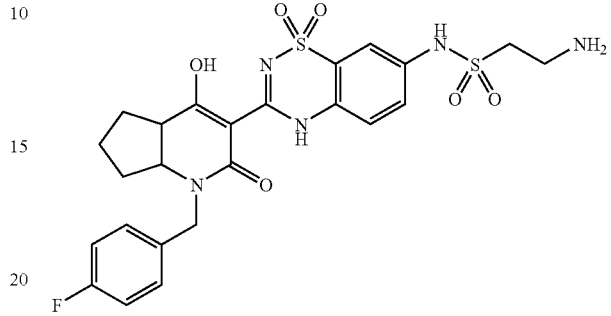

a) 2-Amino-5-iodo-benzenesulfonamide

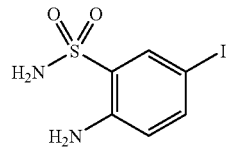

2-Amino-benzenesulfonamide (5.15 g, 29.3 mmol) was dissolved in chloroform (87 mL), and N-iodosuccinimide (7.29 g, 30.77 mmol) was added under a nitrogen atmosphere. The mixture was heated at reflux for 24 h, allowed to cool to 25° C., and filtered through a sinter funnel. The solid was washed with chloroform and 10% methanol/chloroform (3-8 times) to afford the desired product, 2-amino-5-iodo-benzenesulfonamide (6.78 g, 22.75 mmol, 78%) as a brown crystalline solid. ¹H NMR (400 MHz, DMSO-d₆): 5.98 (s, 2H), 6.62 (d, 1H, J=8.8 Hz), 7.31 (s, 2H), 7.45 (dd, 1H, J=8.8, 2.4 Hz), 7.73 (d, 1H, J=2.0 Hz).

b) (7-Iodo-1,1-dioxo-1,4-dihydro-1λ⁶-benzo[1,2,4]thiadiazin-3-yl)-acetic acid

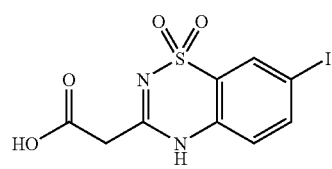

2-Amino-5-iodo-benzenesulfonamide (2.0 g, 6.71 mmol) was dissolved in N,N-dimethylacetamide (5 mL) and diethyl ether (7 mL). Ethyl 3-chloro-3-oxo-propionate (0.916 g, 6.71 mmol) was added and the reaction mixture was stirred at 25° C. for 2 h. The reaction mixture was diluted with diethyl ether (10 mL) and water (20 mL). Upon mixing vigorously, a precipitate formed. The solid was collected by vacuum filtration, rinsed with 1.0 M aqueous hydrochloric acid solution (2×10 mL) and dried in vacuo for 2 h. The solid was dissolved in 8% aqueous sodium hydroxide solution (50 mL) and stirred at 100° C. for 15 min. Upon cooling to 25° C., the solution was neutralized with 6.0 M aqueous hydrochloric acid solution. Additional 1.0 M aqueous hydrochloric acid solution (20 mL) was added and the desired product precipitated. The solid was collected by vacuum filtration, rinsed with 1.0 M aqueous hydrochloric acid solution (2×10 mL) and dried in vacuo for 16 h to afford the desired product, (7-iodo-1,1-dioxo-1,4-dihydro-1$\lambda^6$-benzo[1,2,4]thiadiazin-3-yl)-acetic acid (2.0 g, 5.46 mmol, 81%) as a pale pink powder. $^1$H NMR (400 MHz, DMSO-d$_6$) δ: 3.58 (3H, s), 7.13 (1H, d, J=8.5 Hz), 7.98 (1H, dd, J$_1$=8.6 Hz, J$_2$=1.7 Hz), 8.03 (1H, d, J=2.5 Hz), 12.33 (1H, bs), 13.05 (1H, bs). LC-MS (ESI) calcd for C$_9$H$_7$IN$_2$O$_4$S 365.92, found 366.95 [M+H$^+$].

c) cis-1-(4-Fluoro-benzyl)-4-hydroxy-3-(7-iodo-1,1-dioxo-1,4-dihydro-1$\lambda^6$-benzo[1,2,4]thiadiazin-3-yl)-1,4a,5,6,7,7a-hexahydro-[1]pyrindin-2-one

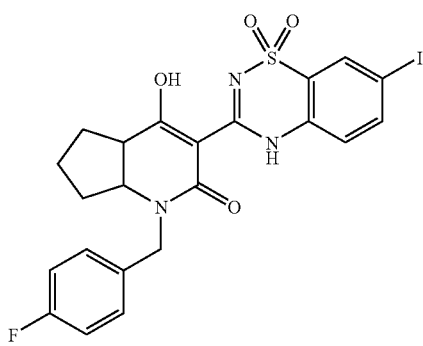

To a stirred solution of cis-2-(4-fluoro-benzylamino)-cyclopentanecarboxylic acid ethyl ester (prepared as described in Example 11, 1.33 g, 5 mmol) and (7-iodo-1,1-dioxo-1,4-dihydro-1$\lambda^6$-benzo[1,2,4]thiadiazin-3-yl)-acetic acid (2.20 g, 6.0 mmol) in anhydrous N,N-dimethylformamide (15 mL) under a nitrogen atmosphere, a 1.0 M solution of N,N'-dicyclohexylcarbodiimide solution in dichloromethane (6.5 mL, 6.5 mmol) was slowly added. After stirring for 1.5 h at 25° C., the mixture was diluted with ethyl acetate, washed with water and saturated aqueous brine solution, dried over magnesium sulfate and filtered. The filtrate was concentrated in vacuo to afford the amide intermediate, which was used directly in the next step without further purification.

Above intermediate was dissolved in ethanol (25 mL), a 21% w/w solution of sodium ethoxide in ethanol (7.41 mL, 20 mmol) was added and the mixture was stirred at 60° C. for 1.5 h. The reaction mixture was allowed to cool to 25° C., and then 2.0 M aqueous hydrochloric acid solution (20 mL) was slowly added, upon which the product precipitated. The solid was collected by vacuum filtration and further dried in vacuo to afford the desired product, cis-1-(4-fluoro-benzyl)-4-hydroxy-3-(7-iodo-1,1-dioxo-1,4-dihydro-1$\lambda^6$-benzo[1,2,4]thiadiazin-3-yl)-1,4a,5,6,7,7a-hexahydro-[1]pyrindin-2-one (1.85 g, 3.26 mmol, 65%), as an off-white solid. $^1$H NMR (400 MHz, DMSO-d$_6$) δ: 1.60-1.44 (3H, m), 2.10-1.94 (3H, m), 3.23 (1H, bs), 3.85 (1H, m), 4.49 (1H, d, J=15.2 Hz), 4.89 (1H, d, J=15.2 Hz), 7.15 (2H, m), 7.39 (3H, m), 8.00 (1H, dd, J=8.8, 2.0 Hz), 8.08 (1H, d, J=1.6 Hz). LC-MS (ESI) calcd for C$_{22}$H$_{19}$FIN$_3$O$_4$S 567.01, found 568.2 [M+H$^+$].

d) cis-2-Amino-ethanesulfonic acid {3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-amide

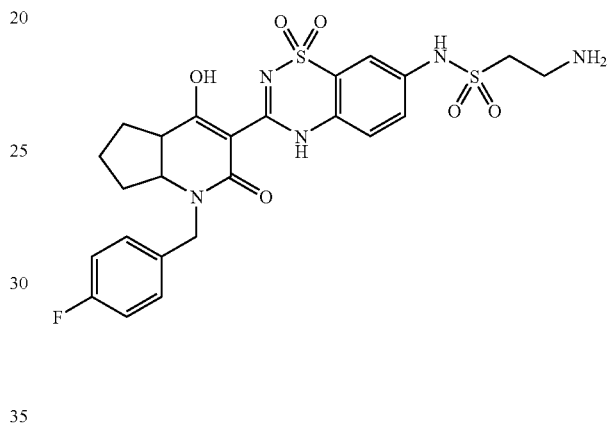

A reaction flask was charged with copper(I) iodide (268 mg, 1.41 mmol), sarcosine (N-methyl glycine) (188 mg, 2.11 mmol), 2-amino-ethanesulfonic acid amide (1.80 g, 11.2 mmol), cis-1-(4-fluoro-benzyl)-4-hydroxy-3-(7-iodo-1,1-dioxo-1,4-dihydro-1$\lambda^6$-benzo[1,2,4]thiadiazin-3-yl)-1,4a,5,6,7,7a-hexahydro-[1]pyrindin-2-one (1.0 g, 1.76 mmol) and potassium phosphate (2.61 g, 12.32 mmol). The flask was degassed and backfilled with nitrogen, and then anhydrous N,N-dimethylformamide (16 mL) was added. The resulting suspension was vigorously stirred at 100° C. for 2 h and then at 120° C. for 1.5 h, cooled to 25° C., passed through a plug of Celite and rinsed with 10% methanol-dichloromethane. The filtrate was concentrated in vacuo, and the residue was purified by prep-HPLC [Column ODS-A 5μ 100 Å, 150×21.2 mm, 5 micron, 30%-100% in 13.5 min @ 22 mL/min flow rate, 0.05% trifluoroacetic acid in acetonitrile/0.05% trifluoroacetic acid in water] to afford the desired product, cis-2-amino-ethanesulfonic acid {3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-amide (100 mg, 0.178 mmol, 10%), as a yellow solid. $^1$H NMR (400 MHz, DMSO-d$_6$) δ: 1.52 (3H, m), 1.99 (2H, m), 2.06 (1H, m), 3.17 (2H, m), 3.30 (1H, m), 3.46 (2H, t, J=6.8 Hz), 3.86 (1H, bs), 4.48 (1H, bs), 4.90 (1H, d, J=14.8 Hz), 7.16 (2H, m), 7.39 (2H, m), 7.51 (1H, m), 7.61 (2H, m), 7.82 (3H, s), 10.55 (1H, s). LC-MS (ESI) calcd for C$_{24}$H$_{26}$FN$_5$O$_6$S$_2$ 563.13, found 564.2 [M+H$^+$].

EXAMPLE 25 cis-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,4]thiazin-7-yl}-methanesulfonamide

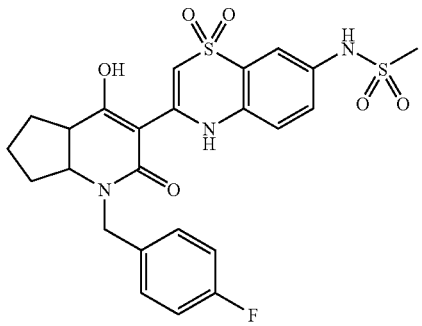

a) 2-Amino-5-nitro-benzenethiol

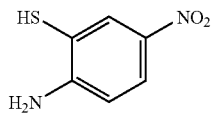

A solution of 6-nitrobenzothiazole (5 g, 27.7 mmol) in ethanol (50 mL) was treated with mono hydrazine hydrate (19 g, 388 mmol). The reaction mixture was stirred for 3 h at 25° C. and concentrated in vacuo. The resulting red oil was taken up in ethyl acetate, carefully acidified with 0.1 M aqueous hydrochloric acid solution until the solution turned light yellow. The reaction mixture was extracted with ethyl acetate, dried over magnesium sulfate, filtered, and concentrated in vacuo. The resulting orange solid was triturated with diethyl ether and dried in vacuo to afford the desired product, 2-amino-5-nitro-benzenethiol (4.1 g, 23.9 mmol, 86%) as a yellow solid. $^1$H NMR (400 MHz, Acetone-$d_6$) δ 6.43 (bs, 2H), 6.82 (d, 1H, J=8.7 Hz), 7.65 (d, 1H, J=2.2 Hz), 7.88 (dd, 1H, $J_1$=8.9 Hz, $J_2$=2.7 Hz). LC-MS (ESI) calcd for $C_6H_6N_2O_2S$ [M+H$^+$] 171.01, found 193.20 [M+Na$^+$].

b) (7-Nitro-4H-benzo[1,4]thiazin-3-yl)-acetic acid ethyl ester

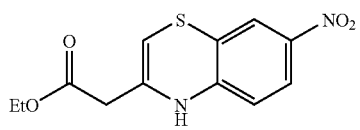

A solution of 2-amino-5-nitro-benzenethiol (4.1 g, 23.9 mmol) in tetrahydrofuran (60 mL) was treated with triethylamine (4.8 g, 47.8 mmol) and ethyl chloroacetoacetate (4.3 g, 26.3 mmol). The reaction mixture was stirred at 25° C. for 12 h, concentrated in vacuo, taken up in ethyl acetate, and heated at 80° C. for 3 h. The reaction mixture was allowed to cool to 25° C., washed with saturated aqueous brine solution, dried over sodium sulfate, and concentrated in vacuo. The resulting brown solid was triturated with diethyl ether to afford the desired product, (7-nitro-4H-benzo[1,4]thiazin-3-yl)-acetic acid ethyl ester (5.8 g, 20.7 mmol, 87%) as a yellow solid. $^1$H NMR (400 MHz, CDCl$_3$) δ 1.32 (t, 3H, J=7.1 Hz), 3.49 (s, 2H), 4.21 (q, 2H, J=7.0 Hz), 4.89 (s, 1H), 6.91 (d, 1H, J=8.7 Hz), 8.00 (dd, 1H, $J_1$=9.5 Hz, $J_2$=2.3 Hz), 8.12 (d, 1H, J=3.1 Hz), 10.95 (bs, 1H). LC-MS (ESI) calcd for $C_{12}H_{12}N_2O_4S$ [M+H$^+$] 281.05, found 281.23 [M+H$^+$].

c) (7-Amino-4H-benzo[1,4]thiazin-3-yl)-acetic acid ethyl ester

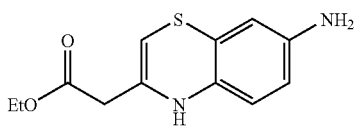

A solution of (7-nitro-4H-benzo[1,4]thiazin-3-yl)-acetic acid ethyl ester (5.8 g, 20.7 mmol) in ethanol (90 mL) was treated with tin (II) chloride and 1.0 M aqueous hydrochloric acid solution (3 mL). The reaction mixture was heated at 100° C. for 3 h. The suspension was allowed to cool and was concentrated in vacuo. The crude material was suspended in ethyl acetate (90 mL) and treated with 6.0 M aqueous sodium hydroxide solution (90 mL). The resulting precipitate was filtered. The filter cake was thoroughly washed with ethyl acetate, the filtrated was washed with saturated aqueous brine solution, and concentrated in vacuo. The crude oil was purified by flash column chromatography (Merck silica gel 60, 40-63 µm, ethyl acetate/hexanes) to afford the desired product, (7-amino-4H-benzo[1,4]thiazin-3-yl)-acetic acid ethyl ester (2.38 g, 9.51 mmol, 46%) as a white solid. $^1$H NMR (400 MHz, CDCl$_3$) δ 1.21 (t, 3H, J=7.1 Hz), 3.30 (s, 2H), 3.43 (bs, 2H), 4.08 (q, 2H, J=7.1 Hz), 4.52 (s, 1H), 6.39 (dd, 1H, $J_1$=8.3 Hz, $J_2$=2.7 Hz), 6.46 (d, 1H, J=2.3 Hz), 6.62 (d, 1H, J=7.6 Hz), 10.38 (bs, 1H). LC-MS (ESI) calcd for $C_{12}H_{14}N_2O_2S$ [M+H$^+$] 251.08, found 251.23 [M+H$^+$].

d) (7-Methanesulfonylamino-4H-benzo[1,4]thiazin-3-yl)-acetic acid ethyl ester

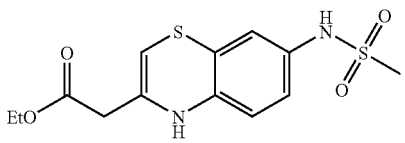

A solution of (7-amino-4H-benzo[1,4]thiazin-3-yl)-acetic acid ethyl ester (2.38 g, 9.51 mmol) in dichloromethane (80 mL) was cooled to 0° C. and treated with triethylamine (3.1 g, 30.4 mmol) followed by dropwise addition of methanesulfonyl chloride (1.37 g, 9.51 mmol). The reaction mixture was stirred at 0° C. for 0.5 h and allowed to warm to 25° C. The reaction mixture was concentrated in vacuo and purified by flash column chromatography (Merck silica gel 60, 40-63 µm, ethyl acetate/hexanes) to afford the desired product, (7-methanesulfonylamino-4H-benzo[1,4]thiazin-3-yl)-acetic acid ethyl ester (2.2 g, 6.7 mmol, 71%) as a light tan solid. $^1$H NMR (400 MHz, CDCl$_3$) δ 1.31 (t, 3H, J=7.0 Hz), 3.00 (s, 3H), 3.43 (s, 2H), 4.19 (quartet, 2H, J=7.1 Hz), 4.73 (s, 1H), 6.28 (s, 1H), 6.85 (d, 1H, J=8.5 Hz), 6.99 (dd, 1H, J$_1$=8.5 Hz, J$_2$=2.4 Hz), 7.12 (d, 1H, J=2.3 Hz), 10.64 (bs, 1H). LC-MS (ESI) calcd for C$_{13}$H$_{16}$N$_2$O$_4$S [M+H$^+$] 329.06, found 329.10 [M+H$^+$].

e) [7-(Methanesulfonyl-tert-butyloxycarbonyl-amino)-4-tert-butyloxycarbonyl-4H-benzo[1,4]thiazin-3-yl]-acetic acid ethyl ester

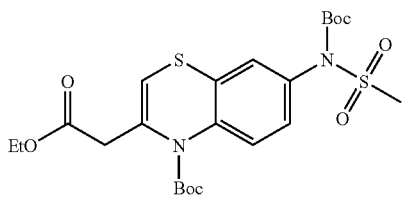

A solution of (7-methanesulfonylamino-4H-benzo[1,4]thiazin-3-yl)-acetic acid ethyl ester (2.2 g, 6.7 mmol) in anhydrous tetrahydrofuran (60 mL) was treated with di-tert-butyl-dicarbonate (3.2 g, 14.7 mmol) and 4-(dimethylamino)pyridine (0.82 g, 6.7 mmol). The reaction mixture was stirred at 25° C. under a nitrogen atmosphere for 3 h. The solvent was removed in vacuo and the residue was dissolved in dichloromethane. The resulting solution was washed with 1.0 M aqueous hydrochloric acid solution, the organic layer was dried over sodium sulfate, filtered, and concentrated in vacuo. The crude oil was purified by flash column chromatography (Merck silica gel 60, 40-63 μm, ethyl acetate/hexanes) to afford the desired product, [7-(methanesulfonyl-tert-butyloxycarbonyl-amino)-4-tert-butyloxycarbonyl-4H-benzo[1,4]thiazin-3-yl]-acetic acid ethyl ester (1.59 g, 3.01 mmol, 45%) as a colorless resin. $^1$H NMR (400 MHz, CDCl$_3$) δ 1.16 (t, 3H, J=7.0 Hz), 1.48 (s, 9H), 1.52 (s, 9H), 3.42 (s, 3H), 3.67 (bs, 2H), 4.07 (q, 2H, J=7.3 Hz), 6.26 (s, 1H), 7.09 (1,1H, J$_1$=0.0 Hz, J$_2$=0.0 Hz), 7.08-7.11 (m, 2H), 7.42 (d, 1H, J=7.8 Hz). LC-MS (ESI) calcd for C$_{23}$H$_{32}$N$_2$O$_8$S$_2$ [M+H$^+$] 529.16, found 429.48 [M-Boc$^+$].

f) [7-(Methanesulfonyl-tert-butyloxycarbonyl-amino)-4-tert-butyloxycarbonyl-1,1-dioxo-1,4-dihydro-1λ$^6$-benzo[1,4]thiazin-3-yl]-acetic acid ethyl ester

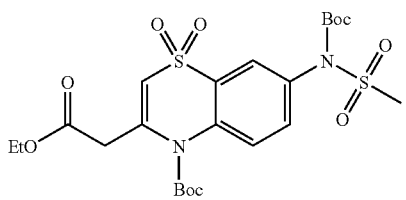

A solution of [7-(methanesulfonyl-tert-butyloxycarbonyl-amino)-4-tert-butyloxycarbonyl-4H-benzo[1,4]thiazin-3-yl]-acetic acid ethyl ester (1.59 g, 3.01 mmol) in dichloromethane (50 mL) was treated with 3-chloroperoxybenzoic acid (2.23 g, 12.9 mmol). The reaction mixture was stirred for 12 h at 25° C. A solution of aqueous sodium thiosulfate (2.0 g, 12.9 mmol) was added, and the reaction was stirred for an additional 0.5 h. The organic layer was separated, washed sequentially with 1.0 M aqueous sodium hydroxide solution, 1.0 M aqueous hydrochloric acid solution, saturated aqueous sodium bicarbonate solution, and saturated aqueous brine solution, dried over sodium sulfate, filtered, and concentrated in vacuo. The crude oil was purified by flash column chromatography (Merck silica gel 60, 40-63 μm, ethyl acetate/hexanes) to afford the desired product, [7-(methanesulfonyl-tert-butyloxycarbonyl-amino)-4-tert-butyloxycarbonyl-1,1-dioxo-1,4-dihydro-1λ$^6$-benzo[1,4]thiazin-3-yl]-acetic acid ethyl ester (1.1 g, 1.96 mmol, 64%) as a white solid. $^1$H NMR (400 MHz, CDCl$_3$) δ 1.23 (t, 3H, J=7.0 Hz), 1.50 (s, 9H), 1.56 (s, 9H), 3.46 (s, 3H), 3.81 (s, 2H), 4.15 (q, 2H, J=7.4 Hz), 6.40 (s, 1H), 7.45 (dd, 1H, J$_1$=9.1 Hz, J$_2$=2.7 Hz), 7.72 (d, 1H, J=2.3 Hz), 7.91 (d, 1H, J=8.6 Hz). LC-MS (ESI) calcd for C$_{23}$H$_{32}$N$_2$O$_8$S$_2$ [M+H$^+$] 560.16, found 361.18 [M-(2× Boc)$^+$].

g) (7-Methanesulfonylamino-1,1-dioxo-1,4-dihydro-1λ$^6$-benzo[1,4]thiazin-3-yl)-acetic acid ethyl ester

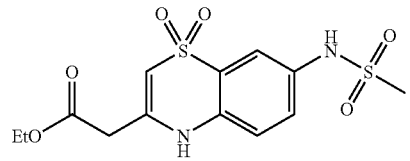

A solution of [7-(methanesulfonyl-tert-butyloxycarbonyl-amino)-4-tert-butyloxycarbonyl-1,1-dioxo-1,4-dihydro-1λ$^6$-benzo[1,4]thiazin-3-yl]-acetic acid ethyl ester (0.30 g, 0.54 mmol) in 1:1 dichloromethane/trifluoroacetic acid was stirred at 25° C. for 2 h. The reaction mixture was concentrated in vacuo and the residue was dissolved in ethyl acetate. The solution was washed with saturated aqueous sodium bicarbonate solution and saturated aqueous brine solution. The organic layer was dried over sodium sulfate, filtered, and concentrated in vacuo to afford the desired product, (7-methanesulfonylamino-1,1-dioxo-1,4-dihydro-1λ$^6$-benzo[1,4]thiazin-3-yl)-acetic acid ethyl ester (0.17 g, 0.47 mmol, 86%) as a yellow solid. $^1$H NMR (400 MHz, CDCl$_3$) δ 1.32 (t, 3H, J=6.9 Hz), 3.03 (s, 3H), 4.02 (s, 2H), 4.21 (q, 2H, J=7.0 Hz), 5.02 (s, 1H), 6.96 (s, 1H), 7.02 (d, 1H, J=8.4 Hz), 7.53 (dd, 1H, J$_1$=8.7 Hz, J$_2$=2.4 Hz), 7.65 (d, 1H, J=2.2 Hz), 10.73 (s, 1H). LC-MS (ESI) calcd for C$_{13}$H$_{16}$N$_2$O$_6$S$_2$ [M+H$^+$] 361.04, found 361.18 [M+H$^+$].

h) (7-Methanesulfonylamino-1,1-dioxo-1,4-dihydro-1λ$^6$-benzo[1,4]thiazin-3-yl)-acetic acid

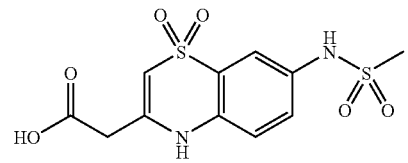

A solution of (7-methanesulfonylamino-1,1-dioxo-1,4-dihydro-1λ$^6$-benzo[1,4]thiazin-3-yl)-acetic acid ethyl ester (0.245 g, 0.680 mmol) in methanol (15 mL) was cooled to 0° C. in an ice-water bath and treated with 2.0 M aqueous lithium hydroxide solution (1.7 mL, 3.40 mmol). The reaction mixture was allowed to warm to 25° C. and stirred for 1 h. The reaction was poured into 0.5 M aqueous hydrochloric acid solution (50 mL) on ice, extracted with ethyl acetate (3×50 mL), dried over magnesium sulfate, filtered, and concentrated in vacuo to give an orange solid. The crude solid was triturated with diethyl ether to afford the desired product, (7-methanesulfonylamino-1,1-dioxo-1,4-dihydro-1λ⁶-benzo[1,4]thiazin-3-yl)-acetic acid (0.175 g, 0.526 mmol, 77%) as a light orange solid. LC-MS (ESI) calcd for $C_{11}H_{12}N_2O_6S_2$ 332.4, found 333.3 [M+H⁺].

i) cis-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,4]thiazin-7-yl}-methanesulfonamide

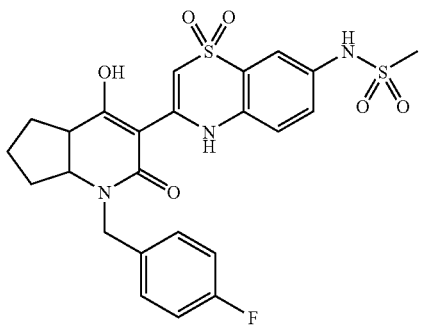

A solution of cis-2-(4-fluoro-benzylamino)-cyclopentanecarboxylic acid ethyl ester (prepared as described in Example 11, 154 mg, 0.580 mmol), (7-methanesulfonylamino-1,1-dioxo-1,4-dihydro-1λ⁶-benzo[1,4]thiazin-3-yl)-acetic acid (175 mg, 0.527 mmol), and 1-(3-dimethylaminopropyl)-3-ethylcarbodiimide hydrochloride (117 mg, 0.609 mmol) in anhydrous N,N-dimethylformamide (6 mL) was treated with N-methylmorpholine (123 mg, 134 µL, 1.22 mmol). The reaction was stirred for 1 h at 25° C., diluted with 1.0 M aqueous hydrochloric acid solution (20 mL), and extracted with ethyl acetate (3×50 mL). The combined organic layers were dried over magnesium sulfate, filtered, and concentrated in vacuo. The residue was taken up in ethanol (6 mL) and treated with a 60% oil dispersion of sodium hydride (93 mg, 3.87 mmol). The reaction was heated at 70° C. for 1 h, allowed to cool to 25° C., and quenched with 1.0 M aqueous hydrochloric acid solution (50 mL). The resulting mixture was extracted with ethyl acetate (3×50 mL), and the combined organic layers were dried over magnesium sulfate, filtered, and concentrated in vacuo. The crude oil was purified by prep-HPLC [Column: Thomson C18 ODSA, 5 micron, 50×21.2 mm ID; 45-70% acetonitrile in water; 30 mL/min flow rate for 4 min run] to afford the desired product, cis-N-{3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,4]thiazin-7-yl}-methanesulfonamide (60 mg, 0.112 mmol, 21%), as a light yellow solid. ¹H NMR (400 MHz, CDCl₃) ¹H NMR (400 MHz, Acetone-d₆) δ: 1.34-1.47 (m, 1H), 1.50-1.91 (m, 4H), 2.32-2.42 (m, 1H), 2.96-3.03 (m, 1H), 3.11 (s, 3H), 3.83-3.94 (m, 1H), 4.54-4.67 (m, 1H), 4.97-5.07 (m, 1H), 5.37-5.78 (m, 2H), 7.07-7.14 (m, 2H), 7.36-7.54 (m, 3H), 7.66-7.71 (m, 1H), 7.81-7.83 (m, 1H), 8.95 (bs, 1H). LC-MS calcd for $C_{24}H_{24}FN_3O_6S_2$ 533.6, found 534.3 [M+H⁺].

EXAMPLE 26

(4aS,7aR)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide

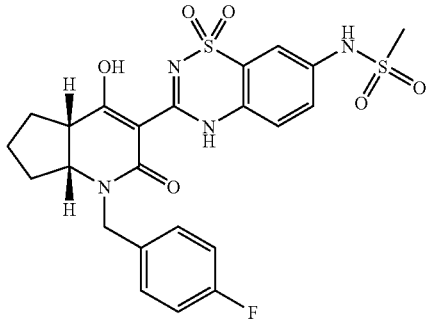

a) (1S,2R)-2-Amino-cyclopentanecarboxylic acid methyl ester hydrochloride

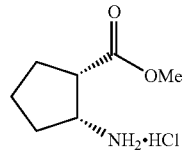

(1S,2R)-2-Amino-cyclopentanecarboxylic acid hydrochloride (126 mg, 0.76 mmol) was dissolved in a 1:1 mixture of benzene and methanol (8 mL). The mixture was cooled to 0° C. A 2.0 M solution of (trimethylsilyl)diazomethane in hexanes (0.57 mL, 1.14 mmol) was added and the reaction was stirred at 25° C. for 30 min. The mixture was concentrated and dried in vacuo. The crude product was directly used in the next step.

b) (1S,2R)-2-(4-Fluoro-benzylamino)-cyclopentanecarboxylic acid methyl ester

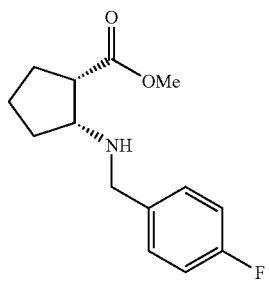

To a solution of (1S,2R)-2-amino-cyclopentanecarboxylic acid methyl ester hydrochloride (136 mg, 0.76 mmol) in tetrahydrofuran (10 mL) at 25° C. was added magnesium sulfate (200 mg), triethylamine (0.11 mL, 0.80 mmol), and 4-fluorobenzaldehyde (0.17 mL, 1.56 mmol) sequentially.

The reaction was stirred at 25° C. for 16 h. The mixture was passed through a short pad of Celite and the filtrate was concentrated and dried in vacuo. The residue was re-dissolved in methanol (10 mL) at 25° C. To this solution was added slowly sodium borohydride (59 mg, 1.56 mmol). The mixture was stirred at 25° C. for 1 h. It was then poured into a saturated aqueous sodium bicarbonate solution (10 mL) and the mixture was extracted into ethyl acetate (20 mL). The organic layer was dried over magnesium sulfate, filtered, and concentrated in vacuo to afford a clear oil. Purification by flash column chromatography (Merck silica gel 60, 40-63 µm; 0-15% ethyl acetate in hexanes) afforded the desired product, (1S,2R)-2-(4-fluoro-benzylamino)-cyclopentanecarboxylic acid methyl ester (116 mg, 0.46 mmol, 79%), as a clear oil. $^1$H NMR (400 MHz, CDCl$_3$) δ: 1.55-1.73 (2H, m), 1.83-1.93 (3H, m), 1.99-2.08 (1H, m), 2.97 (1H, dd, J$_1$=14.4 Hz, J$_2$=8.0 Hz), 3.31 (1H, dd, J$_1$=14.4 Hz, J$_2$=7.2 Hz), 3.70 (3H, s), 3.77 (2H, dd, J$_1$=19.6 Hz, J$_2$=12.0 Hz), 4.67 (1H, s), 6.96-7.06 (2H, m), 7.26-7.35 (2H, m). LC-MS (ESI) calcd for C$_{14}$H$_{18}$FNO$_2$ 251.30, found 252.1 [M+H$^+$].

c) (4aS,7aR)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

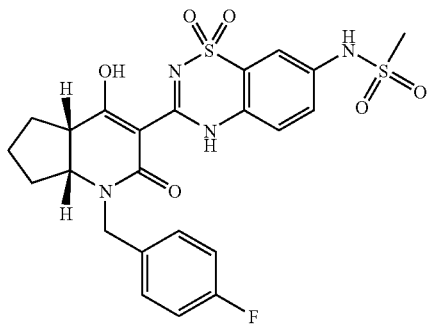

(1S,2R)-2-(4-Fluoro-benzylamino)-cyclopentanecarboxylic acid methyl ester (97 mg, 0.39 mmol) and (7-methanesulfonylamino-1,1-dioxo-1,4-dihydro-1λ$^6$-benzo[1,2,4]thiadiazin-3-yl)-acetic acid (prepared as described in Example 1j, 143 mg, 0.43 mmol) were dissolved in a 1:1 mixture of dichloromethane and N,N'-dimethylformamide (6 mL). 4-Dimethylaminopyridine (12 mg, 0.10 mmol) was then added. The mixture was stirred until everything dissolved, approximately 5 min. 1-(3-Dimethylaminopropyl)-3-ethylcarbodiimide hydrochloride (0.15 g, 0.78 mmol) was added and the mixture was stirred at 25° C. for 4 h. The reaction was stirred at 25° C. for 16 h. The reaction was quenched via addition of saturated aqueous sodium bicarbonate solution (20 mL). The mixture was extracted with ethyl acetate (3×30 mL). The organic layers were combined and washed with saturated aqueous brine solution (20 mL). The resulting solution was dried over magnesium sulfate, filtered, and concentrated in vacuo to afford a golden oil.

The oil was dissolved in ethanol (10 mL). A 21% w/w solution of sodium ethoxide in ethanol (0.12 mL, 0.31 mmol) was added. The reaction was stirred at 60° C. The reaction was quenched via the addition of a 1.0 M aqueous hydrochloric acid solution (10 mL). The mixture was extracted with ethyl acetate (3×20 mL). The organic layer was further washed with saturated sodium bicarbonate solution (2×20 mL), saturated aqueous brine solution (20 mL), dried over magnesium sulfate, filtered, and concentrated in vacuo to afford a clear oil. The crude material was purified by flash column chromatography (Merck silica gel 60, 40-63 µm; 0-5% methanol in dichloromethane) to afford the desired product, (4aS,7aR)-N-{3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide (60 mg, 0.11 mmol, 28%), as a white solid. $^1$H NMR (400 MHz, DMSO-d$_6$) δ: 1.46-1.61 (4H, m), 1.95-2.12 (2H, m), 3.07 (3H, s), 3.85 (1H, bs), 4.48 (1H, bs), 4.91 (1H, d, J=14.8 Hz), 7.16 (2H, t, J=8.4 Hz), 7.40 (2H, bs), 7.50-7.61 (3H, m), 10.18 (1H, s). LC-MS (ESI) calcd for C$_{23}$H$_{23}$FN$_4$O$_6$S$_2$ 534.58, found 535.1 [M+H].

EXAMPLE 27

(4aR,7aS)-N-{3-[1-(3,4-Difluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

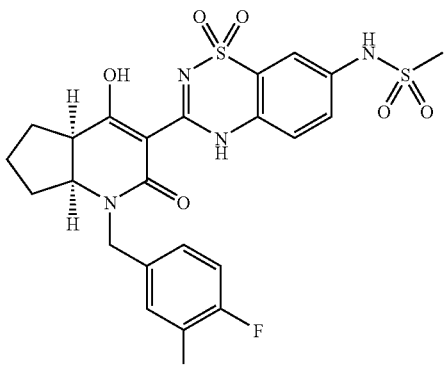

a) (1R,2S)-2-(3,4-Difluoro-benzylamino)-cyclopentanecarboxylic acid methyl ester

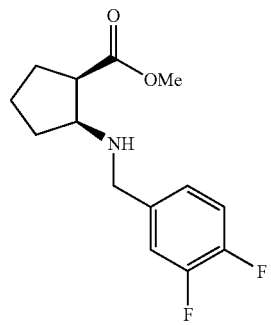

The crude (1R,2S)-2-amino-cyclopentanecarboxylic acid methyl ester hydrochloride (prepared as described in Example 11a, 0.54 mmol) was dissolved in tetrahydrofuran (6 mL). Magnesium sulfate (185 mg), triethylamine (80 µL, 0.57 mmol) and 3,4-difluoro-benzaldehyde (122 µL, 1.11 mmol) were added at 25° C. and the resulted mixture was stirred at 25° C. for 16 h. The solid was filtered off and the filtrate was concentrated in vacuo to give an oil. This oil was dissolved in methanol (10 mL) and sodium borohydride (42 mg, 1.11 mmol) was then added portionwise. The mixture was stirred at 25° C. for 1 h. Saturated aqueous sodium bicarbonate solution (2 mL), water (2 mL) and saturated aqueous brine solution (1 mL) were added. The mixture was extracted with ethyl acetate (3×10 mL) and the organic layer was dried over anhydrous sodium sulfate, filtered, and concentrated in vacuo to afford the desired product, (1R,2S)-2-(3,4-difluoro-benzylamino)-cyclopentanecarboxylic acid methyl ester (126.1 mg, 0.469 mmol, 86.7% over two steps). This crude product was directly used in next step without further purification. LC-MS (ESI) calcd for $C_{14}H_{17}F_2NO_2$ 269.1, found 270.1 [M+H$^+$].

c) (1R,2S)-2-{(3,4-Difluoro-benzyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid methyl ester

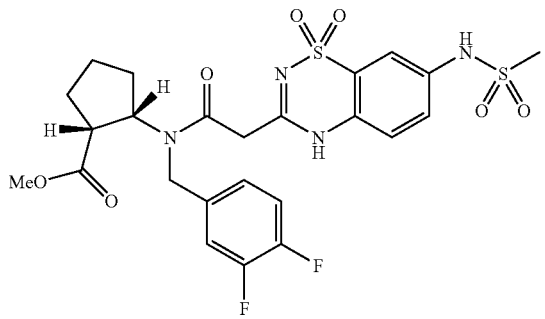

(1R,2S)-2-(3,4-Difluoro-benzylamino)-cyclopentanecarboxylic acid methyl ester (126.1 mg, 0.47 mmol) was mixed with (7-methanesulfonylamino-1,1-dioxo-1,4-dihydro-1λ$^6$-benzo[1,2,4]thiadiazin-3-yl)-acetic acid (prepared as described in Example 1j, 157 mg, 0.47 mmol) and dissolved in N,N-dimethylformamide (6 mL). A 1.0 M solution of N,N'-dicyclohexylcarbodiimide in dichloromethane (0.52 mL, 0.52 mmol) was added at 25° C. The reaction mixture was stirred at 25° C. for 16 h. LC-MS analysis confirmed the formation of both the desired product, (1R,2S)-2-{(3,4-difluoro-benzyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid methyl ester along with a small amount of the cyclized product, (4aR,7aS)-N-{3-[1-(3,4-difluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide. LC-MS (ESI) calcd for $C_{24}H_{26}F_2N_4O_7S_2$ 584.1, found 585.2 [M+H$^+$].

d) (4aR,7aS)-N-{3-[1-(3,4-Difluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

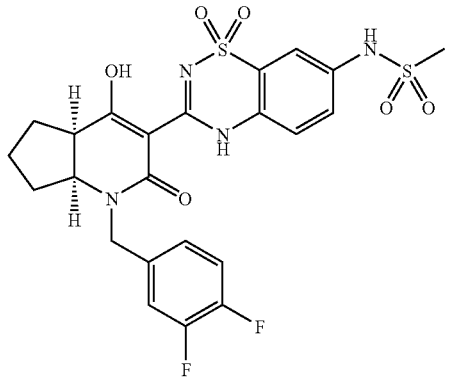

Triethylamine (0.13 mL, 0.94 mmol) was added into the crude reaction mixture containing (1R,2S)-2-{(3,4-difluoro-benzyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid methyl ester along with a small amount of the cyclized product, (4aR,7aS)-N-{3-[1-(3,4-difluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide. The resulting mixture was stirred at 25° C. for 2 days. A solid precipitated out and was removed by vacuum filtration. The filtrate was concentrated in vacuo and was further purified by prep-HPLC to afford the desired product, (4aR,7aS)-N-{3-[1-(3,4-difluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide (72.5 mg, 0.131 mmol, 27.9% over two steps). $^1$H NMR (DMSO-d$_6$) δ: 1.43-1.62 (m, 3H), 1.95-2.16 (m, 3H), 3.06 (s, 3H), 3.30-3.40 (m, 1H), 3.82-3.92 (m, 1H), 4.42-4.52 (m, 1H), 4.89 (d, 1H, J=14.8 Hz), 7.17-7.23 (m, 1H), 7.34-7.46 (m, 2H), 7.51 (dd, 1H, $J_1$=8.8 Hz, $J_2$=2.4 Hz), 7.56-7.61 (m, 2H), δ 10.18 (s, 1H). LC-MS (ESI) calcd for $C_{23}H_{22}F_2N_4O_6S_2$ 552.1, found 553.2 [M+H$^+$]. Anal. calcd for $C_{23}H_{22}F_2N_4O_6S_2$ 0.5H$_2$O: C, 49.19; H, 4.13; N, 9.98; found: C, 49.01; H, 3.90; N, 10.06. [α]$_D$=−49.6 (1.93 mg/mL in CH$_3$CN).

EXAMPLE 28

(4aR,7aS)-N-{3-[4-Hydroxy-1-(3-methyl-butyl)-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

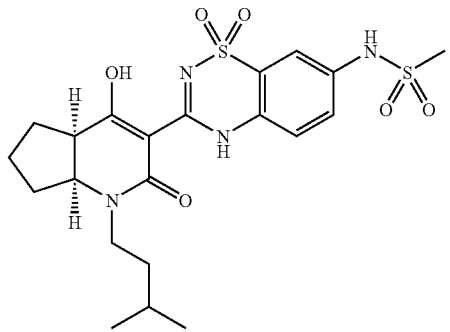

a) (1R,2S)-2-(4'-Fluorobenzylamino)cyclopentanecarboxylic acid ethyl ester complex with (S)-(+)-mandelic Acid

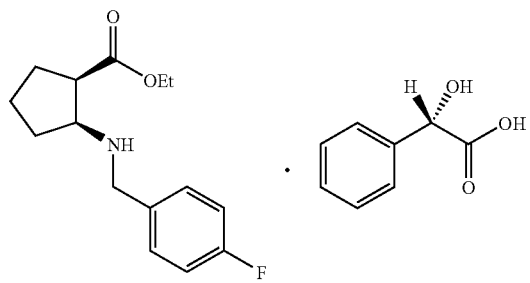

A solution of (S)-(+)-mandelic acid (11.40 g, 74.9 mmol, 1.0 equiv) in ethyl acetate (150 mL) was slowly poured over 1 min into a solution of cis-2-(4'-fluorobenzylamino)-cyclopentanecarboxylic acid ethyl ester (prepared as described in Example 11, 19.9 g, 74.9 mmol) in ethyl acetate (200 mL) at 23° C. The resulting suspension was stirred at 23° C. for 19 h, and then was filtered through a medium frit. The collected white powder was washed with diethyl ether (1×40 mL) and was air-dried. Recrystallization of this material from ethyl acetate afforded the desired product, (1R,2S)-2-(4'-fluorobenzylamino)-cyclopentanecarboxylic acid ethyl ester complex with (S)-(+)-mandelic acid (12.4 g, 29.7 mmol, 40%, >99% de) as white needles. $^1$H NMR (CDCl$_3$) δ: 1.26 (3H, t, J=7.4), 1.58-1.67 (1H, m), 1.73-1.86 (2H, m), 1.89-2.08 (3H, m), 2.93-2.98 (1H, m), 3.44-3.49 (1H, m), 3.86 (1H, d, J=13.0), 4.06 (1H, d, J=12.7), 4.08-4.20 (2H, m), 4.97 (1H, s), 6.77 (2H, bs), 6.89-6.95 (2H, m), 7.18-7.21 (2H, m), 7.25-7.27 (1H, m), 7.29-7.33 (2H, m), 7.45-7.48 (2H, m). The diastereomeric purity of this material was assessed by careful examination of the compound's $^1$H NMR spectrum obtained at 400 MHz in CDCl$_3$ at 23° C. These conditions enabled the resolution of the compound's resonances and a diastereomeric impurity located at 3.86 and 3.84 ppm, respectively (both doublets; each half of an "AB quartet" spin system). The amount of the impurity present in the compound prior to recrystallization was estimated to be no more than 2.5% by integration of these signals. Resonances associated with the impurity could not be detected by $^1$H NMR following a single recrystallization of the compound.

b) (1R,2S)-2-Amino-cyclopentanecarboxylic acid ethyl ester hydrochloride

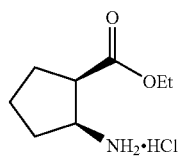

(1R,2S)-2-(4'-Fluorobenzylamino)cyclopentanecarboxylic acid ethyl ester complex with (S)-(+)-mandelic acid (10 g, 24.0 mmol) was dissolved in methanol (200 mL) at 25° C. Palladium on carbon (2.0 g, 5%, "wet") was added and the resulting suspension was maintained under a hydrogen atmosphere (balloon) at 50° C. for 6 h. After cooling to 25° C., the mixture was filtered through Celite and the filtrate was concentrated in vacuo. The residue was partitioned between saturated aqueous sodium bicarbonate solution (150 mL) and ethyl acetate (2×150 mL). The organic layers were dried over sodium sulfate and were concentrated in vacuo. The residue was dissolved in ethyl acetate (30 mL) and a 4.0 M solution of hydrochloric acid in 1,4-dioxane (10 mL) was slowly added at 25° C. After 1 h, the mixture was concentrated in vacuo to afford the desired product, (1R,2S)-2-amino-cyclopentanecarboxylic acid ethyl ester hydrochloride (4.41 g, 22.8 mmol, 95%), as a white solid. LC-MS (ESI) calcd for C$_8$H$_{15}$NO$_2$ 157.11, found 158.2 [M+H$^+$].

c) (1R,2S)-2-(3-Methyl-butylamino)-cyclopentanecarboxylic acid ethyl ester

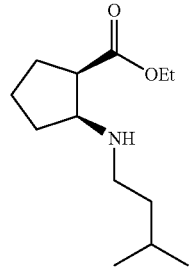

(1R,2S)-2-Amino-cyclopentanecarboxylic acid ethyl ester hydrochloride (0.81 g, 4.18 mmol) was dissolved in methanol (40 mL). Sodium acetate (0.69 g, 8.36 mmol) was added followed by 4 Å powdered molecular sieve (0.81 g). Isovaleraldehyde (0.36 g, 4.18 mmol) was then added followed by sodium cyanoborohydride (0.6 g, 10.45 mmol). The reaction mixture stirred at 25° C. for 16 h. The mixture was poured into saturated aqueous sodium bicarbonate solution (150 mL). The aqueous layer was extracted with ethyl acetate (2×150 mL). The organic layer was dried over sodium sulfate and concentrated in vacuo to afford the crude product, (1R,2S)-2-(3-methyl-butylamino)-cyclopentanecarboxylic acid ethyl ester (0.58 g, 2.55 mmol, 61%), as a clear oil. LC-MS (ESI) calcd for C$_{13}$H$_{25}$NO$_2$ 227.19, found 228.2 [M+H$^+$].

d) (1R,2S)-2-[[2-(7-Methanesulfonylamino-1,1-dioxo-1,4-dihydro-1λ$^6$-benzo[1,2,4]thiadiazin-3-yl)-acetyl]-(3-methyl-butyl)-amino]-cyclopentanecarboxylic acid ethyl ester

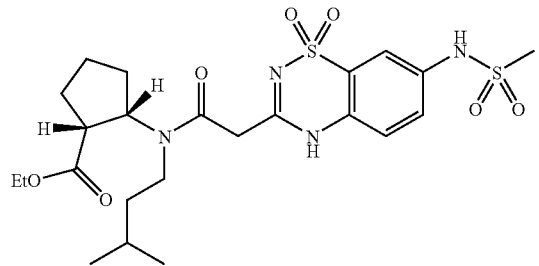

(7-Methanesulfonylamino-1,1-dioxo-1,4-dihydro-1λ$^6$-benzo[1,2,4]thiadiazin-3-yl)-acetic acid (prepared as described in Example 1j, 0.1 g, 0.3 mmol) was dissolved in anhydrous N,N-dimethylformamide (3 mL). (1R,2S)-2-(3-Methyl-butylamino)-cyclopentanecarboxylic acid ethyl ester (0.068 g, 0.3 mmol) was added followed by 1-(3-dimethylaminopropyl)-3-ethylcarbodiimide hydrochloride (0.06 g, 0.315 mmol). Then N-methylmorpholine (0.064 g, 0.63 mmol) was added into the above reaction mixture. The mixture was stirred at 25° C. for 7 h. The solution was poured into a 1.0 M aqueous hydrochloric acid solution (50 mL). The aqueous layer was extracted with ethyl acetate (2×50 mL). The organic layer was dried over sodium sulfate and concentrated in vacuo to afford the crude product, (1R,2S)-2-[[2-(7-methanesulfonylamino-1,1-dioxo-1,4-dihydro-1λ$^6$-benzo[1,2,4]thiadiazin-3-yl)-acetyl]-(3-methyl-butyl)-amino]-cyclopentanecarboxylic acid ethyl ester (0.3 mmol), as a light yellow oil, which was used directly for next step. LC-MS (ESI) calcd for C$_{23}$H$_{34}$N$_4$O$_7$S$_2$ 542.19, found 543.3 [M+H$^+$].

e) (4aR,7aS)-N-{3-[4-Hydroxy-1-(3-methyl-butyl)-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide

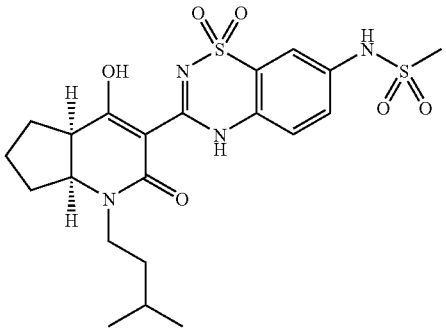

(1R,2S)-2-[[2-(7-Methanesulfonylamino-1,1-dioxo-1,4-dihydro-1λ⁶-benzo[1,2,4]thiadiazin-3-yl)-acetyl]-(3-methyl-butyl)-amino]-cyclopentanecarboxylic acid ethyl ester (0.3 mmol) was dissolved in ethanol (3 mL), a 21% w/w solution of sodium ethoxide in ethanol (0.56 mL, 1.5 mmol) was added into the above solution. The mixture was stirred at 60° C. for 2 h and allowed to cool to 25° C. The mixture was poured into 0.5 M aqueous hydrochloric acid solution (50 mL). The aqueous layer was extracted with ethyl acetate (2×50 mL). The organic layer was dried over sodium sulfate and concentrated in vacuo to afford the crude product, which was purified by flash column chromatography (Teledyne Isco RediSep Column; 100% ethyl acetate in hexanes) to afford the desired product, (4aR,7aS)-N-{3-[4-hydroxy-1-(3-methyl-butyl)-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide (0.054 g, 0.109 mmol, 36.3% over two steps), as an off-white solid. $^1$H NMR (400 MHz, DMSO-$d_6$) δ: 0.93 (6H, d, J=6.1 Hz), 1.35-1.65 (7H, m), 2.06-2.18 (2H, m), 3.06 (3H, s), 3.17-3.34 (3H, m), 3.65-3.73 (1H, m), 3.92 (1H, bs), 7.49-7.56 (3H, m), 10.16 (1H, bs). LC-MS (ESI) calcd for $C_{21}H_{28}N_4O_6S_2$ 496.15, found 497.4 [M+H⁺].

EXAMPLE 29

(4aR,7aS)-N-{3-[1-(3,3-Dimethyl-butyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4-]thiadiazin-7-yl}-methanesulfonamide

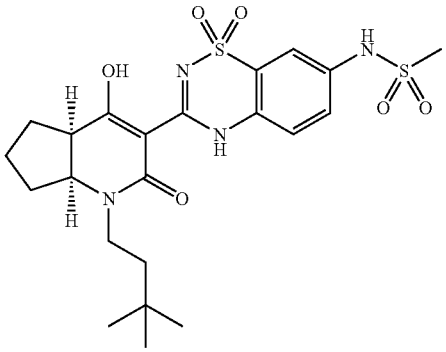

a) (1R,2S)-2-(3,3-Dimethyl-butylamino)-cyclopentanecarboxylic acid ethyl ester

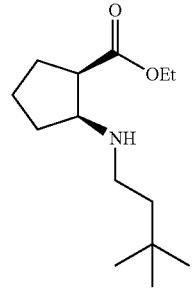

Sodium acetate (0.423 g, 5.16 mmol), powdered 4 Å molecular sieves (1.0 g), 3,3-dimethylbutyraldehyde (0.324 mL, 2.58 mmol) and sodium cyanoborohydride (0.324 mg, 5.16 mmol) were added sequentially to a solution of (1R,2S)-2-amino-cyclopentanecarboxylic acid ethyl ester hydrochloride (prepared as described in Example 28b, 0.500 g, 2.58 mmol) in methanol (13 mL) at 25° C. The reaction mixture was stirred at 25° C. for 3.5 h, and then was diluted with ethyl acetate (50 mL) and half-saturated aqueous sodium bicarbonate solution (100 mL). After stirring for 20 min at 25° C., the mixture was filtered through Celite and the filtrate was partitioned between half-saturated aqueous sodium bicarbonate solution (50 mL) and ethyl acetate (2×100 mL). The organic layers were washed with saturated aqueous brine solution (100 mL), dried over sodium sulfate, filtered, and were concentrated in vacuo. The residue was purified by flash column chromatography (Analogix SuperFlash Column; 0-40% ethyl acetate in hexanes) to afford the desired product, (1R,2S)-2-(3,3-dimethyl-butylamino)-cyclopentanecarboxylic acid ethyl ester (0.210 g, 0.87 mmol, 33%), as a clear oil. $^1$H NMR (400 MHz, CDCl$_3$) δ: 0.90 (s, 9H), 1.28 (t, 3H, J=7.1 Hz), 1.31-1.40 (m, 2H), 1.55-1.66 (m, 3H), 1.82-2.02 (m, 5H), 2.58 (septet, 2H, J=3.3 Hz), 2.94 (q, 1H, J=7.1 Hz), 3.27 (q, 1H, J=7.0 Hz), 4.14 (q, 2H, J=7.3 Hz). LC-MS (ESI) calcd for $C_{14}H_{27}NO_2$ 241.2, found 242.2 [M+H⁺].

b) (4aR,7aS)-N-{3-[1-(3,3-Dimethyl-butyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide

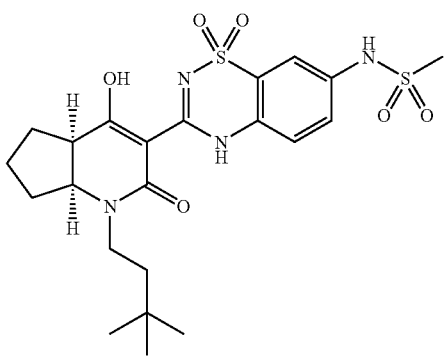

(7-Methanesulfonylamino-1,1-dioxo-1,4-dihydro-1λ$^6$-benzo[1,2,4]thiadiazin-3-yl)-acetic acid (prepared as described in Example 1j, 0.100 g, 0.300 mmol), 1-(3-dimethylaminopropyl)-3-ethylcarbodiimide hydrochloride (0.060 g, 0.315 mmol) and N-methylmorpholine (0.070 mL, 0.630 mmol) were added sequentially to a solution of (1R,2S)-2-(3,3-dimethyl-butylamino)-cyclopentanecarboxylic acid ethyl ester (0.072 g, 0.300 mmol) in N,N-dimethylformamide (4 mL) at 25° C. The reaction mixture was stirred at 25° C. for 3 h, and then was partitioned between 1.0 M aqueous hydrochloric acid solution (110 mL) and ethyl acetate (2×110 mL). The organic layers were washed with saturated aqueous brine solution (100 mL), dried over sodium sulfate, filtered, and were concentrated in vacuo. The residue was dissolved in ethanol (4 mL) at 25° C. A 21% w/w solution of sodium ethoxide in ethanol (0.244 mL, 0.600 mmol) was added and the reaction mixture was heated to 60° C. for 2 h. After cooling to 25° C. and stirring for 16 h, the reaction mixture was slowly added to 1.0 M aqueous hydrochloric acid solution (50 mL) at 0° C. The resulting precipitate was collected by filtration and dried in vacuo, then was triturated with a small amount of methanol (ca. 0.5 mL) to afford the desired product, (4aR,7aS)-N-{3-[1-(3,3-dimethyl-butyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide (0.083 g, 0.163 mmol, 54%), as a white solid. $^1$H NMR (400 MHz, CDCl$_3$) δ: 1.00 (s, 9H), 1.50-1.82 (m, 6H), 1.94-2.47 (m, 4H), 2.94-3.39 (m, 2H), 3.06 (s, 3H), 3.68-3.82 (m, 2H), 6.99 (bs, 1H), 7.21 (dd, 1H, J$_1$=28.7 Hz, J$_2$=8.4 Hz), 7.63 (t, 1H, J=8.9 Hz), 7.67-7.69 (m, 1H). LC-MS (ESI) calcd for C$_{22}$H$_{30}$N$_4$O$_6$S$_2$ 510.16, found 511.4 [M+H$^+$].

EXAMPLE 30

(4aR,7aS)-N-[3-(1-Cyclopropylmethyl-4-hydroxy-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide

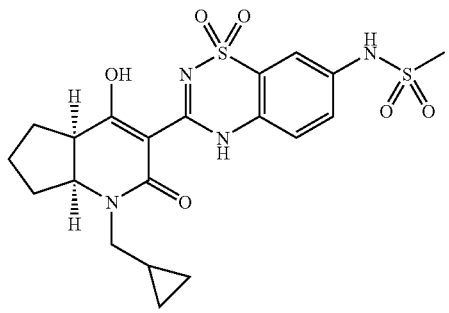

a) (1R,2S)-2-(Cyclopropylmethyl-amino)-cyclopentanecarboxylic acid ethyl ester

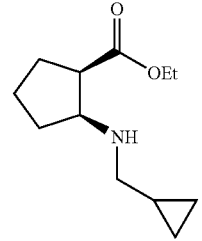

Sodium acetate (0.423 g, 5.16 mmol), powdered 4 Å molecular sieves (0.60 g), cyclopropanecarboxaldehyde (0.193 mL, 2.58 mmol) and sodium cyanoborohydride (0.324 mg, 5.16 mmol) were added sequentially to a solution of (1R,2S)-2-amino-cyclopentanecarboxylic acid ethyl ester hydrochloride (prepared as described in Example 28b, 0.500 g, 2.58 mmol) in methanol (15 mL) at 25° C. The reaction mixture was stirred at 25° C. for 16 h, then was acidified to pH=2 by the addition of 1.0 M aqueous hydrochloric acid solution. After stirring for 5 min at 25° C., the mixture was partitioned between half-saturated aqueous sodium bicarbonate solution (150 mL) and ethyl acetate (3×50 mL). The organic layers were washed with saturated aqueous brine solution (100 mL), dried over sodium sulfate, filtered, and were concentrated in vacuo. The residue was purified by flash column chromatography (Analogix SuperFlash Column; 0-40% ethyl acetate in hexanes) to afford the desired product, (1R,2S)-2-(cyclopropylmethyl-amino)-cyclopentanecarboxylic acid ethyl ester (0.101 g, 0.478 mmol, 18%), as a clear oil. $^1$H NMR (400 MHz, CDCl$_3$) δ: 0.00-0.07 (m, 2H), 0.38-0.43 (m, 2H), 0.84-0.91 (m, 1H), 1.23 (t, 3H, J=7.2 Hz), 1.48-1.61 (m, 2H), 1.76-1.87 (m, 3H), 1.91-1.98 (m, 1H), 2.29-2.34 (m, 1H), 2.46-2.51 (m, 1H), 2.84-2.90 (m, 1H), 3.20-3.26 (m, 1H), 3.63 (s, 1H), 4.09 (q, 2H, J=7.0 Hz). LC-MS (ESI) calcd for C$_{12}$H$_{21}$NO$_2$ 211.16, found 212.4 [M+H$^+$].

b) (4aR,7aS)-N-[3-(1-Cyclopropylmethyl-4-hydroxy-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide

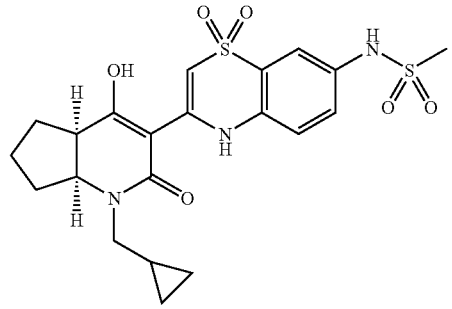

(7-Methanesulfonylamino-1,1-dioxo-1,4-dihydro-1λ$^6$-benzo[1,2,4]thiadiazin-3-yl)-acetic acid (prepared as described in Example 1j, 0.075 g, 0.225 mmol), 1-(3-dimethylaminopropyl)-3-ethylcarbodiimide hydrochloride (0.045 g, 0.236 mmol) and N-methylmorpholine (0.052 mL, 0.473 mmol) were added sequentially to a solution of (1R,2S)-2-(cyclopropylmethyl-amino)-cyclopentanecarboxylic acid ethyl ester (0.048 g, 0.225 mmol) in N,N-dimethylformamide (3 mL) at 25° C. The reaction mixture was stirred at 25° C. for 16 h, and then was partitioned between 1.0 M aqueous hydrochloric acid solution (100 mL) and ethyl acetate (2×100 mL). The organic layers were washed with saturated aqueous brine solution (100 mL), dried over sodium sulfate, filtered, and were concentrated in vacuo. The residue was dissolved in ethanol (4 mL) at 25° C. A 21% w/w solution of sodium ethoxide in ethanol (0.167 mL, 0.450 mmol) was added and the reaction mixture was heated to 60° C. for 1.5 h. After cooling to 25° C., the reaction mixture was partitioned between 1.0 M aqueous hydrochloric acid solution (100 mL) and ethyl acetate (2×75 mL). The organic layers were washed with saturated aqueous brine solution (100 mL), dried over sodium sulfate, filtered, and were concentrated in vacuo. The residue was purified by flash column chromatography (Analogix SuperFlash Column; 30-80% ethyl acetate in hexanes) to afford the desired product, (4aR,7aS)-N-[3-(1-cyclopropylmethyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide (0.065 g, 0.135 mmol, 60%), as a white solid. $^1$H NMR (400 MHz, CDCl$_3$) δ: 0.28-0.40 (m, 2H), 0.56-0.68 (m, 2H), 1.02-1.18 (m, 1H), 1.60-1.83 (m, 4H), 1.95-2.51 (m, 3H), 2.99-3.06 (m, 1H), 3.06 (d, 3H, J=3.3 Hz), 3.16-3.26 (m, 1H), 3.58-3.64 (m, 1H), 3.92 (q, 1H, J=7.7 Hz), 7.00 (s, 1H), 7.22 (d, 1H, J=8.4 Hz), 7.62-7.66 (m, 1H), 7.68-7.70 (m, 1H). LC-MS (ESI) calcd for C$_{20}$H$_{24}$N$_4$O$_6$S$_2$ 480.11, found 481.2 [M+H$^+$].

EXAMPLE 31

(4aS, 8aR)-N-{3-[1-(4-Fluoro-benzyl)-4-hydroxy-2-oxo-1,2,4a,5,6,7,8,8a-octahydro-quinolin-3-yl]-1,1-dioxo-1,4-dihydro-1$\lambda^6$-benzo[1,2,4]thiadiazin-7-yl}-methanesulfonamide

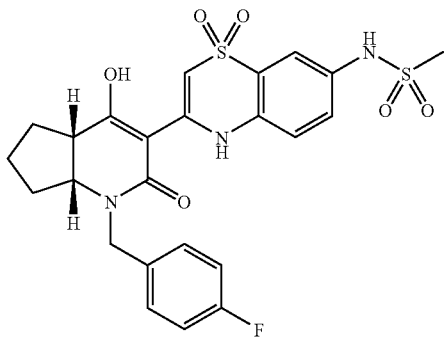

a) (1S,2R)-2-tert-Butoxycarbonylamino-1-cyclohexanecarboxylic acid methyl ester

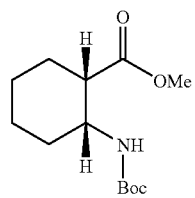

A 2.0 M solution of (trimethylsilyl)diazomethane in diethyl ether (5.0 mL, 10.0 mmol) was added over 10 min to a solution of (1S,2R)-2-tert-butoxycarbonylamino-1-cyclohexanecarboxylic acid (0.994 g, 4.09 mmol; purchased from NeoMPS) in a 1:1 mixture of benzene and methanol (50 mL) at 25° C. The resulting mixture was stirred at 25° C. for 30 min, and then was partitioned between half-saturated sodium bicarbonate solution (150 mL) and ethyl acetate (2×150 mL). The combined organic layers were dried over sodium sulfate, decanted, and were concentrated in vacuo to afford the desired product, (1S,2R)-2-tert-butoxycarbonylamino-1-cyclohexanecarboxylic acid methyl ester (1.00 g, 3.89 mmol, 95%), as a colorless oil. $^1$H NMR (400 MHz, CDCl$_3$) δ: 1.44 (9H, s), 1.58-1.68 (3H, m), 1.72-1.81 (2H, m), 1.98-2.05 (2H, m), 2.77-2.80 (1H, m), 3.69 (3H, s), 3.82-3.90 (1H, m), 5.29-5.31 (1H, m). LC-MS (ESI) calcd for C$_{13}$H$_{23}$NO$_4$ 257.16, found 258.2 [M+H$^+$].

b) (1S,2R)-2-Amino-cyclohexanecarboxylic acid methyl ester

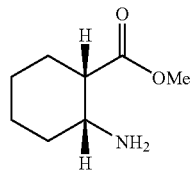

A 4.0 M solution of hydrochloric acid in 1,4-dioxane (20 mL) was added to a solution of (1S,2R)-2-tert-butoxycarbonylamino-1-cyclohexanecarboxylic acid methyl ester (1.28 g, 4.97 mmol) in 1,4-dioxane (15 mL) at 25° C. The reaction mixture was stirred at 25° C. for 2 h, then toluene (40 mL) was added and the volatiles were removed in vacuo. The residue was partitioned between saturated sodium bicarbonate solution (150 mL) and ethyl acetate (2×150 mL). The combined organic layers were dried over sodium sulfate, decanted, and were concentrated in vacuo to afford the crude product, (1S,2R)-2-amino-cyclohexanecarboxylic acid methyl ester as a yellow oil, which was used directly in the next step without further purification.

c) (1S,2R)-2-(4-Fluoro-benzylamino)-cyclohexanecarboxylic acid methyl ester

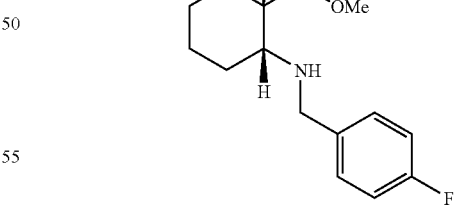

The crude (1S,2R)-2-amino-cyclohexanecarboxylic acid methyl ester (4.97 mmol) was dissolved in methanol (15 mL) at 25° C. and 4-fluorobenzaldehyde (0.533 mL, 4.97 mmol), glacial acetic acid (1 mL) and sodium cyanoborohydride (0.781 g, 12.4 mmol) were added sequentially. The reaction mixture was stirred at 25° C. for 19 h, and then was partitioned between saturated sodium bicarbonate solution (150 mL) and ethyl acetate (2×150 mL). The combined organic layers were dried over sodium sulfate, decanted, and were concentrated in vacuo to afford the crude product, (1S,2R)-2-(4-fluoro-benzylamino)-cyclohexanecarboxylic acid methyl ester as a yellow oil, which was used directly in the next step without further purification.

d) (1S,2R)-2-{(4-Fluoro-benzyl)-[2-(7-methane-sulfonylamino-1,1-dioxo-1,4-dihydro-1λ⁶-benzo[1,2,4]thiadiazin-3-yl)-acetyl]-amino}-cyclohexanecarboxylic acid methyl ester

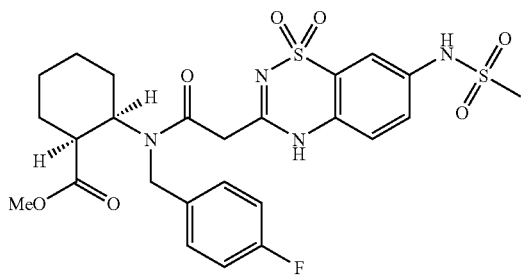

The crude (1S,2R)-2-(4-fluoro-benzylamino)-cyclohexanecarboxylic acid methyl ester (4.97 mmol) was dissolved in N,N-dimethylformamide (40 mL) at 25° C. and (7-methanesulfonylamino-1,1-dioxo-1,4-dihydro-1λ⁶-benzo[1,2,4]thiadiazin-3-yl)-acetic acid (prepared as described in Example 1j, 1.47 g, 4.41 mmol), 1-(3-dimethylaminopropyl)-3-ethylcarbodiimide hydrochloride (0.887, 4.63 mmol), and N-methylmorpholine (1.01 mL, 9.19 mmol) were added sequentially. The reaction mixture was stirred at 25° C. for 2 h, and then was concentrated in vacuo. The residue was partitioned between 1.0 M aqueous hydrochloric acid solution (150 mL) and ethyl acetate (2×150 mL). The combined organic layers were dried over sodium sulfate, decanted, and were concentrated in vacuo to afford the crude product, (1S,2R)-2-{(4-fluoro-benzyl)-[2-(7-methanesulfonylamino-1,1-dioxo-1,4-dihydro-1λ⁶-benzo[1,2,4]thiadiazin-3-yl)-acetyl]-amino}-cyclohexanecarboxylic acid methyl ester as a yellow oil, which was used directly in the next step without further purification.

e) (4aS, 8aR)-N-{3-[1-(4-Fluoro-benzyl)-4-hydroxy-2-oxo-1,2,4a,5,6,7,8,8a-octahydro-quinolin-3-yl]-1,1-dioxo-1,4-dihydro-1λ⁶-benzo[1,2,4]thiadiazin-7-yl}-methanesulfonamide

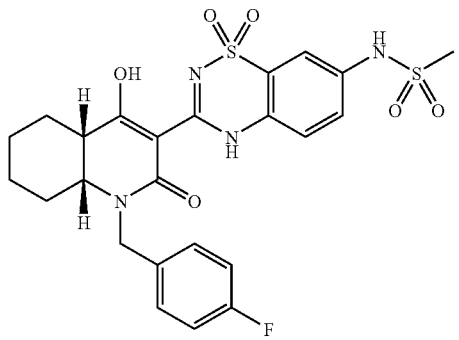

The crude (1S,2R)-2-{(4-fluoro-benzyl)-[2-(7-methanesulfonylamino-1,1-dioxo-1,4-dihydro-1λ⁶-benzo[1,2,4]thiadiazin-3-yl)-acetyl]-amino}-cyclohexanecarboxylic acid methyl ester (4.97 mmol) was dissolved in ethanol (50 mL) at 25° C. and a 21% w/w solution of sodium ethoxide in ethanol (2.86 mL) was added. The reaction mixture was heated to 60° C. for 8 h, then was cooled to 25° C. and partitioned between 1.0 M aqueous hydrochloric acid solution (150 mL) and ethyl acetate (2×150 mL). The combined organic layers were dried over sodium sulfate, decanted, and were concentrated in vacuo. The residue was purified by flash column chromatography (Teledyne Isco RediSep Flash Column 150 g; 0-6% methanol in dichloromethane) to afford the desired product, (4aS,8aR)-N-{3-[1-(4-fluoro-benzyl)-4-hydroxy-2-oxo-1,2,4a,5,6,7,8,8a-octahydro-quinolin-3-yl]-1,1-dioxo-1,4-dihydro-1λ⁶-benzo[1,2,4]thiadiazin-7-yl}-methanesulfonamide (0.96 g, 1.75 mmol, 40% over 4 steps), as a pale yellow foam. $^1$H NMR (400 MHz, DMSO-d$_6$) δ: 1.10-1.26 (3H, m), 1.36-1.48 (3H, m), 1.61-1.64 (1H, m), 1.77-1.80 (1H, m), 2.27-2.31 (1H, m), 3.06 (3H, s), 3.59 (1H, bs), 4.32 (1H, bs), 4.45 (1H, s), 4.99 (1H, d, J=15.3 Hz), 7.07-7.11 (1H, m), 7.12-7.17 (2H, m), 7.29-7.33 (1H, m), 7.39-7.42 (1H, m), 7.51 (1H, dd, J$_1$=2.3 Hz, J$_2$=8.5 Hz), 7.57 (1H, s), 7.58-7.59 (1H, m), 10.17 (1H, s), 13.80 (1H, s). LC-MS (ESI) calcd for $C_{24}H_{25}FN_4O_6S_2$ 548.12, found 549.4 [M+H⁺]. >99.5% e.e. as determined by chiral HPLC analysis: column: Chiralpak AS-RH 4.6×250 mm ID 5 um, solvent: acetonitrile+0.05% trifluoroacetic acid (mobile phase B); water+0.05% trifluoroacetic acid (mobile phase A), gradient: 50% to 90% mobile phase B over 15 min.

EXAMPLE 32

N-{3-[1-(3,3-Dimethyl-butyl)-4-hydroxy-2-oxo-2,4a,5,6,7,8,9,9a-octahydro-1H-cyclohepta[b]pyridin-3-yl]-1,1-dioxo-1,4-dihydro-1λ⁶-benzo[1,2,4]thiadiazin-7-yl}-methanesulfonamide

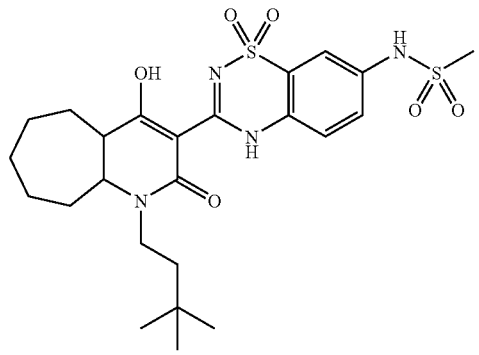

a) cis-2-(3,3-Dimethyl-butylamino)-cycloheptanecarboxylic acid methyl ester

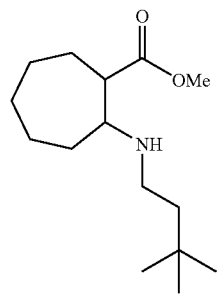

Sodium acetate (0.197 g, 2.40 mmol), powdered 4 Å molecular sieves (0.60 g), 3,3-dimethylbutyraldehyde (0.151 mL, 1.20 mmol) and sodium cyanoborohydride (0.151 mg, 2.40 mmol) were added sequentially to a solution of cis-2- amino-cycloheptanecarboxylic acid methyl ester hydrochloride (prepared as described in Example 2a, 0.250 g, 1.20 mmol) in methanol (10 mL) at 25° C. The reaction mixture was stirred at 25° C. for 3 h, and then was partitioned between half-saturated aqueous sodium bicarbonate solution (100 mL) and ethyl acetate (2×150 mL). The organic layers were washed sequentially with half-saturated aqueous sodium bicarbonate solution (100 mL) and saturated aqueous brine solution (100 mL), then were dried over sodium sulfate, filtered, and were concentrated in vacuo. The residue was purified by flash column chromatography (Analogix SuperFlash Column; 0-25% ethyl acetate in hexanes) to afford the desired product, cis-2-(3,3-dimethyl-butylamino)-cycloheptanecarboxylic acid methyl ester (0.090 g, 0.352 mmol, 29%), as a clear oil. $^1$H NMR (400 MHz, CDCl$_3$) δ: 0.90 (s, 9H), 1.33-1.37 (m, 2H), 1.43-1.50 (m, 3H), 1.58-1.87 (m, 7H), 2.46-2.53 (m, 1H), 2.58-2.65 (m, 1H), 2.81-2.85 (m, 1H), 2.95-2.99 (m, 1H), 3.67 (s, 3H). LC-MS (ESI) calcd for C$_{15}$H$_{29}$NO$_2$ 255.22, found 256.3 [M+H$^+$].

b) N-{3-[1-(3,3-Dimethyl-butyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide

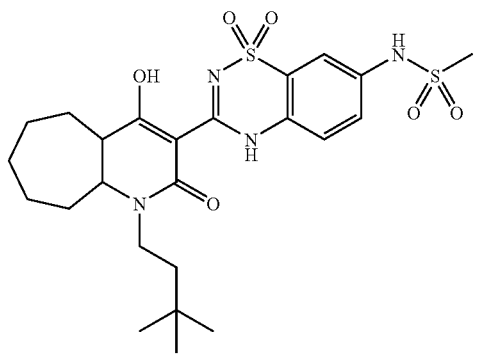

(7-Methanesulfonylamino-1,1-dioxo-1,4-dihydro-1λ$^6$-benzo[1,2,4]thiadiazin-3-yl)-acetic acid (prepared as described in Example 1j, 0.100 g, 0.300 mmol), 1-(3-dimethylaminopropyl)-3-ethylcarbodiimide hydrochloride (0.060 g, 0.315 mmol) and N-methylmorpholine (0.070 mL, 0.630 mmol) were added sequentially to a solution of cis-2-(3,3-dimethyl-butylamino)-cycloheptanecarboxylic acid methyl ester (0.076 g, 0.300 mmol) in N,N-dimethylformamide (4 mL) at 25° C. The reaction mixture was stirred at 25° C. for 2 h, and then was partitioned between 1.0 M aqueous hydrochloric acid solution (100 mL) and ethyl acetate (2×100 mL). The organic layers were washed with saturated aqueous brine solution (100 mL), dried over sodium sulfate, filtered, and were concentrated in vacuo. The residue was dissolved in ethanol (4 mL) at 25° C. A 21% w/w solution of sodium ethoxide in ethanol (0.244 mL, 0.600 mmol) was added and the reaction mixture was heated to 60° C. for 2 h. After cooling to 25° C. and stirring for 16 h, the reaction mixture was slowly added to 1.0 M aqueous hydrochloric acid solution (50 mL) at 0° C. The resulting precipitate was collected by filtration and dried in vacuo, then was triturated with a small amount of methanol (ca. 0.5 mL) to afford the desired product, N-{3-[1-(3,3-dimethyl-butyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide (0.096 g, 0.178 mmol, 59%), as a white solid. $^1$H NMR (400 MHz, CDCl$_3$) δ: 1.01 (s, 9H), 1.41-2.25 (m, 12H), 2.72-3.00 (m, 1H), 3.06 (d, 3H, J=3.6 Hz), 3.06-3.33 (m, 1H), 3.40-3.50 (m, 1H), 3.94-4.10 (m, 1H), 7.02 (d, 1H, J=18.0 Hz), 7.20 (dd, 1H, J$_1$=22.7 Hz, J$_2$=13.4 Hz), 7.64 (t, 1H, J=7.5 Hz), 7.69 (d, 1H, J=7.7 Hz). LC-MS (ESI) calcd for C$_{24}$H$_{34}$N$_4$O$_6$S$_2$ 538.19, found 539.4 [M+H$^+$].

EXAMPLE 33

N-{3-[4-Hydroxy-1-(3-methyl-butyl)-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide

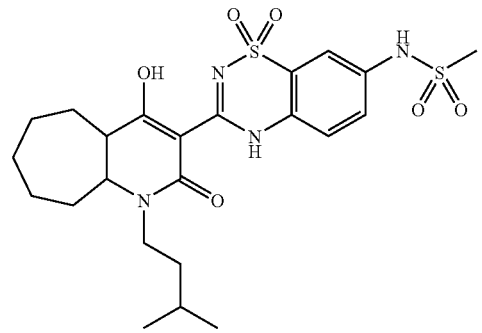

a) cis-2-(3-Methyl-butylamino)-cycloheptanecarboxylic acid methyl ester

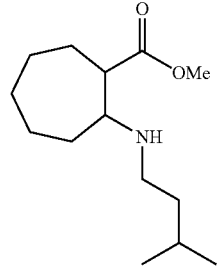

Sodium acetate (0.328 g, 4.00 mmol), powdered 4 Å molecular sieves (1.0 g), isovaleraldehyde (0.216 mL, 2.00 mmol) and sodium cyanoborohydride (0.251 mg, 4.00 mmol) were added sequentially to a solution of cis-2-amino-cycloheptanecarboxylic acid methyl ester hydrochloride (prepared as described in Example 2a, 0.415 g, 2.00 mmol) in methanol (10 mL) at 25° C. The reaction mixture was stirred at 25° C. for 16 h, then was acidified to pH=2 by the addition of 1.0 M aqueous hydrochloric acid solution. After stirring for 5 min at 25° C., the mixture was partitioned between half-saturated aqueous sodium bicarbonate solution (100 mL) and ethyl acetate (3×50 mL). The organic layers were washed sequentially with half-saturated aqueous sodium bicarbonate solution (100 mL) and saturated aqueous brine solution (100 mL), then were dried over sodium sulfate, filtered, and were concentrated in vacuo. The residue was purified by flash column chromatography (Analogix SuperFlash Column; 0-40% ethyl acetate in hexanes) to afford the desired product, cis-2-(3-methyl-butylamino)-cycloheptanecarboxylic acid methyl ester (0.340 g, 1.41 mmol, 70%), as a clear oil. $^1$H NMR (400 MHz, CDCl$_3$) δ: 0.89 (d, 6H, J=6.5 Hz), 1.33 (q, 2H, J=7.3 Hz), 1.43-1.50 (m, 3H), 1.57-1.66 (m, 3H), 1.72-1.79 (m, 3H), 1.81-1.87 (m, 2H), 2.47-2.54 (m, 1H), 2.59-2.66 (m, 1H), 2.79-2.84 (m, 1H), 2.95-2.99 (m, 1H), 3.67 (s, 3H). LC-MS (ESI) calcd for C$_{14}$H$_{27}$NO$_2$ 241.20, found 242.4 [M+H$^+$].

b) N-{3-[4-Hydroxy-1-(3-methyl-butyl)-2-oxo-2,4a, 5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide

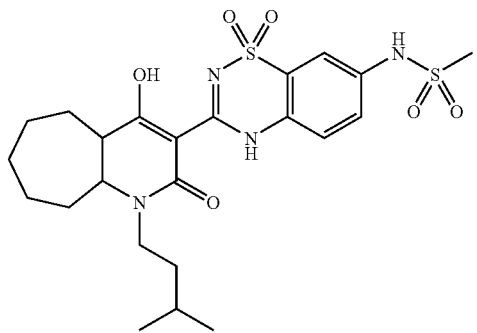

(7-Methanesulfonylamino-1,1-dioxo-1,4-dihydro-1λ$^6$-benzo[1,2,4]thiadiazin-3-yl)-acetic acid (prepared as described in Example 1j, 0.200 g, 0.600 mmol), 1-(3-dimethylaminopropyl)-3-ethylcarbodiimide hydrochloride (0.121 g, 0.630 mmol) and N-methylmorpholine (0.139 mL, 1.26 mmol) were added sequentially to a solution of cis-2-(3-methyl-butylamino)-cycloheptanecarboxylic acid methyl ester (0.144 g, 0.600 mmol) in N,N-dimethylformamide (7 mL) at 25° C. The reaction mixture was stirred at 25° C. for 1 h, and then was partitioned between 1.0 M aqueous hydrochloric acid solution (100 mL) and ethyl acetate (2×100 mL). The organic layers were washed with saturated aqueous brine solution (100 mL), dried over sodium sulfate, filtered, and were concentrated in vacuo. The residue was dissolved in ethanol (5 mL) at 25° C. A 21% w/w solution of sodium ethoxide in ethanol (0.448 mL, 1.20 mmol) was added and the reaction mixture was heated to 60° C. for 2 h. After cooling to 25° C., the reaction mixture was partitioned between 1.0 M aqueous hydrochloric acid solution (100 mL) and ethyl acetate (2×75 mL). The organic layers were washed with saturated aqueous brine solution (100 mL), dried over sodium sulfate, filtered, and were concentrated in vacuo. The residue was purified by flash column chromatography (Analogix SuperFlash Column; 25-80% ethyl acetate in hexanes) to afford the desired product, N-{3-[4-hydroxy-1-(3-methyl-butyl)-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide (0.186 g, 0.354 mmol, 59%), as a white solid. $^1$H NMR (400 MHz, CDCl$_3$) δ: 0.98-1.01 (m, 6H), 1.41-2.24 (m, 15H), 2.75-3.01 (m, 1H), 3.05-3.09 (m, 1H), 3.06 (d, 3H, J=3.9 Hz), 3.41-3.52 (m, 1H), 3.96-4.09 (m, 1H), 7.16-7.23 (m, 1H), 7.62-7.66 (m, 1H), 7.69-7.71 (m, 1H). LC-MS (ESI) calcd for C$_{23}$H$_{32}$N$_4$O$_6$S$_2$ 524.18, found 525.4 [M+H$^+$].

EXAMPLE 34

N-{3-[4-Hydroxy-1-(3-methyl-butyl)-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-N-methyl-methanesulfonamide

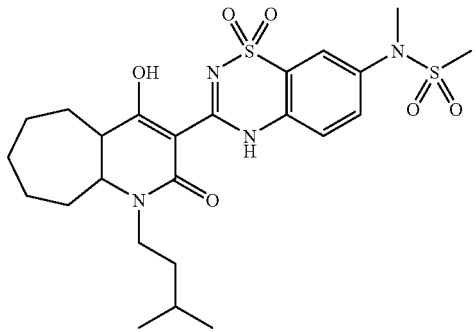

Potassium carbonate (0.067 g, 0.488 mmol) and iodomethane (0.017 mL, 0.268 mmol) were added sequentially to a solution of N-{3-[4-hydroxy-1-(3-methyl-butyl)-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide (prepared as described in Example 33b, 0.128 g, 0.244 mmol) in N,N-dimethylformamide (4 mL) at 25° C. The reaction mixture was stirred at 25° C. for 2 h, and then was partitioned between ethyl acetate (30 mL) and water (2×20 mL). The organic layers were washed with saturated aqueous brine solution (50 mL), dried over sodium sulfate, filtered, and were concentrated in vacuo. The residue was purified by flash column chromatography (Analogix SuperFlash Column; 30-80% ethyl acetate in hexanes) to afford the desired product, N-{3-[4-hydroxy-1-(3-methyl-butyl)-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-N-methyl-methanesulfonamide (0.045 g, 0.084 mmol, 34%), as a white solid. $^1$H NMR (400 MHz, CDCl$_3$) δ: 1.00 (d, 6H, J=7.1 Hz), 1.40-2.24 (m, 14H), 2.88 (d, 3H, J=2.1 Hz), 2.94-3.09 (m, 1H), 3.30-3.53 (m, 2H), 3.37 (d, 3H, J=3.1 Hz), 3.95-4.09 (m, 1H), 7.17-7.23 (m, 1H), 7.67-7.73 (m, 1H), 7.77-7.80 (m, 1H). LC-MS (ESI) calcd for C$_{24}$H$_{34}$N$_4$O$_6$S$_2$ 538.19, found 539.4 [M+H$^+$].

EXAMPLE 35

N-{3-[1-(3,3-Dimethyl-butyl)-4-hydroxy-2-oxo-1,2,4a,5,6,7,8,9,10,10a-decahydro-cycloocta[b]pyridin-3-yl]-1,1-dioxo-1,4-dihydro-1λ$^6$-benzo[1,2,4]thiadiazin-7-yl}-methanesulfonamide

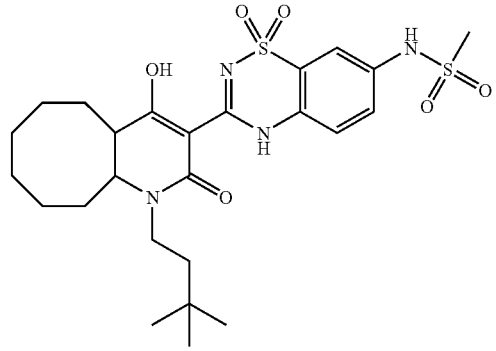

a) cis-2-(3,3-Dimethyl-butylamino)-cyclooctanecarboxylic acid methyl ester

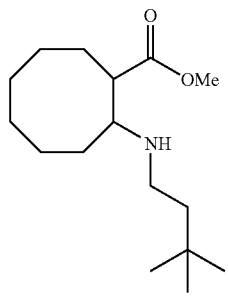

cis-2-Amino-cyclooctanecarboxylic acid methyl ester hydrochloride (0.25 g, 1.35 mmol) was dissolved in methanol (10 mL). Sodium acetate (0.22 g, 2.70 mmol) was added followed by 4 Å powdered molecular sieves (0.20 g) and 3,3-dimethyl-butyraldehyde (0.17 mL, 1.35 mmol). Sodium cyanoborohydride (0.17 g, 2.70 mmol) was added and the mixture was stirred at 25° C. for 16 h. The mixture was poured into a mixture of saturated aqueous sodium bicarbonate solution (20 mL) and ethyl acetate (30 mL). After shaking, both layers were passed through a plug of Celite. The organic layer was further washed with saturated aqueous sodium bicarbonate solution (10 mL), saturated aqueous brine solution (10 mL), dried over magnesium sulfate, filtered, and concentrated in vacuo to afford the crude product, cis-2-(3,3-dimethyl-butylamino)-cyclooctanecarboxylic acid methyl ester (0.34 g, 1.26 mmol, 93%), as a clear oil. LC-MS (ESI) calcd for $C_{16}H_{31}NO_2$ 269.42, found [M+H$^+$].

b) N-{3-[1-(3,3-Dimethyl-butyl)-4-hydroxy-2-oxo-1,2,4a,5,6,7,8,9,10,10a-decahydro-cycloocta[b]pyridin-3-yl]-1,1-dioxo-1,4-dihydro-1λ$^6$-benzo[1,2,4]thiadiazin-7-yl}-methanesulfonamide

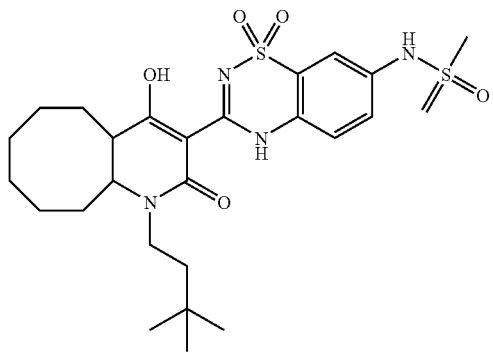

cis-2-(3,3-Dimethyl-butylamino)-cyclooctanecarboxylic acid methyl ester (0.18 g, 0.67 mmol) was dissolved in anhydrous N,N-dimethylformamide (8 mL). (7-Methanesulfonylamino-1,1-dioxo-1,4-dihydro-1λ$^6$-benzo[1,2,4]thiadiazin-3-yl)-acetic acid (prepared as described in Example 1j, 0.23 g, 0.67 mmol) was added followed by N-methylmorpholine (0.15 mL, 1.40 mmol). The mixture was stirred until everything dissolved, approximately 5 min. 1-(3-Dimethylaminopropyl)-3-ethylcarbodiimide hydrochloride (0.13 g, 0.70 mmol) was added and the mixture was stirred at 25° C. for 4 h. Triethylamine (0.28 mL, 2.00 mmol) was added and the mixture was stirred at 50° C. for 16 h. Upon cooling to 25° C., the solution was diluted with ethyl acetate (50 mL) and washed with 1.0 M aqueous hydrochloric acid solution (2×50 mL), saturated aqueous brine solution (20 mL), dried over magnesium sulfate, filtered, and concentrated in vacuo to afford a golden oil. Purification by flash column chromatography (Teledyne Isco RediSep Flash Column; 0-20% ethyl acetate in dichloromethane) afforded the desired product, N-{3-[1-(3,3-dimethyl-butyl)-4-hydroxy-2-oxo-1,2,4a,5,6,7,8,9,10,10a-decahydro-cycloocta[b]pyridin-3-yl]-1,1-dioxo-1,4-dihydro-1λ$^6$-benzo[1,2,4]thiadiazin-7-yl}-methanesulfonamide (0.18 g, 0.32 mmol, 48%), as a white powder. $^1$H NMR (400 MHz, DMSO-d$_6$) δ: 1.02 (9H, s), 1.42-2.21 (14H, m), 2.80-2.86 (1H, m), 3.06 (3H, s), 3.11-3.15 (1H, m), 3.66-3.70 (1H, m), 3.99-4.04 (1H, m), 6.57 (1H, s), 7.22-7.26 (1H, m), 7.60-7.66 (2H, m). LC-MS (ESI) calcd for $C_{25}H_{36}N_4O_6S_2$ 552.71, found 553.3 [M+H$^+$].

EXAMPLE 36

N-{3-[1-(3,3-Dimethyl-butyl)-4-hydroxy-2-oxo-1,2,4a,5,6,7,8,9,10,10a-decahydro-cycloocta[b]pyridin-3-yl]-1,1-dioxo-1,4-dihydro-1λ$^6$-benzo[1,2,4]thiadiazin-7-yl}-N-methyl-methanesulfonamide

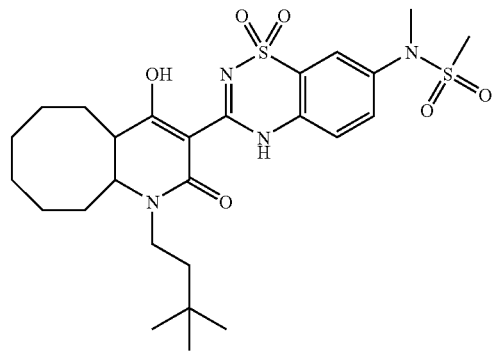

N-{3-[1-(3,3-Dimethyl-butyl)-4-hydroxy-2-oxo-1,2,4a,5,6,7,8,9,10,10a-decahydro-cycloocta[b]pyridin-3-yl]-1,1-dioxo-1,4-dihydro-1λ$^6$-benzo[1,2,4]thiadiazin-7-yl}-methanesulfonamide (prepared as described in Example 35b, 0.20 g, 0.36 mmol) was dissolved in N,N-dimethylformamide (12 mL). Potassium carbonate (0.10 g, 0.72 mmol) and iodomethane (0.025 mL, 0.40 mmol) were added sequentially. The reaction was stirred at 25° C. for 3 h. The reaction was quenched via the addition of 1.0 M aqueous hydrochloric acid solution (20 mL). The mixture was extracted with ethyl acetate (3×30 mL). The organic layers were combined and washed with saturated aqueous brine solution (20 mL) before they were dried over magnesium sulfate, filtered, and concentrated in vacuo to afford a golden oil. Purification by flash column chromatography (Teledyne Isco RediSep Flash Column 12 g; 0-20% ethyl acetate in dichloromethane) afforded the desired product, N-{3-[1-(3,3-dimethyl-butyl)-4-hydroxy-2-oxo-1,2,4a,5,6,7,8,9,10,10a-decahydro-cycloocta[b]pyridin-3-yl]-1,1-dioxo-1,4-dihydro-1λ$^6$-benzo[1,2,4]thiadiazin-7-yl}-N-methyl-methanesulfonamide (0.018 g, 0.23 mmol, 9%), as a white powder. $^1$H NMR (400 MHz, DMSO-d$_6$) δ: 1.00-1.02 (9H, m), 1.35-1.80 (14H, m), 2.87-2.88 (3H, m), 3.00-3.35 (2H, m), 3.36-3.38 (3H, m), 3.86-

4.15 (2H, m), 7.20-7.28 (1H, m), 7.64-7.79 (2H, m). LC-MS (ESI) calcd for $C_{26}H_{38}N_4O_6S_2$ 566.73, found 567.4 [M+H$^+$].

EXAMPLE 37 cis-N-{3-[1-(4-Fluoro-benzyl)-4-hydroxy-2-oxo-1,2,4a,5,8,8a-hexahydro-quinolin-3-yl]-1,1-dioxo-1,4-dihydro-1$\lambda^6$-benzo[1,2,4]thiadiazin-7-yl}-methanesulfonamide

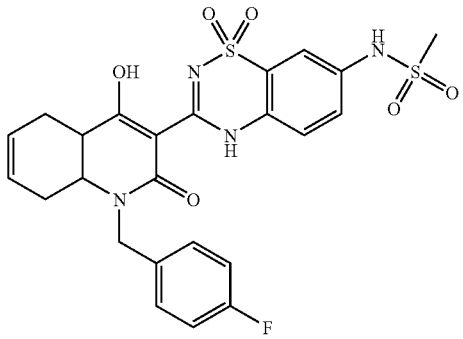

a) 6-(4-Fluoro-benzylamino)-cyclohex-3-enecarboxylic acid ethyl ester

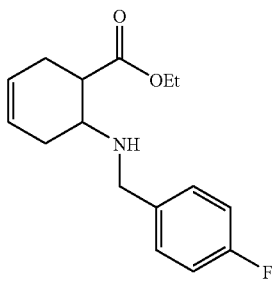

cis-6-Amino-cyclohex-3-enecarboxylic acid ethyl ester hydrochloride (411.4 mg, 2 mmol) and anhydrous tetrahydrofuran (20 mL) were mixed to form slurry. Triethylamine (295 µL, 2.1 mmol), magnesium sulfate (685 mg), and 4-fluoro-benzaldehyde (450 µL, 4.1 mmol) were added at 25° C. and the resulted mixture was stirred at 25° C. for 16 h. The precipitated solid was filtered off and the filtrate was concentrated in vacuo at 25° C. to give an oil. This oil was dissolved in methanol (35 mL) and sodium borohydride (155 mg, 4.1 mmol) was then added portionwise at 25° C. The mixture was stirred at 25° C. for 1 h. Saturated aqueous sodium bicarbonate solution (15 mL) was added, extracted with ethyl acetate (3×40 mL) and the organic layer was dried over sodium sulfate, filtered, and concentrated in vacuo to afford the desired product, 6-(4-fluoro-benzylamino)-cyclohex-3-enecarboxylic acid ethyl ester (537.6 mg, 1.94 mmol, 96.9%). This crude product was directly used in next step without further purification. LC-MS (ESI) calcd for $C_{16}H_{20}FNO_2$ 277.2, found 278.2 [M+H$^+$].

b) 6-{(4-Fluoro-benzyl)-[2-(7-methanesulfonylamino-1,1-dioxo-1,4-dihydro-1$\lambda^6$-benzo[1,2,4]thiadiazin-3-yl)-acetyl]-amino}-cyclohex-3-enecarboxylic acid ethyl ester

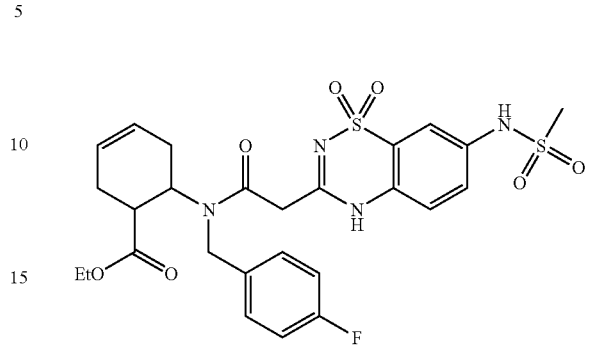

The crude 6-(4-fluoro-benzylamino)-cyclohex-3-enecarboxylic acid ethyl ester (113.7 mg, 0.41 mmol) was mixed with (7-methanesulfonylamino-1,1-dioxo-1,4-dihydro-1$\lambda^6$-benzo[1,2,4]thiadiazin-3-yl)-acetic acid (prepared as described in Example 1j, 150 mg, 0.45 mmol) and dissolved in N,N-dimethylformamide (3.4 mL). N-methylmorpholine (100 µL, 0.9 mmol) was added followed by 1-(3-dimethylaminopropyl)-3-ethylcarbodiimide hydrochloride (86 mg, 0.45 mmol). The reaction mixture was stirred at 25° C. for 16 h. LC-MS analysis indicated that the reaction was incomplete and thus additional (7-methanesulfonylamino-1,1-dioxo-1,4-dihydro-1$\lambda^6$-benzo[1,2,4]thiadiazin-3-yl)-acetic acid (30 mg) and 1-(3-dimethylaminopropyl)-3-ethylcarbodiimide hydrochloride (17 mg) were added and the resulted mixture was stirred at 25° C. for 1.5 h. A 1.0 M aqueous hydrochloric acid solution (6.7 mL) was added. The product was extracted with ethyl acetate (3×15 mL) and the combined organic layers were washed with water (10 mL) and saturated aqueous brine solution (15 mL), dried over anhydrous sodium sulfate, filtered and concentrated in vacuo and further dried under high vacuum for 16 h to afford the crude product, 6-{(4-fluoro-benzyl)-[2-(7-methanesulfonylamino-1,1-dioxo-1,4-dihydro-1$\lambda^6$-benzo[1,2,4]thiadiazin-3-yl)-acetyl]-amino}-cyclohex-3-enecarboxylic acid ethyl ester (295.4 mg). LC-MS (ESI) calcd for $C_{26}H_{29}FN_4O_7S_2$ 592.15, found 593.4 [M+H$^+$]. This crude product was directly used in next step without further purification.

c) cis-N-{3-[1-(4-Fluoro-benzyl)-4-hydroxy-2-oxo-1,2,4a,5,8,8a-hexahydro-quinolin-3-yl]-1,1-dioxo-1,4-dihydro-1$\lambda^6$-benzo[1,2,4]thiadiazin-7-yl}-methanesulfonamide

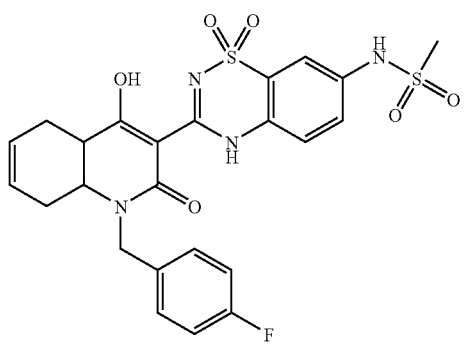

The crude 6-{(4-fluoro-benzyl)-[2-(7-methanesulfonylamino-1,1-dioxo-1,4-dihydro-1λ⁶-benzo[1,2,4]thiadiazin-3-yl)-acetyl]-amino}-cyclohex-3-enecarboxylic acid ethyl ester (0.41 mmol) was dissolved in ethanol (2 mL) and a 21% w/w solution of sodium ethoxide in ethanol (0.64 mL, 1.73 mmol) was added at 25° C. The reaction mixture was stirred at 60° C. under a nitrogen atmosphere for 1.5 h. A 1.0 M aqueous hydrochloric acid solution (5 mL) was added at 0° C. (pH=1) and the mixture was stirred at 0° C. for 20 min. The precipitated solid was collected, washed with water (3×5 mL) and recrystallized from ethyl acetate and hexanes to give a first batch of the desired product, N-{3-[1-(4-fluoro-benzyl)-4-hydroxy-2-oxo-1,2,4a,5,8,8a-hexahydro-quinolin-3-yl]-1,1-dioxo-1,4-dihydro-1λ⁶-benzo[1,2,4]thiadiazin-7-yl}-methanesulfonamide (123.6 mg). The filtrate was then extracted with ethyl acetate and the combined organic layers were concentrated in vacuo to give a second batch of the crude desired product, N-{3-[1-(4-fluoro-benzyl)-4-hydroxy-2-oxo-1,2,4a,5,8,8a-hexahydro-quinolin-3-yl]-1,1-dioxo-1,4-dihydro-1λ⁶-benzo[1,2,4]thiadiazin-7-yl}-methanesulfonamide (96.9 mg). The combined batches of the crude product were further purified by prep-HPLC (30-100% acetonitrile in water with 0.05% trifluoroacetic acid as gradient) to afford two isomers of the desired product. cis-N-{3-[1-(4-fluoro-benzyl)-4-hydroxy-2-oxo-1,2,4a,5,8,8a-hexahydro-quinolin-3-yl]-1,1-dioxo-1,4-dihydro-1λ⁶-benzo[1,2,4]thiadiazin-7-yl}-methanesulfonamide (66 mg, 0.121 mmol, 29.5% over two steps). ¹H NMR (DMSO-d₆, 400 MHz): δ 2.05-2.30 (m, 4H), 2.69-2.83 (m, 1H), 3.05 (s, 3H), 3.88 (bs, 1H), 4.42-4.62 (m, 1H), 4.91 (d, 1H, J=15.2 Hz), 5.47-5.56 (m, 1H), 5.59-5.66 (m, 1H), 7.17 (t, 2H, J=8.8 Hz), 7.43-7.51 (m, 3H), 7.56-7.58 (m, 2H), 10.14 (s, 1H), 13.67 (bs, 1H). LC-MS (ESI) calcd for $C_{24}H_{23}FN_4O_6S_2$ 546.1, found 547.2 [M+H⁺]. Anal. calcd for $C_{24}H_{23}FN_4O_6S_2$ 0.5H₂O: C, 51.88; H, 4.35; N, 10.08; found: C, 52.23; H, 4.40; N, 10.19. trans-N-{3-[1-(4-fluoro-benzyl)-4-hydroxy-2-oxo-1,2,4a,5,8,8a-hexahydro-quinolin-3-yl]-1,1-dioxo-1,4-dihydro-1λ⁶-benzo[1,2,4]thiadiazin-7-yl}-methanesulfonamide (14.8 mg, 0.027 mmol, 6.6% over two steps). ¹H NMR (DMSO-d₆, 400 MHz): δ 1.78-2.02 (m, 2H), 2.09-2.27 (m, 2H), 2.50-2.62 (m, 1H), 3.07 (s, 3H), 3.60-3.72 (m, 1H), 4.58 (d, 1H, J=15.2 Hz), 5.04 (d, 1H, J=15.6 Hz), 5.54-5.62 (m, 1H), 5.66-5.74 (m, 1H), 7.14 (t, 2H, J=8.6 Hz), 7.29-7.37 (m, 2H), 7.52 (d, 1H, J=8.4 Hz), 7.57-7.65 (m, 2H), 10.18 (bs, 1H), 11.65 (bs, 1H), 13.97 (bs, 1H). LC-MS (ESI) calcd for $C_{24}H_{23}FN_4O_6S_2$ 546.1, found 547.2 [M+H⁺].

EXAMPLE 38 cis-N-[3-(1-Dimethylamino-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide hydrochloride

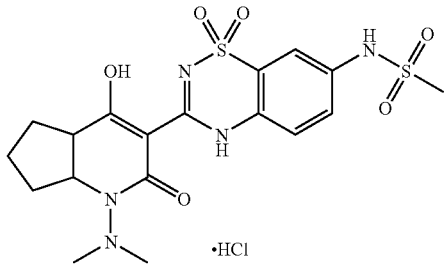

a) Ethyl 2-(2,2-dimethylhydrazono)cyclopentanecarboxylate

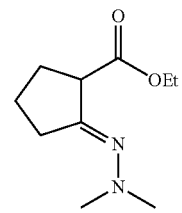

2-Oxo-cyclopentanecarboxylic acid ethyl ester (1.00 mL, 6.91 mmol) was dissolved in ethanol (10 mL). N,N-Dimethylhydrazine (0.53 mL, 6.91 mmol) was added. The reaction was stirred at 25° C. for 16 h. The resulting mixture was concentrated in vacuo to afford the crude product, ethyl 2-(2,2-dimethylhydrazono)cyclopentane-carboxylate, which was used in the next step without further purification. LC-MS (ESI) calcd for $C_{10}H_{18}N_2O_2$ 198.26, found 199.2 [M+H⁺].

b) Ethyl 2-(2,2-dimethylhydrazinyl)cyclopentanecarboxylate

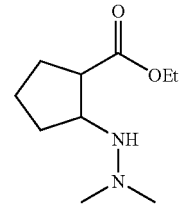

The crude ethyl 2-(2,2-dimethylhydrazono)cyclopentanecarboxylate (6.91 mmol) was dissolved in acetic acid (10 mL) and water (10 mL). Sodium cyanoborohydride was added and the reaction was stirred at 25° C. for 16 h. The mixture was neutralized with saturated aqueous sodium bicarbonate solution until pH=8 was reached and was diluted with ethyl acetate (30 mL). After shaking, both layers were passed through a plug of Celite. The organic layer was further washed with saturated aqueous sodium bicarbonate solution (10 mL), saturated aqueous brine solution (10 mL), then dried over magnesium sulfate, filtered, and concentrated in vacuo to afford the crude product, ethyl 2-(2,2-dimethylhydrazinyl) cyclopentanecarboxylate as a clear oil, which was used directly in the next step without any further purification. LC-MS (ESI) calcd for $C_{10}H_{20}N_2O_2$ 200.28, found 201.3 [M+H⁺].

c) cis-N-[3-(1-Dimethylamino-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide hydrochloride

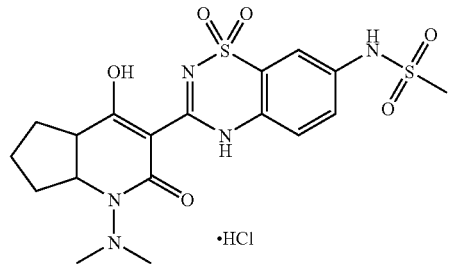

Ethyl 2-(2,2-dimethylhydrazinyl)cyclopentanecarboxylate (0.16 g, 0.82 mmol) was dissolved in anhydrous N,N-dimethylformamide (8 mL). (7-Methanesulfonylamino-1,1-dioxo-1,4-dihydro-1$\lambda^6$-benzo[1,2,4]thiadiazin-3-yl)-acetic acid (prepared as described in Example 1j, 0.27 g, 0.82 mmol) was added followed by N-methylmorpholine (0.19 mL, 1.72 mmol). The mixture was stirred until everything dissolved, approximately 5 min. 1-(3-Dimethylaminopropyl)-3-ethylcarbodiimide hydrochloride (0.16 g, 0.86 mmol) was added and the mixture was stirred at 25° C. for 16 h. The reaction was quenched via addition of saturated aqueous sodium bicarbonate solution (20 mL). The mixture was extracted with ethyl acetate (3×30 mL). The organic layers were combined and washed with saturated aqueous brine solution (20 mL). The resulting solution was dried over magnesium sulfate, filtered, and concentrated in vacuo to afford a golden oil. The residue was triturated with ethyl acetate to afford the desired product, cis-N-[3-(1-dimethylamino-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide hydrochloride (0.22 g, 0.43 mmol, 52%), as a white powder. $^1$H NMR (400 MHz, DMSO-d$_6$) δ: 1.48-1.73 (2H, m), 1.88-2.20 (4H, m), 2.82 (6H, s), 3.06 (3H, s), 4.01 (1H, s), 7.49-7.74 (3H, m), 10.18 (1H, s). LC-MS (ESI) calcd for $C_{18}H_{23}N_5O_6S_2$ 469.54, found 470.2 [M+H$^+$].

EXAMPLE 39

(4aR,7aS)-1-(4-Fluoro-benzyl)-4-hydroxy-3-(7-iodo-1,1-dioxo-1,4-dihydro-1$\lambda^6$-benzo[1,2,4]thiadiazin-3-yl)-1,4a,5,6,7,7a-hexahydro-[1]pyrindin-2-one

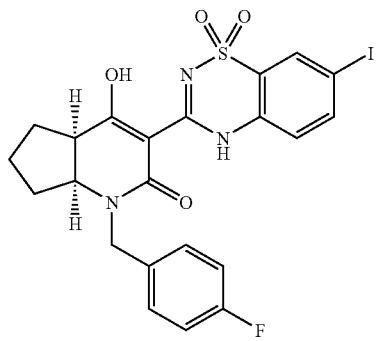

a) Methyl (1R,2S)-2-aminocyclopentanecarboxylate hydrochloride

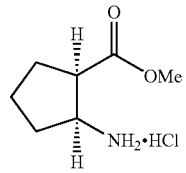

Thionyl chloride (2.64 mL, 36.22 mmol) was added slowly to anhydrous methanol (50 mL) at 0° C. under a nitrogen atmosphere. (1R,2S)-2-Amino-cyclopentanecarboxylic acid (4.0 g, 24.15 mmol) was added to above solution. The resulting mixture was allowed to warm to 25° C. and stirred for 5 h. The reaction mixture was concentrated in vacuo to afford the desired product, methyl (1R,2S)-2-aminocyclopentanecarboxylate hydrochloride (4.32 g, 24.15 mmol, quantitative), as a clear oil. The crude product was used directly in the next step. $^1$H NMR (400 MHz, CD$_3$OD) δ: 1.72-2.05 (4H, m), 2.16 (2H, m), 3.13 (1H, m), 3.75 (3H, s), 3.77 (1H, m).

b) Methyl (1R,2S)-2-(4-fluoro-benzylamino)-cyclopentanecarboxylate

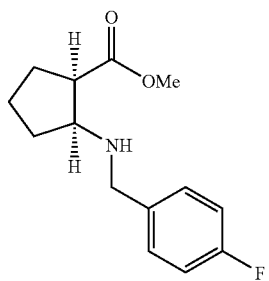

Methyl (1R,2S)-2-aminocyclopentanecarboxylate hydrochloride (4.32 g, 24.15 mmol) was dissolved in methanol (120 mL). Sodium acetate (3.96 g, 48.3 mmol) was added followed by 4 Å powdered molecular sieves (5.0 g) and 4-fluoro-benzaldehyde (2.55 mL, 24.15 mmol). Sodium cyanoborohydride (3.04 g, 48.3 mmol) was added and the mixture was stirred at 25° C. for 16 h. The mixture was poured into a mixture of saturated aqueous sodium bicarbonate solution (200 mL) and ethyl acetate (400 mL). After shaking, both layers were passed through a plug of Celite. The organic layer was further washed with saturated aqueous sodium bicarbonate solution (100 mL), saturated aqueous brine solution (100 mL), dried over magnesium sulfate, filtered, and concentrated in vacuo to afford the crude product, methyl (1R,2S)-2-(4-fluoro-benzylamino)-cyclopentanecarboxylate (5.38 g, 21.4 mmol, 89%), as a clear oil. $^1$H NMR (400 MHz, CDCl$_3$) δ: 1.55-1.72 (2H, m), 1.89 (3H, m), 2.05 (1H, m), 2.97 (1H, m), 3.32 (1H, m), 3.71 (3H, s), 3.77 (2H, m), 7.00 (2H, m), 7.28 (2H, m). LC-MS (ESI) calcd for $C_{14}H_{18}FNO_2$ 251.13, found 252.2 [M+H$^+$].

c) (4aR,7aS)-1-(4-Fluoro-benzyl)-4-hydroxy-3-(7-iodo-1,1-dioxo-1,4-dihydro-1$\lambda^6$-benzo[1,2,4]thiadiazin-3-yl)-1,4a,5,6,7,7a-hexahydro-[1]pyrindin-2-one

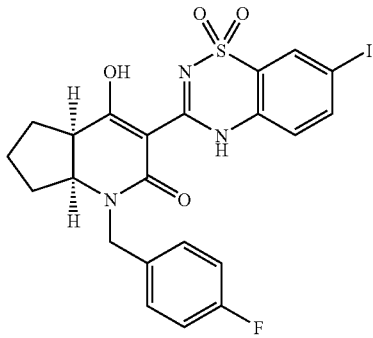

To a stirred solution of methyl (1R,2S)-2-(4-fluoro-benzylamino)-cyclopentanecarboxylate (2.50 g, 10 mmol) in anhydrous N,N-dimethylformamide (25 mL) under a nitrogen atmosphere, (7-iodo-1,1-dioxo-1,4-dihydro-1λ⁶-benzo[1,2,4]thiadiazin-3-yl)-acetic acid (prepared as described in Example 24b, 3.66 g, 10 mmol), N-methylmorpholine (2.20 mL, 20 mmol) and 1-(3-dimethylaminopropyl)-3-ethylcarbodiimide hydrochloride (1.92 g, 10 mmol) were added sequentially. After stirring at 25° C. for 16 h, the reaction mixture was diluted with ethyl acetate, washed with a 1.0 M aqueous hydrochloric acid solution and saturated aqueous brine solution, dried over sodium sulfate and filtered. The filtrate was concentrated in vacuo to afford the crude amide intermediate.

The above intermediate was dissolved in absolute ethanol (50 mL), and a 21% w/w solution of sodium ethoxide in ethanol (14.8 mL, 40 mmol) was added. The mixture was stirred at 60° C. for 2 h, and then was allowed to cool to 25° C. A 2.0 M aqueous hydrochloric acid solution (30 mL) was added slowly to the mixture, and white solid precipitated upon stirring. The solid was collected by filtration, washed with water and dried in vacuo to afford the desired product, (4aR,7aS)-1-(4-fluoro-benzyl)-4-hydroxy-3-(7-iodo-1,1-dioxo-1,4-dihydro-1λ⁶-benzo[1,2,4]thiadiazin-3-yl)-1,4a,5,6,7,7a-hexahydro-[1]pyrindin-2-one (2.90 g, 5.11 mmol, 51%), as an off-white solid. $^1$H NMR (400 MHz, DMSO-d$_6$) δ: 1.44-1.60 (3H, m), 1.97 (2H, m), 2.11 (1H, m), 3.25 (1H, m), 3.85 (1H, m), 4.48 (1H, m), 4.90 (1H, d, J=15.2 Hz), 7.15 (2H, m), 7.39 (3H, m), 7.99 (1H, m), 8.08 (1H, s). LC-MS (ESI) calcd for $C_{22}H_{19}FIN_3O_4S$ 567.01, found 568.2 [M+H⁺].

EXAMPLE 40

(4aR,7aS)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-benzenesulfonamide

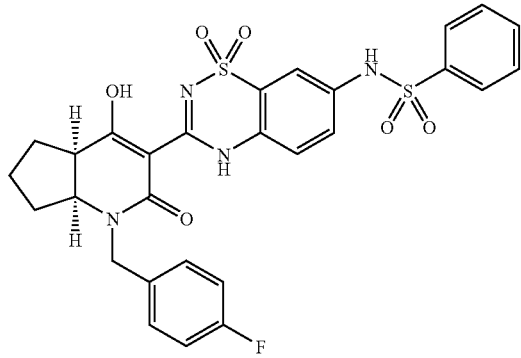

A reaction flask was charged with copper iodide (50.4 mg, 0.265 mmol), sarcosine (N-methyl glycine) (37.7 mg, 0.42 mmol), benzenesulfonamide (251 mg, 1.59 mmol), (4aR,7aS)-1-(4-fluoro-benzyl)-4-hydroxy-3-(7-iodo-1,1-dioxo-1,4-dihydro-1λ⁶-benzo[1,2,4]thiadiazin-3-yl)-1,4a,5,6,7,7a-hexahydro-[1]pyrindin-2-one (prepared as described in Example 39c, 300 mg, 0.53 mmol) and potassium phosphate (338 mg, 1.59 mmol). The flask was degassed and backfilled with nitrogen, and then anhydrous N,N-dimethylformamide (8 mL) was added. The resulting suspension was vigorously stirred at 100° C. for 16 h, and then allowed to cool to 25° C. The mixture was passed through a plug of Celite and washed with 10% methanol/dichloromethane. The filtrate was concentrated in vacuo, and the residue was purified by prep-HPLC [Column Luna 5μ C18 (2) 100 Å AXIA 50×21.2 mm, 5 micron, 40%-95% in 7 min @ 30 mL/min flow rate, 0.05% trifluoroacetic acid in acetonitrile/0.05% trifluoroacetic acid in water] to afford the desired product, (4aR,7aS)-N-[3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-benzenesulfonamide (110 mg, 0.19 mmol, 35%), as a white solid. $^1$H NMR (400 MHz, DMSO-d$_6$) δ: 1.40-1.60 (2H, m), 1.94 (1H, m), 2.05 (1H, m), 3.29 (1H, bs), 3.84 (1H, bs), 4.46 (1H, bs), 4.86 (1H, d, J=14.4 Hz), 7.14 (2H, t, J=9.6 Hz), 7.35-7.43 (4H, m), 7.47-7.62 (4H, m), 7.74 (2H, m), 10.75 (1H, s). LC-MS (ESI) calcd for $C_{28}H_{25}FN_4O_6S_2$ 596.12, found 597.2 [M+H⁺].

EXAMPLE 41 cis-N-[3-(1-Cyclobutylamino-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide trifluoroacetic acid salt

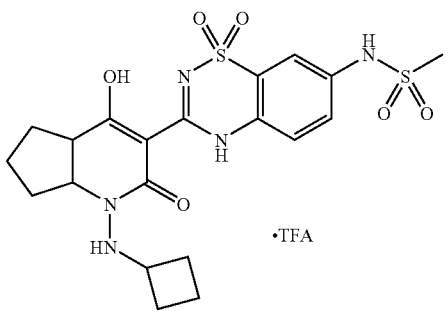

a) N'-Cyclobutyl-hydrazinecarboxylic acid tert-butyl ester

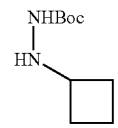

Cyclobutanone (8.19 g, 116.85 mmol) was dissolved in ethanol (60 mL). tert-Butyl carbazate (15.64 g, 118.34 mmol) was added. The reaction was stirred at 25° C. for 2.5 h before it was concentrated in vacuo. The residue was re-dissolved in ethanol (60 mL). Acetic acid (14.09 mL, 246.14 mmol) and sodium cyanoborohydride (15.46 g, 246.02 mmol) were added. The reaction was stirred at 25° C. for 48 h. The reaction was quenched via slow addition of saturated aqueous sodium bicarbonate solution (until pH 8 was reached). The resulting mixture was extracted with ethyl acetate (3×150 mL). The organic layers were combined, dried over magnesium sulfate, filtered and concentrated in vacuo to afford a yellow oil. Purification by flash column chromatography (Teledyne Isco RediSep Column; 0-30% ethyl acetate in hexanes) afforded the desired product, N'-cyclobutyl-hydrazinecarboxylic acid tert-butyl ester (5.42 g, 29.10 mmol, 25%), as a white powder. $^1$H NMR (400 MHz, CDCl$_3$) δ: 1.48 (9H, s), 1.62-1.70 (1H, m), 1.73-1.82 (1H, m), 1.84-1.94 (2H, m), 2.07-2.15 (2H, m), 3.56-3.63 (1H, m).

b) N'-Allyl-N'-cyclobutyl-hydrazinecarboxylic acid tert-butyl ester

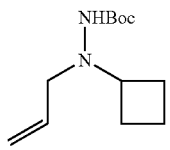

N'-cyclobutyl-hydrazinecarboxylic acid tert-butyl ester (0.88 g, 4.72 mmol) was dissolved in ethanol (45 mL). Allyl bromide (0.82 mL, 9.44 mmol), potassium carbonate (0.65 g, 4.72 mmol), and lithium iodide (0.063 g, 0.47 mmol) were added sequentially. The reaction was stirred at reflux for 18 h. The mixture was cooled to 25° C., concentrated in vacuo, taken up in water (20 mL) and extracted with ethyl acetate (3×20 mL). The organic layers were combined, dried over magnesium sulfate, filtered, and concentrated in vacuo to afford a yellow oil. Purification by flash column chromatography (Teledyne Isco RediSep Column; 0-20% ethyl acetate in hexanes) afforded the desired product, N'-allyl-N'-cyclobutyl-hydrazinecarboxylic acid tert-butyl ester (0.98 g, 4.34 mmol, 92%), as a white powder. $^1$H NMR (400 MHz, DMSO-$d_6$) δ: 1.36 (9H, s), 1.50-1.62 (2H, m), 1.82-1.88 (4H, m), 3.13 (2H, d, J=6.0 Hz), 3.34-3.39 (1H, m), 5.03 (1H, d, J=10.0 Hz), 5.14 (1H, d, J=16.8 Hz), 5.71-5.81 (1H, m), 7.59 (1H, bs). LC-MS (ESI) calcd for $C_7H_{14}N_2$ (free hydrazine) 126.20, found 127.0 [M+H$^+$].

c) N'-Allyl-N'-cyclobutyl-hydrazine hydrochloride

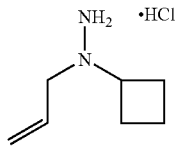

Acetyl chloride (1.45 mL, 20.41 mmol) was added dropwise into methanol (10 mL) at 0° C. The resulting mixture was stirred at 25° C. for 30 min. N'-allyl-N'-cyclobutyl-hydrazinecarboxylic acid tert-butyl ester (0.40 g, 1.77 mmol) was added in one portion. The reaction was stirred at 25° C. for 18 h. The mixture was concentrated in vacuo and used directly in the next step.

d) 2-(N'-Allyl-N'-cyclobutyl-hydrazino)-cyclopentanecarboxylic acid ethyl ester

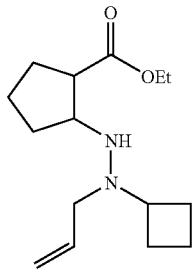

N'-Allyl-N'-cyclobutyl-hydrazine hydrogen chloride (288 mg, 1.77 mmol) was dissolved in methanol (20 mL). 2-Oxocyclopentanecarboxylic acid ethyl ester (0.26 mL, 1.77 mL), sodium acetate (290 mg, 3.54 mmol), sodium cyanoborohydride (222 mg, 3.54 mmol) and 4 Å molecular sieves (400 mg) were added sequentially. The reaction was stirred at 25° C. for 18 h before it was quenched via the addition of saturated aqueous sodium bicarbonate solution (20 mL). The mixture was extracted with ethyl acetate (3×20 mL). The organic layers were combined, dried over magnesium sulfate, filtered and concentrated in vacuo to afford a yellow oil. Purification by flash column chromatography (Teledyne Isco RediSep Column; 0-30% ethyl acetate in hexanes) afforded the desired product, 2-(N'-allyl-N'-cyclobutyl-hydrazino)-cyclopentanecarboxylic acid ethyl ester (333 mg, 1.25 mmol, 71%), as a white powder. $^1$H NMR (400 MHz, CDCl$_3$) δ: 1.25-1.38 (2.2H, m), 1.60-1.68 (3.1H, m), 1.74-1.88 (5.2H, m), 1.94-2.06 (4.8H, m), 2.14-2.21 (3.6H, m), 3.42 (2.5H, d, J=6.8 Hz), 3.51-3.58 (1.3H, m), 3.64-3.69 (0.4H, m), 3.76-3.80 (0.5H, m), 4.10-4.20 (1.2H, m), 4.36-4.41 (0.3H, m), 5.36 (2.2H, bs), 5.45-5.51 (2.7H, m), 5.74-5.85 (1H, m). LC-MS (ESI) calcd for $C_{15}H_{26}N_2O_2$ 266.38, found 267.2 [M+H$^+$].

e) cis-N-{3-[1-(Allyl-cyclobutyl-amino)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

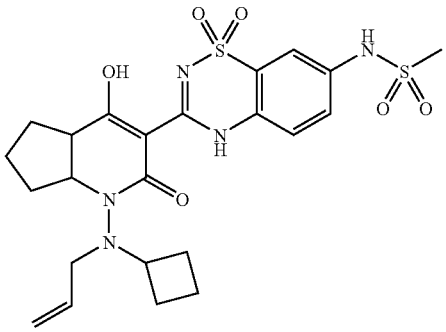

2-(N'-Allyl-N'-cyclobutyl-hydrazino)-cyclopentanecarboxylic acid ethyl ester (333 mg, 1.25 mmol) was dissolved in anhydrous N,N-dimethylformamide (10 mL). (7-Methanesulfonylamino-1,1-dioxo-1,4-dihydro-1λ$^6$-benzo[1,2,4]thiadiazin-3-yl)-acetic acid (416 mg, 1.25 mmol) was added followed by N-methylmorpholine (0.29 mL, 2.62 mmol). The mixture was stirred until everything dissolved, approximately 5 min. 1-(3-Dimethylaminopropyl)-3-ethylcarbodiimide hydrochloride (251 mg, 1.31 mmol) was added and the mixture was stirred at 25° C. for 16 h. The reaction was quenched via addition of saturated aqueous sodium bicarbonate solution (20 mL). The mixture was extracted with ethyl acetate (3×30 mL). The organic layers were combined and washed with saturated aqueous brine solution (20 mL). The resulting solution was dried over magnesium sulfate, filtered, and concentrated in vacuo to afford a golden oil. The oil was dissolved in ethanol (8 mL). A 21% w/w solution of sodium ethoxide in ethanol (1.40 mL, 3.75 mmol) was added. The reaction was refluxed for 16 h. The reaction was quenched via the addition of saturated aqueous ammonium chloride solution (10 mL). The mixture was extracted with ethyl acetate (3×20 mL). The organic layer was further washed with saturated aqueous sodium bicarbonate solution (2×20 mL), saturated aqueous brine solution (20 mL), dried over magnesium sulfate, filtered, and concentrated in vacuo to afford a clear oil. Purification by flash column chromatography (Teledyne Isco RediSep Column; 0-5% methanol in dichloromethane) afford the desired product, cis-N-{3-[1-(allyl-cyclobutyl-amino)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide (83 g, 0.16 mmol, 13%), as a white powder. $^1$H NMR (400 MHz, DMSO-$d_6$) δ: 1.50-1.71 (7H, m), 1.80-2.33 (5H, m), 3.06 (3H, s), 3.67 (2H, s), 3.89-4.05 (2H, m), 5.05-5.12 (1H, m), 5.18-5.22 (1H, m), 5.82-5.90 (1H, m), 7.50-7.57 (3H, m), 10.18 (1H, bs). LC-MS (ESI) calcd for $C_{23}H_{29}N_5O_6S_2$ 535.64, found 536.4 [M+H$^+$].

f) cis-N-[3-(1-Cyclobutylamino-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide trifluoroacetic acid salt

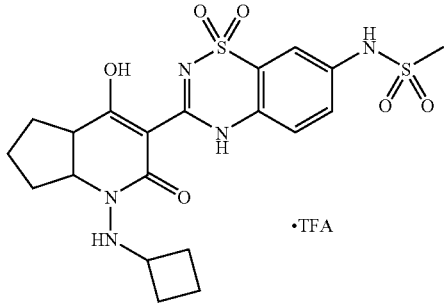

cis-N-{3-[1-(Allyl-cyclobutyl-amino)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide (62 mg, 0.12 mmol) was dissolved in dichloromethane (5 mL). The solution was degassed and backfilled with nitrogen. Tetrakis(triphenylphosphine)palladium(0) (14 mg, 0.012 mmol) and N,N'-dimethylbarbituric acid (56 mg, 0.36 mmol) were added sequentially. The reaction was stirred at 35° C. for 18 h. The mixture was cooled to 25° C. and concentrated in vacuo. Purification by prep-HPLC [Column Luna 5µ C18 (2) 100 Å AXIA 150×21.2 mm, 5 micron, 25%-100% in 12 min @ 30 mL/min flow rate, 0.05% trifluoroacetic acid in acetonitrile/0.05% trifluoroacetic acid in water] afforded the desired product, cis-N-[3-(1-cyclobutylamino-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide trifluoroacetic acid salt (25 mg, 0.04 mmol, 33%), as a white solid. $^1$H NMR (400 MHz, DMSO-d$_6$) δ: 1.53-1.70 (4H, m), 1.84-1.95 (8H, m), 1.97-2.13 (6H, m), 3.06 (3H, s), 3.45-3.70 (2H, m), 7.50-7.57 (3H, m), 10.18 (1H, s), 13.88 (1H, s). LC-MS (ESI) calcd for $C_{20}H_{25}N_5O_6S_2$ (free hydrazine) 495.57, found 496.3 [M+H$^+$].

EXAMPLE 42

(4aR,7aS)-3-(1,1-Dioxo-7-piperidin-1-yl-1,4-dihydro-1$\lambda^6$-benzo[1,2,4]thiadiazin-3-yl)-1-(4-fluorobenzyl)-4-hydroxy-1,4a,5,6,7,7a-hexahydro-[1]pyrindin-2-one

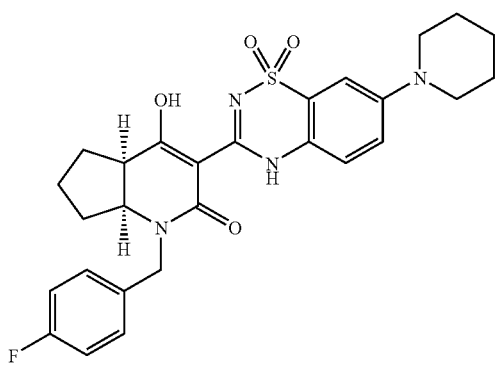

A reaction flask was charged with L-proline (24.3 mg, 0.21 mmol), potassium carbonate (146.3 mg, 1.06 mmol), copper iodide (21 mg, 0.11 mmol) and (4aR,7aS)-1-(4-fluoro-benzyl)-4-hydroxy-3-(7-iodo-1,1-dioxo-1,4-dihydro-1$\lambda^6$-benzo[1,2,4]thiadiazin-3-yl)-1,4a,5,6,7,7a-hexahydro-[1]pyrindin-2-one (prepared as described in Example 39c, 300 mg, 0.53 mmol). The flask was degassed and backfilled with nitrogen, and then anhydrous dimethylsulfoxide (5 mL) was added followed by addition of piperidine (0.16 mL, 1.60 mmol). The resulting suspension was vigorously stirred at 90° C. for 60 h, and then allowed to cool to 25° C. The mixture was passed through a plug of Celite and rinsed with 10% methanol/dichloromethane. The filtrate was concentrated in vacuo, and the residue was purified by prep-HPLC [Column Luna 5µ C18 (2) 100 Å AXIA 50×21.2 mm, 5 micron, 40%-95% in 7 min @ 30 mL/min flow rate, 0.05% trifluoroacetic acid in acetonitrile/0.05% trifluoroacetic acid in water] to afford the desired product, (4aR,7aS)-3-(1,1-dioxo-7-piperidin-1-yl-1,4-dihydro-1$\lambda^6$-benzo[1,2,4]thiadiazin-3-yl)-1-(4-fluorobenzyl)-4-hydroxy-1,4a,5,6,7,7a-hexahydro-[1]pyrindin-2-one (160 mg, 0.31 mmol, 58%), as a yellow solid. $^1$H NMR (400 MHz, DMSO-d$_6$) δ: 1.40-1.63 (9H, m), 1.96 (2H, m), 2.06 (1H, m), 3.23 (4H, m), 3.32 (1H, m), 3.83 (1H, m), 4.45 (1H, d, J=15.6 Hz), 4.89 (1H, d, J=14.8 Hz), 7.14 (3H, m), 7.32-7.44 (4H, m), 13.86 (1H, s). LC-MS (ESI) calcd for $C_{27}H_{29}FN_4O_4S$ 524.19, found 525.3 [M+H$^+$]. e.e. >97% based on the e.e. of the commercially available (1R,2S)-2-amino-cyclopentanecarboxylic acid (Example 40a).

EXAMPLE 43 cis-N-[3-(1-Cyclohexyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide

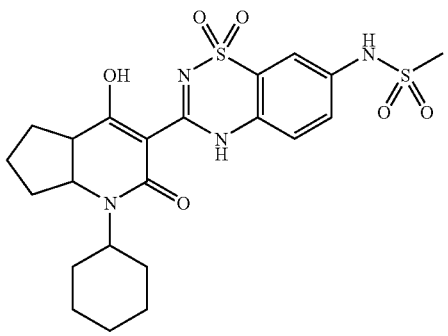

a) 2-Cyclohexylamino-cyclopentanecarboxylic acid ethyl ester

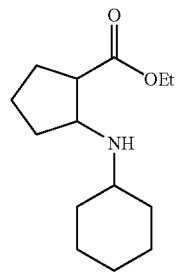

A solution of 2-oxo-cyclopentanecarboxylic acid ethyl ester (2.01 g, 12.9 mmol) in ethanol (20 mL) was treated with cyclohexylamine (1.75 mL, 12.1 mmol), sodium cyanoborohydride (1.39 g, 22.2 mmol), and glacial acetic acid (10 drops) and stirred for 16 h at 50° C. After cooling to 25° C. the solvent was removed in vacuo, the crude material was redissolved in ethyl acetate (100 mL), washed with saturated aqueous sodium bicarbonate solution (100 mL). The aqueous layer was discarded and the organic layer was washed with 1.0 M aqueous hydrochloric acid solution (50 mL). The organic layer was discarded, 1.0 M aqueous sodium hydroxide solution (75 mL) was added and the aqueous layer was extracted with ethyl acetate (100 mL). The organic layer was dried over sodium sulfate, filtered and the solvent was removed in vacuo to afford the desired product 2-cyclohexylamino-cyclopentanecarboxylic acid ethyl ester (2.10 g, 8.77 mmol, 86.9%), as a light yellow oil. LC-MS (ESI) calcd for $C_{14}H_{25}NO_2$ 239.19, found 240.2 [M+H$^+$].

b) cis-N-[3-(1-Cyclohexyl-4-hydroxy-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide

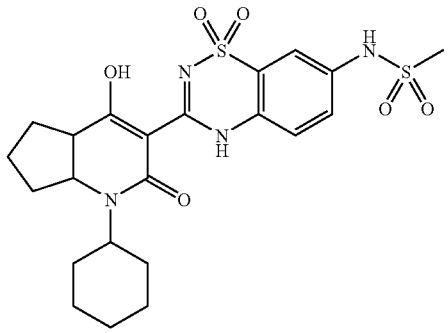

A solution of (7-methanesulfonylamino-1,1-dioxo-1,4-dihydro-1λ$^6$-benzo[1,2,4] thiadiazin-3-yl)-acetic acid (prepared as described in Example 1j, 0.100 g, 0.300 mmol) and 2-cyclohexylamino-cyclopentanecarboxylic acid ethyl ester (0.072 g, 0.300 mmol) in N,N-dimethylformamide (1.5 mL) was treated with N-methylmorpholine (72.8 mg, 0.72 mmol), 1-(3-dimethylaminopropyl)-3-ethylcarbodiimide hydrochloride (69.0 mg, 0.36 mmol) and stirred at 25° C. for 4 h. The solvent was removed in vacuo. The crude material was redissolved in ethyl acetate (75 mL) and washed twice with 1.0 M aqueous hydrochloric acid solution (50 mL). The organic layer was then dried over sodium sulfate, filtered and concentrated in vacuo. The crude intermediate was redissolved in ethanol (5 mL) and treated with a 21% w/w solution of sodium ethoxide in ethanol (448 μL, 1.2 mmol) and stirred for 2 h at 60° C. The reaction was allowed to cool to 25° C., treated with glacial acetic acid (0.4 mL), the solvents were removed in vacuo, and the residue was and purified by prep-HPLC [Column Luna 5μ C18 (2) 100 Å AXIA 50×21.2 mm, 5 micron, 30%-90% in 7 min @ 30 mL/min flow rate, 0.05% trifluoroacetic acid in acetonitrile/0.05% trifluoroacetic acid in water] to afford the desired product, cis-N-[3-(1-cyclohexyl-4-hydroxy-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide (48 mg, 0.094 mmol, 31.5%), as a white solid. $^1$H NMR (400 MHz, DMSO-d$_6$) δ: 1.13-1.19 (2H, m), 1.31-1.40 (2H, m), 1.48-2.04 (12H, m), 3.06 (3H, s), 3.26-3.35 (1H, m), 3.91-4.05 (1H, m), 4.23-4.35 (1H, m), 7.50-7.57 (3H, m), 10.18 (1H, bs). LC-MS (ESI) calcd for $C_{22}H_{28}N_4O_6S_2$ 508.15, found 509.2 [M+H$^+$].

EXAMPLE 44

(4aR,7aS)-3-[7-(1,1-Dioxo-4,5-dihydro-1H-1λ$^6$-thiophen-2-yl)-1,1-dioxo-1,4-dihydro-1λ$^6$-benzo[1,2,4]thiadiazin-3-yl]-1-(4-fluoro-benzyl)-4-hydroxy-1,4a,5,6,7,7a-hexahydro-[1]pyrindin-2-one

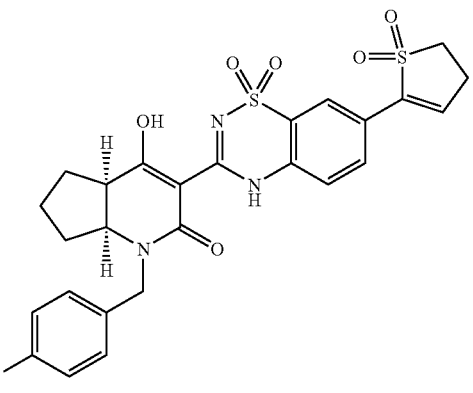

To a solution of (4aR,7aS)-1-(4-fluoro-benzyl)-4-hydroxy-3-(7-iodo-1,1-dioxo-1,4-dihydro-1λ$^6$-benzo[1,2,4]thiadiazin-3-yl)-1,4a,5,6,7,7a-hexahydro-[1]pyrindin-2-one (prepared as described in Example 39c, 284 mg, 0.50 mmol) and tributyl-(1,1-dioxo-4,5-dihydro-1H-1%-thiophen-2-yl)-stannane (380 mg, 0.93 mmol) in anhydrous N,N-dimethylformamide (8 mL) under a nitrogen atmosphere, tetrakis(triphenylphosphine)-palladium(0) (60 mg, 0.05 mmol) was added. The resulting mixture was stirred at 90° C. for 20 h, and then allowed to cool to 25° C. The reaction mixture was concentrated in vacuo and the residue was purified by prep-HPLC [Column Luna 5μ C18 (2) 100 Å AXIA 50×21.2 mm, 5 micron, 40%-95% in 7 min @ 30 mL/min flow rate, 0.05% trifluoroacetic acid in acetonitrile/0.05% trifluoroacetic acid in water] to afford the desired product, (4aR,7aS)-3-[7-(1,1-dioxo-4,5-dihydro-1H-1λ$^6$-thiophen-2-yl)-1,1-dioxo-1,4-dihydro-1λ$^6$-benzo[1,2,4]thiadiazin-3-yl]-1-(4-fluoro-benzyl)-4-hydroxy-1,4a,5,6,7,7a-hexahydro-[1]pyrindin-2-one (84 mg, 0.15 mmol, 30%), as a yellow solid. $^1$H NMR (400 MHz, DMSO-d$_6$) δ: 1.44-1.60 (3H, m), 1.97 (2H, m), 2.11 (1H, m), 2.97 (2H, m), 3.32 (1H, bs), 3.53 (2H, t, J=6.4 Hz), 3.87 (1H, m), 4.48 (1H, d, J=13.2 Hz), 4.90 (1H, d, J=15.6 Hz), 7.16 (2H, m), 7.41 (3H, m), 7.69 (1H, d, J=8.4 Hz), 7.96 (1H, dd, J=8.4, 1.6 Hz), 8.10 (1H, d, J=1.2 Hz). LC-MS (ESI) calcd for $C_{26}H_{24}FN_3O_6S_2$ 557.11, found 558.1 [M+H$^+$]. e.e. >97% based on the e.e. of the commercially available (1R,2S)-2-amino-cyclopentanecarboxylic acid (Example 40a).

EXAMPLE 45

(4aR,7aS)-3-[7-(1,1-Dioxo-tetrahydro-1λ⁶-thiophen-2-yl)-1,1-dioxo-1,4-dihydro-1λ⁶-benzo[1,2,4]thiadiazin-3-yl]-1-(4-fluoro-benzyl)-4-hydroxy-1,4a,5,6,7,7a-hexahydro-[1]pyrindin-2-one

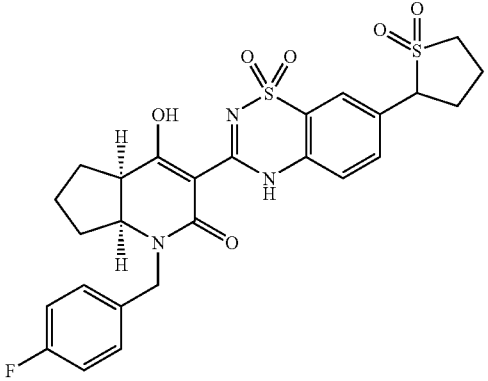

(4aR,7aS)-3-[7-(1,1-Dioxo-4,5-dihydro-1H-1λ⁶-thiophen-2-yl)-1,1-dioxo-1,4-dihydro-1λ⁶-benzo[1,2,4]thiadiazin-3-yl]-1-(4-fluoro-benzyl)-4-hydroxy-1,4a,5,6,7,7a-hexahydro-[1]pyrindin-2-one (prepared as described in Example 44, 45 mg, 0.081 mmol) was dissolved in a 1:5 mixture of N,N-dimethylformamide and methanol (12 mL). 5% Palladium on charcoal (100 mg) was added. The flask was degassed and backfilled with hydrogen gas via balloon. The mixture was stirred at 25° C. for 16 h. The mixture was passed through a plug of Celite, washed with 10% methanol/dichloromethane, and the filtrate was concentrated in vacuo. The residue was purified by prep-HPLC [Column Luna 5μ C18 (2) 100 Å AXIA 50×21.2 mm, 5 micron, 40-95% in 7 min @ 30 mL/min flow rate, 0.05% trifluoroacetic acid in acetonitrile/0.05% trifluoroacetic acid in water] to afford the desired product as an inseparable mixture of two diastereomers, (4aR,7aS)-3-[7-(1,1-dioxo-tetrahydro-1λ⁶-thiophen-2-yl)-1,1-dioxo-1,4-dihydro-1λ⁶-benzo[1,2,4]thiadiazin-3-yl]-1-(4-fluoro-benzyl)-4-hydroxy-1,4a,5,6,7,7a-hexahydro-[1]pyrindin-2-one (20 mg, 0.036 mmol, 44%), as a white powder. ¹H NMR (400 MHz, DMSO-d₆) δ: 1.44-1.60 (3H, m), 1.95-2.40 (10H, m), 3.22-3.36 (3H, m), 3.86 (1H, bs), 4.47 (1H, d, J=14.4 Hz), 4.56 (1H, dd, J=12.4, 8.0 Hz), 4.91 (1H, d, J=15.2 Hz), 7.15 (2H, t, J=8.4 Hz), 7.39 (2H, m), 7.61 (1H, d, J=8.8 Hz), 7.71 (1H, dd, J=8.4, 2.4 Hz), 7.82 (1H, s). LC-MS (ESI) calcd for $C_{26}H_{26}FN_3O_6S_2$ 559.12, found 560.3 [M+H⁺].

EXAMPLE 46

1-(4-Fluoro-benzyl)-4-hydroxy-3-(7-iodo-1,1-dioxo-1,4-dihydro-1λ⁶-benzo[1,2,4]thiadiazin-3-yl)-1,4a,5,6,7,8,9,9a-octahydro-cyclohepta[b]pyridin-2-one

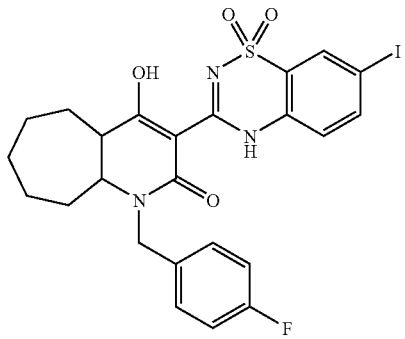

(7-Iodo-1,1-dioxo-1,4-dihydro-1λ⁶-benzo[1,2,4]thiadiazin-3-yl)-acetic acid (prepared as described in Example 24b, 0.959 g, 2.62 mmol), 1-(3-dimethylaminopropyl)-3-ethylcarbodiimide hydrochloride (0.527 g, 2.75 mmol) and N-methylmorpholine (0.605 mL, 5.50 mmol) were added sequentially to a solution of cis-2-(4-fluoro-benzylamino)-cycloheptanecarboxylic acid methyl ester (prepared as described in Example 2b, 0.732 g, 2.62 mmol) in N,N-dimethylformamide (20 mL) at 25° C. The reaction mixture was stirred at 25° C. for 3 h, and then was concentrated in vacuo. The residue was partitioned between 1.0 M aqueous hydrochloric acid solution (150 mL) and ethyl acetate (2×150 mL). The organic layers were dried over sodium sulfate, filtered and concentrated in vacuo. The residue was dissolved in ethanol (60 mL) at 25° C. A 21% w/w solution of sodium ethoxide in ethanol (3.40 mL, 10.4 mmol) was added and the reaction mixture was heated to 60° C. for 1 h. After cooling to 25° C., the reaction mixture was partitioned between 1.0 M aqueous hydrochloric acid solution (150 mL) and ethyl acetate (2×150 mL). The organic layers were dried over sodium sulfate, filtered and concentrated in vacuo. The residue was purified by flash column chromatography (Teledyne Isco RediSep Column; 10-70% ethyl acetate in hexanes) to afford the desired product, 1-(4-fluoro-benzyl)-4-hydroxy-3-(7-iodo-1,1-dioxo-1,4-dihydro-1λ⁶-benzo[1,2,4]thiadiazin-3-yl)-1,4a,5,6,7,8,9,9a-octahydro-cyclohepta[b]pyridin-2-one (0.534 g, 0.891 mmol, 34%) as a beige foam. ¹H NMR (400 MHz, DMSO-d₆) δ: 1.25-1.42 (2H, m), 1.50-1.57 (3H, m), 1.76-1.98 (1H, m), 1.93 (3H, s), 3.30 (1H, bs), 3.55-3.59 (1H, m), 4.27 (1H, d, J=15.1 Hz), 5.02 (1H, d, J=14.9 Hz), 7.11-7.18 (2H, m), 7.25-7.29 (1H, m), 7.30-7.32 (1H, m), 7.39-7.42 (2H, m), 7.91-7.96 (1H, m), 8.02 (1H, s). LC-MS (ESI) calcd for $C_{24}H_{23}FN_3O_4S$ 595.04, found 596.2 [M+H⁺].

EXAMPLE 47 cis-N-[3-(1-Cyclobutylmethyl-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide

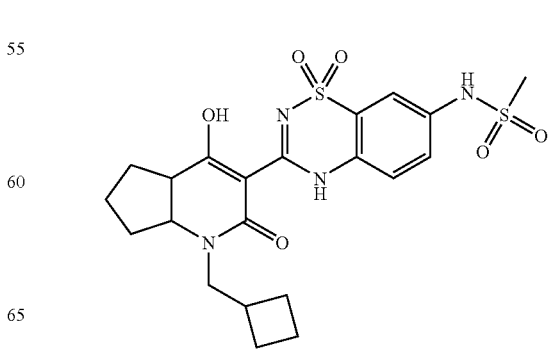

a) 2-(Cyclobutylmethyl-amino)-cyclopentanecarboxylic acid ethyl ester

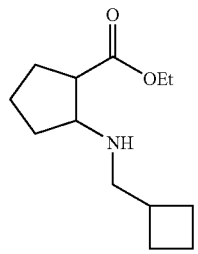

2-Oxo-cyclopentanecarboxylic acid ethyl ester (0.24 mL, 1.64 mmol) and C-cyclobutyl-methylamine hydrochloride (0.20 g, 1.64 mmol) were dissolved in methanol (8 mL). Sodium acetate (0.27 g, 3.28 mmol) was added followed by 4 Å powdered molecular sieves (0.20 g) and sodium cyanoborohydride (0.21 g, 3.28 mmol). The reaction was stirred at 25° C. for 16 h. The mixture was poured into a mixture of saturated aqueous sodium bicarbonate solution (20 mL) and ethyl acetate (30 mL). After shaking, both layers were passed through a plug of Celite. The organic layer was further washed with saturated aqueous sodium bicarbonate solution (10 mL), saturated aqueous brine solution (10 mL), dried over magnesium sulfate, filtered, and concentrated in vacuo to afford the crude product, 2-(cyclobutylmethyl-amino)-cyclopentanecarboxylic acid ethyl ester (0.29 g, 1.30 mmol, 79%) as a clear oil. LC-MS (ESI) calcd for $C_{13}H_{23}NO_2$ 225.33, found 226.2 [M+H$^+$].

b) cis-N-[3-(1-Cyclobutylmethyl-4-hydroxy-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide

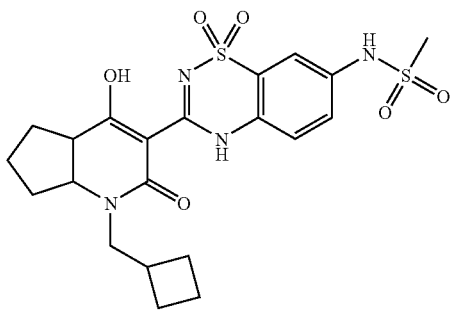

2-(Cyclobutylmethyl-amino)-cyclopentanecarboxylic acid ethyl ester (0.22 g, 0.96 mmol) was dissolved in anhydrous N,N-dimethylformamide (10 mL). (7-Methanesulfonylamino-1,1-dioxo-1,4-dihydro-1λ$^6$-benzo[1,2,4]thiadiazin-3-yl)-acetic acid (prepared as described in Example 1j, 0.32 g, 0.96 mmol) was added followed by N-methylmorpholine (0.22 mL, 2.02 mmol). The mixture was stirred until everything dissolved, approximately 5 min. 1-(3-Dimethylaminopropyl)-3-ethylcarbodiimide hydrochloride (0.19 g, 1.01 mmol) was added and the mixture was stirred at 25° C. for 16 h. The reaction was quenched via addition of saturated aqueous ammonium chloride solution (20 mL). The mixture was extracted with ethyl acetate (3×30 mL). The organic layers were combined and washed with saturated aqueous brine solution (20 mL). The resulting solution was dried over magnesium sulfate, filtered, and concentrated in vacuo to afford a golden oil. The oil was dissolved in ethanol (10 mL). A 21% w/w solution of sodium ethoxide in ethanol (1.08 mL, 2.88 mmol) was added. The reaction was refluxed for 16 h. The reaction was quenched via the addition of saturated aqueous ammonium chloride solution (10 mL). The mixture was extracted with ethyl acetate (3×20 mL). The organic layer was further washed with saturated aqueous sodium bicarbonate solution (2×20 mL), saturated aqueous brine solution (20 mL), dried over magnesium sulfate, filtered, and concentrated in vacuo to afford a clear oil. Purification by flash column chromatography (Teledyne Isco RediSep Column; 0-5% methanol in dichloromethane) afforded the desired product, cis-N-[3-(1-cyclobutylmethyl-4-hydroxy-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide (0.14 g, 0.28 mmol, 29%) as a pale yellow powder. $^1$H NMR (400 MHz, DMSO-d$_6$) δ: 1.42-1.64 (4H, m), 1.72-1.87 (5H, m), 1.90-2.05 (2H, m), 2.08-2.19 (2H, m), 2.66 (1H, bs), 3.06 (3H, s), 3.74-3.79 (1H, m), 3.86 (1H, bs), 7.13-7.17 (2H, m), 7.49-7.57 (3H, m), 10.16 (1H, s). LC-MS (ESI) calcd for $C_{21}H_{26}N_4O_6S_2$ 494.58, found 495.4 [M+H$^+$].

EXAMPLE 48 cis-N-[3-(4-Hydroxy-2-oxo-1-phenyl-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide

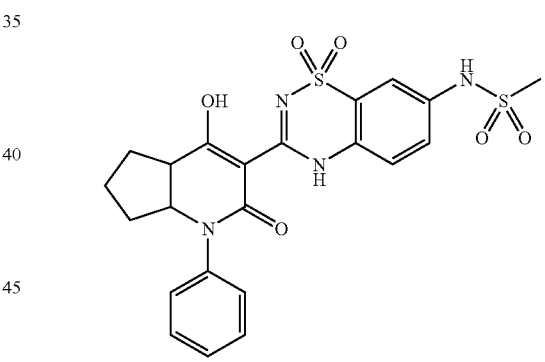

a) 2-Phenylamino-cyclopentanecarboxylic acid ethyl ester

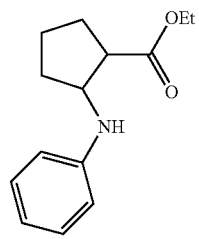

A solution of 2-oxo-cyclopentanecarboxylic acid ethyl ester (2.01 g, 12.9 mmol) in ethanol (20 mL) was treated with aniline (0.98 mL, 10.7 mmol), sodium cyanoborohydride (1.48 g, 23.6 mmol), and glacial acetic acid (10 drops) and stirred for 16 h at 50° C. After cooling to 25° C. the solvent was removed in vacuo, the crude material was redissolved in ethyl acetate (100 mL), washed with saturated aqueous sodium bicarbonate solution (100 mL). The aqueous layer was discarded and the organic layer was washed with 1.0 M aqueous hydrochloric acid solution (50 mL). The organic layer was discarded, 1.0 M aqueous sodium hydroxide solution (75 mL) was added and the aqueous layer was extracted with ethyl acetate (100 mL). The organic layer was dried over sodium sulfate, filtered and the solvent was removed in vacuo to afford the desired product, 2-cyclopentylamino-cyclopentanecarboxylic acid ethyl ester (1.40 g, 6.00 mmol, 56.1%), as a light yellow oil. LC-MS (ESI) calcd for $C_{14}H_{19}NO_2$ 233.14, found 234.2 [M+H$^+$].

b) cis-N-[3-(4-Hydroxy-2-oxo-1-phenyl-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide

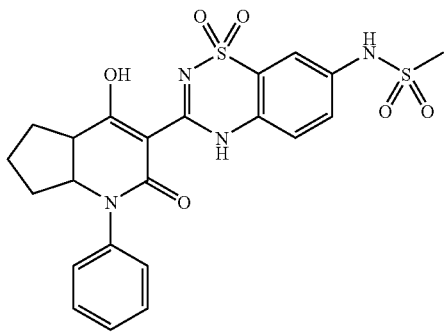

A solution of (7-methanesulfonylamino-1,1-dioxo-1,4-dihydro-1$\lambda^6$-benzo[1,2,4] thiadiazin-3-yl)-acetic acid (prepared as described in Example 1j, 0.100 g, 0.300 mmol) and 2-phenylamino-cyclopentanecarboxylic acid ethyl ester (0.070 g, 0.300 mmol) in N,N-dimethylformamide (1.5 mL) was treated with N-methylmorpholine (72.8 mg, 0.72 mmol), 1-(3-dimethylaminopropyl)-3-ethylcarbo-diimide hydrochloride (69.0 mg, 0.36 mmol) and stirred at 25° C. for 4 h. The solvent was removed in vacuo. The crude material was redissolved in ethyl acetate (75 mL) and washed twice with 1.0 M aqueous hydrochloric acid solution (50 mL). The organic layer was then dried over sodium sulfate, filtered and concentrated in vacuo. The crude intermediate was redissolved in ethanol (5 mL) and treated with a 21% w/w solution of sodium ethoxide in ethanol (448 µL, 1.2 mmol) and stirred for 2 h at 60° C. The reaction was allowed to cool to 25° C., treated with glacial acetic acid (0.4 mL), the solvents were removed in vacuo, and the residue was and purified by prep-HPLC [Column Luna 5µ C18 (2) 100 Å AXIA 50×21.2 mm, 5 micron, 30%-90% in 7 min @ 30 mL/min flow rate, 0.05% trifluoroacetic acid in acetonitrile/0.05% trifluoroacetic acid in water] to afford the desired product, cis-N-[3-(4-Hydroxy-2-oxo-1-phenyl-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide (25 mg, 0.050 mmol, 16.6%), as a white solid. $^1$H NMR (400 MHz, CDCl$_3$) δ: 1.65-1.72 (1H, m), 1.76-1.88 (2H, m), 1.93-2.00 (1H, m), 2.26-2.31 (2H, m), 3.04 (3H, s), 3.26 (1H, dd, J$_1$=15.5 Hz, J$_2$=7.7 Hz), 4.26 (1H, dd, J$_1$=13.1 Hz, J$_2$=5.4 Hz), 7.10 (1H, d, J=8.5 Hz), 7.22-7.29 (2H, m), 7.39 (1H, t, J=7.4 Hz), 7.49 (2H, t, J=8.0 Hz), 7.56-7.59 (1H, m), 7.69 (1H, d, J=2.5 Hz). LC-MS (ESI) calcd for $C_{22}H_{22}N_4O_6S_2$ 502.10, found 503.2 [M+H$^+$].

EXAMPLE 49

N-[3-(1-Cyclohexyl-4-hydroxy-2-oxo-1,2,4a,5,6,7,8,8a-octahydro-quinolin-3-yl)-1,1-dioxo-1,4-dihydro-1$\lambda^6$-benzo[1,2,4]thiadiazin-7-yl]-methanesulfonamide

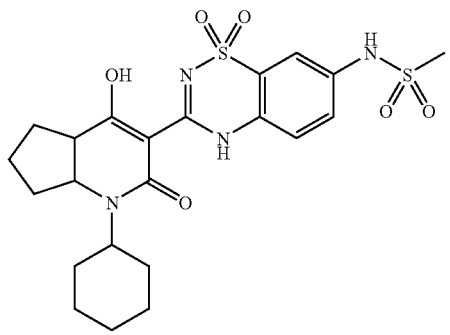

a) 2-Cyclohexylamino-cyclohexanecarboxylic acid ethyl ester

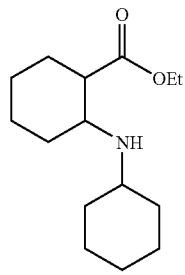

cis-2-Amino-cyclohexanecarboxylic acid ethyl ester hydrochloride (0.5 g, 2.407 mmol) was dissolved in methanol (25 mL). Cyclohexanone (0.236 g, 2.407 mmol) was added followed by acetic acid (0.1 mL). The solution was stirred at 25° C. for 10 min. Sodium cyanoborohydride (0.378 g, 6.018 mmol) was added and the mixture was stirred at 25° C. for 16 h. The mixture was poured into 1/2 saturated aqueous sodium bicarbonate solution (300 mL). The aqueous layer was extracted with ethyl acetate (3×100 mL). The combined organic layers were dried over sodium sulfate, filtered and concentrated in vacuo to afford the crude product, 2-cyclohexylamino-cyclohexanecarboxylic acid ethyl ester (0.38 g, 1.5 mmol, 62.4%), as a clear oil. LC-MS (ESI) calcd for $C_{15}H_{27}NO_2$ 253.20, found 253.9 [M+H$^+$].

b) 2-{Cyclohexyl-[2-(7-methanesulfonylamino-1,1-dioxo-1,4-dihydro-1λ⁶-benzo[1,2,4]thiadiazin-3-yl)-acetyl]-amino}-cyclohexanecarboxylic acid ethyl ester

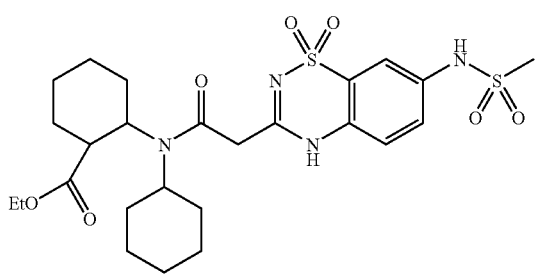

(7-Methanesulfonylamino-1,1-dioxo-1,4-dihydro-1λ⁶-benzo[1,2,4]thiadiazin-3-yl)-acetic acid (prepared as described in Example 1j, 0.333 g, 1.0 mmol) was dissolved in anhydrous N,N-dimethylformamide (5 mL). 2-Cyclohexylamino-cyclohexanecarboxylic acid ethyl ester (0.253 g, 1.0 mmol) was added followed by 1-(3-dimethylaminopropyl)-3-ethylcarbodiimide hydrochloride (0.201 g, 1.05 mmol). Then N-methylmorpholine (212 mg, 2.1 mmol) was added. The mixture was stirred at 25° C. for 5 h. The solution was poured into 1.0 M aqueous hydrochloric acid solution (100 mL). The aqueous layer was extracted with ethyl acetate (2×100 mL). The organic layer was dried over sodium sulfate, filtered and concentrated in vacuo to afford the crude product, 2-{cyclohexyl-[2-(7-methanesulfonylamino-1,1-dioxo-1,4-dihydro-1λ⁶-benzo[1,2,4]thiadiazin-3-yl)-acetyl]-amino}-cyclohexanecarboxylic acid ethyl ester (0.48 g, 0.845 mmol, 84.5%), as a yellow oil. LC-MS (ESI) calcd for $C_{25}H_{36}N_4O_7S_2$ 568.20, found 569.3 [M+H⁺].

c) N-[3-(1-Cyclohexyl-4-hydroxy-2-oxo-1,2,4a,5,6,7,8,8a-octahydro-quinolin-3-yl)-1,1-dioxo-1,4-dihydro-1λ⁶-benzo[1,2,4]thiadiazin-7-yl]-methanesulfonamide

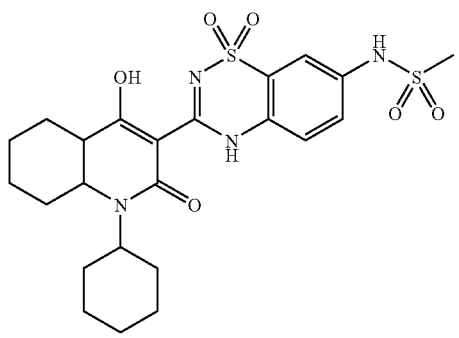

2-{Cyclohexyl-[2-(7-methanesulfonylamino-1,1-dioxo-1,4-dihydro-1λ⁶-benzo[1,2,4]thiadiazin-3-yl)-acetyl]-amino}-cyclohexanecarboxylic acid ethyl ester (0.48 g, 0.845 mmol) was dissolved in ethanol (15 mL), a 21% w/w solution of sodium ethoxide in ethanol (1.095 g, 3.38 mmol) was added. The mixture was stirred at 60° C. for 4 h and allowed to cool to 25° C. The mixture was poured into a 1.0 M aqueous hydrochloric acid solution (50 mL). The product started to precipitate and was collected by vacuum filtration. The precipitate was washed with water and dried under high vacuum to afford the pure product, N-[3-(1-cyclohexyl-4-hydroxy-2-oxo-1,2,4a,5,6,7,8,8a-octahydro-quinolin-3-yl)-1,1-dioxo-1,4-dihydro-1λ⁶-benzo[1,2,4]thiadiazin-7-yl]-methanesulfonamide (0.183 g, 0.35 mmol, 41.4%), as a tan solid. ¹H NMR (400 MHz, DMSO-d₆) δ: 1.07-1.89 (18H, m), 2.32 (1H, bs), 3.05 (3H, s), 3.61-4.33 (3H, m), 7.47-7.60 (3H, m), 7.49-7.57 (3H, m), 10.15 (1H, s), 13.88 (1H, s). LC-MS (ESI) calcd for $C_{23}H_{30}N_4O_6S_2$ 522.16, found 523.4 [M+H⁺].

EXAMPLE 50

1-(4-Fluoro-benzyl)-4-hydroxy-3-(7-iodo-1,1-dioxo-1,4-dihydro-1λ⁶-benzo[1,2,4]thiadiazin-3-yl)-4a,5,6,7,8,8a-hexahydro-1H-quinolin-2-one

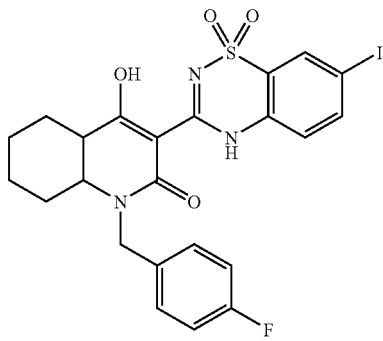

a) 2-(4-Fluoro-benzylamino)-cyclohexanecarboxylic acid ethyl ester

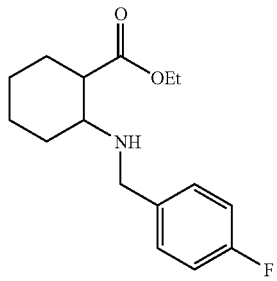

To a solution of cis-2-amino-cyclohexanecarboxylic acid ethyl ester hydrochloride (2.80 g, 12.81 mmol) in tetrahydrofuran (100 mL) at 25° C. was added magnesium sulfate (4.0 g), triethylamine (1.36 g, 13.48 mmol), and 4-fluorobenzaldehyde (3.26 g, 26.29 mmol) sequentially. The reaction was stirred at 25° C. for 16 h. The mixture was passed through a short pad of Celite and the filtrate was concentrated and dried in vacuo. The residue was re-dissolved in methanol (100 mL) at 25° C. To this solution was slowly added sodium borohydride (1.0 g, 26.29 mmol). The mixture was stirred at 25° C. for 1 h. It was then poured into a 1/2 saturated aqueous sodium bicarbonate solution and the mixture was extracted into ethyl acetate (3×100 mL). The organic layer was dried over sodium sulfate, filtered, and concentrated in vacuo to afford a clear oil. Purification by flash column chromatography (Teledyne Isco RediSep Column; 0-50% ethyl acetate in hexanes) afforded the desired product, 2-(4-fluoro-benzylamino)-cyclohexanecarboxylic acid ethyl ester (4.47 g, 16.0 mmol, >100%, product still contains ethyl acetate), as a clear oil which was directly used in the next step. LC-MS (ESI) calcd for $C_{16}H_{22}FNO_2$ 279.16, found 280.0 [M+H$^+$].

b) 2-{(4-Fluoro-benzyl)-[2-(7-iodo-1,1-dioxo-1,4-dihydro-1λ$^6$-benzo[1,2,4]thiadiazin-3-yl)-acetyl]-amino}-cyclohexanecarboxylic acid ethyl ester

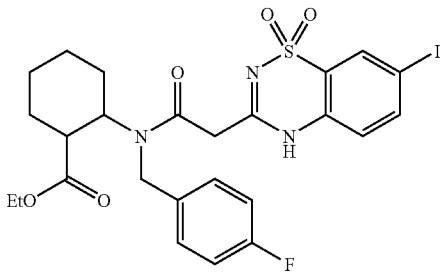

(7-Iodo-1,1-dioxo-1,4-dihydro-1λ$^6$-benzo[1,2,4]thiadiazin-3-yl)-acetic acid (prepared as described in Example 24b, 2.62 g, 7.16 mmol) was dissolved in anhydrous N,N-dimethylformamide (30 mL). 2-(4-Fluoro-benzylamino)-cyclohexanecarboxylic acid ethyl ester (2.0 g, 7.16 mmol) was added followed by 1-(3-dimethylaminopropyl)-3-ethylcarbodiimide hydrochloride (1.44 g, 7.52 mmol). Then N-methylmorpholine (1.52 g, 15.04 mmol) was added into the above reaction mixture. The mixture stirred at 25° C. for 24 h. The solution was diluted with ethyl acetate (200 mL), washed with 1.0 M aqueous hydrochloric acid solution, saturated aqueous sodium bicarbonate solution and saturated aqueous brine solution. The organic layer was dried over sodium sulfate and concentrated in vacuo to afford the crude product, 2-{(4-fluoro-benzyl)-[2-(7-iodo-1,1-dioxo-1,4-dihydro-1λ$^6$-benzo[1,2,4]thiadiazin-3-yl)-acetyl]-amino}-cyclohexanecarboxylic acid ethyl ester, as a yellow oil, which was used directly in the next step without further purification. LC-MS (ESI) calcd for $C_{25}H_{27}FIN_3O_5S$ 627.07, found 628.3 [M+H$^+$].

c) 1-(4-Fluoro-benzyl)-4-hydroxy-3-(7-iodo-1,1-dioxo-1,4-dihydro-1λ$^6$-benzo[1,2,4]thiadiazin-3-yl)-4a,5,6,7,8,8a-hexahydro-1H-quinolin-2-one

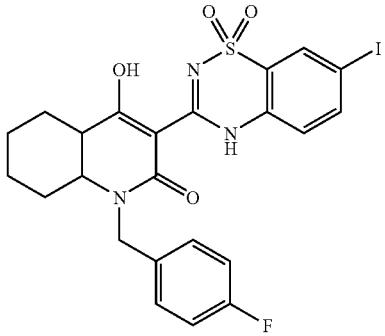

A solution of the crude 2-{(4-fluoro-benzyl)-[2-(7-iodo-1,1-dioxo-1,4-dihydro-1λ$^6$-benzo[1,2,4]thiadiazin-3-yl)-acetyl]-amino}-cyclohexanecarboxylic acid ethyl ester in ethanol (20 mL) was treated with a 21% w/w solution of sodium ethoxide in ethanol (9.28 g, 28.64 mmol) and stirred for 16 h at 60° C. Upon cooling, the reaction mixture was then quenched with 1.0 M aqueous hydrochloric acid solution (20 mL) and extracted with ethyl acetate (2×50 mL). The combined organic layers were washed with saturated aqueous sodium bicarbonate solution, dried over sodium sulfate, filtered, and dried in vacuo. The residue was purified by flash column chromatography (Teledyne Isco RediSep Column; 0-50% ethyl acetate in hexanes) to afford the desired product, 1-(4-fluoro-benzyl)-4-hydroxy-3-(7-iodo-1,1-dioxo-1,4-dihydro-1λ$^6$-benzo[1,2,4]thiadiazin-3-yl)-4a,5,6,7,8,8a-hexahydro-1H-quinolin-2-one (516 mg, 0.888 mmol, 12.4% over two steps), as an off-white solid. $^1$H NMR (400 MHz, DMSO-d$_6$) δ: 1.07-1.81 (8H, m), 2.21-2.34 (1H, m), 3.50-5.03 (3H, m), 7.11-8.03 (7H, m). LC-MS (ESI) calcd for $C_{23}H_{21}FIN_3O_4S$ 581.03, found 582.1 [M+H$^+$].

EXAMPLE 51

3-(1,1-Dioxo-1,4-dihydro-1λ$^6$-benzo[1,2,4]thiadiazin-3-yl)-1-(4-fluoro-benzyl)-4-hydroxy-1,4a,5,6,7,7a-hexahydro-[1]pyrindin-2-one

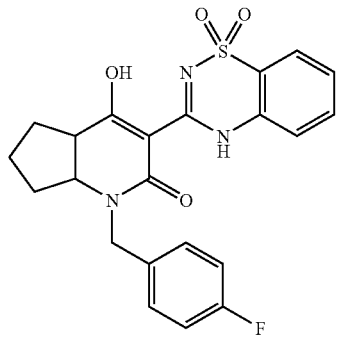

a) (1,1-Dioxo-1,4-dihydro-1λ$^6$-benzo[1,2,4]thiadiazin-3-yl)-acetic acid

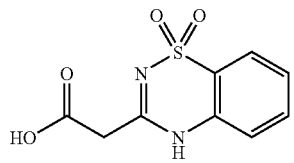

Methyl 3-chloro-3-oxopropionate (3.36 mL, 31.3 mmol) was added to a solution of 2-aminobenzenesulfonamide (4.91 g, 28.5 mmol) in a 1:1 mixture of N,N-dimethylacetamide and diethylether (100 mL) at 0° C. The cloudy reaction mixture was stirred at 0° C. for 3 h, and then was partitioned between half-saturated aqueous sodium bicarbonate (150 mL) and ethyl acetate (2×150 mL). The organic layers were dried over sodium sulfate, filtered and were concentrated in vacuo. The residue was then dissolved in water (75 mL) containing sodium hydroxide (3.42 g, 85.5 mmol) at 25° C. The mixture was heated at 100° C. for 1 h, and then was cooled to 0° C. Concentrated (12.0 M) aqueous hydrochloric acid solution (10.0 mL, 120 mmol) was added dropwise via addition funnel over 10 min, resulting in the formation of a white precipitate. The reaction mixture was stirred at 0° C. for an additional 15 min, and then was filtered through a medium frit. The collected material was washed with water (30 mL) and was air-dried overnight to afford the desired product, (1,1-dioxo-1,4-dihydro-1λ⁶-benzo[1,2,4]thiadiazin-3-yl)-acetic acid (6.37 g, 26.6 mmol, 93%), as a white solid. ¹H NMR (400 MHz, DMSO-d₆) δ: 3.58 (2H, s), 7.30 (1H, d, J=7.4 Hz), 7.44 (1H, t, J=8.2 Hz), 7.64-7.68 (1H, m), 7.79 (1H, dd, J₁=1.5 Hz, J₂=7.8 Hz), 12.19 (1H, s).

b) 2-[[2-(1,1-Dioxo-1,4-dihydro-1λ⁶-benzo[1,2,4]thiadiazin-3-yl)-acetyl]-(4-fluoro-benzyl)-amino]-cyclopentanecarboxylic acid ethyl ester

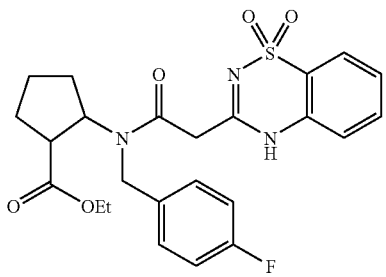

2-(4-Fluoro-benzylamino)-cyclopentanecarboxylic acid ethyl ester (prepared as described in Example 11, 133.5 mg, 0.503 mmol) was mixed with (1,1-dioxo-1,4-dihydro-1λ⁶-benzo[1,2,4]thiadiazin-3-yl)-acetic acid (132.9 mg, 0.554 mmol) in N,N-dimethylformamide (4.6 mL). N-methylmorpholine (122 μL, 1.11 mmol) was added followed by 1-(3-dimethylaminopropyl)-3-ethylcarbodiimide hydrochloride (106.2 mg, 0.554 mmol). The reaction mixture was shaken at 25° C. for 16 h. A 1.0 M aqueous hydrochloric acid solution (4.6 mL) was added at 25° C., and the aqueous layer was extracted with ethyl acetate (3×15 mL). The combined organic layers were washed with saturated aqueous brine solution (10 mL). The organic layer was dried over sodium sulfate, filtered, concentrated and dried in vacuo to afford the crude product, 2-[[2-(1,1-dioxo-1,4-dihydro-1λ⁶-benzo[1,2,4]thiadiazin-3-yl)-acetyl]-(4-fluoro-benzyl)-amino]-cyclopentanecarboxylic acid ethyl ester, as a pale yellow oil, which was directly used in the next step without further purification. LC-MS (ESI) calcd for C₂₄H₂₆FN₃O₅S 487.16, found 488.3 [M+H⁺].

c) 3-(1,1-Dioxo-1,4-dihydro-1λ⁶-benzo[1,2,4]thiadiazin-3-yl)-1-(4-fluoro-benzyl)-4-hydroxy-1,4a,5,6,7,7a-hexahydro-[1]pyrindin-2-one

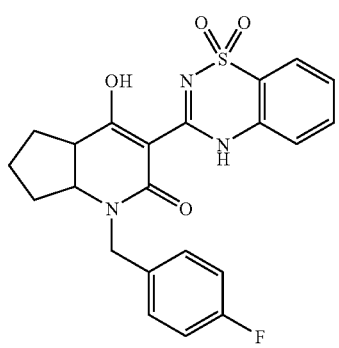

The crude 2-[[2-(1,1-dioxo-1,4-dihydro-1λ⁶-benzo[1,2,4]thiadiazin-3-yl)-acetyl]-(4-fluoro-benzyl)-amino]-cyclopentanecarboxylic acid ethyl ester (0.503 mmol) was dissolved in ethanol (4 mL). A 21% w/w solution of sodium ethoxide in ethanol (1.8 mL) was added and the resulting reaction mixture was shaken for 16 h. A 1.0 M aqueous hydrochloric acid solution (9 mL) was added and the mixture was extracted with ethyl acetate (3×20 mL). The combined organic layers were dried over sodium sulfate, filtered, and concentrated in vacuo to afford the crude product, which was further purified by flash chromatography (Teledyne Isco RediSep Column; 0-100% ethyl acetate in hexanes) to afford the desired product, 3-(1,1-dioxo-1,4-dihydro-1λ⁶-benzo[1,2,4]thiadiazin-3-yl)-1-(4-fluoro-benzyl)-4-hydroxy-1,4a,5,6,7,7a-hexahydro-[1]pyrindin-2-one (114.2 mg, 0.259 mmol, 51.5% over two steps), as an off-white solid. LC-MS (ESI) calcd for C₂₂H₂₀FN₃O₄S 441.12, found 442.4 [M+H⁺]. The ¹H NMR spectrum indicated a 4:1 mixture of cis- and trans-isomers. ¹H NMR (CDCl₃, 400 MHz): δ 1.54-1.77 (m, 3H), 1.87-2.13 (m, 2H), 2.26-2.34 (m, 1H, 80%), 2.36-2.49 (m, 1H, 20%), 2.88-2.93 (m, 1H, 20%), 3.11-3.16 (m. 1H, 80%), 3.69-3.77 (m, 1H), 4.30 (d, 1H, 80%, J=14.8 Hz), 4.43 (d, 1H, 20%, J=14.8 Hz), 5.00 (d, 1H, 20%, J=14.8 Hz), 5.09 (d, 1H, 80%, J=15.2 Hz), 7.03-7.10 (m, 2H), 7.17-7.35 (m, 3H), 7.36-7.42 (m, 1H), 7.55-7.60 (m, 1H), 7.91-7.95 (m, 1H). Anal. calcd for C₂₂H₂₀FN₃O₄S H₂O: C, 57.50; H, 4.83; N, 9.15; found: C, 57.54; H, 4.53; N, 8.79.

EXAMPLE 52

(4aR,7aS)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-C-phenyl-methanesulfonamide

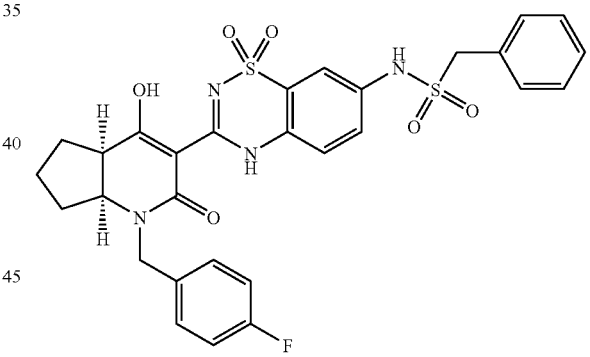

(4aR,7aS)-1-(4-Fluoro-benzyl)-4-hydroxy-3-(7-iodo-1,1-dioxo-1,4-dihydro-1λ⁶-benzo[1,2,4]thiadiazin-3-yl)-1,4a,5,6,7,7a-hexahydro-[1]pyrindin-2-one (prepared as described in Example 39c, 301 mg, 0.53 mmol), α-toluenesulfonamide (272 mg, 1.59 mmol) copper(I) iodide (50.4 mg, 0.265 mmol) potassium phosphate (338 mg, 1.59 mmol), and sarcosine (N-methyl glycine) (37.4 mg, 0.42 mmol) were suspended in N,N-dimethylformamide (8 mL). The mixture was degassed and backfilled with nitrogen (3×). The resulting mixture was stirred at 100° C. for 20.5 h. The mixture was filtered through a plug of Celite. The Celite was washed with 10% methanol in dichloromethane and the combined filtrates were concentrated in vacuo to afford the crude product which was further purified by prep-HPLC [Column ODS-A 5μ 100 Å, 150×21.2 mm, 5 micron, 30%-100% in 13.5 min @ 22 mL/min flow rate, 0.05% trifluoroacetic acid in acetonitrile/0.05% trifluoroacetic acid in water] to afford the desired product, (4aR,7aS)-N-{3-[1-(4-fluoro-benzyl)-4-hydroxy-2-oxo-2,4a,5,6, 7,7a-hexahydro-1H-[1]pyrindin-3-yl]-1,1-dioxo-1,4-dihydro-1λ$^6$-benzo[1,2,4]thiadiazin-7-yl}-C-phenyl-methanesulfonamide 120.4 mg, 0.197 mmol, 37.2%, as a light purple solid. The estimated e.e. is 97% based on the chiral amino acid starting material used. $^1$H NMR (DMSO-d$_6$, 400 MHz): δ 1.44-1.62 (m, 3H), 1.94-2.11 (m, 3H), 2.77 (t, 1H, J=7.4 Hz), 3.01 (t, 1H, J=7.4 Hz), 4.40-4.52 (m, 1H), 4.54 (s, 2H), 4.90 (d, 1H, J=15.6 Hz), 7.15 (t, 2H, J=8.8 Hz), 7.24-7.26 (m, 2H), 7.29-7.32 (m, 4H), 7.36-7.46 (m, 3H), 7.50-7.58 (m, 3H), 10.27-10.29 (m, 1H). LC-MS (ESI) calcd for C$_{29}$H$_{27}$FN$_4$O$_6$S$_2$ 610.14, found 611.5 [M+H$^+$]. Anal. calcd for C$_{29}$H$_{27}$FN$_4$O$_6$S$_2$H$_2$O: C, 55.40; H, 4.65; N, 8.91; found: C, 55.41; H, 4.38; N, 9.11.

EXAMPLE 53 cis-N-[3-(4-Hydroxy-1-methyl-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide

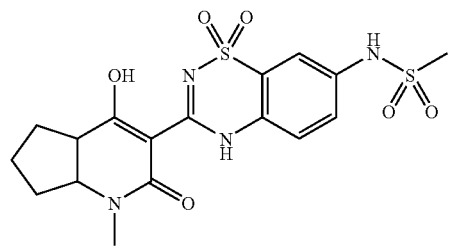

a) 2-Methylamino-cyclopent-1-enecarboxylic acid ethyl ester

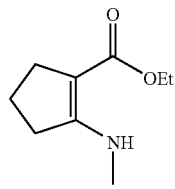

A solution of 2-oxo-cyclopentanecarboxylic acid ethyl ester (3.00 g, 19.2 mmol) in ethanol (20 mL) was treated with methylamine hydrochloride (1.296 g, 19.2 mmol), sodium cyanoborohydride (2.42 g, 38.4 mmol), and glacial acetic acid (10 drops) and stirred for 16 h at 50° C. After cooling to 25° C. the solvent was removed in vacuo, the crude material was redissolved in ethyl acetate (100 mL) and washed with saturated aqueous sodium bicarbonate solution (100 mL). The aqueous layer was discarded and the organic layer was washed with 1.0 M aqueous hydrochloric acid solution (50 mL). The organic layer was discarded, 1.0 M aqueous sodium hydroxide solution (75 mL) was added and the aqueous layer was extracted with ethyl acetate (100 mL). The organic layer was dried over sodium sulfate, filtered and the solvent was removed in vacuo to afford the crude product, 2-methylamino-cyclopent-1-enecarboxylic acid ethyl ester, as a light yellow oil. LC-MS (ESI) calcd for C$_9$H$_{15}$NO$_2$ 169.11, found 170.2 [M+H$^+$].

b) 2-Methylamino-cyclopentanecarboxylic acid ethyl ester

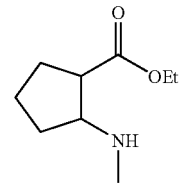

2-Methylamino-cyclopent-1-enecarboxylic acid ethyl ester (1.28 g, 7.57 mmol) was dissolved in glacial acetic acid (20 mL) and sodium triacetoxyborohydride (4.81 g, 22.71 mmol) was added at 0° C. The solution was allowed to warm to 25° C. and stirred for 3 h. The acetic acid was removed in vacuo and the residue was dissolved in dichloromethane. The solution was washed with saturated aqueous sodium bicarbonate solution followed by saturated aqueous brine solution. The organic layer was dried over sodium sulfate, filtered and concentrated in vacuo to afford the desired product, 2-methylamino-cyclopentanecarboxylic acid ethyl ester (285 mg, 1.67 mmol, 22.1%), as a yellowish oil. LC-MS (ESI) calcd for C$_9$H$_{17}$NO$_2$ 171.13, found 172.1 [M+H$^+$].

c) 2-{[2-(7-Methanesulfonylamino-1,1-dioxo-1,4-dihydro-1λ$^6$-benzo[1,2,4]thiadiazin-3-yl)-acetyl]-methyl-amino}-cyclopentanecarboxylic acid ethyl ester

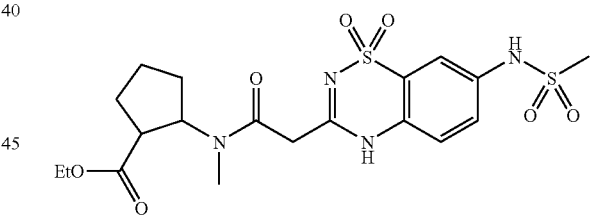

(7-Methanesulfonylamino-1,1-dioxo-1,4-dihydro-1λ$^6$-benzo[1,2,4]thiadiazin-3-yl)-acetic acid (prepared as described in Example 1j, 0.1665 g, 0.5 mmol) was dissolved in anhydrous N,N-dimethylformamide (3 mL). 2-Methylamino-cyclopentanecarboxylic acid ethyl ester (0.0856 g, 0.5 mmol) was added followed by 1-(3-dimethylaminopropyl)-3-ethylcarbodiimide hydrochloride (0.1003 g, 0.525 mmol). Then N-methylmorpholine (115 µL, 1.05 mmol) was added. The mixture was stirred at 25° C. for 5 h. The solution was poured into 1.0 M aqueous hydrochloric acid solution (100 mL). The aqueous layer was extracted with ethyl acetate (2×100 mL). The organic layer was dried over sodium sulfate, filtered and concentrated in vacuo to afford the crude product, 2-{[2-(7-methanesulfonylamino-1,1-dioxo-1,4-dihydro-1λ$^6$-benzo[1,2,4]thiadiazin-3-yl)-acetyl]-methyl-amino}-cyclopentanecarboxylic acid ethyl ester, as a yellow oil. LC-MS (ESI) calcd for C$_{19}$H$_{26}$N$_4$O$_7$S$_2$ 486.12, found 487.2 [M+H$^+$].

d) cis-N-[3-(4-Hydroxy-1-methyl-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide

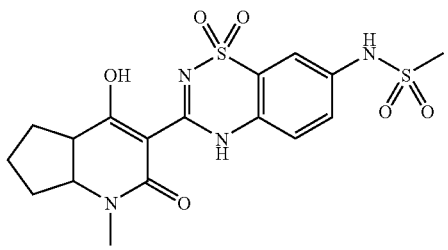

A solution of the crude 2-{[2-(7-methanesulfonylamino-1,1-dioxo-1,4-dihydro-1λ⁶-benzo[1,2,4]thiadiazin-3-yl)-acetyl]-methyl-amino}-cyclopentanecarboxylic acid ethyl ester in ethanol (20 mL) was treated with a 21% w/w solution of sodium ethoxide in ethanol (0.648 g) and stirred for 16 h at 60° C. Upon cooling, the reaction mixture was then quenched with 1.0 M aqueous hydrochloric acid solution (20 mL) and extracted with ethyl acetate (2×50 mL). The combined organic layers were washed with saturated aqueous sodium bicarbonate solution, dried over sodium sulfate, filtered, and dried in vacuo. The residue was purified by prep-HPLC [Column ODS-A 5μ 100 Å, 150×21.2 mm, 5 micron, 50%-100% in 13.5 min @ 22 mL/min flow rate, 0.05% trifluoroacetic acid in acetonitrile/0.05% trifluoroacetic acid in water] to afford the desired product, cis-N-[3-(4-hydroxy-1-methyl-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide (7.5 mg, 0.017 mmol, 3.4% over two steps), as a white solid. ¹H NMR (400 MHz, DMSO-d₆) δ: 1.49-1.69 (4H, m), 1.85-2.22 (3H, m), 2.88-3.20 (3H, m) 3.05 (3H, s), 3.90 (1H, bs), 7.50-7.64 (3H, m), 10.17 (1H, s). LC-MS (ESI) calcd for $C_{17}H_{20}N_4O_6S_2$ 440.08, found 441.2 [M+H⁺].

EXAMPLE 54 cis-N-[3-(1-Ethyl-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide

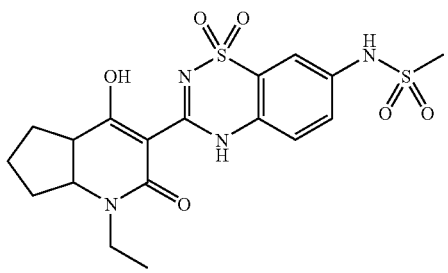

a) 2-Ethylamino-cyclopent-1-enecarboxylic acid ethyl ester

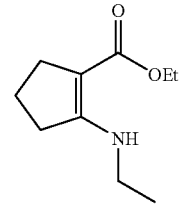

A solution of 2-oxo-cyclopentanecarboxylic acid ethyl ester (3.00 g, 19.2 mmol) in ethanol (20 mL) was treated with a 2.0 M solution of ethylamine in tetrahydrofuran (9.6 mL, 19.2 mmol), sodium cyanoborohydride (2.42 g, 38.4 mmol), and glacial acetic acid (10 drops) and stirred for 16 h at 50° C. After cooling to 25° C. the solvent was removed in vacuo, the crude material was redissolved in ethyl acetate (100 mL) and washed with saturated aqueous sodium bicarbonate solution (100 mL). The aqueous layer was discarded and the organic layer was washed with 1.0 M aqueous hydrochloric acid solution (50 mL). The organic layer was discarded, 1.0 M aqueous sodium hydroxide solution (75 mL) was added and the aqueous layer was extracted with ethyl acetate (100 mL). The organic layer was dried over sodium sulfate, filtered and the solvent was removed in vacuo to afford the crude product, 2-ethylamino-cyclopent-1-enecarboxylic acid ethyl ester (1.52 g, 8.30 mmol, 43.2%), as a light yellow oil. LC-MS (ESI) calcd for $C_{10}H_{17}NO_2$ 183.13, found 184.1 [M+H⁺].

b) 2-Ethylamino-cyclopentanecarboxylic acid ethyl ester

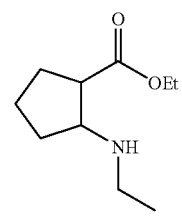

2-Ethylamino-cyclopent-1-enecarboxylic acid ethyl ester (1.52 g, 8.30 mmol) was dissolved in glacial acetic acid (25 mL) and sodium triacetoxyborohydride (5.28 g, 24.9 mmol) was added at 0° C. The solution was allowed to warm to 25° C. and stirred for 3 h. The acetic acid was removed in vacuo and the residue was dissolved in dichloromethane. The solution was washed with saturated aqueous sodium bicarbonate solution followed by saturated aqueous brine solution. The organic layer was dried over sodium sulfate, filtered and concentrated in vacuo to afford the desired product, 2-ethylamino-cyclopentanecarboxylic acid ethyl ester (435.1 mg, 2.35 mmol, 28.3%), as a yellow oil. LC-MS (ESI) calcd for $C_{10}H_{19}NO_2$ 185.14, found 186.1 [M+H⁺].

c) 2-{Ethyl-[2-(7-methanesulfonylamino-1,1-dioxo-1,4-dihydro-1λ⁶-benzo[1,2,4]thiadiazin-3-yl)-acetyl]-amino}-cyclopentanecarboxylic acid ethyl ester

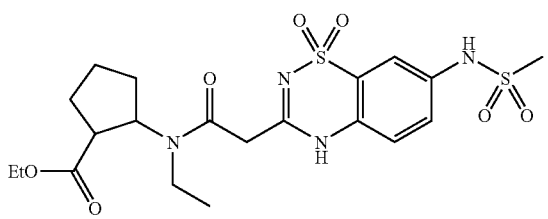

(7-Methanesulfonylamino-1,1-dioxo-1,4-dihydro-1λ$^6$-benzo[1,2,4]thiadiazin-3-yl)-acetic acid (prepared as described in Example 1j, 0.1665 g, 0.5 mmol) was dissolved in anhydrous N,N-dimethylformamide (3 mL). 2-Ethylamino-cyclopentanecarboxylic acid ethyl ester (0.0926 g, 0.5 mmol) was added followed by 1-(3-dimethylaminopropyl)-3-ethylcarbodiimide hydrochloride (0.1003 g, 0.525 mmol). Then N-methylmorpholine (115 µL, 1.05 mmol) was added. The mixture was stirred at 25° C. for 5 h. The solution was poured into 1.0 M aqueous hydrochloric acid solution (100 mL). The aqueous layer was extracted with ethyl acetate (2×100 mL). The organic layer was dried over sodium sulfate, filtered and concentrated in vacuo to afford the crude product, 2-{ethyl-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester, as a yellow oil. LC-MS (ESI) calcd for $C_{20}H_{28}N_4O_7S_2$ 500.14, found 501.2 [M+H$^+$].

d) cis-N-[3-(1-Ethyl-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide

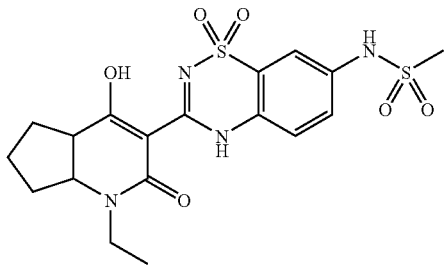

A solution of the crude 2-{ethyl-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester in ethanol (20 mL) was treated with a 21% w/w solution of sodium ethoxide in ethanol (0.648 g) and stirred for 16 h at 60° C. Upon cooling, the reaction mixture was then quenched with 1.0 M aqueous hydrochloric acid solution (20 mL) and extracted with ethyl acetate (2×50 mL). The combined organic layers were washed with saturated aqueous sodium bicarbonate solution, dried over sodium sulfate, filtered, and dried in vacuo. The residue was purified by prep-HPLC [Column ODS-A 5µ 100 Å, 150×21.2 mm, 5 micron, 50%-100% in 13.5 min @ 22 mL/min flow rate, 0.05% trifluoroacetic acid in acetonitrile/0.05% trifluoroacetic acid in water] to afford the desired product, cis-N-[3-(1-ethyl-4-hydroxy-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide (54.3 mg, 0.120 mmol, 23.9% over two steps), as a white solid. $^1$H NMR (400 MHz, DMSO-d$_6$) δ: 1.08-1.30 (3H, m), 1.48-1.70 (4H, m), 1.99-2.24 (3H, m), 3.05 (3H, s), 3.64 (1H, bs), 3.87-4.45 (2H, m), 7.49-7.60 (3H, m), 10.16 (1H, s). LC-MS (ESI) calcd for $C_{18}H_{22}N_4O_6S_2$ 454.10, found 455.2 [M+H$^+$].

EXAMPLE 55 cis-N-[3-(4-Hydroxy-1-isopropyl-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide

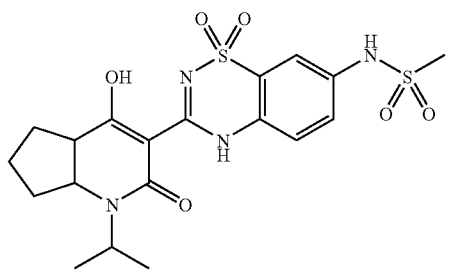

a) 2-Isopropylamino-cyclopent-1-enecarboxylic acid ethyl ester

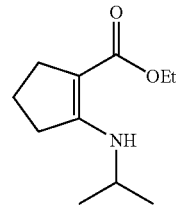

A solution of 2-oxo-cyclopentanecarboxylic acid ethyl ester (3.00 g, 19.2 mmol) in ethanol (20 mL) was treated with isopropylamine (1.135 g, 19.2 mmol), sodium cyanoborohydride (2.42 g, 38.4 mmol), and glacial acetic acid (10 drops) and stirred for 16 h at 50° C. After cooling to 25° C. the solvent was removed in vacuo, the crude material was redissolved in ethyl acetate (100 mL) and washed with saturated aqueous sodium bicarbonate solution (100 mL). The aqueous layer was discarded and the organic layer was washed with 1.0 M aqueous hydrochloric acid solution (50 mL). The organic layer was discarded, 1.0 M aqueous sodium hydroxide solution (75 mL) was added and the aqueous layer was extracted with ethyl acetate (100 mL). The organic layer was dried over sodium sulfate, filtered and the solvent was removed in vacuo to afford the crude product, 2-isopropylamino-cyclopent-1-enecarboxylic acid ethyl ester (2.44 g, 12.38 mmol, 64.5%), as a light yellow oil. LC-MS (ESI) calcd for $C_{11}H_{19}NO_2$ 197.14, found 198.1 [M+H$^+$].

b) 2-Isopropylamino-cyclopentanecarboxylic acid ethyl ester

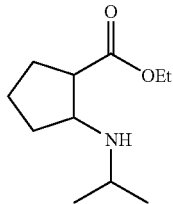

2-Isopropylamino-cyclopent-1-enecarboxylic acid ethyl ester (2.44 g, 12.38 mmol) was dissolved in glacial acetic acid (30 mL) and sodium triacetoxyborohydride (7.87 g, 37.13 mmol) was added at 0° C. The solution was allowed to warm to 25° C. and stirred for 3 h. The acetic acid was removed in vacuo and the residue was dissolved in dichloromethane. The solution was washed with saturated aqueous sodium bicarbonate solution followed by saturated aqueous brine solution. The organic layer was dried over sodium sulfate, filtered and concentrated in vacuo to afford the desired product, 2-isopropylamino-cyclopentanecarboxylic acid ethyl ester (1.5 g, 7.53 mmol, 60.8%), as a yellowish oil. LC-MS (ESI) calcd for $C_{11}H_{21}NO_2$ 199.16, found 200.2 [M+H$^+$].

c) 2-{Isopropyl-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester

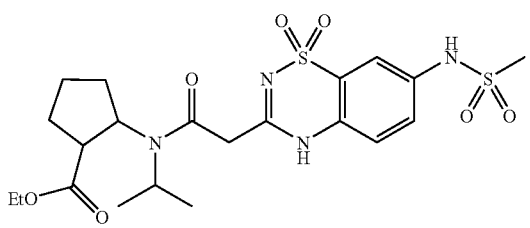

(7-Methanesulfonylamino-1,1-dioxo-1,4-dihydro-1λ$^6$-benzo[1,2,4]thiadiazin-3-yl)-acetic acid (prepared as described in Example 1j, 0.1665 g, 0.5 mmol) was dissolved in anhydrous N,N-dimethylformamide (3 mL). 2-Isopropylamino-cyclopentanecarboxylic acid ethyl ester (0.0996 g, 0.5 mmol) was added followed by 1-(3-dimethylaminopropyl)-3-ethylcarbodiimide hydrochloride (0.1003 g, 0.525 mmol). Then N-methylmorpholine (115 μL, 1.05 mmol) was added. The mixture was stirred at 25° C. for 5 h. The solution was poured into 1.0 M aqueous hydrochloric acid solution (100 mL). The aqueous layer was extracted with ethyl acetate (2×100 mL). The organic layer was dried over sodium sulfate, filtered and concentrated in vacuo to afford the crude product, 2-{isopropyl-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester, as a yellow oil. LC-MS (ESI) calcd for $C_{21}H_{30}N_4O_7S_2$ 514.16, found 515.3 [M+H$^+$].

d) cis-N-[3-(4-Hydroxy-1-isopropyl-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide

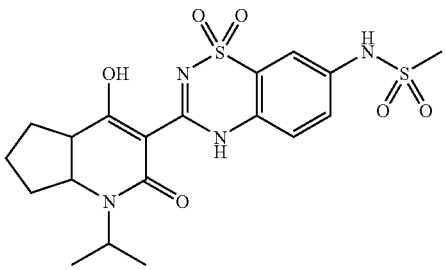

A solution of the crude 2-{isopropyl-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester in ethanol (20 mL) was treated with a 21% w/w solution of sodium ethoxide in ethanol (0.648 g) and stirred for 16 h at 60° C. Upon cooling, the reaction mixture was then quenched with 1.0 M aqueous hydrochloric acid solution (20 mL) and extracted with ethyl acetate (2×50 mL). The combined organic layers were washed with saturated aqueous sodium bicarbonate solution, dried over sodium sulfate, filtered, and dried in vacuo. The residue was purified by prep-HPLC [Column ODS-A 5μ 100 Å, 150×21.2 mm, 5 micron, 50%-100% in 13.5 min @ 22 mL/min flow rate, 0.05% trifluoroacetic acid in acetonitrile/0.05% trifluoroacetic acid in water] to afford the desired product, cis-N-[3-(4-hydroxy-1-isopropyl-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide (77.6 mg, 0.166 mmol, 33.2% over two steps), as a white solid. $^1$H NMR (400 MHz, DMSO-$d_6$) δ: 1.10-1.32 (6H, m), 1.46-2.13 (7H, m), 2.28 (1H, bs), 3.06 (3H, s), 3.95 (1H, bs), 4.54-5.10 (1H, m), 7.49-7.63 (3H, m), 10.17 (1H, s). LC-MS (ESI) calcd for $C_{19}H_{24}N_4O_6S_2$ 468.11, found 469.3 [M+H$^+$].

EXAMPLE 56 cis-N-{3-[1-(4-Chloro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

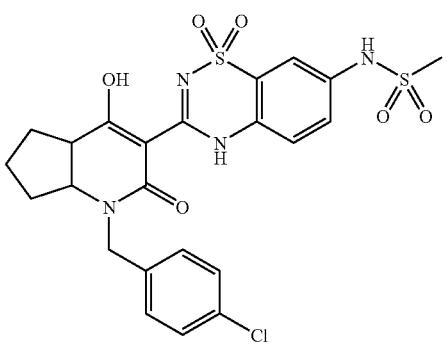

a) 2-(4-Chloro-benzylamino)-cyclopent-1-enecarboxylic acid ethyl ester

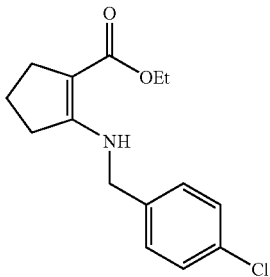

A solution of 2-oxo-cyclopentanecarboxylic acid ethyl ester (3.00 g, 19.2 mmol) in ethanol (20 mL) was treated with 4-chlorobenzylamine (2.72 g, 19.2 mmol), sodium cyanoborohydride (2.42 g, 38.4 mmol), and glacial acetic acid (10 drops) and stirred for 16 h at 50° C. After cooling to 25° C. the solvent was removed in vacuo, the crude material was redissolved in ethyl acetate (100 mL) and washed with saturated aqueous sodium bicarbonate solution (100 mL). The aqueous layer was discarded and the organic layer was washed with 1.0 M aqueous hydrochloric acid solution (50 mL). The organic layer was discarded, 1.0 M aqueous sodium hydroxide solution (75 mL) was added and the aqueous layer was extracted with ethyl acetate (100 mL). The organic layer was dried over sodium sulfate, filtered and the solvent was removed in vacuo to afford the crude product, 2-(4-chloro-benzylamino)-cyclopent-1-enecarboxylic acid ethyl ester (2.98 g, 10.68 mmol, 55.6%), as a light yellow oil. LC-MS (ESI) calcd for $C_{15}H_{18}ClNO_2$ 279.10, found 280.1 [M+H$^+$].

b) 2-(4-Chloro-benzylamino)-cyclopentanecarboxylic acid ethyl ester

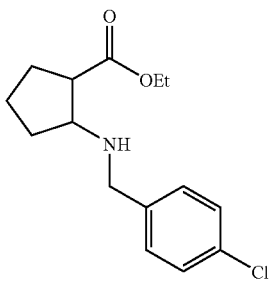

2-(4-Chloro-benzylamino)-cyclopent-1-enecarboxylic acid ethyl ester (2.98 g, 10.68 mmol) was dissolved in glacial acetic acid (20 mL) and sodium triacetoxyborohydride (6.79 g, 32.04 mmol) was added at 0° C. The solution was allowed to warm to 25° C. and stirred for 3 h. The acetic acid was removed in vacuo and the residue was dissolved in dichloromethane. The solution was washed with saturated aqueous sodium bicarbonate solution followed by saturated aqueous brine solution. The organic layer was dried over sodium sulfate, filtered and concentrated in vacuo to afford the desired product, 2-(4-chloro-benzylamino)-cyclopentanecarboxylic acid ethyl ester (2.43 g, 8.64 mmol, 80.9%), as a yellow oil. LC-MS (ESI) calcd for $C_{15}H_{20}ClNO_2$ 281.12, found 282.0 [M+H$^+$].

c) 2-{(4-Chloro-benzyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester

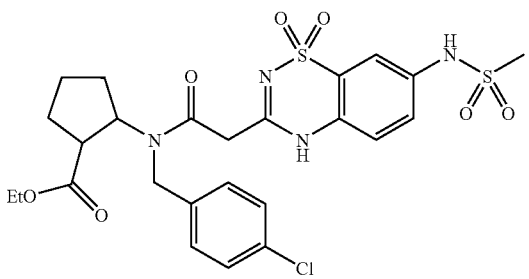

(7-Methanesulfonylamino-1,1-dioxo-1,4-dihydro-1λ$^6$-benzo[1,2,4]thiadiazin-3-yl)-acetic acid (prepared as described in Example 1j, 0.1665 g, 0.5 mmol) was dissolved in anhydrous N,N-dimethylformamide (3 mL). 2-(4-Chloro-benzylamino)-cyclopentanecarboxylic acid ethyl ester (0.1406 g, 0.5 mmol) was added followed by 1-(3-dimethylaminopropyl)-3-ethylcarbodiimide hydrochloride (0.1003 g, 0.525 mmol). Then N-methylmorpholine (115 μL, 1.05 mmol) was added. The mixture was stirred at 25° C. for 5 h. The solution was poured into 1.0 M aqueous hydrochloric acid solution (100 mL). The aqueous layer was extracted with ethyl acetate (2×100 mL). The organic layer was dried over sodium sulfate and concentrated in vacuo to afford the crude product, 2-{(4-chloro-benzyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester, as a yellow oil. LC-MS (ESI) calcd for $C_{25}H_{29}ClN_4O_7S_2$ 596.12, found 597.2 [M+H$^+$].

d) cis-N-{3-[1-(4-Chloro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

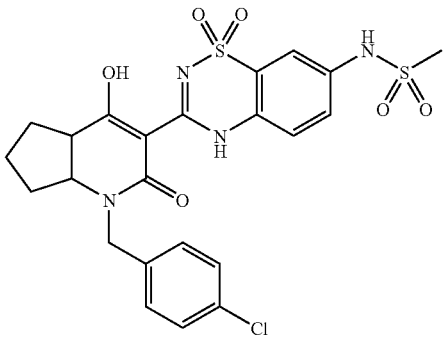

A solution of the crude 2-{(4-chloro-benzyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid ethyl ester in ethanol (20 mL) was treated with a 21% w/w solution of sodium ethoxide in ethanol (0.648 g) and stirred for 16 h at 60° C. Upon cooling, the reaction mixture was then quenched with 1.0 M aqueous hydrochloric acid solution (20 mL) and extracted with ethyl acetate (2×50 mL). The combined organic layers were washed with saturated aqueous sodium bicarbonate solution, dried over sodium sulfate, filtered, and dried in vacuo. The residue was purified by prep-HPLC [Column ODS-A 5μ 100 Å, 150×21.2 mm, 5 micron, 50%-100% in 13.5 min @ 22 mL/min flow rate, 0.05% trifluoroacetic acid in acetonitrile/0.05% trifluoroacetic acid in water] to afford the desired product, cis-N-{3-[1-(4-chloro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide (72.1 mg, 0.131 mmol, 26.2% over two steps), as a white solid. $^1$H NMR (400 MHz, DMSO-d$_6$) δ: 1.44-1.62 (4H, m), 1.91-2.18 (3H, m), 3.06 (3H, s), 3.78-3.94 (1H, m), 4.39-4.62 (1H, m), 4.90 (1H, d, J=15.6 Hz), 7.35-7.64 (7H, m), 10.19 (1H, s). LC-MS (ESI) calcd for $C_{23}H_{23}ClN_4O_6S_2$ 550.07, found 551.4 [M+H$^+$].

EXAMPLE 57 cis-N-{3-[1-(4-Fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-benzo[1,4]thiazin-7-yl}-methanesulfonamide

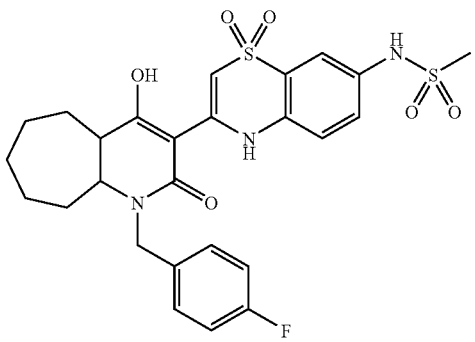

(7-Methanesulfonylamino-1,1-dioxo-1,4-dihydro-1λ$^6$-benzo[1,4]thiazin-3-yl)-acetic acid (prepared as described in Example 25 h, 0.365 g, 1.10 mmol), 1-(3-dimethylaminopropyl)-3-ethylcarbodiimide hydrochloride (0.223 g, 1.16 mmol) and N-methylmorpholine (0.256 mL, 2.33 mmol) were added sequentially to a solution of cis-2-(4-fluoro-benzylamino)-cycloheptanecarboxylic acid methyl ester (prepared as described in Example 2b, 0.310 g, 1.10 mmol) in N,N-dimethylformamide (6 mL) at 25° C. The reaction mixture was stirred at 25° C. for 2 h, and then was partitioned between 1.0 M aqueous hydrochloric acid solution (150 mL) and ethyl acetate (2×150 mL). The organic layers were dried over sodium sulfate, filtered and concentrated in vacuo. The residue was dissolved in ethanol (30 mL) at 25° C. A 21% w/w solution of sodium ethoxide in ethanol (1.44 mL, 4.44 mmol) was added and the reaction mixture was heated to 60° C. for 1 h. After cooling to 25° C., the reaction mixture was partitioned between 1.0 M aqueous hydrochloric acid solution (150 mL) and ethyl acetate (2×150 mL). The organic layers were dried over sodium sulfate, filtered and concentrated in vacuo. The residue was purified by flash column chromatography (Teledyne Isco RediSep Column; 30-100% ethyl acetate in hexanes) to afford cis-N-{3-[1-(4-fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-benzo[1,4]thiazin-7-yl}-methanesulfonamide (0.340 g, 0.610 mmol, 55%) as a yellow solid. $^1$H NMR (400 MHz, DMSO-d$_6$) δ: (1:1 mixture of tautomers) 0.86-0.90 (m), 1.15-1.19 (m), 1.27-1.36 (m), 1.46-1.66 (m), 2.01-2.05 (m), 3.06 (s), 3.31 (s), 3.50-3.54 (m), 3.98-4.41 (1H, m), 4.26-4.33 (m), 4.95-5.05 (m), 5.52 (d, J=16.1 Hz), 5.61 (d, J=15.9 Hz), 5.69 (d, J=15.4 Hz), 5.89 (d, J=16.4 Hz), 7.15-7.26 (m), 7.40-7.41 (m), 7.48-7.51 (m), 7.57-7.61 (m), 10.14 (s), 10.18 (s). LC-MS (ESI) calcd for $C_{26}H_{28}FN_3O_6S_2$ 561.14, found 562.4 [M+H$^+$].

EXAMPLE 58

N-{3-[1-(2-Cyclopropyl-ethyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide

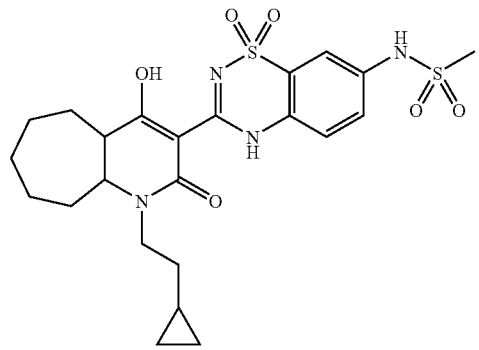

a) cis-2-(2-Cyclopropyl-ethylamino)-cycloheptanecarboxylic acid methyl ester and cis-2-amino-cycloheptanecarboxylic acid methyl ester

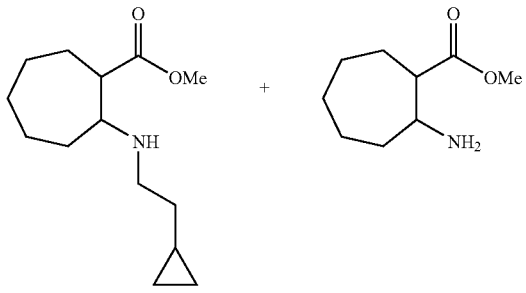

cis-2-Amino-cycloheptanecarboxylic acid methyl ester hydrochloride (prepared as described in Example 2a, 1.027 g, 4.96 mmol) was dissolved in methanol (23 mL), cyclopropylacetaldehyde (prepared as described in Example 19a, as a 1.40 M solution in dichloromethane, 3.54 mL, 4.96 mmol) was added at 25° C. followed by glacial acetic acid (0.94 mL). Sodium triacetoxyborohydride (2.63 g, 12.4 mmol) was added in portions at 0° C. The mixture was stirred at 0° C. to 25° C. for 16 h. Saturated aqueous sodium bicarbonate solution (40 mL) was added to neutralize the solution (pH ~8), and the mixture was extracted with ethyl acetate (3×60 mL). The combined organic layers were washed with brine (40 mL), dried over sodium sulfate, filtered and concentrated and then dried at 25° C. in vacuo for 5 h to afford the crude product, cis-2-(2-cyclopropyl-ethylamino)-cycloheptanecarboxylic acid methyl ester, as a yellow oil (911.1 mg, 3.81 mmol, 76.8% crude yield over two steps) which contained neutralized unreacted cis-2-amino-cycloheptanecarboxylic acid methyl ester. This crude product was directly used in the next step without further purification. LC-MS (ESI) calcd for $C_{14}H_{25}NO_2$ 239.19, found 240.3 [M+H$^+$].

b) 2-{(2-Cyclopropyl-ethyl)-[2-(7-methanesulfonylamino-1,1-dioxo-1,4-dihydro-1λ$^6$-benzo[1,2,4]thiadiazin-3-yl)-acetyl]-amino}-cycloheptanecarboxylic acid methyl ester and 2-[2-(7-Methanesulfonylamino-1,1-dioxo-1,4-dihydro-1λ$^6$-benzo[1,2,4]thiadiazin-3-yl)-acetylamino]-cycloheptanecarboxylic acid methyl ester

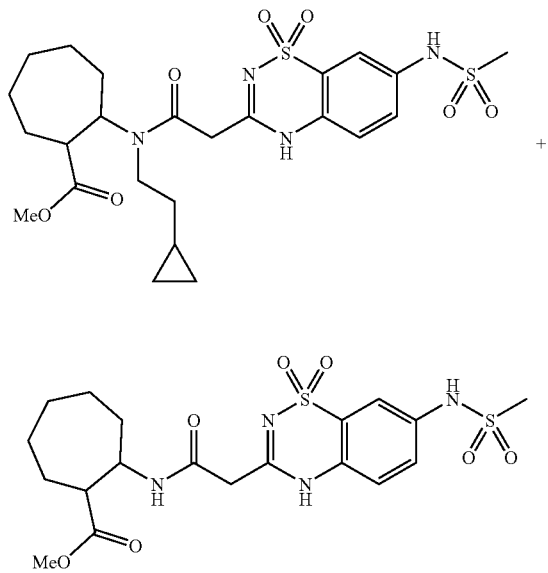

The crude cis-2-(2-cyclopropyl-ethylamino)-cycloheptanecarboxylic acid methyl ester (260.5 mg, 1.09 mmol) was mixed with (7-methanesulfonylamino-1,1-dioxo-1,4-dihydro-1λ$^6$-benzo[1,2,4]thiadiazin-3-yl)-acetic acid (prepared as described in Example 1j, 399 mg, 1.2 mmol) and dissolved in N,N-dimethylformamide (9 mL). N-Methylmorpholine (264 µL, 2.4 mmol) was added followed by 1-(3-dimethylaminopropyl)-3-ethylcarbodiimide hydrochloride (230 mg, 1.2 mmol). The resulting mixture was shaken at 25° C. overnight. A 1.0 M aqueous hydrochloric acid solution (11 mL) was added (pH=2) and the mixture was extracted with ethyl acetate (3×50 mL). The combined organic layers were washed with brine (40 mL), dried over sodium sulfate, filtered, and concentrated in vacuo. The residue was further dried in vacuo for 5.5 h to afford the crude product, 2-{(2-cyclopropyl-ethyl)-[2-(7-methanesulfonylamino-1,1-dioxo-1,4-dihydro-1λ$^6$-benzo[1,2,4]thiadiazin-3-yl)-acetyl]-amino}-cycloheptanecarboxylic acid methyl ester, containing 2-[2-(7-methanesulfonylamino-1,1-dioxo-1,4-dihydro-1λ$^6$-benzo[1,2,4]thiadiazin-3-yl)-acetylamino]-cycloheptanecarboxylic acid methyl ester as a side product, as a brown oil. This crude product was directly used in the next step without further purification. LC-MS (ESI) calcd for $C_{24}H_{34}N_4O_7S_2$ 554.19, found 555.3 [M+H$^+$] and LC-MS (ESI) calcd for $C_{19}H_{26}N_4O_7S_2$ 486.12, found 487.3 [M+H$^+$]$^+$.

c) N-{3-[1-(2-Cyclopropyl-ethyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide

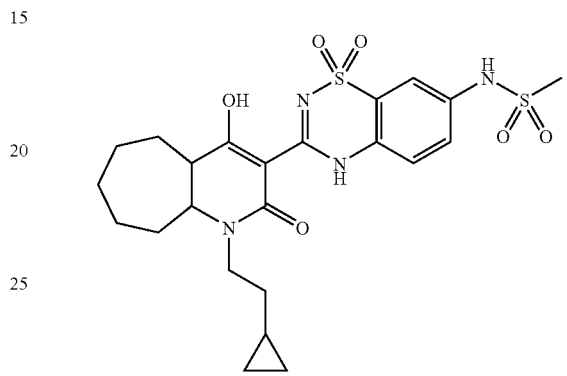

The above crude mixture of 2-{(2-cyclopropyl-ethyl)-[2-(7-methanesulfonylamino-1,1-dioxo-1,4-dihydro-1λ$^6$-benzo[1,2,4]thiadiazin-3-yl)-acetyl]-amino}-cycloheptanecarboxylic acid methyl ester and 2-[2-(7-methanesulfonylamino-1,1-dioxo-1,4-dihydro-1λ$^6$-benzo[1,2,4]thiadiazin-3-yl)-acetylamino]-cycloheptanecarboxylic acid methyl ester (1.09 mmol) was dissolved in absolute ethanol (9 mL). A 21% w/w solution of sodium ethoxide in ethanol (1.9 mL) was added and the resulting mixture was shaken at 25° C. for 2 days. LC-MS analysis indicated completion of the reaction, along with the formation of a side product (see Example 60 below). A 1.0 M aqueous hydrochloric acid solution (18 mL) was added (pH=1) and the mixture was extracted with ethyl acetate (3×20 mL), dried over sodium sulfate, filtered, and concentrated in vacuo. The crude product was further purified by prep-HPLC [Column ODS-A 5µ 100 Å, 150×21.2 mm, 5 micron, 30%-100% in 13.5 min @ 22 mL/min flow rate, 0.05% trifluoroacetic acid in acetonitrile/0.05% trifluoroacetic acid in water] to afford the desired product, N-{3-(2-cyclopropyl-ethyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide as an inseparable mixture of cis- and trans-isomers (55.6 mg, 0.106 mmol, 9.8% over two steps), as an off-white solid. LC-MS (ESI) calcd for $C_{23}H_{30}N_4O_6S_2$ 522.16, found 523.5 [M+H$^+$]. The $^1$H NMR spectrum indicated a mixture of cis- and trans-isomers with a ratio of 45:55. $^1$H NMR (CDCl$_3$, 400 MHz): δ 0.12-0.18 (m, 2H), 0.5-0.59 (m, 2H), 0.68-0.79 (m, 1H), 1.32-1.62 (m, 5H), 1.70-1.95 (m, 4H), 1.95-2.25 (m, 3H), 2.80-2.89 (m, 1H, 55%), 2.99-3.04 (m, 1H, 55%), 3.05 (s, 3H, 45%), 3.06 (s, 3H, 55%), 3.08-3.14 (m, 1H, 45%), 3.36 (q, 1H, 45%, J=8 Hz), 3.48-3.61 (m, 1H), 4.07-4.18 (m, 1H), 6.87 (d, 1H, J=13.6 Hz), 7.21 (dd, 1H, J$_1$=14.0 Hz, J$_2$=8.8 Hz), 7.60-7.70 (m, 2H), 13.95 (s, br, 1H).

EXAMPLE 59

N-[3-(4-Hydroxy-2-oxo-2,4a,5,6,7,8,9,9a-octahydro-1H-cyclohepta[b]pyridin-3-yl)-1,1-dioxo-1,4-dihydro-1λ⁶-benzo[1,2,4]thiadiazin-7-yl]-methanesulfonamide

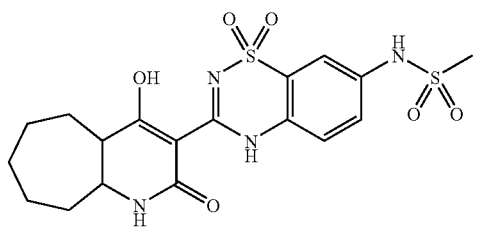

The crude reaction mixture from Example 59c was further purified by prep-HPLC [Column ODS-A 5μ 100 Å, 150×21.2 mm, 5 micron, 30%-100% in 13.5 min @ 22 mL/min flow rate, 0.05% trifluoroacetic acid in acetonitrile/0.05% trifluoroacetic acid in water] to afford the desired product, N-[3-(4-hydroxy-2-oxo-2,4a,5,6,7,8,9,9a-octahydro-1H-cyclohepta[b]pyridin-3-yl)-1,1-dioxo-1,4-dihydro-1λ⁶-benzo[1,2,4]thiadiazin-7-yl]-methanesulfonamide (87.6 mg, 0.193 mmol, 17.7% over two steps), as an off-white solid. LC-MS (ESI) calcd for $C_{18}H_{22}N_4O_6S_2$ 454.10, found 455.4 [M+H⁺]. ¹H NMR (DMSO-d₆, 300 MHz): δ 1.2-1.8 (m, 10H), 3.02 (s, 3H), 3.26-3.41 (m, 2H), 3.94-4.16 (m, 1H), 7.37 (d, 1H, J=9.9 Hz), 7.50-7.56 (m, 2H), 8.30-8.38 (m, 1H), 10.12 (s, 1H), 12.20 (s, 1H).

EXAMPLE 60

N-[3-(1-Cyclobutylamino-4-hydroxy-2-oxo-2,4a,5,6,7,8,9,9a-octahydro-1H-cyclohepta[b]pyridin-3-yl)-1,1-dioxo-1,4-dihydro-1λ⁶-benzo[1,2,4]thiadiazin-7-yl]-methanesulfonamide trifluoroacetic acid salt

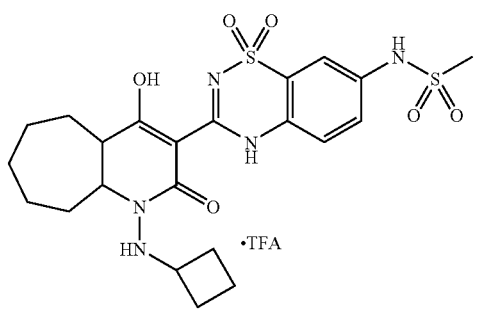

a) 2-(N'-Allyl-N'-cyclobutyl-hydrazino)-cycloheptanecarboxylic acid methyl ester

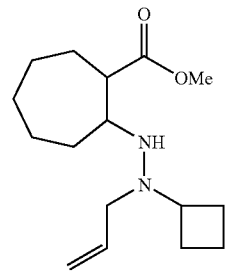

N'-Allyl-N'-cyclobutyl-hydrazine hydrochloride (2.01 g, 12.37 mmol) was dissolved in methanol (40 mL). 2-Oxo-cycloheptanecarboxylic acid methyl ester (1.93 mL, 12.37 mmol), sodium acetate (2.04 g, 24.74 mmol), sodium cyanoborohydride (1.55 g, 24.74 mmol) and 4 Å molecular sieves (2.80 g) were added sequentially. The reaction was stirred at 25° C. for 18 h before it was quenched via the addition of saturated aqueous sodium bicarbonate solution (30 mL). The mixture was extracted with ethyl acetate (3×40 mL). The organic layers were combined, dried over magnesium sulfate, filtered and concentrated in vacuo to afford the crude product, 2-(N'-allyl-N'-cyclobutyl-hydrazino)-cycloheptanecarboxylic acid methyl ester, as a yellow oil. The residue was used directly in the next step. LC-MS (ESI) calcd for $C_{16}H_{28}N_2O_2$ 280.41, found 281.2 [M+H⁺].

b) N-{3-[1-(Allyl-cyclobutyl-amino)-4-hydroxy-2-oxo-2,4a,5,6,7,8,9,9a-octahydro-1H-cyclohepta[b]pyridin-3-yl]-1,1-dioxo-1,4-dihydro-1λ⁶-benzo[1,2,4]thiadiazin-7-yl}-methanesulfonamide

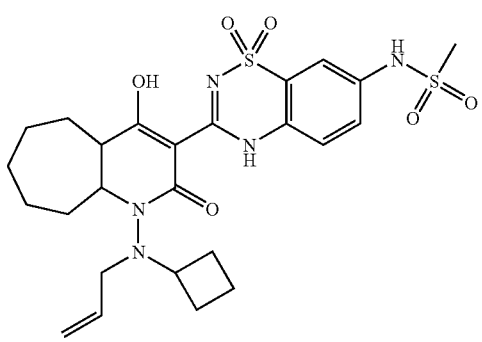

2-(N'-Allyl-N'-cyclobutyl-hydrazino)-cycloheptanecarboxylic acid methyl ester (0.60 g, 2.16 mmol) was dissolved in anhydrous N,N-dimethylformamide (10 mL). (7-Methanesulfonylamino-1,1-dioxo-1,4-dihydro-1λ⁶-benzo[1,2,4]thiadiazin-3-yl)-acetic acid (prepared as described in Example 1j, 0.72 mg, 2.16 mmol) was added followed by N-methylmorpholine (0.50 mL, 4.54 mmol). The mixture was stirred until everything dissolved, approximately 5 min. 1-(3-Dimethylaminopropyl)-3-ethylcarbodiimide hydrochloride (0.44 mg, 2.27 mmol) was added and the mixture was stirred at 25° C. for 16 h. The reaction was quenched via addition of saturated aqueous sodium bicarbonate solution (20 mL). The mixture was extracted with ethyl acetate (3×30 mL). The organic layers were combined and washed with brine (20 mL). The resulting solution was dried over magnesium sulfate, filtered, and concentrated in vacuo to afford a golden oil. The oil was dissolved in ethanol (20 mL). A 21% w/w solution of sodium ethoxide in ethanol (2.42 mL, 6.48 mmol) was added. The reaction was heated at reflux for 16 h. The reaction was quenched via the addition of saturated aqueous ammonium chloride solution (40 mL). The mixture was extracted with ethyl acetate (3×40 mL). The organic layer was further washed with saturated sodium bicarbonate solution (2×20 mL), aqueous saturated brine solution (20 mL), dried over magnesium sulfate, filtered, and concentrated in vacuo to afford a clear oil. Purification by flash column chromatography (Teledyne Isco RediSep Column; 0-5% methanol in dichloromethane) afford the desired product, N-{3-[1-(allyl-cyclobutyl-amino)-4-hydroxy-2-oxo-2,4a,5,6,7,8,9,9a-octahydro-1H-cyclohepta[b]pyridin-3-yl]-1,1-dioxo-1,4-dihydro-1$\lambda^6$-benzo[1,2,4]thiadiazin-7-yl}-methanesulfonamide (0.39 g, 0.69 mmol, 32%) as a white powder. $^1$H NMR (400 MHz, CDCl$_3$) δ: 1.38-2.14 (17H, m), 2.90-3.05 (3H, m), 3.14-3.97 (4H, m), 5.09-5.95 (3H, m), 7.16-8.02 (3H, m). LC-MS (ESI) calcd for C$_{25}$H$_{33}$N$_5$O$_6$S$_2$ 563.69, found 564.5 [M+H$^+$].

c) N-[3-(1-Cyclobutylamino-4-hydroxy-2-oxo-2,4a,5,6,7,8,9,9a-octahydro-1H-cyclohepta[b]pyridin-3-yl)-1,1-dioxo-1,4-dihydro-1$\lambda^6$-benzo[1,2,4]thiadiazin-7-yl]-methanesulfonamide trifluoroacetic acid salt

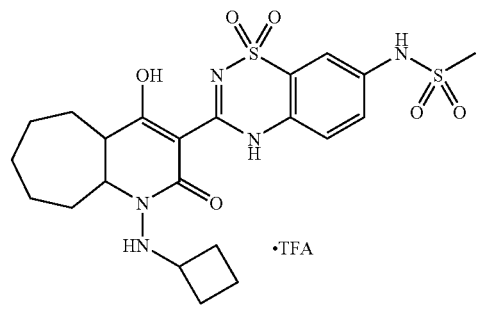

N-{3-[1-(Allyl-cyclobutyl-amino)-4-hydroxy-2-oxo-2,4a,5,6,7,8,9,9a-octahydro-1H-cyclohepta[b]pyridin-3-yl]-1,1-dioxo-1,5-dihydro-1$\lambda^6$-benzo[1,2,4]thiadiazin-7-yl}-methanesulfonamide (0.39 g, 0.69 mmol) was dissolved in dichloromethane (20 mL). The solution was degassed and refilled with nitrogen. Tetrakis(triphenylphosphine)palladium(0) (80 mg, 0.07 mmol) and N,N'-dimethylbarbituric acid (0.32 mg, 2.07 mmol) were added sequentially. The reaction was stirred at 35° C. for 18 h. The mixture was cooled to 25° C. and concentrated in vacuo. Purification by prep-HPLC [Column Luna 5μ C18 (2) 100 Å AXIA 150×21.2 mm, 5 micron, 25%-100% in 12 min @ 30 mL/min flow rate, 0.05% trifluoroacetic acid in acetonitrile/0.05% trifluoroacetic acid in water] afforded the desired product, N-[3-(1-cyclobutylamino-4-hydroxy-2-oxo-2,4a,5,6,7,8,9,9a-octahydro-1H-cyclohepta[b]pyridin-3-yl)-1,1-dioxo-1,4-dihydro-1$\lambda^6$-benzo[1,2,4]thiadiazin-7-yl]-methanesulfonamide trifluoroacetic acid salt (134 mg, 0.21 mmol, 30%) as a yellow solid. $^1$H NMR (400 MHz, DMSO-d$_6$) δ: 1.18-2.06 (17H, m), 3.06 (3H, s), 3.45-3.69 (2H, m), 7.50-7.60 (3H, m), 10.17 (1H, s), 13.73 (1H, s). LC-MS (ESI) calcd for C$_{22}$H$_{29}$N$_5$O$_6$S$_2$ (free hydrazine) 523.63, found 524.3 [M+H$^+$].

Biological Testing

The ability of compounds of Formula I to inhibit HCV replication can be demonstrated in the following in vitro assays.

Compounds were tested for HCV polymerase inhibition. Assays were performed in a 96-well streptavidin-coated FlashPlate using 20 nM enzyme, 0.5 μCi of [α-$^{33}$P]GTP, 0.6 μM GTP, and 250 nM 5'biotinylated oligo (rG$_{13}$)/poly rC in 20 mM Tris-HCl, pH 7.5, 5 mM MgCl$_2$, 5 mM dithiothreitol, 0.1 g/L bovine serum albumin, and 100 U/mL RNAse inhibitor. The reaction was stopped by aspiration after 75 min at 28° C. and the plate was washed several times. After washing and drying the plate, incorporated radioactivity was counted using a Microbeta scintillation counter. IC$_{50}$ values were calculated relative to the uninhibited control and inhibition data were fitted to a 4-parameter IC$_{50}$ equation. For very potent inhibitors, the data were fitted to a tight binding quadratic equation to obtain IC$_{50}$ values.

Test results (IC$_{50}$ values) for compounds of Formula I are summarized in Table 1, wherein ++++ means NS5B polymerase inhibition with IC$_{50}$ values less than 0.02+M, +++ means IC$_{50}$ values between 0.02 μM and 0.1 μM, ++ means IC$_{50}$ values between 0.1 μM and 1 μM, and + means IC$_{50}$ values between 1 μM and 100 μM.

TABLE 1

| Example # | Structure | Name | IC50 |
|---|---|---|---|
| 1 | 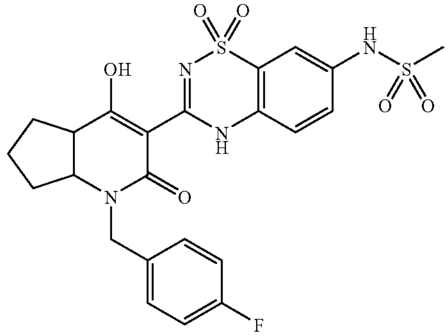 | cis-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide | ++++ |

TABLE 1-continued

| Example # | Structure | Name | IC50 |
|---|---|---|---|
| 2 | 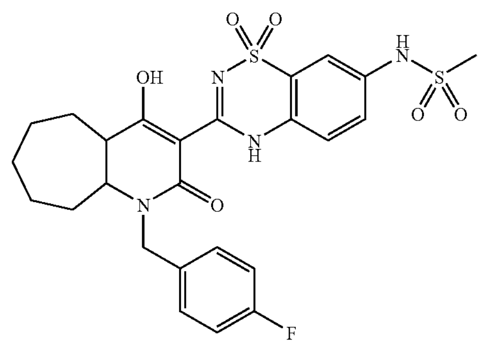 | N-{3-[1-(4-Fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide | +++ |
| 3 | 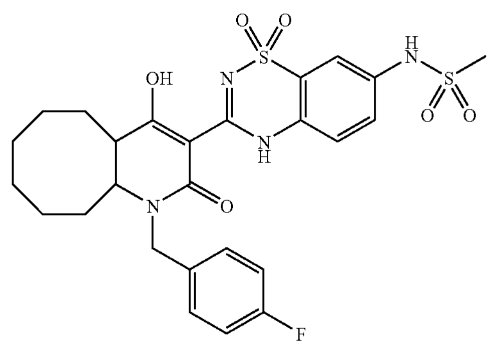 | N-{3-[1-(4-Fluoro-benzyl)-4-hydroxy-2-oxo-1,2,4a,5,6,7,8,9,10,10a-decahydro-cycloocta[b]pyridin-3-yl]-1,1-dioxo-1,4-dihydro-1λ$^6$-benzo[1,2,4]thiadiazin-7-yl}-methanesulfonamide | ++ |
| 4 | 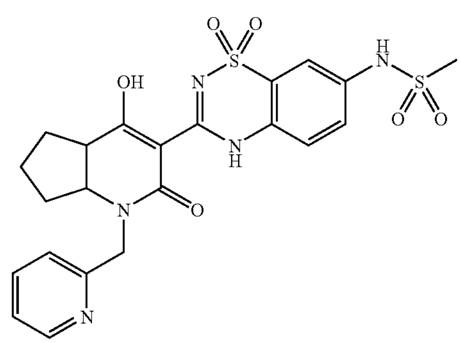 | cis-N-[3-(4-Hydroxy-2-oxo-1-pyridin-2-ylmethyl-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide | ++ |
| 5 | 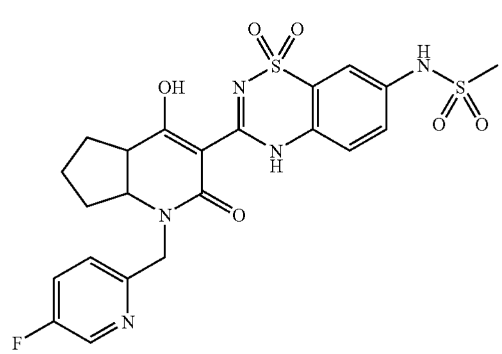 | cis-N-{3-[1-(5-Fluoro-pyridin-2-ylmethyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide | ++ |

TABLE 1-continued

| Example # | Structure | Name | IC50 |
|---|---|---|---|
| 6 | 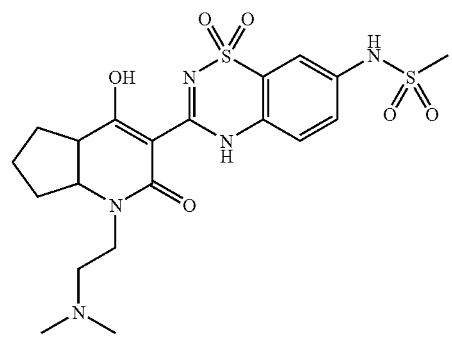 | cis-N-{3-[1-(2-Dimethylamino-ethyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}1-methanesulfonamide | + |
| 7 | 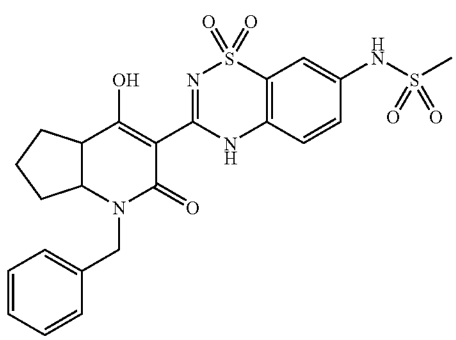 | cis-N-[3-(1-Benzyl-4-hydroxy-2-oxo-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide | +++ |
| 8 | 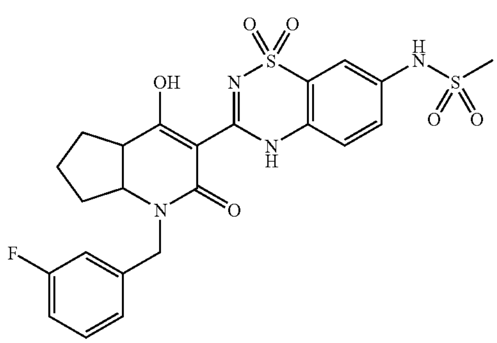 | cis-N-{3-[1-(3-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide | ++++ |
| 9 | 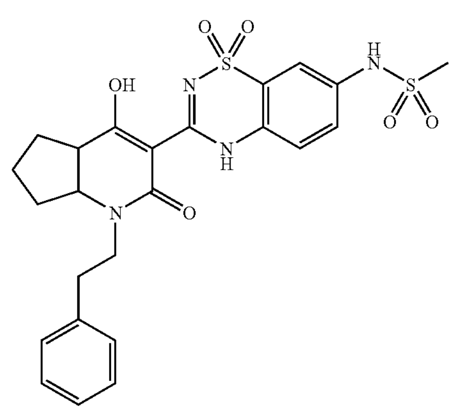 | cis-N-[3-(4-Hydroxy-2-oxo-1-phenethyl-2,4a,5,6,7,7a-hexahydro-1H-[1]pyrindin-3-yl)-1,1-dioxo-1,4-dihydro-1λ⁶-benzo[1,2,4]thiadiazin-7-yl]-methanesulfonamide | ++ |

TABLE 1-continued

| Example # | Structure | Name | IC50 |
|---|---|---|---|
| 10 | 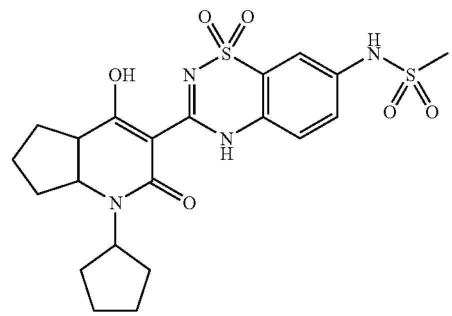 | cis-N-[3-(1-Cyclopentyl-4-hydroxy-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide | + |
| 11 | 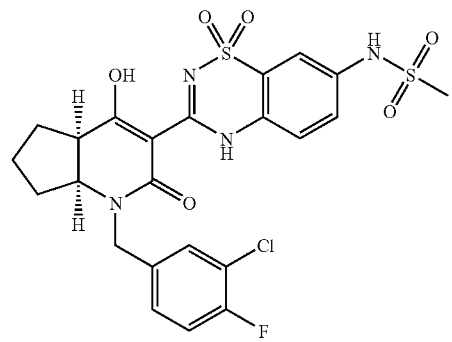 | (4aR,7aS)-N-{3-[1-(3-Chloro-4-fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}1-methanesulfonamide | ++++ |
| 12 | 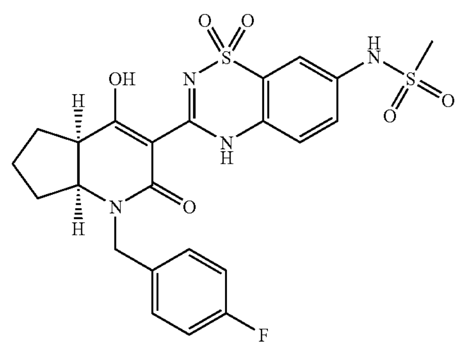 | (4aR,7aS)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide | ++++ |
| 13 | 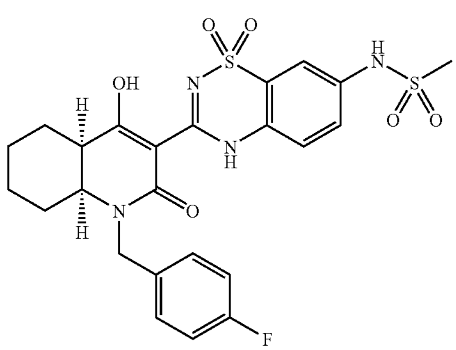 | (4aR,8aS)-N-{3-[1-(4-Fluoro-benzyl)-4-hydroxy-2-oxo-1,2,4a,5,6,7,8,8a-octahydro-quinolin-3-yl]-1,1-dioxo-1,4-dihydro-1λ$^6$-benzo[1,2,4]thiadiazin-7-yl}-methanesulfonamide | +++ |

TABLE 1-continued

| Example # | Structure | Name | IC50 |
|---|---|---|---|
| 14 | 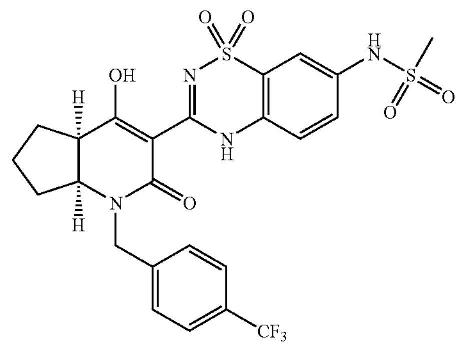 | (4aR,7aS)-N-{3-[4-Hydroxy-2-oxo-1-(4-trifluoromethyl-benzyl)-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide | ++ |
| 15 | 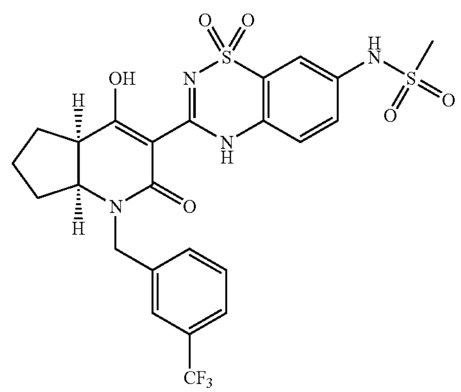 | (4aR,7aS)-N-{3-[4-Hydroxy-2-oxo-1-(3-trifluoromethyl-benzyl)-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide | ++ |
| 16 | 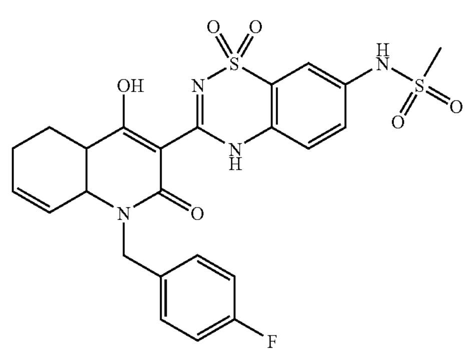 | N-{3-[1-(4-Fluoro-benzyl)-4-hydroxy-2-oxo-1,2,4a,5,6,8a-hexahydro-quinolin-3-yl]-1,1-dioxo-1,4-dihydro-1λ⁶-benzo[1,2,4]thiadiazin-7-yl}-methanesulfonamide | ++++ |
| 17 | 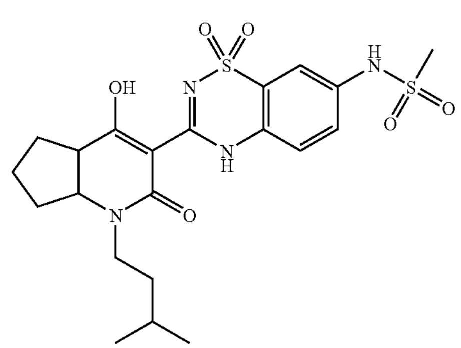 | cis-N-{3-[2-(3-Methylbutyl)-5-hydroxy-3-oxo-2-aza-bicyclo[4.3.0]non-4-en-4-yl]-1,1-dioxo-1,4-dihydro-1λ⁶-benzo[1,2,4]thiadiazin-7-yl}-methanesulfonamide | ++++ |

TABLE 1-continued

| Example # | Structure | Name | IC50 |
|---|---|---|---|
| 18 | 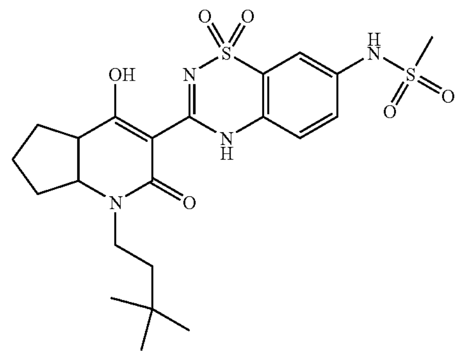 | cis-N-{3-[2-(3,3-Dimethylbutyl)-5-hyroxy-3-oxo-2-aza-bicyclo[4.3.0]non-4-en-4-yl]-1,1-dioxo-1,4-dihydro-1$\lambda^6$-benzo[1,2,4]thiadiazin-7-yl}-methanesulfonamide | |
| 19 | 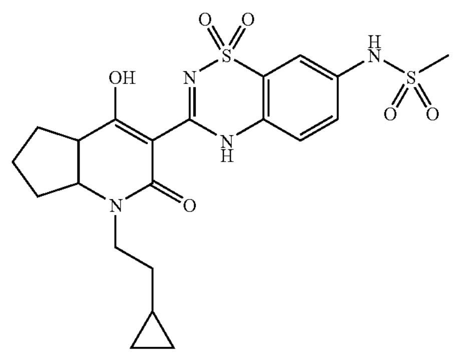 | cis-N-{3-[2-Cyclopropylethyl-5-hydroxy-3-oxo-2-aza-bicyclo[4.3.0]non-4-en-4-yl]-1,1-dioxo-1,4-dihydro-1$\lambda^6$-benzo[1,2,4]thiadiazin-7-yl}-methanesulfonamide | +++ |
| 20 | 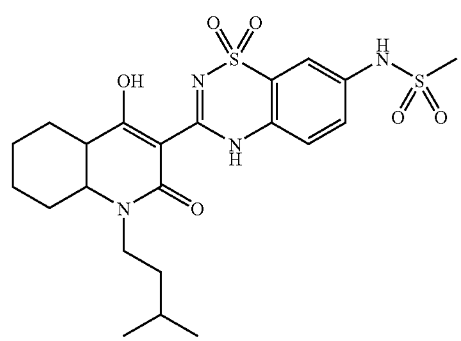 | N-{3-[2-(3-Methylbutyl)-5-hydroxy-3-oxo-2-aza-bicyclo[4.4.0]dec-4-en-4-yl]-1,1-dioxo-1,4-dihydro-1$\lambda^6$-benzo[1,2,4]thiadiazin-7-yl}-methanesulfonamide | +++ |
| 21 | 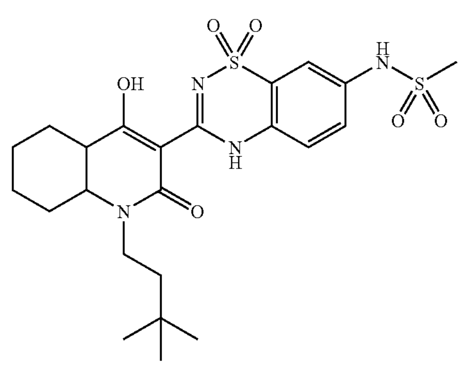 | N-{3-[2-(3,3-Dimethylbutyl)-5-hydroxy-3-oxo-2-aza-bicyclo[4.4.0]dec-4-en-4-yl]-1,1-dioxo-1,4-dihydro-1$\lambda^6$-benzo[1,2,4]thiadiazin-7-yl}-methanesulfonamide | +++ |

TABLE 1-continued

| Example # | Structure | Name | IC50 |
|---|---|---|---|
| 22 | 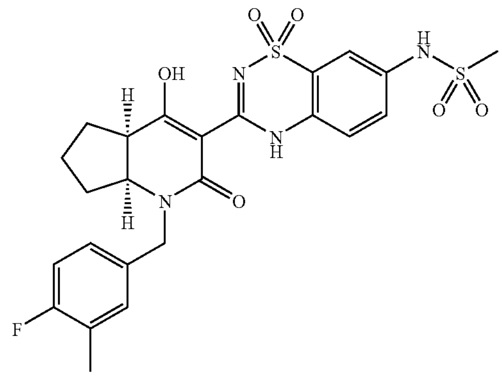 | (4aR,7aS)-N-{3-[1-(4-Fluoro-3-methyl-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide | ++++ |
| 23 | 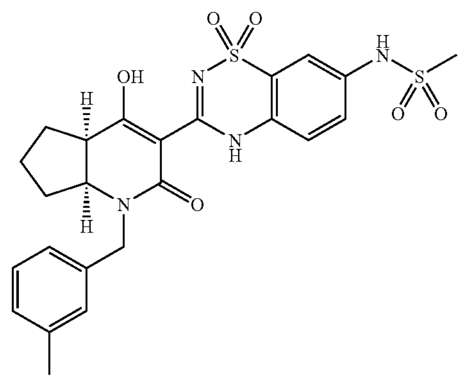 | (4aR,7aS)-N-{3-[4-Hydroxy-1-(3-methyl-benzyl)-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide | ++++ |
| 24 | 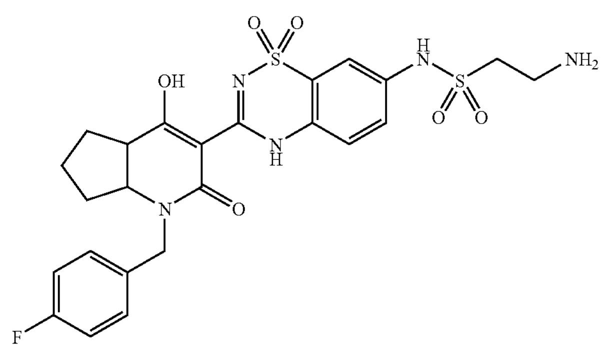 | cis-2-Amino-ethanesulfonic acid {3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-amide | +++ |
| 25 | 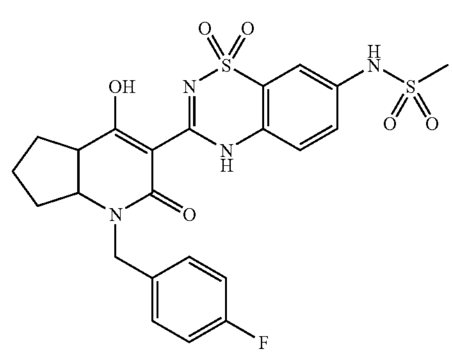 | cis-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,4]thiazin-7-yl}-methanesulfonamide | +++ |

TABLE 1-continued

| Example # | Structure | Name | IC50 |
|---|---|---|---|
| 26 | 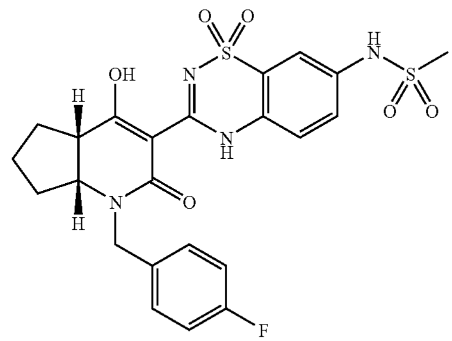 | (4aS,7aR)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide | +++ |
| 27 | 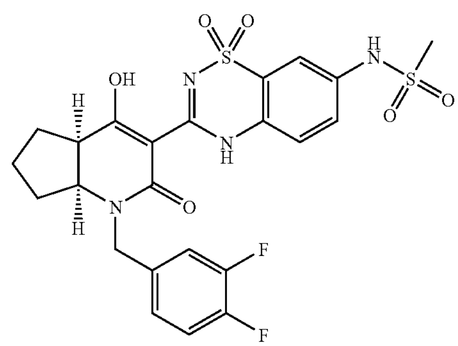 | (4aR,7aS)-N-{3-[1-(3,4-Difluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide | ++++ |
| 28 | 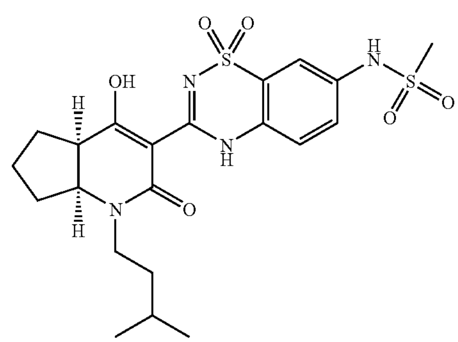 | (4aR,7aS)-N-{3-[4-Hydroxy-1-(3-methyl-butyl)-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide | ++++ |
| 29 | 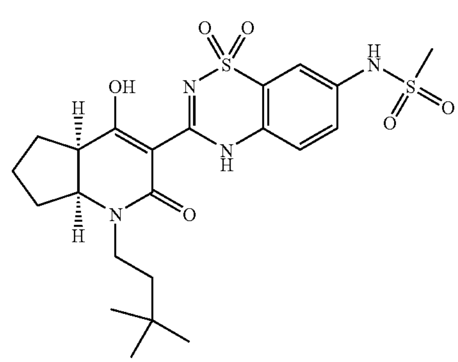 | (4aR,7aS)-N-{3-[1-(3,3-Dimethyl-butyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methane sulfonamide | ++++ |

TABLE 1-continued

| Example # | Structure | Name | IC50 |
|---|---|---|---|
| 30 | 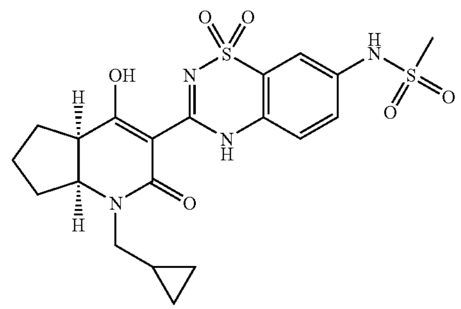 | (4aR,7aS)-N-[3-(1-Cyclopropylmethyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide | ++ |
| 31 | 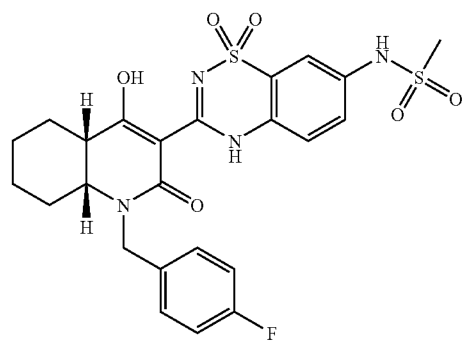 | (4aS,8aR)-N-{3-[1-(4-Fluoro-benzyl)-4-hydroxy-2-oxo-1,2,4a,5,6,7,8,8a-octahydro-quinolin-3-yl]-1,1-dioxo-1,4-dihydro-1$\lambda^6$-benzo[1,2,4]thiadiazin-7-yl}-methanesulfonamide | +++ |
| 32 | 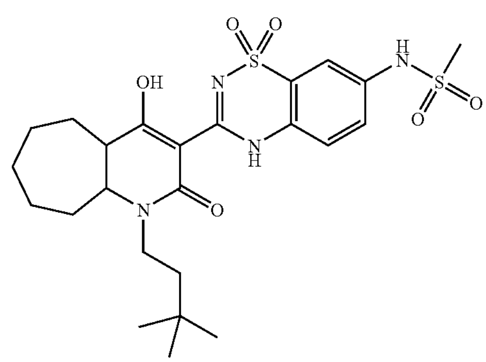 | N-{3-[1-(3,3-Dimethyl-butyl)-4-hydroxy-2-oxo-2,4a,5,6,7,8,9,9a-octahydro-1H-cyclohepta[b]pyridin-3-yl]-1,1-dioxo-1,4-dihydro-1$\lambda^6$-benzo[1,2,4]thiadiazin-7-yl}-methanesulfonamide | +++ |
| 33 | 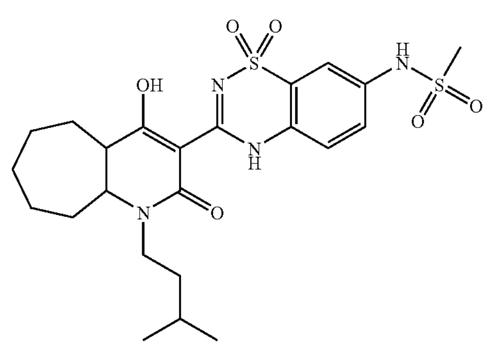 | N-{3-[4-Hydroxy-1-(3-methyl-butyl)-2-oxo-2,4a,5,6,7,8,9,9a-octahydro-1H-cyclohepta[b]pyridin-3-yl]-1,1-dioxo-1,4-dihydro-1$\lambda^6$-benzo[1,2,4]thiadiazin-7-yl}-methanesulfonamide | +++ |

TABLE 1-continued

| Example # | Structure | Name | IC50 |
|---|---|---|---|
| 34 | 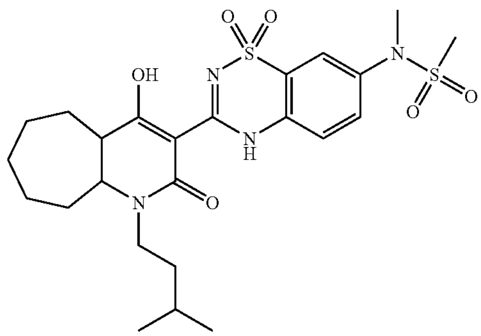 | N-{3-[4-Hydroxy-1-(3-methyl-butyl)-2-oxo-2,4a,5,6,7,8,9,9a-octahydro-1H-cyclohepta[b]pyridin-3-yl]-1,1-dioxo-1,4-dihydro-1$\lambda^6$-benzo[1,2,4]thiadiazin-7-yl}-N-methyl-methanesulfonamide | ++ |
| 35 | 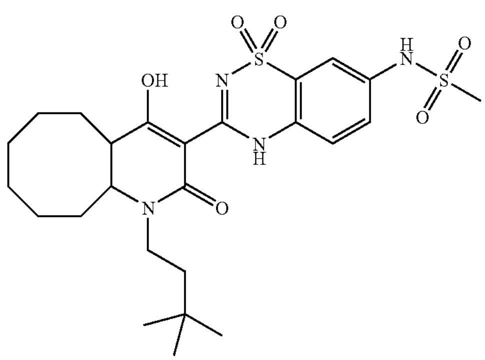 | N-{3-[1-(3,3-Dimethyl-butyl)-4-hydroxy-2-oxo-1,2,4a,5,6,7,8,9,10,10a-decahydro-cycloocta[b]pyridin-3-yl]-1,1-dioxo-1,4-dihydro-1$\lambda^6$-benzo[1,2,4]thiadiazin-7-yl}-methanesulfonamide | + |
| 36 | 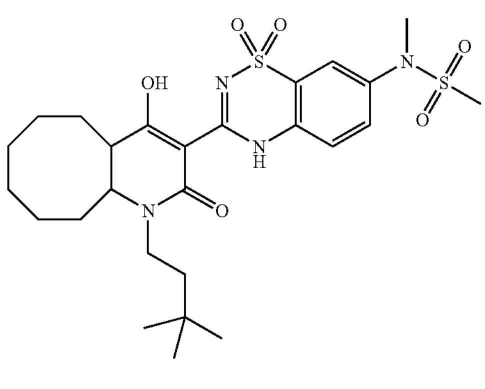 | N-{3-[1-(3,3-Dimethyl-butyl)-4-hydroxy-2-oxo-1,2,4a,5,6,7,8,9,10,10a-decahydro-cycloocta[b]pyridin-3-yl]-1,1-dioxo-1,4-dihydro-1$\lambda^6$-benzo[1,2,4]thiadiazin-7-yl}-N-methyl-methanesulfonamide | + |

TABLE 1-continued

| Example # | Structure | Name | IC50 |
|---|---|---|---|
| 37 | 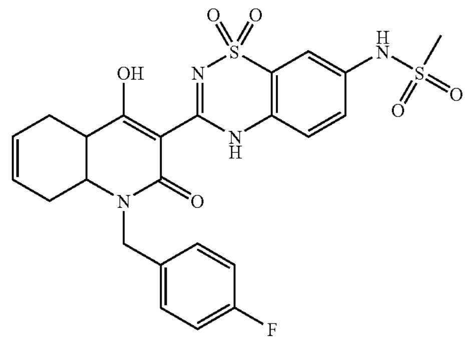 | cis-N-{3-[1-(4-Fluoro-benzyl)-4-hydroxy-2-oxo-1,2,4a,5,8,8a-hexahydro-quinolin-3-yl]-1,1-benzo[1,2,4]thiadiazin-7-yl}-methanesulfonamide | +++ |
| 38 | 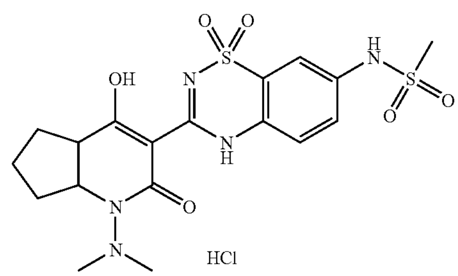 | cis-N-[3-(1-Dimethylamino-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide hydrochloride | + |
| 39 | 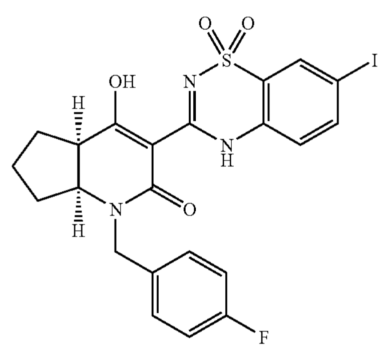 | (4aR,7aS)-1-(4-Fluoro-benzyl)-4-hydroxy-3-(7-iodo-1,1-dioxo-1,4-dihydro-1$\lambda^6$-benzo[1,2,4]thiadiazin-3-yl)-1,4a,5,6,7,7a-hexahydro-[1]pyrindin-2-one | + |
| 40 | 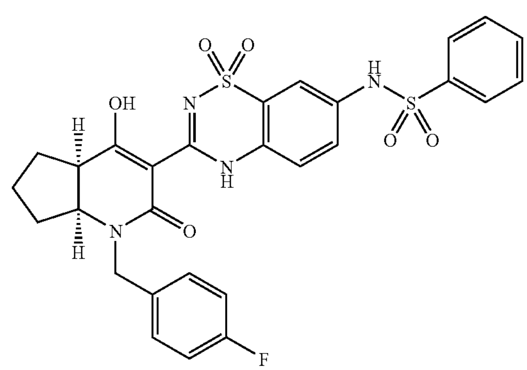 | (4aR,7aS)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-benzenesulfonamide | +++ |

TABLE 1-continued

| Example # | Structure | Name | IC50 |
|---|---|---|---|
| 41 | 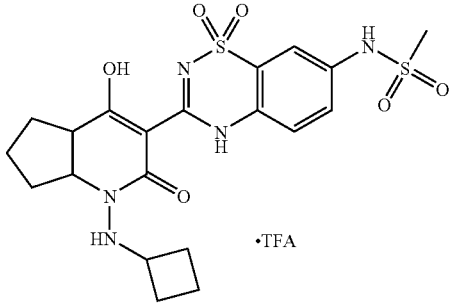 | cis-N-[3-(1-Cyclobutylamino-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide trifluoroacetic acid salt | +++ |
| 42 | 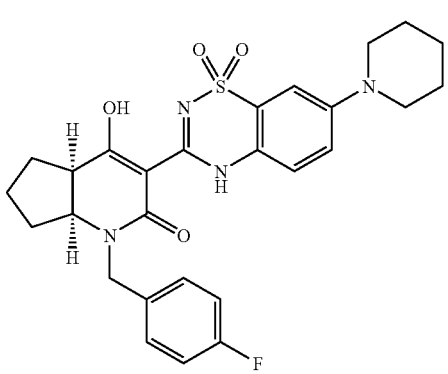 | (4aR,7aS)-3-(1,1-Dioxo-7-piperidin-1-yl-1,4-dihydro-1$\lambda^6$-benzo[1,2,4]thiadiazin-3-yl)-1-(4-fluoro-benzyl)-4-hydroxy-1,4a,5,6,7,7a-hexahydro-[1]pyrindin-2-one | + |
| 43 | 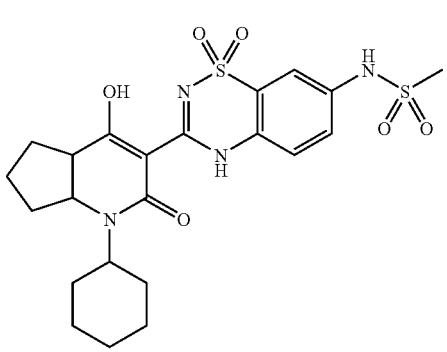 | cis-N-[3-(1-Cyclohexyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide | ++ |
| 44 | 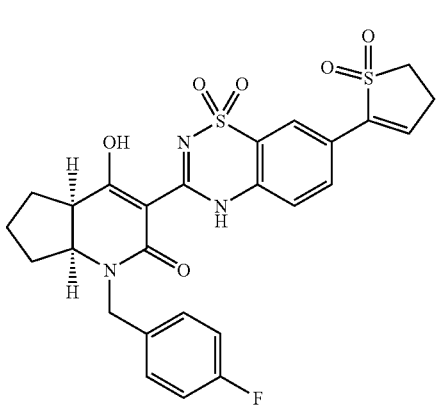 | (4aR,7aS)-3-[7-(1,1-Dioxo-4,5-dihydro-1H-1$\lambda^6$-thiophen-2-yl)-1,1-dioxo-1,4-dihydro-1$\lambda^6$-benzo[1,2,4]thiadiazin-3-yl]-1-(4-fluoro-benzyl)-4-hydroxy-1,4a,5,6,7,7a-hexahydro-[1]pyrindin-2-one | ++ |

TABLE 1-continued

| Example # | Structure | Name | IC50 |
|---|---|---|---|
| 45 | 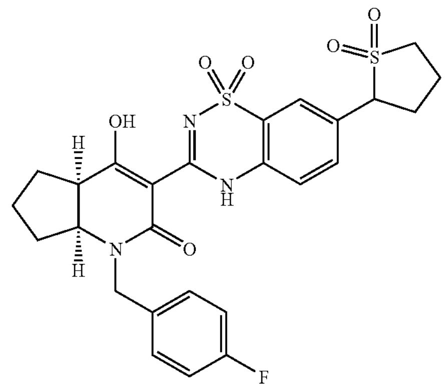 | (4aR,7aS)-3-[7-(1,1-Dioxo-tetrahydro-1$\lambda^6$-thiophen-2-yl)-1,1-dioxo-1,4-dihydro-1$\lambda^6$-benzo[1,2,4]thiadiazin-3-yl]-1-(4-fluoro-benzyl)-4-hydroxy-1,4a,5,6,7,7a-hexahydro-[1]pyrindin-2-one | +++ |
| 46 | 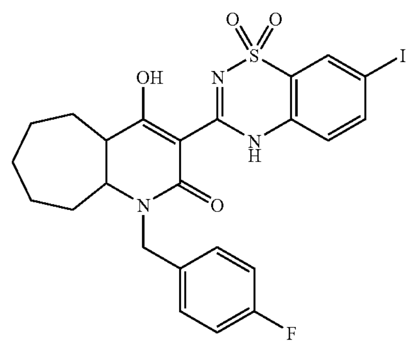 | 1-(4-Fluoro-benzyl)-4-hydroxy-3-(7-iodo-1,1-dioxo-1,4-dihydro-1$\lambda^6$-benzo[1,2,4]thiadiazin-3-yl)-1,4a,5,6,7,8,9,9a-octahydro-cyclohepta[b]pyridin-2-one | + |
| 47 | 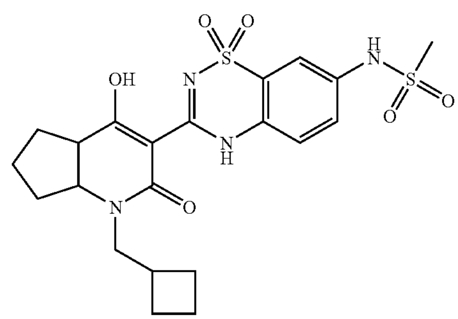 | cis-N-[3-(1-Cyclobutylmethyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide | +++ |
| 48 | 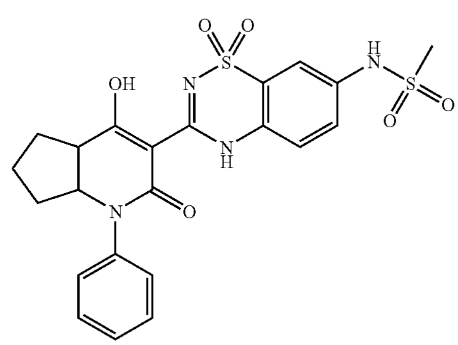 | cis-N-[3-(4-Hydroxy-2-oxo-1-phenyl-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide | + |

TABLE 1-continued

| Example # | Structure | Name | IC50 |
|---|---|---|---|
| 49 | 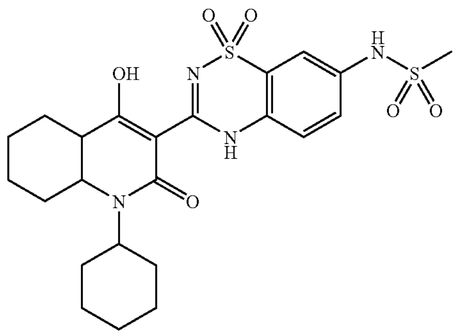 | N-[3-(1-Cyclohexyl-4-hydroxy-2-oxo-1,2,4a,5,6,7,8,8a-octahydro-quinolin-3-yl)-1,1-dioxo-1,4-dihydro-1$\lambda^6$-benzo[1,2,4]thiadiazin-7-yl]-methanesulfonamide | ++ |
| 50 | 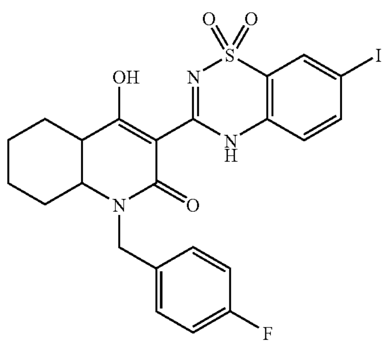 | 1-(4-Fluoro-benzyl)-4-hydroxy-3-(7-iodo-1,1-dioxo-1,4-dihydro-1$\lambda^6$-benzo[1,2,4]thiadiazin-3-yl)-4a,5,6,7,8,8a-hexahydro-1H-quinolin-2-one | + |
| 51 | 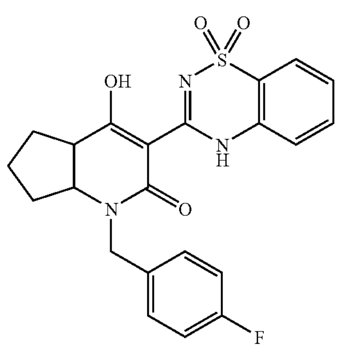 | 3-(1,1-Dioxo-1,4-dihydro-1$\lambda^6$-benzo[1,2,4]thiadiazin-3-yl)-1-(4-fluoro-benzyl)-4-hydroxy-1,4a,5,6,7,7a-hexahydro-[1]pyrindin-2-one | ++ |
| 52 | 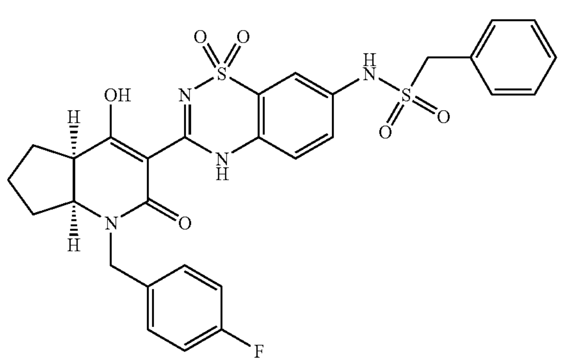 | (4aR,7aS)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-C-phenyl-methanesulfonamide | ++ |

TABLE 1-continued

| Example # | Structure | Name | IC50 |
|---|---|---|---|
| 53 | 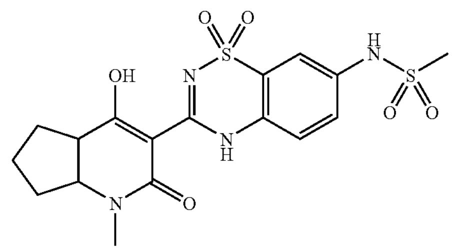 | cis-N-[3-(4-Hydroxy-1-methyl-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide | + |
| 54 | 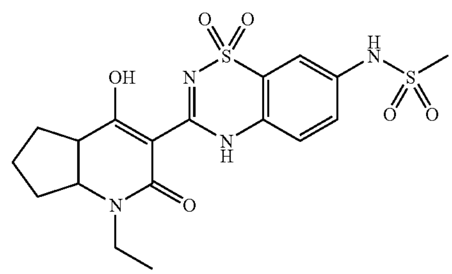 | cis-N-[3-(1-Ethyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide | ++ |
| 55 | 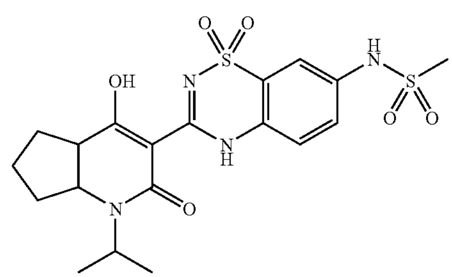 | cis-N-[3-(4-Hydroxy-1-isopropyl-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide | ++ |
| 56 | 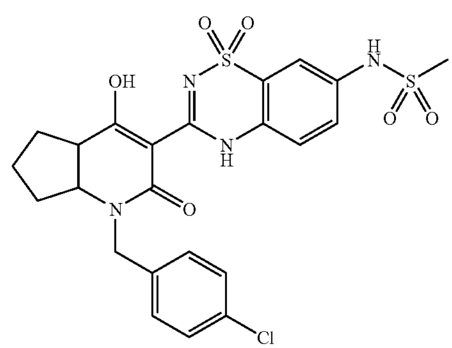 | cis-N-{3-[1-(4-Chloro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide | ++++ |
| 57 | 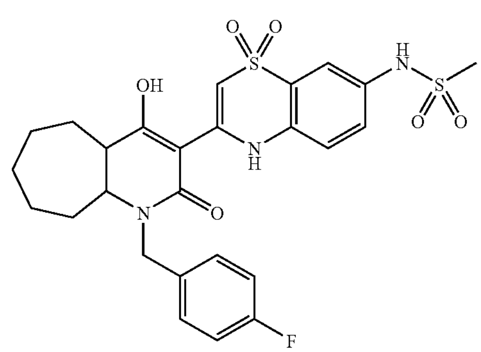 | cis-N-{3-[1-(4-Fluoro-benzyl)-4-octahydro-1H-cyclohepta[b]pyridin-3-yl]-1,1-dioxo-1,4-dihydro-1$\lambda^6$-benzo[1,4]thiazin-7-yl}-methanesulfonamide | ++++ |

TABLE 1-continued

| Example # | Structure | Name | IC50 |
|---|---|---|---|
| 58 | 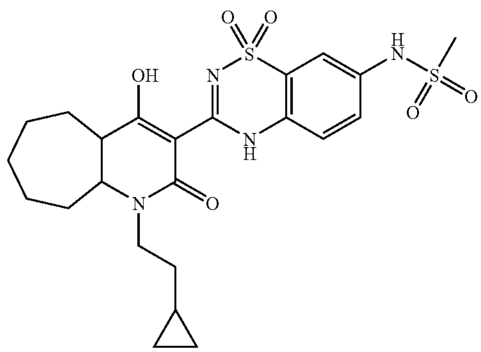 | N-{3-[1-(2-Cyclopropyl-ethyl)-4-hydroxy-2-oxo-2,4a,5,6,7,8,9,9a-octahydro-1H-cyclohepta[b]pyridin-3-yl]-1,1-dioxo-1,4-dihydro-1$\lambda^6$-benzo[1,2,4]thiadiazin-7-yl}-methanesulfonamide | +++ |
| 59 | 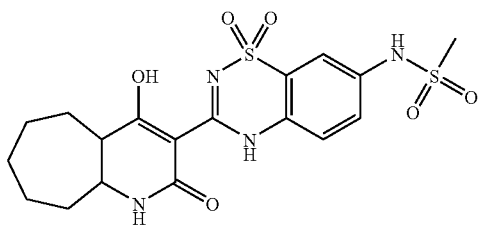 | N-[3-(4-Hydroxy-2-oxo-2,4a,5,6,7,8,9,9a-octahydro-1H-cyclohepta[b]pyridin-3-yl)-1,1-dioxo-1,4-dihydro-1$\lambda^6$-benzo[1,2,4]thiadiazin-7-yl]-methanesulfonamide | + |
| 60 | 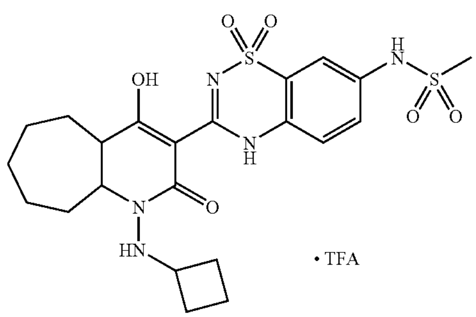 | N-[3-(1-Cyclobutylamino-4-hydroxy-2-oxo-2,4a,5,6,7,8,9,9a-octahydro-1H-cyclohepta[b]pyridin-3-yl)-1,1-dioxo-1,4-dihydro-1$\lambda^6$-benzo[1,2,4]thiadiazin-7-yl]-methanesulfonamide trifluoroacetic acid salt | +++ |

HCV Replicon Assay (Replicon $EC_{50}$ (µM))

The cell culture component of the assay is performed essentially as described by Bartenschlager et al., *Hepatology* 2002, 35, 694-703, wherein exponentially growing HCV Huh-7/C24 replicon cells are seeded at $4.5 \times 10^3$ cells/well in 96 well plates and 24 hours later are treated with six point half-log concentration of compound. After 72 hours exposure the media is discarded from the compound assay plate and the cell monolayers are lysed by addition of 150l lysis mixture (Genospectra) with incubation at 53° C. for 45 minutes. Following incubation, each lysate is thoroughly mixed and 5 µl (NS3 probe) or 10 µl (GAPDH probe) of each lysate is then transferred to the capture plate and analyzed by bDNA assay.

Branched DNA (bDNA) Assay

Based on provided sequences for NS3 [AJ242652], Genospectra (Fremont, Calif., USA) designed and synthesized probes to these analytes (together with GAPDH). Cellular bDNA analysis is carried out essentially as described in the Genospectra protocol (details in Shyamala, V. et al., *Anal Biochem* 1999, 266, 140-7), wherein target specific capture extenders, label extenders and blocking probes are added to the capture plate after the addition of 5 or 10 µl cell lysate. After annealing overnight, during which the target RNA is captured to the plate via interaction with the capture extenders, the plate is washed, and then amplifier (which binds via the label extenders) and label probe are sequentially added.

After subsequent addition of the chemilumigenic substrate (dioxetan), each plate is read by luminometer (Wallac 1420 Multilabel HTS Counter Victor 2). The luminescence signal is proportional to the amount of mRNA present in each lysate. In addition to the samples, cell lysate only (no probe) background controls are also included on each bDNA assay plate and the average signal from these control wells is subtracted from the sample reading prior to analysis. Percent of no drug control is determined for both the NS3 and GAPDH signals for each compound also. Percent inhibition is determined for each compound concentration in relation to the no drug control to calculate the $EC_{50}$.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention.

What is claimed is:
1. A compound of Formula I

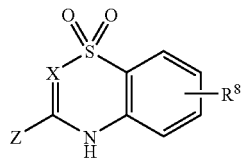

wherein
Z is

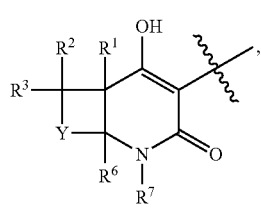

X is N,
Y is —$(CR^4R^5)_n$—,
n is 2, 3, 4, or 5,
$R^1$ and $R^6$ are independently H or $C_1$-$C_6$ alkyl,
$R^2$, $R^3$, $R^4$, and $R^5$ are independently H, $C_1$-$C_6$ alkyl, halo, or $R^2$ and $R^3$ or $R^4$ and $R^5$ combine with the atom to which they are attached to form a 3- to 6-membered spirocyclic ring,
$R^7$ is H, $C_1$-$C_6$ alkyl, $C_3$-$C_8$ cycloalkyl, —$C_1$-$C_6$ alkylene($C_3$-$C_8$ cycloalkyl), —$C_1$-$C_6$ alkylene(aryl), —$C_1$-$C_6$ alkylene(heterocyclyl), aryl, heterocyclyl, or —$NR^{10}R^{11}$, wherein $R^{10}$ and $R^{11}$ are independently H, $C_1$-$C_6$ alkyl, $C_3$-$C_8$ cycloalkyl, or $C_2$-$C_6$ alkenyl
$R^8$ is H, halo, nitro, —$CHR^{12}S(O)_2R^{13}$, —$C(S(O)_2R^{13})$=$CHR^{12}$—, —$NR^{13}R^{14}$, —$NR^{12}S(O)_2R^{13}$, or —$NR^{12}S(O)_2NR^{13}R^{14}$, wherein $R^{12}$, $R^{13}$, and $R^{14}$ are independently H, $C_1$-$C_6$ alkyl $C_3$-$C_8$ cycloalkyl, aryl, or heterocyclyl, or $R^{12}$ and $R^{13}$ or $R^{13}$ and $R^{14}$ combine with the atom(s) to which they are attached to form a 5- or 6-membered heterocyclyl ring,
wherein the above alkyl, alkylene, aryl, cycloalkyl, or heterocyclyl moieties provided in $R^1$, $R^2$, $R^3$, $R^4$, $R^5$, $R^6$, $R^7$, $R^{10}$, $R^{11}$, $R^{12}$, $R^{13}$, and $R^{14}$ are each optionally and independently substituted by 1-3 substituents selected from
alkylamine,
amino,
aryl, cycloalkyl, heterocyclyl,
$C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms,
carboxyl,
cyano,
halo,
hydroxy,
nitro,
—C(O)OH, —$C(O)_2$—($C_1$-$C_6$ alkyl), —$C(O)_2$—($C_3$-$C_8$ cycloalkyl), —$C(O)_2$-(aryl), —$C(O)_2$-(heterocyclyl), —$C(O)_2$—($C_1$-$C_6$ alkylene)aryl, —$C(O)_2$—($C_1$-$C_6$ alkylene)heterocyclyl, —$C(O)_2$—($C_1$-$C_6$ alkylene)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkylene)aryl, —C(O)($C_1$-$C_6$ alkylene)heterocyclyl, and —C(O)($C_1$-$C_6$ alkylene)cycloalkyl,
wherein each of the above optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents,
or a pharmaceutically acceptable salt, hydrate, tautomer or stereoisomer thereof.

2. The compound according to claim 1 wherein $R^8$ is —$NR^{12}S(O)_2R^{13}$, wherein $R^{12}$ and $R^{13}$ are independently H, $C_1$-$C_6$ alkyl or $C_3$-$C_8$ cycloalkyl.

3. The compound according to claim 2 wherein $R^8$ is selected from

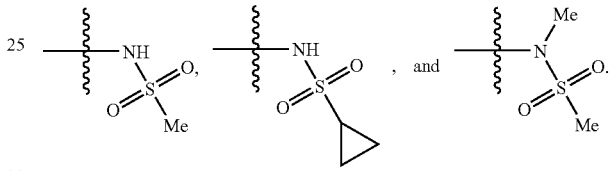

4. The compound according to claim 3 wherein $R^8$ is selected from

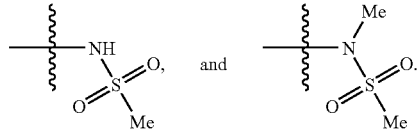

5. The compound according to claim 1 wherein $R^7$ is selected from

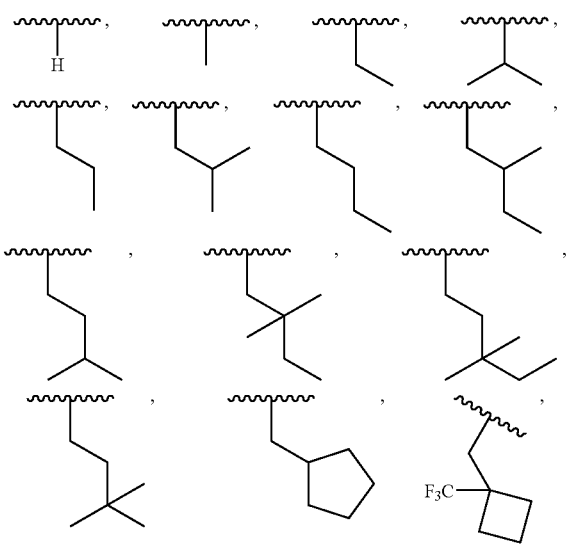

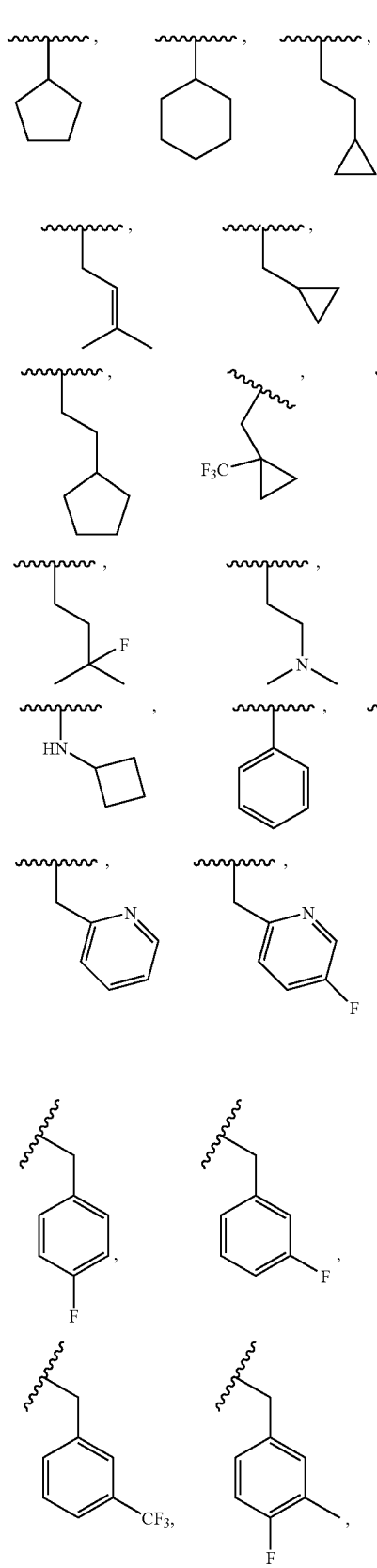
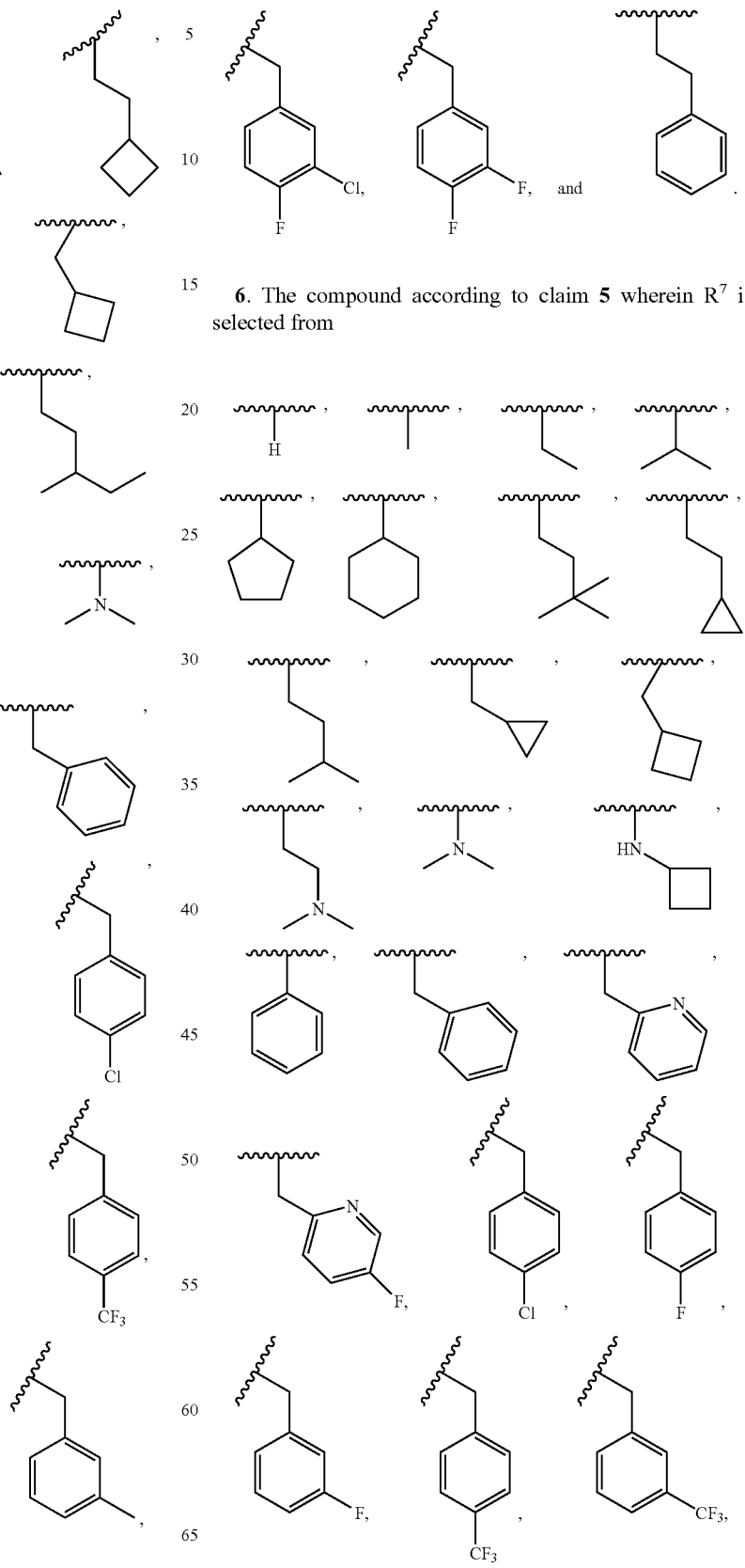
6. The compound according to claim 5 wherein $R^7$ is selected from -continued

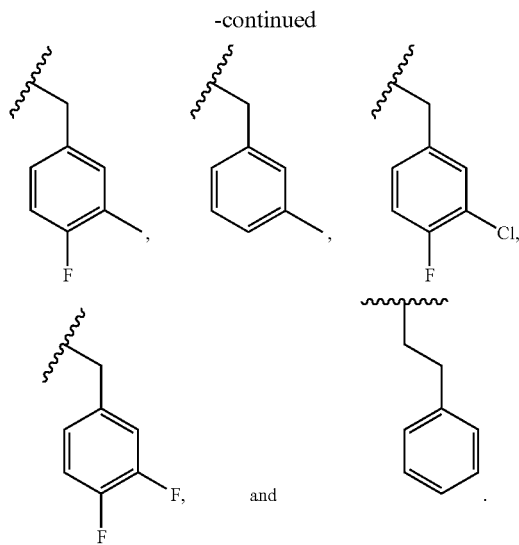

7. The compound according claim 6 wherein $R^7$ is selected from

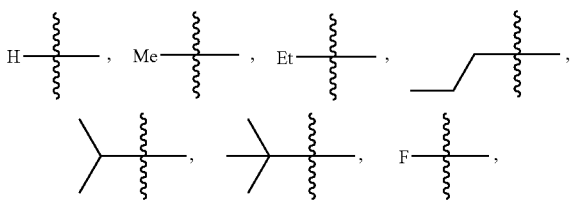

8. The compound according to claim 1 wherein $R^1$ and $R^6$ are H.

9. The compound according to claim 1 wherein $R^2$, $R^3$, $R^4$, and $R^5$ are independently selected from

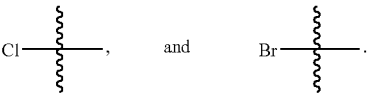

10. The compound according to claim 9 wherein $R^2$, $R^3$, $R^4$, and $R^5$ are independently selected from

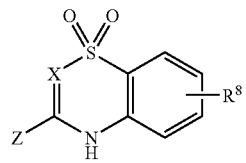

11. The compound according to claim 10 wherein $R^2$, $R^3$, $R^4$, and $R^5$ are H.

12. The compound according to claim 1 wherein n is 2 or 3.

13. A compound of Formula I

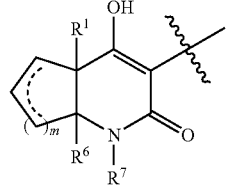

I wherein
Z is with one carbon-carbon double bond among the bonds indicated by the dotted line,
X is N,
m is 1 or 2,
$R^1$ and $R^6$ are independently H or $C_1$-$C_6$ alkyl,
$R^7$ is H, $C_1$-$C_6$ alkyl, $C_3$-$C_8$ cycloalkyl, —$C_1$-$C_6$ alkylene ($C_3$-$C_8$ cycloalkyl), —$C_1$-$C_6$ alkylene(aryl), —$C_1$-$C_6$ alkylene(heterocyclyl), aryl, heterocyclyl, or —$NR^{10}R^{11}$, wherein $R^{10}$ and $R^{11}$ are independently H, $C_1$-$C_6$ alkyl, $C_3$-$C_8$ cycloalkyl, or $C_2$-$C_6$-alkenyl
$R^8$ is H, halo, nitro, —$CHR^{12}S(O)_2R^{13}$, —$C(S(O)_2R^{13})$ =$CHR^{12}$—, —$NR^{13}R^{14}$, —$NR^{12}S(O)_2R^{13}$, or —$NR^{12}S(O)_2NR^{13}R^{14}$, wherein $R^{12}$, $R^{13}$, and $R^{14}$ are independently H, $C_1$-$C_6$ alkyl, $C_3$-$C_8$ cycloalkyl, aryl, or heterocyclyl, or $R^{12}$ and $R^{13}$ or $R^{13}$ and $R^{14}$ combine with the atom(s) to which they are attached to form a 5- or 6-membered heterocyclyl ring,
wherein the above alkyl, alkylene, aryl, cycloalkyl, or heterocyclyl moieties provided in $R^1$, $R^6$, $R^7$, $R^{10}$, $R^{11}$, $R^{12}$, $R^{13}$, and $R^{14}$ are each optionally and independently substituted by 1-3 substituents selected from
alkylamine,
amino,
aryl, cycloalkyl, heterocyclyl,
$C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms,
carboxyl,
cyano, halo,
hydroxy,
nitro,
—C(O)OH, —C(O)$_2$—(C$_1$-C$_6$ alkyl), —C(O)$_2$—(C$_3$-C$_8$ cycloalkyl), —C(O)$_2$-(aryl), —C(O)$_2$-(heterocyclyl), —C(O)$_2$—(C$_1$-C$_6$ alkylene)aryl, —C(O)$_2$—(C$_1$-C$_6$ alkylene)heterocyclyl,
—C(O)$_2$—(C$_1$-C$_6$ alkylene)cycloalkyl, —C(O)(C$_1$-C$_6$ alkyl), —C(O)(C$_3$-C$_8$ cycloalkyl),
—C(O)(aryl), —C(O)(heterocyclyl), —C(O)(C$_1$-C$_6$ alkylene)aryl, —C(O)(C$_1$-C$_6$ alkylene)heterocyclyl, and —C(O)(C$_1$-C$_6$ alkylene)cycloalkyl,
wherein each of the above optional substituents can be further optionally substituted by 1-5 substituents selected from amino, cyano, halo, hydroxy, nitro, C$_1$-C$_6$ alkylamine, C$_1$-C$_6$ dialkylamine, C$_1$-C$_6$ alkyl, C$_1$-C$_6$ alkoxy, C$_1$-C$_6$ alkenyl, and C$_1$-C$_6$ hydroxyalkyl, wherein each alkyl is optionally substituted by one or more halo substituents,
or a pharmaceutically acceptable salt, hydrate, tautomer or stereoisomer thereof.

14. The compound according to claim 13 wherein m is 2.

15. A compound selected from
cis-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
N-{3-[1-(4-Fluoro-benzyl)-4-hydroxy-2-oxo-2,4a,5,6,7,8,9,9a-octahydro-1H-cyclohepta[b]pyridin-3-yl]-1,1-dioxo-1,4-dihydro-1λ$^6$-benzo[1,2,4]thiadiazin-7-yl}-methanesulfonamide,
N-{3-[1-(4-Fluoro-benzyl)-4-hydroxy-2-oxo-1,2,4a,5,6,7,8,9,10,10a-decahydro-cycloocta[b]pyridin-3-yl]-1,1-dioxo-1,4-dihydro-1λ$^6$-benzo[1,2,4]thiadiazin-7-yl}-methanesulfonamide,
cis-N-[3-(4-Hydroxy-2-oxo-1-pyridin-2-ylmethyl-2,4a,5,6,7,7a-hexahydro-1H-[1]pyrindin-3-yl)-1,1-dioxo-1,4-dihydro-1λ6-benzo[1,2,4]thiadiazin-7-yl]-methanesulfonamide,
cis-N-{3-[1-(5-Fluoro-pyridin-2-ylmethyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
cis-N-{3-[1-(2-Dimethylamino-ethyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
cis-N-[3-(1-Benzyl-4-hydroxy-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide,
cis-N-{3-[1-(3-Fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
cis-N-[3-(4-Hydroxy-2-oxo-1-phenethyl-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide,
cis-N-[3-(1-Cyclopentyl-4-hydroxy-2-oxo-2,4a,5,6,7,7a-hexahydro-1H-[1]pyrindin-3-yl)-1,1-dioxo-1,4-dihydro-1λ$^6$-benzo[1,2,4]thiadiazin-7-yl]-methanesulfonamide,
(4aR,7aS)-N-{3-[1-(3-Chloro-4-fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
(4aR,7aS)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
(4aR,8aS)-N-{3-[1-(4-Fluoro-benzyl)-4-hydroxy-2-oxo-1,2,4a,5,6,7,8,8a-octahydro-quinolin-3-yl]-1,1-dioxo-1,4-dihydro-1λ$^6$-benzo[1,2,4]thiadiazin-7-yl}-methanesulfonamide,
(4aR,7aS)-N-{3-[4-Hydroxy-2-oxo-1-(4-trifluoromethyl-benzyl)-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
(4aR,7aS)-N-{3-[4-Hydroxy-2-oxo-1-(3-trifluoromethyl-benzyl)-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
N-{3-[1-(4-Fluoro-benzyl)-4-hydroxy-2-oxo-1,2,4a,5,6,8a-hexahydro-quinolin-3-yl]-1,1-dioxo-1,4-dihydro-1λ$^6$-benzo[1,2,4]thiadiazin-7-yl}-methanesulfonamide,
cis-N-{3-[2-(3-Methylbutyl)-5-hydroxy-3-oxo-2-aza-bicyclo[4.3.0]non-4-en-4-yl]-1,1-dioxo-1,4-dihydro-1λ$^6$-benzo[1,2,4]thiadiazin-7-yl}-methanesulfonamide,
cis-N-{3-[2-(3,3-Dimethylbutyl)-5-hydroxy-3-oxo-2-aza-bicyclo[4.3.0]non-4-en-4-yl]-1,1-dioxo-1,4-dihydro-1λ$^6$-benzo[1,2,4]thiadiazin-7-yl}-methanesulfonamide,
cis-N-{3-[2-Cyclopropylethyl-5-hydroxy-3-oxo-2-aza-bicyclo[4.3.0]non-4-en-4-yl]-1,1-dioxo-1,4-dihydro-1λ$^6$-benzo[1,2,4]thiadiazin-7-yl}-methanesulfonamide,
N-{3-[2-(3-Methylbutyl)-5-hydroxy-3-oxo-2-aza-bicyclo[4.4.0]dec-4-en-4-yl]-1,1-dioxo-1,4-dihydro-1λ$^6$-benzo[1,2,4]thiadiazin-7-yl}-methanesulfonamide,
N-{3-[2-(3,3-Dimethylbutyl)-5-hydroxy-3-oxo-2-aza-bicyclo[4.4.0] dec-4-en-4-yl]-1,1-dioxo-1,4-dihydro-1λ$^6$-benzo[1,2,4]thiadiazin-7-yl}-methanesulfonamide,
(4aR,7aS)-N-{3-[1-(4-Fluoro-3-methyl-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
(4aR,7aS)-N-{3-[4-Hydroxy-1-(3-methyl-benzyl)-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
cis-2-Amino-ethanesulfonic acid {3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-amide,
(4aS,7aR)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
(4aR,7aS)-N-{3-[1-(3,4-Difluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
(4aR,7aS)-N-{3-[4-Hydroxy-1-(3-methyl-butyl)-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide,
(4aR,7aS)-N-{3-[1-(3,3-Dimethyl-butyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide, (4aR,7aS)-N-[3-(1-Cyclopropylmethyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide, (4aS,8aR)-N-{3-[1-(4-Fluoro-benzyl)-4-hydroxy-2-oxo-1,2,4a,5,6,7,8,8a-octahydro-quinolin-3-yl]-1,1-dioxo-1,4-dihydro-1$\lambda^6$-benzo[1,2,4]thiadiazin-7-yl}-methanesulfonamide, N-{3-[1-(3,3-Dimethyl-butyl)-4-hydroxy-2-oxo-2,4a,5,6,7,8,9,9a-octahydro-1H-cyclohepta[b]pyridin-3-yl]-1,1-dioxo-1,4-dihydro-1$\lambda^6$-benzo[1,2,4]thiadiazin-7-yl}-methanesulfonamide, N-{3-[4-Hydroxy-1-(3-methyl-butyl)-2-oxo-2,4a,5,6,7,8,9,9a-octahydro-1H-cyclohepta[b]pyridin-3-yl]-1,1-dioxo-1,4-dihydro-1$\lambda^6$-benzo[1,2,4]thiadiazin-7-yl}-methanesulfonamide, N-{3-[4-Hydroxy-1-(3-methyl-butyl)-2-oxo-2,4a,5,6,7,8,9,9a-octahydro-1H-cyclohepta[b]pyridin-3-yl]-1,1-dioxo-1,4-dihydro-1$\lambda^6$-benzo[1,2,4]thiadiazin-7-yl}-N-methyl-methanesulfonamide, N-{3-[1-(3,3-Dimethyl-butyl)-4-hydroxy-2-oxo-1,2,4a,5,6,7,8,9,10,10a-decahydro-cycloocta[b]pyridin-3-yl]-1,1-dioxo-1,4-dihydro-1$\lambda^6$-benzo[1,2,4]thiadiazin-7-yl}-methanesulfonamide, N-{3-[1-(3,3-Dimethyl-butyl)-4-hydroxy-2-oxo-1,2,4a,5,6,7,8,9,10,10a-decahydro-cycloocta[b]pyridin-3-yl]-1,1-dioxo-1,4-dihydro-1$\lambda^6$-benzo[1,2,4]thiadiazin-7-yl}-N-methyl-methanesulfonamide, cis-N-{3-[1-(4-Fluoro-benzyl)-4-hydroxy-2-oxo-1,2,4a,5,8,8a-hexahydro-quinolin-3-yl]-1,1-dioxo-1,4-dihydro-1$\lambda^6$-benzo[1,2,4]thiadiazin-7-yl}-methanesulfonamide, cis-N-[3-(1-Dimethylamino-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide hydrochloride, (4aR,7aS)-1-(4-Fluoro-benzyl)-4-hydroxy-3-(7-iodo-1,1-dioxo-1,4-dihydro-1$\lambda^6$ benzo[1,2,4]thiadiazin-3-yl)-1,4a,5,6,7,7a-hexahydro-[1]pyrindin-2-one, (4aR,7aS)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-benzenesulfonamide, cis-N-[3-(1-Cyclobutylamino-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide trifluoroacetic acid salt, (4aR,7aS)-3-(1,1-Dioxo-7-piperidin-1-yl-1,4-dihydro-1$\lambda^6$-benzo[1,2,4]thiadiazin-3-yl)-1-(4-fluoro-benzyl)-4-hydroxy-1,4a,5,6,7,7a-hexahydro-[1]pyrindin-2-one, cis-N-[3-(1-Cyclohexyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide, (4aR,7aS)-3-[7-(1,1-Dioxo-4,5-dihydro-1H-1$\lambda^6$-thiophen-2-yl)-1,1-dioxo-1,4-dihydro-1$\lambda^6$-benzo[1,2,4]thiadiazin-3-yl]-1-(4-fluoro-benzyl)-4-hydroxy-1,4a,5,6,7,7a-hexahydro-[1]pyrindin-2-one, (4aR,7aS)-3-[7-(1,1-Dioxo-tetrahydro-1$\lambda^6$-thiophen-2-yl)-1,1-dioxo-1,4-dihydro-1$\lambda^6$-benzo[1,2,4]thiadiazin-3-yl]-1-(4-fluoro-benzyl)-4-hydroxy-1,4a,5,6,7,7a-hexahydro-[1]pyrindin-2-one, 1-(4-Fluoro-benzyl)-4-hydroxy-3-(7-iodo-1,1-dioxo-1,4-dihydro-1$\lambda^6$-benzo[1,2,4]thiadiazin-3-yl)-1,4a,5,6,7,8,9,9a-octahydro-cyclohepta[b]pyridin-2-one, cis-N-[3-(1-Cyclobutylmethyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide, cis-N-[3-(4-Hydroxy-2-oxo-1-phenyl-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide, N-[3-(1-Cyclohexyl-4-hydroxy-2-oxo-1,2,4a,5,6,7,8,8a-octahydro-quinolin-3-yl)-1,1-dioxo-1,4-dihydro-1$\lambda^6$-benzo[1,2,4]thiadiazin-7-yl]-methanesulfonamide, 1-(4-Fluoro-benzyl)-4-hydroxy-3-(7-iodo-1,1-dioxo-1,4-dihydro-1$\lambda^6$-benzo[1,2,4]thiadiazin-3-yl)-4a,5,6,7,8,8a-hexahydro-1H-quinolin-2-one, 3-(1,1-Dioxo-1,4-dihydro-1$\lambda^6$-benzo[1,2,4]thiadiazin-3-yl)-1-(4-fluoro-benzyl)-4-hydroxy-1,4a,5,6,7,7a-hexahydro-[1]pyrindin-2-one, (4aR,7aS)-N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-C-phenyl-methanesulfonamide, cis-N-[3-(4-Hydroxy-1-methyl-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide, cis-N-[3-(1-Ethyl-4-hydroxy-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide, cis-N-[3-(4-Hydroxy-1-isopropyl-2-oxo-2,4a,5,6,7,7a-hexahydro-1H-[1]pyrindin-3-yl)-1,1-dioxo-1,4-dihydro-1$\lambda^6$-benzo[1,2,4]thiadiazin-7-yl]-methanesulfonamide, cis-N-{3-[1-(4-Chloro-benzyl)-4-hydroxy-2-oxo-2,4a,5,6,7,7a-hexahydro-1H-[1]pyrindin-3-yl]-1,1-dioxo-1,4-dihydro-1$\lambda^6$-benzo[1,2,4]thiadiazin-7-yl}-methanesulfonamide, N-{3-[1-(2-Cyclopropyl-ethyl)-4-hydroxy-2-oxo-2,4a,5,6,7,8,9,9a-octahydro-1H-cyclohepta[b]pyridin-3-yl]-1,1-dioxo-1,4-dihydro-1$\lambda^6$-benzo[1,2,4]thiadiazin-7-yl}-methanesulfonamide, N-[3-(4-Hydroxy-2-oxo-2,4a,5,6,7,8,9,9a-octahydro-1H-cyclohepta[b]pyridin-3-yl)-1,1-dioxo-1,4-dihydro-1$\lambda^6$-benzo[1,2,4]thiadiazin-7-yl]-methanesulfonamide, and N-[3-(1-Cyclobutylamino-4-hydroxy-2-oxo-2,4a,5,6,7,8,9,9a-octahydro-1H-cyclohepta[b]pyridin-3-yl)-1,1-dioxo-1,4-dihydro-1$\lambda^6$-benzo[1,2,4]thiadiazin-7-yl]-methanesulfonamide trifluoroacetic acid salt.

16. A pharmaceutically acceptable composition comprising a compound of claim 1 and a pharmaceutically acceptable carrier.

17. A method for treating hepatitis C virus infection in a mammal in need thereof, comprising administering to the mammal a therapeutically effective amount of a compound of claim 1.

18. The method of claim 17 wherein the mammal is a human.

19. The method of claim 17 further comprising administering an additional therapeutic agent to the mammal.

20. The method of claim 19 wherein the additional therapeutic agent is selected from the group consisting of an antibiotic, an antiemetic agent, an antidepressant, an antifungal agent, an anti-inflammatory agent, an antiviral agent, an anticancer agent, an immunomodulatory agent, an α-interferon, a β-interferon, a ribavirin, an alkylating agent, a hormone, a cytokine and a toll receptor-like modulator.

* * * * *